United States Patent
Boehme et al.

(10) Patent No.: US 8,895,547 B2
(45) Date of Patent: Nov. 25, 2014

(54) SUBSTITUTED PHENYL-OXATHIAZINE DERIVATIVES, METHOD FOR PRODUCING THEM, DRUGS CONTAINING SAID COMPOUNDS AND THE USE THEREOF

(75) Inventors: Thomas Boehme, Frankfurt am Main (DE); Christian Engel, Frankfurt am Main (DE); Stefan Guessregen, Frankfurt am Main (DE); Torsten Haack, Frankfurt am Main (DE); Kurt Ritter, Frankfurt am Main (DE); Georg Tschank, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/003,329

(22) PCT Filed: Mar. 7, 2012

(86) PCT No.: PCT/EP2012/053940
§ 371 (c)(1),
(2), (4) Date: Sep. 5, 2013

(87) PCT Pub. No.: WO2012/120057
PCT Pub. Date: Sep. 13, 2012

(65) Prior Publication Data
US 2013/0338066 A1 Dec. 19, 2013

(30) Foreign Application Priority Data
Mar. 8, 2011 (EP) .................................. 11305245

(51) Int. Cl.
| | | |
|---|---|---|
| A61K 31/51 | (2006.01) | |
| C07D 419/14 | (2006.01) | |
| C07D 291/08 | (2006.01) | |
| C07D 419/10 | (2006.01) | |
| A61K 31/551 | (2006.01) | |
| A61K 31/54 | (2006.01) | |
| C07D 419/04 | (2006.01) | |
| C07D 515/10 | (2006.01) | |
| A61K 31/541 | (2006.01) | |
| A61K 31/547 | (2006.01) | |
| A61K 45/06 | (2006.01) | |
| C07D 291/06 | (2006.01) | |
| C07D 419/12 | (2006.01) | |

(52) U.S. Cl.
CPC ............ *C07D 291/06* (2013.01); *C07D 419/14* (2013.01); *C07D 291/08* (2013.01); *C07D 419/10* (2013.01); *A61K 31/551* (2013.01); *A61K 31/54* (2013.01); *C07D 419/04* (2013.01); *C07D 515/10* (2013.01); *A61K 31/541* (2013.01); *A61K 31/547* (2013.01); *A61K 45/06* (2013.01); *C07D 419/12* (2013.01)
USPC .......................... 514/222.5; 514/222.2; 544/2

(58) Field of Classification Search
None
See application file for complete search history.

(56) References Cited

U.S. PATENT DOCUMENTS

2013/0345127 A1* 12/2013 Boehme et al. ................ 514/6.5

FOREIGN PATENT DOCUMENTS

| WO | WO 02/11722 A1 | 2/2002 |
| WO | WO 2008/073956 A2 | 6/2008 |

OTHER PUBLICATIONS

Burgess, E.M. et al., "The fragmentation of substituted 1,4,3,5-oxathiazine dioxides to N-sulfonylamides", J. Org. Chem., (1973), vol. 38, No. 6, pp. 1249-1250.
Suzue,S et al., "Studies on Hypoglycemic Agents. IV. 1) Synthesis of 1,4,3-Benzoxathiazine-4,4-dioxides", Chemical and Pharmaceutical Bulletin, (May 25, 1968), vol. 16, No. 5, pp. 806-813.
Tsuneo, I. et al., "Cycloaddition in Synthesis of Sulfonamide Derivatives. IV. One-Pot Synthesis of 3-Dimethylamino-4,1,2-benzoxathiazine 1,1-Dioxides,3-Methoxy-4-methyl-1,2,4-benzothiadizine 1,1-Dioxiade and 3- Dimethylamino-1,4,2-benzodithiazine 1,1-Dioxides", Chemical and Pharmaceutical Bulletin, (Aug. 25, 1991), vol. 39, No. 8, pp. 1939-1943.
International Search Report dated May 11, 2012 issued in PCT/EP2012/053940, previously submitted on Sep. 5, 2013.

* cited by examiner

*Primary Examiner* — James H Alstrum Acevedo
*Assistant Examiner* — Fred Reynolds
(74) *Attorney, Agent, or Firm* — Scully, Scott, Murphy & Presser, P.C.

(57) ABSTRACT

The invention relates to the compounds of formula (I) and to the physiologically acceptable salts thereof. Said compounds are suitable e.g. for the treatment of hyperglycemia.

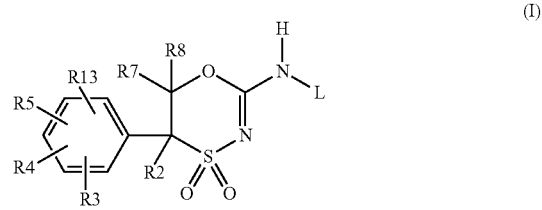

12 Claims, No Drawings

SUBSTITUTED PHENYL-OXATHIAZINE DERIVATIVES, METHOD FOR PRODUCING THEM, DRUGS CONTAINING SAID COMPOUNDS AND THE USE THEREOF

Novel substituted phenyl-oxathiazine derivatives, method for producing them, drugs containing said compounds and the use thereof.

The invention relates to substituted phenyloxathiazine derivatives and to the physiologically compatible salts thereof.

It was an object of the invention to provide compounds which display a therapeutically utilizable action. More particularly, it was a further object to find novel compounds suitable for treatment of diabetes, hyperglycemia, insulin resistance, obesity or lipid metabolism disorders.

The invention therefore relates to compounds of the formula I

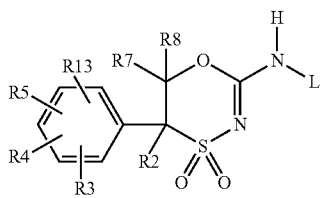

in which

L is R1, —CH(R10)(R11);

R10, R11 are each independently H, F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$, ($C_1$-$C_6$)-alkylene-(R6), ($C_3$-$C_8$)-cycloalkylene-(R6), ($C_1$-$C_6$)-alkylene-($C_3$-$C_8$)-cycloalkylene-(R6), ($C_6$-$C_{10}$-aryl, ($C_1$-$C_6$)-alkylene-(($C_6$-$C_{10}$)-aryl;

where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;

R1 is

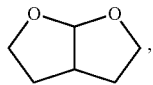

($C_6$-$C_{10}$)-aryl, ($C_3$-$C_8$)-cycloalkyl,
where the

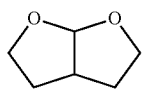

radical, aryl radical or cycloalkyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;

R2 is H, F, ($C_1$-$C_3$)-alkyl where the alkyl radical may be mono- to trisubstituted by fluorine;

R3, R4, R5, R13 are each independently
H, F, Cl, Br, I, OH, $CF_3$, $CHF_2$, $CH_2F$, $NO_2$, CN, $OCF_3$, $OCHF_2$, —($C_1$-$C_6$)-alkylene-(R9), O—($C_1$-$C_6$)-alkylene-(R9), tert-butyl, isopropylene-(R9), (C=O)—($C_1$-$C_6$)-alkylene-(R9), ($C_1$-$C_6$)-alkylene-(R9), $NH_2$, NH($C_1$-$C_6$)-alkylene-(R9), N(($C_1$-$C_6$)-alkylene-R9)$_2$, ($C_1$-$C_6$)-alkylene-$NH_2$, ($C_1$-$C_6$)-alkylene-NH($C_1$-$C_6$)-alkylene-(R9), ($C_1$-$C_6$)-alkylene-N(($C_1$-$C_6$)-alkylene-R9)$_2$, —O—($C_1$-$C_6$)-alkylene-$NH_2$, —O—($C_1$-$C_6$)-alkylene-NH($C_1$-$C_6$)-alkylene-(R9), —O—($C_1$-$C_6$)-alkylene-N(($C_1$-$C_6$)-alkylene-R9)$_2$, —NH—($C_1$-$C_6$)-alkylene-$NH_2$, —NH—($C_1$-$C_6$)-alkylene-NH($C_1$-$C_6$)-alkylene-(R9), —NH—($C_1$-$C_6$)-alkylene-N(($C_1$-$C_6$)-alkylene-R9)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
($C_6$-$C_{10}$)-aryl, —($C_1$-$C_6$)-alkylene-($C_6$-$C_{10}$)-aryl,
where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$, ($C_6$-$C_{10}$-aryl, ($C_3$-$C_8$)-cycloalkyl, 4- to 12-membered heterocycle;
where the ($C_6$-$C_{10}$)-aryl radical, ($C_3$-$C_8$)-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
4- to 12-membered heterocycle, —($C_1$-$C_6$)-alkylene-4- to -12-membered heterocycle,
where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, NH($C_1$-$C_6$)-alkylene-(R9), N(($C_1$-$C_6$)-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—NH($C_1$-$C_6$)-alkylene-(R9), $SO_2$—N(($C_1$-$C_6$)-alkyl)$_2$, COOH, COO—($C_1$-$C_6$)-alkylene-(R9), $CONH_2$, CONH($C_1$-$C_6$)-alkylene-(R9), CON(($C_1$-$C_6$)-alkyl)$_2$, $SF_5$, ($C_6$-$C_{10}$)-aryl, ($C_3$-$C_8$)-cycloalkyl, 4- to 12-membered heterocycle;
where the ($C_6$-$C_{10}$)-aryl radical, ($C_3$-$C_8$)-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;

R6 is H, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—

(C$_1$-C$_6$)-alkyl, CONH$_2$, CONH(C$_1$-C$_6$)-alkyl, CON((C$_1$-C$_6$)-alkyl)$_2$, O—(CO)—NH$_2$, SF$_5$;

R7, R8 are each independently H, (C$_1$-C$_3$)-alkyl, where the alkyl radical may be mono- to trisubstituted by fluorine, or R7 and R8 together with the carbon atom to which they are bonded form a 3-8-membered carbocycle or heterocycle;

R9 is H, OH, OCH$_3$, OCF$_3$, CHF$_2$, CF$_3$;

and pharmaceutically acceptable salts thereof.

Preference is given to compounds of the formula I in which:

L is R1, —CH(R10)(R11);

R10 is F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$, (C$_1$-C$_6$)-alkylene-(R6), (C$_3$-C$_8$)-cycloalkylene-(R6), (C$_1$-C$_6$)-alkylene-(C$_3$-C$_8$)-cycloalkylene-(R6), (C$_6$-C$_{10}$)-aryl, (C$_1$-C$_6$)-alkylene-((C$_6$-C$_{10}$)-aryl;

where the aryl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

R11 is H, F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N(C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$, (C$_1$-C$_6$)-alkylene-(R6), (C$_3$-C$_8$)-cycloalkylene-(R6), (C$_1$-C$_6$)-alkylene-(C$_3$-C$_8$)-cycloalkylene-(R6), (C$_6$-C$_{10}$)-aryl, (C$_1$-C$_6$)-alkylene-(C$_6$-C$_{10}$)-aryl;

where the aryl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

R1 is (C$_3$-C$_8$)-cycloalkyl, where the cycloalkyl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

R2 H, F, (C$_1$-C$_3$)-alkyl where the alkyl radical may be mono- to trisubstituted by fluorine;

R3, R4, R5, R13 are each independently H, F, Cl, Br, I, OH, CF$_3$, CHF$_2$, CH$_2$F, NO$_2$, CN, OCF$_3$, OCHF$_2$, O—(C$_1$-C$_6$)-alkylene-(R9), —(C$_1$-C$_6$)-alkylene-(R9), (C═O)—(C1-C6)-alkylene-(R9), (C$_1$-C$_6$)-alkylene-(R9), NH$_2$, NH(C$_1$-C$_6$)-alkylene-(R9), N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

(C$_6$-C$_{10}$)-aryl, —(C$_1$-C$_6$)-alkylene-(C$_6$-C$_{10}$)-aryl, where the aryl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

4- to 12-membered heterocycle, —(C$_1$-C$_6$)-alkylene-4- to -12-membered heterocycle, where the heterocyclyl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkylene-(R9), (C$_1$-C$_6$)-alkylene-(R9), NH$_2$, NH(C$_1$-C$_6$)-alkylene-(R9), N((C$_1$-C$_6$)-alkyl)$_2$, SO$_2$—(C$_1$-C$_6$)-alkylene-(R9), SO$_2$—C$_2$H$_2$F$_3$, SO$_2$—CH$_3$, SO$_2$—NH$_2$, SO$_2$—NH(C$_1$-C$_6$)-alkylene-(R9), SO$_2$—N((C$_1$-C$_6$)-alkyl)$_2$, COOH, COO—(C$_1$-C$_6$)-alkylene-(R9), CONH$_2$, CONH(C$_1$-C$_6$)-alkylene-(R9), CON((C$_1$-C$_6$)-alkyl)$_2$, SF$_5$, (C$_6$-C$_{10}$)-aryl, (C$_3$-C$_8$)-cycloalkyl, 4- to 12-membered heterocycle;

R6 is H, OH, O—(CO)—NH$_2$, SO$_2$NH$_2$;

R7, R8 are each independently H, (C$_1$-C$_3$)-alkyl where the alkyl radical may be mono- to trisubstituted by fluorine;

R9 is H, OH, OCH$_3$, OCF$_3$, CHF$_2$, CF$_3$;

and pharmaceutically acceptable salts thereof.

Preference is further given to compounds of the formula I in which:

L is R1, —CH(R10)(R11);

R10 is (C$_6$-C$_{10}$)-aryl, (C$_1$-C$_6$)-alkylene-(C$_6$-C$_{10}$)-aryl;

where the aryl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

R11 is F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$, (C$_1$-C$_6$)-alkylene-(R6);

R1 is (C$_3$-C$_8$)-cycloalkyl, where the cycloalkyl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

R2 is H, (C$_1$-C$_3$)-alkyl;

R3, R4, R5, R13 are each independently

H, F, Cl, Br, I, OH, CF$_3$, CHF$_2$, CH$_2$F, NO$_2$, CN, OCF$_3$, OCHF$_2$, O—(C$_1$-C$_6$)-alkylene-(R9), —(C$_1$-C$_6$)-alkylene-(R9), (C═O)—(C1-C6)-alkylene-(R9), (C$_1$-C$_6$)-alkylene-(R9), NH$_2$, NH(C$_1$-C$_6$)-alkylene-(R9), N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

(C$_6$-C$_{10}$)-aryl, —(C$_1$-C$_6$)-alkylene-(C$_6$-C$_{10}$)-aryl, where the aryl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkyl, alkyl, NH$_2$, NH(C$_1$-C$_6$)-alkyl, N((C$_1$-C$_6$)-alkyl)$_2$, SO$_2$—CH$_3$, SO$_2$—NH$_2$, SO$_2$—NH(C$_1$-C$_6$)-alkyl, SO$_2$—N((C$_1$-C$_6$)-alkyl)$_2$, COOH, COO—(C$_1$-C$_6$)-alkyl, CONH$_2$, CONH(C$_1$-C$_6$)-alkyl, CON((C$_1$-C$_6$)-alkyl)$_2$, SF$_5$;

4- to 12-membered heterocycle, —(C$_1$-C$_6$)-alkylene-4- to -12-membered heterocycle, where the heterocyclyl radical may be mono- to trisubstituted by F, Cl, Br, I, OH, CF$_3$, CHF$_2$, CH$_2$F, NO$_2$, CN, OCF$_3$, OCHF$_2$, O—(C$_1$-C$_6$)-alkylene-(R9), (C$_1$-C$_6$)-alkylene-(R9), NH$_2$, NH(C$_1$-C$_6$)-alkylene-(R9), N((C$_1$-C$_6$)-alkyl)$_2$, SO$_2$—(C$_1$-C$_6$)-alkylene-(R9), SO$_2$—C$_2$H$_2$F$_3$, SO$_2$—CH$_3$, SO$_2$—NH$_2$, SO$_2$—NH (C$_1$-C$_6$)-alkylene-(R9), SO$_2$—N((C$_1$-C$_6$)-alkyl)$_2$, COOH, COO—($C_1$-$C_6$)-alkylene-(R9), $CONH_2$, CONH($C_1$-$C_6$)-alkylene-(R9), CON(($C_1$-$C_6$)-alkyl)$_2$, $SF_5$, ($C_6$-$C_{10}$)-aryl, ($C_3$-$C_8$)-cycloalkyl, 4- to 12-membered heterocycle;
R6 is H, OH, O—(CO)—$NH_2$, $SO_2NH_2$;
R7, R8 are each independently ($C_1$-$C_3$)-alkyl;
R9 is H, OH, $OCH_3$, $OCF_3$, $CHF_2$, $CF_3$;
and pharmaceutically acceptable salts thereof.

Preference is further given to compounds of the formula I in which:
L is R1, —CH(R10)(R11);
R10 is phenyl,
  where the phenyl radical may be mono- to trisubstituted by F, Cl, Br, —($C_1$-$C_6$)-alkyl;
R11 is ($C_1$-$C_6$)-alkyl, ($C_1$-$C_6$)-alkylene-(R6);
R1 is ($C_3$-$C_8$)-cycloalkyl,
  where the cycloalkyl radical may be mono- to trisubstituted by F, Cl, Br, OH;
R2 is H, ($C_1$-$C_3$)-alkyl;
R3, R4, R5, R13 are each independently H, F, Cl, Br, I, OH, $CF_3$, $CHF_2$, $CH_2F$, $NO_2$, CN, $OCF_3$, $OCHF_2$, O—($C_1$-$C_6$)-alkylene-(R9), —($C_1$-$C_6$)-alkylene-(R9), (C=O)—(C1-C6)-alkylene-(R9), ($C_1$-$C_6$)-alkylene-(R9), $NH_2$, NH($C_1$-$C_6$)-alkylene-(R9), N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
($C_6$-$C_{10}$)-aryl, —($C_1$-$C_6$)-alkylene-($C_6$-$C_{10}$)-aryl,
  where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
4- to 12-membered heterocycle, —($C_1$-$C_6$)-alkylene-4- to -12-membered heterocycle,
  where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, NH($C_1$-$C_6$)-alkylene-(R9), N(($C_1$-$C_6$)-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—NH($C_1$-$C_6$)-alkylene-(R9), $SO_2$—N(($C_1$-$C_6$)-alkyl)$_2$, COOH, COO—($C_1$-$C_6$)-alkylene-(R9), $CONH_2$, CONH($C_1$-$C_6$)-alkylene-(R9), CON(($C_1$-$C_6$)-alkyl)$_2$, $SF_5$, ($C_6$-$C_{10}$)-aryl, ($C_3$-$C_8$)-cycloalkyl, 4- to 12-membered heterocycle;
R6 is OH;
R7, R8 are each independently ($C_1$-$C_3$)-alkyl;
R9 is H, OH, $OCH_3$, $OCF_3$, $CHF_2$, $CF_3$;
and pharmaceutically acceptable salts thereof.

If radicals or substituents can occur more than once in the compounds of the formula I, they may each independently be defined as specified and be the same or different.

The invention relates to compounds of the formula I in the form of their tautomers, racemates, racemic mixtures, stereoisomer mixtures, pure stereoisomers, diastereoisomer mixtures and pure diastereoisomers. The mixtures are separated, for example, by a chromatographic route.

Owing to their higher water solubility compared to the starting or base compounds, pharmaceutically acceptable salts are particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic acid, phosphoric acid, metaphosphoric acid, nitric acid and sulfuric acid, and of organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion, for example trifluoroacetate, likewise belong within the framework of the invention as useful intermediates for the preparation or purification of pharmaceutically acceptable salts and/or for use in nontherapeutic, for example in vitro, applications.

The compounds of the invention may also exist in various polymorphous forms, for example as amorphous and crystalline polymorphous forms. All polymorphous forms of the inventive compounds are within the scope of the invention and are a further aspect of the invention.

All references to "compound(s) of formula I" hereinafter refer to compound(s) of the formula I as described above, and the salts and solvates thereof, as described herein.

An alkyl radical is understood to mean a straight-chain or branched hydrocarbon chain having one to eight carbons, for example methyl, ethyl, isopropyl, tert-butyl, hexyl, heptyl, octyl. The alkyl radicals may be mono- or polysubstituted as described above.

An alkylene radical is understood to mean a straight-chain or branched hydrocarbon chain having two free valences, for example methylene, ethylene, isopropylene, tert-butylene.

A carbocycle or carbocyclyl radical is understood to mean a ring in saturated or partially unsaturated form (with one or two double bonds), formed exclusively from carbon atoms.

An aryl radical is understood to mean a phenyl, naphthyl, biphenyl, tetrahydronaphthyl, alpha- or beta-tetralonyl, indanyl or indan-1-onyl radical.

The aryl radicals may be mono- or polysubstituted by suitable groups as described above.

"Heterocycle" and "heterocyclic radical" are understood to mean rings and ring systems which, apart from carbon, also contain heteroatoms, for example nitrogen, oxygen or sulfur. In addition, this definition also includes ring systems in which the heterocycle or the heterocyclic radical is fused to a further ring system. The heterocycle or the heterocyclic radical may be saturated, partly saturated or aromatic.

Suitable "heterocycles" or "heterocyclic radicals" are acridinyl, azepanyl, azocinyl, benzimidazolyl, benzofuryl, benzothienyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, 5,6-dihydro-4H-cyclopentathiazol-2-yl, 4,5-dihydrothiazol-2-yl, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, 4,5,6,7-tetrahydrobenzooxazol-2-yl, 4,5,6,7-tetrahydro-benzothiazol-2-yl, 4,5,6,7-tetrahydrobenzoimidazol-2-yl, 4,5,6,7-tetrahydro-pyrazolo[1,5-a]pyridin-2-yl, tetrahydropyranyl, tetrahydropyranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazinyl, triazolyl, tetrazolyl, thiazolo[4,5-b]pyridinyl, thieno[2,3-d]thiazol-2-yl, tropanyl and xanthenyl.

The heterocycles or heterocyclic radicals may be mono- or polysubstituted by suitable groups as described above.

The compound(s) of the formula I can also be administered in combination with further active ingredients.

The amount of a compound of the formula I required to achieve the desired biological effect depends on a number of factors, for example the specific compound chosen, the intended use, the mode of administration and the clinical condition of the patient. In general, the daily dose is in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram per minute. Suitable infusion solutions for these purposes may contain, for example, 0.1 ng to 10 mg, typically 1 ng to 10 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must of course be acceptable in the sense that it is compatible with the other constituents of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Inventive pharmaceutical compositions are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations are also within the scope of the invention. Preference is given to acid- and gastric juice-resistant formulations. Suitable gastric juice-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. For example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the pulverulent compound moistened with an inert liquid diluent in a suitable machine.

Pharmaceutical compositions suitable for peroral (sublingual) administration include lozenges which contain a compound of formula I with a flavoring, typically sucrose, and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable inventive compositions generally contain from 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

Further suitable active ingredients for the combination products are:

All antidiabetics mentioned in the Rote Liste 2006, chapter 12; all weight-reducing agents/appetite suppressants mentioned in the Rote Liste 2006, chapter 1; all lipid-lowering agents mentioned in the Rote Liste 2006, chapter 58. They can be combined with the inventive compound of the formula I, especially for a synergistic improvement in action. The active ingredient combination can be administered either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives, for example Lantus® (see www.lantus.com) or HMR 1964 or Levemir® (insulin detemir), or those as described in WO2005005477 (Novo Nordisk), fast-acting insulins (see U.S. Pat. No. 6,221,633), inhalable insulins, for example Exubera®, or oral insulins, for example IN-105 (Nobex) or Oral-lyn™ (Generex Biotechnology), GLP-1 derivatives, for example exenatide, liraglutide or those which have been disclosed in WO 98/08871, WO2005027978, WO2006037811, WO2006037810 to Novo Nordisk A/S, in WO 01/04156 to Zealand or in WO 00/34331 to Beaufour-Ipsen, pramlintide acetate (Symlin; Amylin Pharmaceuticals), and oral hypoglycemic active ingredients.

The orally active hypoglycemic active ingredients preferably include sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists, potassium channel openers, for example those which have been disclosed in WO 97/26265 and WO 99/03861 to Novo Nordisk A/S, or those described in WO2006045799 (Solvay),
inhibitors of dipeptidyl peptidase-IV (DPP-IV),
insulin sensitizers,
inhibitors of liver enzymes involved in stimulating gluconeogenesis and/or glycogenolysis, modulators of glucose uptake, of glucose transport and of glucose reabsorption,
inhibitors of 11β-HSD1,
inhibitors of protein tyrosine phosphatase-1B (PTP1B),
modulators of sodium-dependent glucose transporter 1 or 2 (SGLT1, SGLT2), compounds which modify the lipid metabolism, such as active antihyperlipidemic ingredients and active antilipidemic ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, L-659699.

In one embodiment of the invention, the compound of the formula I is administered in combination with a cholesterol absorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG).

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with fenofibrate.

In a further embodiment of the invention, the compound of the formula I is administered in combination with a solid combination of fenofibrate with rosuvastatin.

In one embodiment of the invention, the compound of the formula I is administered in combination with ISIS-301012, an antisense oligonucleotide which is capable of regulating the apolipoprotein B gene.

In one embodiment of the invention, the compound of the formula I is administered in combination with a PPAR gamma agonist, for example rosiglitazone, pioglitazone, JTT-501, G1 262570, R-483, CS-01 (rivoglitazone).

In one embodiment of the invention, the compound of the formula I is administered in combination with Competact™, a solid combination of pioglitazone hydrochloride with metformin hydrochloride.

In one embodiment of the invention, the compound of the formula I is administered in combination with Duetact™, a solid combination of pioglitazone hydrochloride with glimepiride.

In one embodiment of the invention, the compound of the formula I is administered in combination with Avandamet®, a solid combination of rosiglitazone maleate with metformin hydrochloride.

In one embodiment of the invention, the compound of the formula I is administered in combination with PPAR alpha agonists, for example GW9578, GW-590735, K-111, LY-674, KRP-101, DRF-10945.

In one embodiment of the invention, the compound of the formula I is administered in combination with a mixed PPAR alpha/gamma agonist, for example naveglitazar, LY-510929, ONO-5129, E-3030, AVE 8042, AVE 8134, AVE 0847, or as described in PCT/US 00/11833, PCT/US 00/11490, DE10142734.4 or in J. P. Berger et al., TRENDS in Pharmacological Sciences 28(5), 244-251, 2005.

In one embodiment of the invention, the compound of the formula I is administered in combination with a PPAR delta agonist, for example GW-501516.

In one embodiment, the compound of the formula I is administered in combination with metaglidasen or with MBX-2044 or other partial PPAR gamma agonists/antagonists.

In a further embodiment of the invention, the compound of the formula I is administered in combination with an activator of AMP-activated protein kinase (AMPK), for example A-769662 or those compounds as described in US20050038068.

In one embodiment of the invention, the compound of the formula I is administered in combination with a fibrate, for example fenofibrate, clofibrate, bezafibrate.

In one embodiment of the invention, the compound of the formula I is administered in combination with an MTP inhibitor, for example implitapide, BMS-201038, R-103757 or those as described in WO2005085226, WO2005121091, WO2006010423.

In one embodiment of the invention, the compound of the formula I is administered in combination with a CETP inhibitor, for example torcetrapib or JTT-705, or those as described in WO2006002342, WO2006010422, WO2006012093.

In one embodiment of the invention, the compound of the formula I is administered in combination with bile acid reabsorption inhibitor (see, for example, U.S. Pat. No. 6,245,744, U.S. Pat. No. 6,221,897 or WO00/61568), for example HMR 1741, or those as described in DE 10 2005 033099.1 and DE 10 2005 033100.9.

In one embodiment of the invention, the compound of the formula I is administered in combination with a polymeric bile acid adsorber, for example cholestyramine, colesevelam.

In one embodiment of the invention, the compound of the formula I is administered in combination with an LDL receptor inducer (see U.S. Pat. No. 6,342,512), for example HMR1171, HMR1586, or those as described in WO2005097738.

In one embodiment, the compound of the formula I is administered in combination with Omacor® (omega-3 fatty acids; highly concentrated ethyl esters of eicosapentaenoic acid and of docosahexaenoic acid).

In one embodiment of the invention, the compound of the formula I is administered in combination with an ACAT inhibitor, for example avasimibe or SMP-797.

In one embodiment of the invention, the compound of the formula I is administered in combination with an antioxidant, for example OPC-14117, probucol, tocopherol, ascorbic acid, β-carotene or selenium.

In one embodiment of the invention, the compound of the formula I is administered in combination with a vitamin, for example vitamin B6 or vitamin B12.

In one embodiment of the invention, the compound of the formula I is administered in combination with a lipoprotein lipase modulator, for example ibrolipim (NO-1886).

In one embodiment of the invention, the compound of the formula I is administered in combination with an ATP citrate lyase inhibitor, for example SB-204990.

In one embodiment of the invention, the compound of the formula I is administered in combination with a squalene synthetase inhibitor, for example BMS-188494, or as described in WO2005077907.

In one embodiment of the invention, the compound of the formula I is administered in combination with a lipoprotein (a) antagonist, for example gemcabene (CI-1027).

In one embodiment of the invention, the compound of the formula I is administered in combination with an agonist of GPR109A (HM74A receptor agonist), for example nicotinic acid or "extended release niacin" in conjunction with MK-0524A, or those compounds as described in WO2006045565, WO2006045564, WO2006069242.

In another embodiment of the invention, the compound of the formula I is administered in combination with an agonist of GPR116, as described, for example, in WO2006067531, WO2006067532.

In one embodiment of the invention, the compound of the formula I is administered in combination with a lipase inhibitor, for example orlistat or cetilistat (ATL-962).

In one embodiment of the invention, the compound of the formula I is administered in combination with insulin.

In one embodiment, the compound of the formula I is administered in combination with a sulfonylurea, for example tolbutamide, glibenclamide, glipizide or glimepiride.

In one embodiment, the compound of the formula I is administered in combination with a substance which enhances insulin secretion, for example KCP-265 (WO2003097064).

In one embodiment, the compound of the formula I is administered in combination with agonists of the glucose-dependent insulinotropic receptor (GDIR), for example APD-668.

In one embodiment, the compound of the formula I is administered in combination with a biguanide, for example metformin.

In yet another embodiment, the compound of the formula I is administered in combination with a meglitinide, for example repaglinide or nateglinide.

In one embodiment, the compound of the formula I is administered in combination with a thiazolidinedione, for example troglitazone, ciglitazone, pioglitazone, rosiglitazone or the compounds disclosed in WO 97/41097 by Dr. Reddy's Research Foundation, especially 5-[[4-[(3,4-dihydro-3-methyl-4-oxo-2-quinazolinylmethoxy]phenyl]methyl]-2,4-thiazolidinedione.

In one embodiment, the compound of the formula I is administered in combination with an α-glucosidase inhibitor, for example miglitol or acarbose.

In one embodiment, the compound of the formula I is administered in combination with an active ingredient which acts on the ATP-dependent potassium channel of the beta cells, for example tolbutamide, glibenclamide, glipizide, glimepiride or repaglinide.

In one embodiment, the compound of the formula I is administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932.

In one embodiment, the compound of the formula I is administered in combination with glucagon receptor antagonists, for example A-770077 or NNC-25-2504 or as described in WO2004100875, WO2005065680.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923.

In one embodiment, the compound of the formula I is administered in combination with an inhibitor of gluconeogenesis, for example FR-225654.

In one embodiment, the compound of the formula I is administered in combination with inhibitors of fructose 1,6-bisphosphatase (FBPase), for example CS-917 (MB-06322) or MB-07803, or those as described in WO2006023515.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidylpeptidase-IV (DPP-IV), for example vildagliptin (LAF-237), sitagliptin (MK-0431), saxagliptin (BMS-477118), GSK-823093, PSN-9301, SYR-322, SYR-619, TA-6666, TS-021, GRC-8200, GW-825964X, KRP-104, DP-893 or as described in WO2003074500, WO2003106456, WO200450658, WO2005058901, WO2005012312, WO2005/012308, WO2006039325, WO2006058064, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, the compound of the formula I is administered in combination with Januvia™, a solid combination of sitagliptin phosphate with metformin hydrochloride.

In one embodiment, the compound of the formula I is administered in combination with inhibitors of 11-beta-hydroxysteroid dehydrogenase 1 (11β-HSD1), for example BVT-2733, JNJ-25918646, INCB-13739, or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109.

In one embodiment, the compound of the formula I is administered in combination with inhibitors of protein tyrosine phosphatase 1B (PTP1B), as described, for example, in WO200119830-31, WO200117516, WO2004506446, WO2005012295, WO2005116003, PCT/EP2005/005311, PCT/EP2005/005321, PCT/EP2005/007151, PCT/EP2005/01294 or DE 10 2004 060542.4.

In one embodiment, the compound of the formula I is administered in combination with modulators of sodium-dependent glucose transporter 1 or 2 (SGLT1, SGLT2), for example KGA-2727, T-1095, SGL-0010, AVE 2268 and SAR 7226, or as described, for example, in WO2004007517, WO200452903, WO200452902, PCT/EP2005/005959, WO2005085237, JP2004359630, WO2005121161, WO2006018150, WO2006035796, WO2006062224, WO2006058597 or by A. L. Handlon in Expert Opin. Ther. Patents (2005) 15(11), 1531-1540.

In one embodiment, the compound of the formula I is administered in combination with GPR40 modulators.

In one embodiment, the compound of the formula I is administered in combination with GPR119b modulators, as described, for example, in WO2004041274.

In one embodiment, the compound of the formula I is administered in combination with GPR119 modulators, as described, for example, in WO2005061489 (PSN-632408).

In one embodiment, the compound of the formula I is administered in combination with inhibitors of hormonesensitive lipase (HSL), as described, for example, in WO2005073199.

In one embodiment, the compound of the formula I is administered in combination with inhibitors of acetyl-CoA carboxylase (ACC), for example those as described in WO199946262, WO200372197, WO2003072197, WO2005044814, WO2005108370, JP2006131559.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of glycogen synthase kinase-3 beta (GSK-3 beta), as described, for example, in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117.

In one embodiment, the compound of the formula I is administered in combination with an inhibitor of protein kinase C beta (PKC beta), for example ruboxistaurin.

In one embodiment, the compound of the formula I is administered in combination with an endothelin A receptor antagonist, for example avosentan (SPP-301).

In one embodiment, the compound of the formula I is administered in combination with inhibitors of "I-kappaB kinase" (IKK inhibitors), as described, for example, in WO2001000610, WO2001030774, WO2004022553, WO2005097129.

In one embodiment, the compound of the formula I is administered in combination with modulators of the glucocorticoid receptor, as described, for example, in WO2005090336.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A);

NPY-5 receptor antagonists such as L-152804, S-2367 or as described, for example, in WO2006001318;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424;

CB1R (cannabinoid receptor 1) antagonists (for example rimonabant, SR147778, SLV-319, AVE-1625, MK-0364 or salts thereof, or those as described in, for example, EP 0656354, WO 00/15609, WO2001/64632, WO2001/64633, WO2001/64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443);

MC4 agonists (for example N-[2-(3a-benzyl-2-methyl-3-oxo-2,3,3a,4,6,7-hexahydropyrazolo[4,3-c]-pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076, WO2004072077, WO2006021655-57;

orexin receptor antagonists (for example 1-(2-methylbenzoxazol-6-yl)-3-[1,5]naphthyridin-4-ylurea hydrochloride (SB-334867-A), or those as described, for example, in WO200196302, WO200185693, WO2004085403, WO2005075458, WO2006067224); histamine H3 receptor agonists (for example 3-cyclohexyl-1-(4,4-dimethyl-1,4,6,7-tetrahydroimidazo[4,5-c]pyridin-5-yl)propan-1-one oxalic acid salt (WO 00/63208), or those as described in WO200064884, WO2005082893);

CRF antagonists (for example [2-Methyl-9-(2,4,6-trimethylphenyl)-9H-1,3,9-triazafluoren-4-yl]dipropylamine (WO 00/66585));

CRF BP antagonists (e.g. urocortin);

urocortin agonists;

agonists of the beta-3 adrenoceptor, for example 1-(4-chloro-3-methanesulfonylmethylphenyl)-2-[2-(2,3-dimethyl-1H-indol-6-yloxy)ethylamino]-ethanol hydrochloride (WO 01/83451) or solabegron (GW-427353) or N-5984 (KRP-204), or those as described in JP2006111553;

MSH (melanocyte-stimulating hormone) agonists;

MCH (melanine-concentrating hormone) receptor antagonists (for example NBI-845, A-761, A-665798, A-798, ATC-0175, T-226296, T-71, GW-803430, or those compounds as described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002089729, WO2002002744, WO2003004027, FR2868780, WO2006010446, WO2006038680, WO2006044293, WO2006044174);

CCK-A agonists (for example {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180), or those as described in WO2005116034;

serotonin reuptake inhibitors (for example dexfenfluramine);

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

5-HT2C receptor agonists (for example lorcaserine hydrochloride (APD-356) or BVT-933, or those as described in WO200077010, WO20077001-02, WO2005019180, WO2003064423, WO200242304, WO2005082859);

5-HT6 receptor antagonists, as described, for example in WO2005058858;

bombesin receptor agonists (BRS-3 agonists);

galanin receptor antagonists;

growth hormone (e.g. human growth hormone or AOD-9604);

growth hormone releasing compounds (tert-butyl 6-benzyloxy-1-(2-diisopropylaminoethylcarbamoyl)-3,4-dihydro-1H-isoquinoline-2-carboxylate (WO 01/85695)); growth hormone secretagogue receptor antagonists (ghrelin antagonists), for example A-778193, or those as described in WO2005030734;

TRH agonists (see, for example, EP 0 462 884);

decoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

dopamine agonists (DA agonists, for example bromocriptine, Doprexin);

lipase/amylase inhibitors (e.g. WO 00/40569);

inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189;

inhibitors of fatty acid synthase (FAS), for example C75, or those as described in WO2004005277;

oxyntomodulin;

oleoyl-estrone or thyroid hormone receptor agonists, for example: KB-2115, or those as described in WO20058279, WO200172692, WO200194293, WO2003084915, WO2004018421, WO2005092316.

In one embodiment, the further active ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the enzyme SIRT1, a member of the human sirtuin enzyme family.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindol or phentermin.

In one embodiment, the further active ingredient is a diphenylazetidinone derivative, as described, for example, in U.S. Pat. No. 6,992,067 or U.S. Pat. No. 7,205,290.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main). Combination with Caromax® is possible in one preparation or by separate administration of compounds of the formula I and Caromax®. Caromax® can also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered by the scope of protection conferred by the present invention.

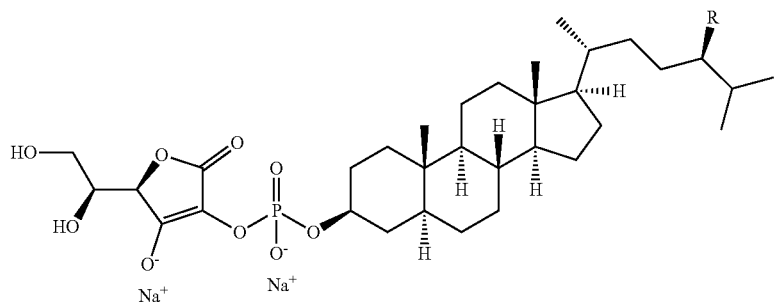
FM-VP4
R = CH₃; CH₂—CH₃
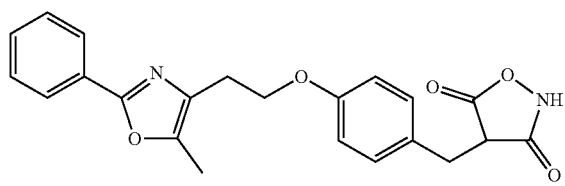
JTT-501
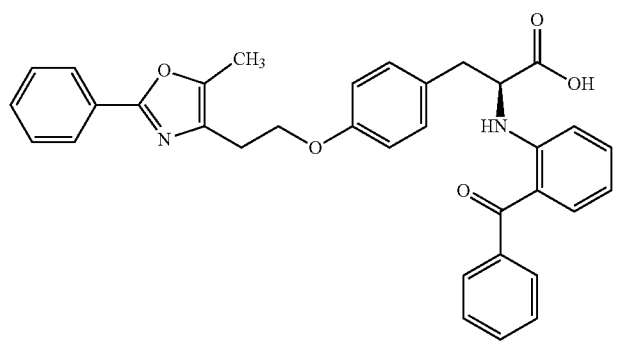
GI 262570
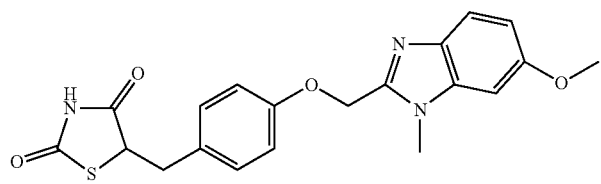
CS-011
Rivoglitazone
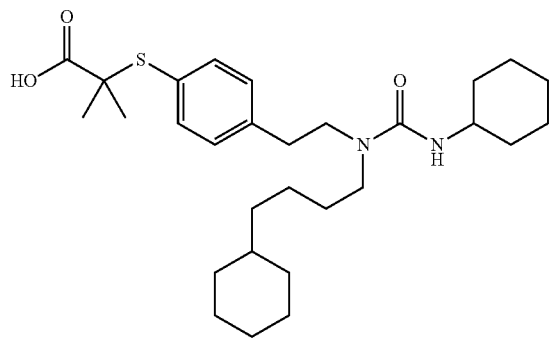
GW-9578

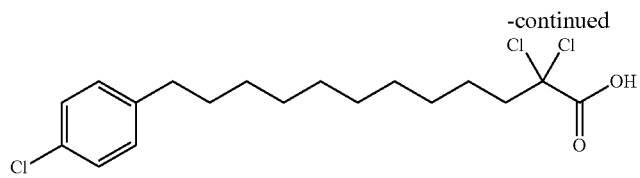
K-111
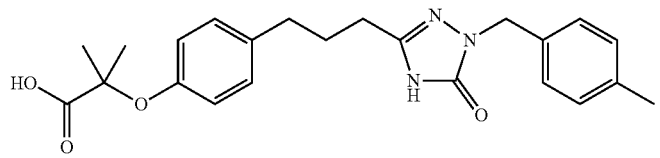
LY-518674
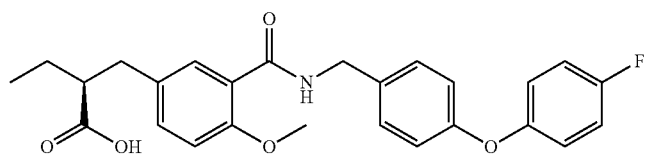
KRP-101
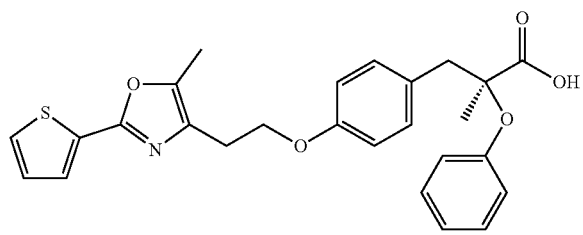
LY-510929
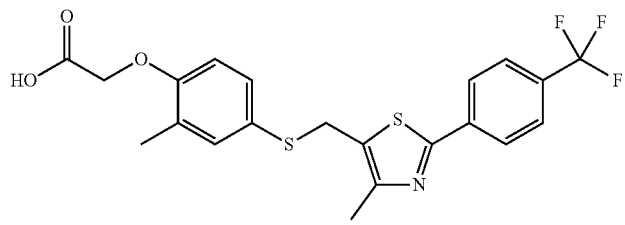
GW-501516
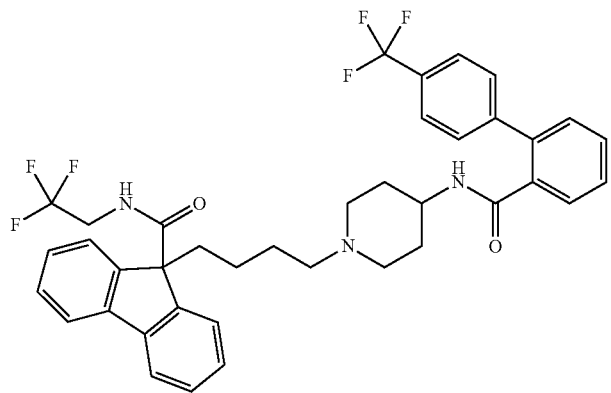
BMS-201038

-continued
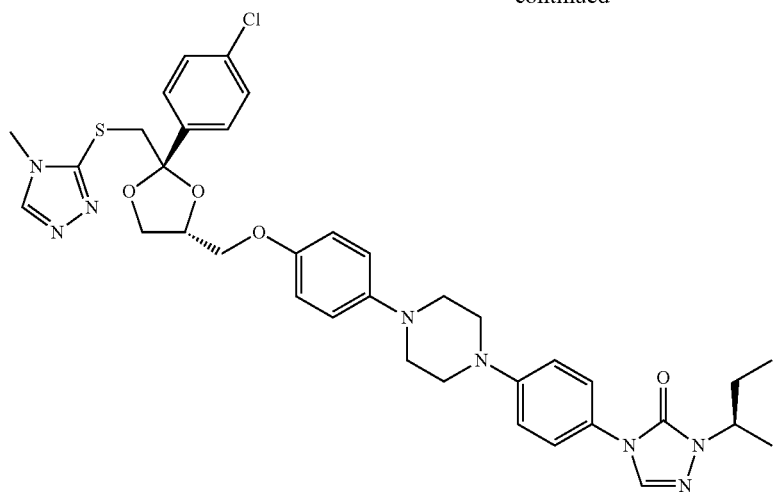
R-103757
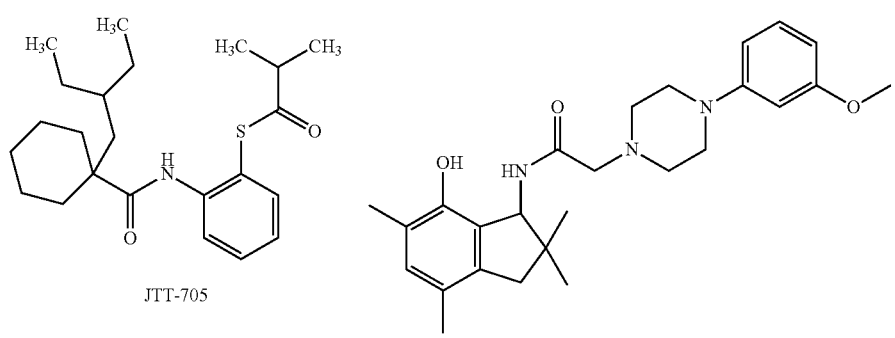
JTT-705    OPC-14117
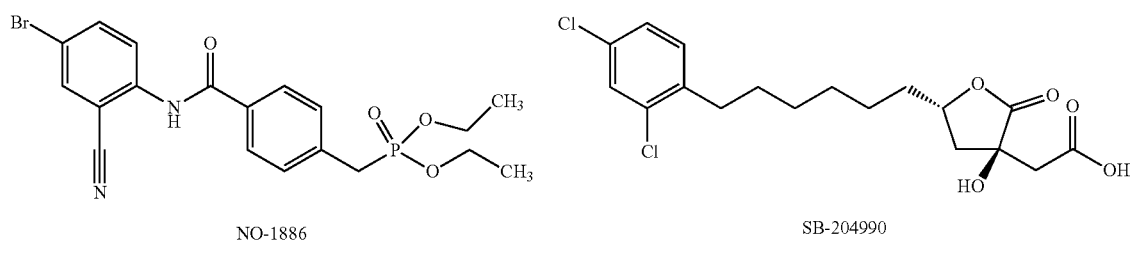
NO-1886    SB-204990
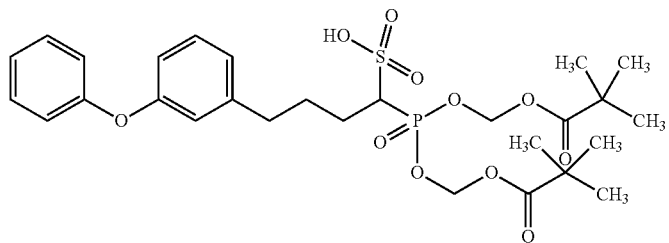
BMS-1888494
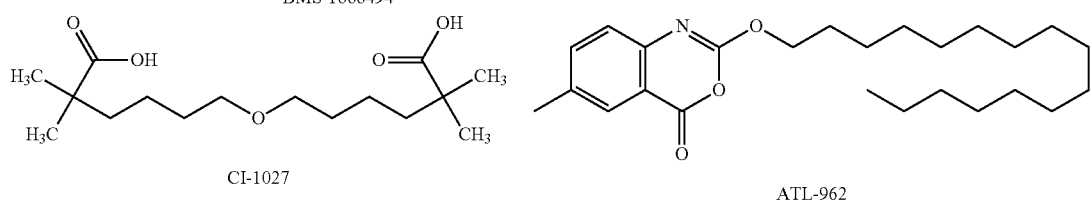
CI-1027    ATL-962

-continued
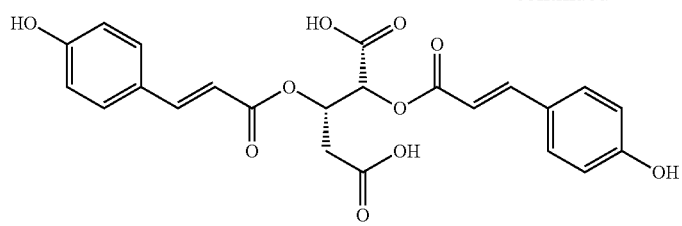
FR-258900
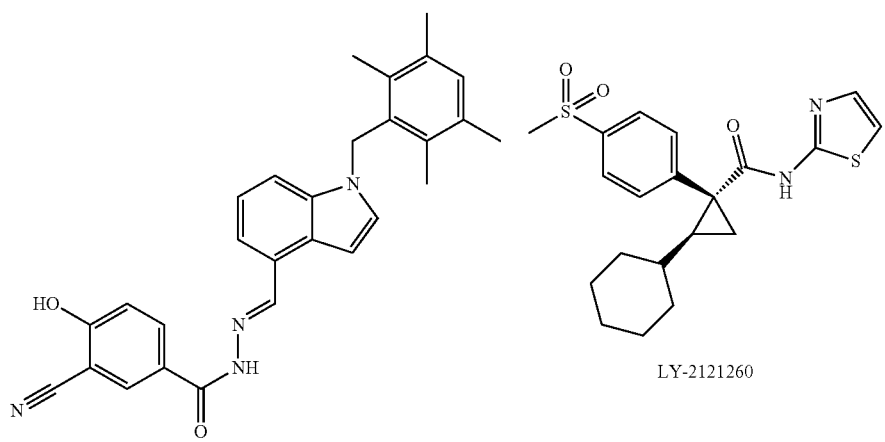
NNC-25-2504
LY-2121260
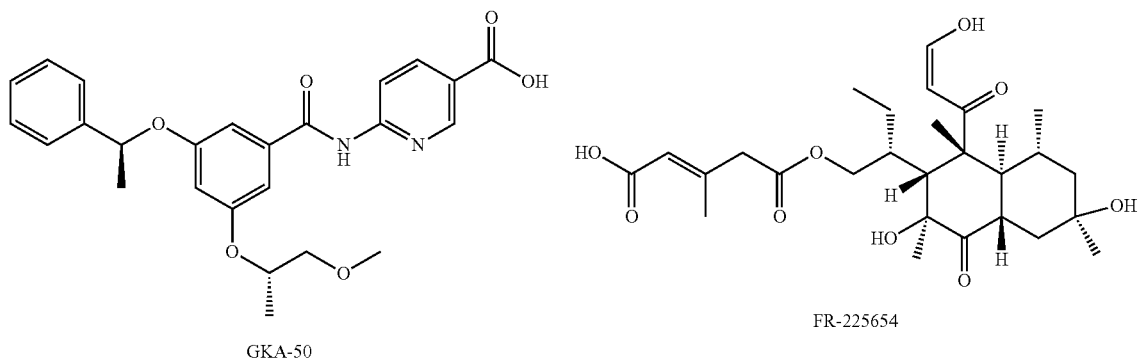
GKA-50
FR-225654
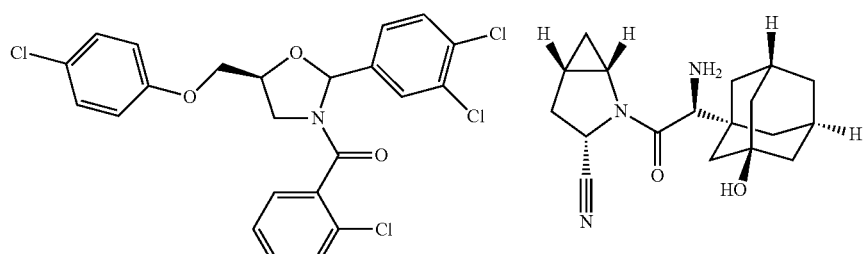
KST-48
BMS-477118

-continued
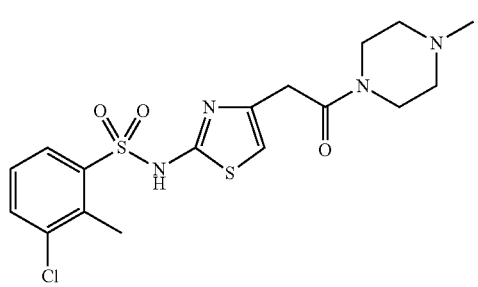
BVT-2733
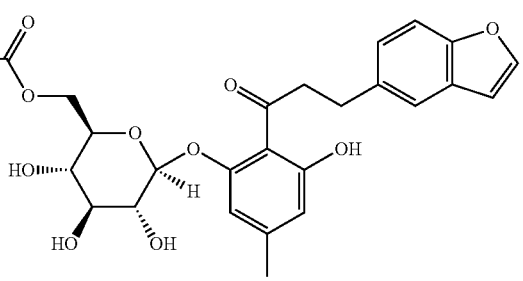
T-1095
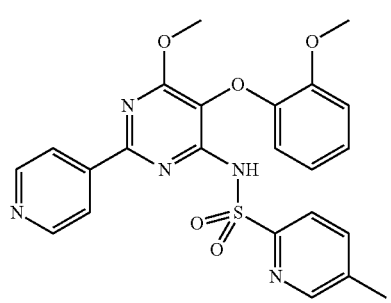
SPP-301
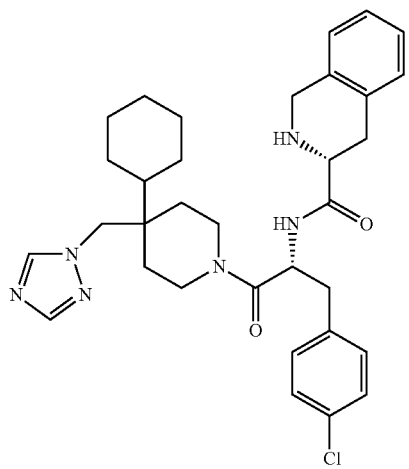
THIQ
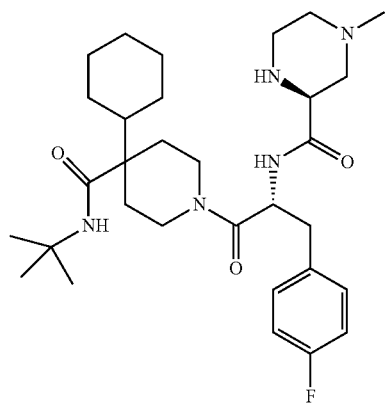
MB243
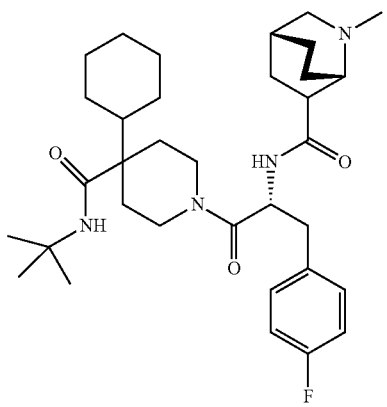
RY764
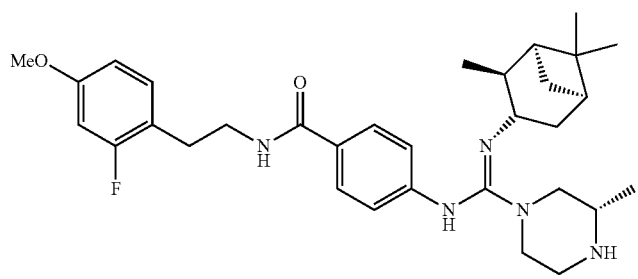
CHIR-785

-continued
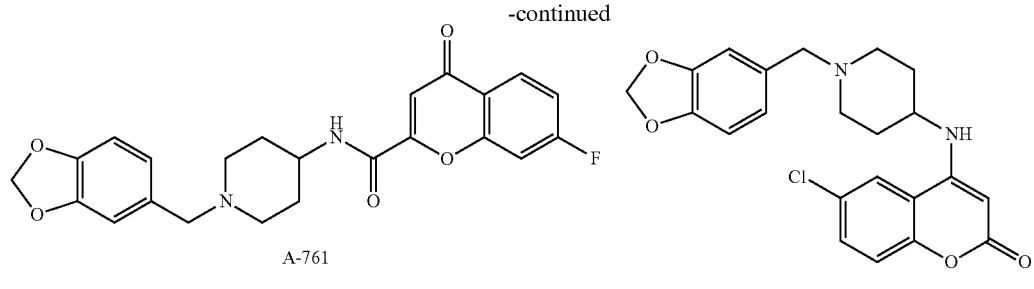
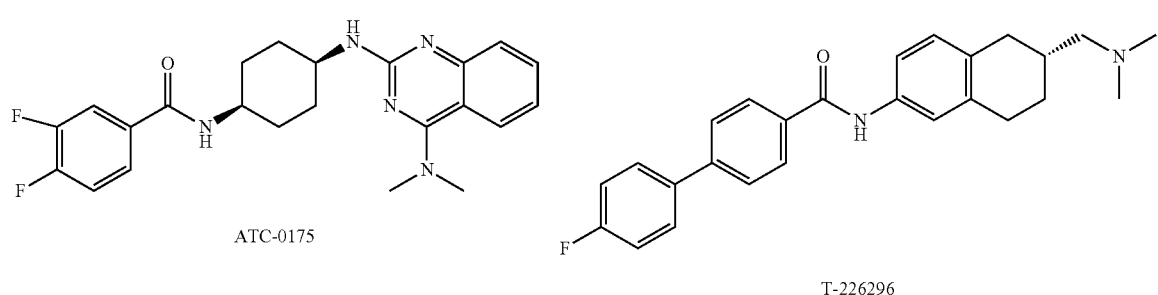
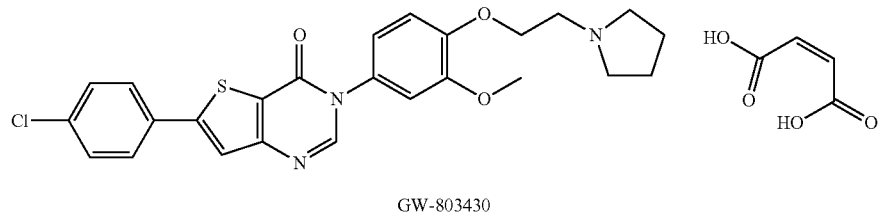
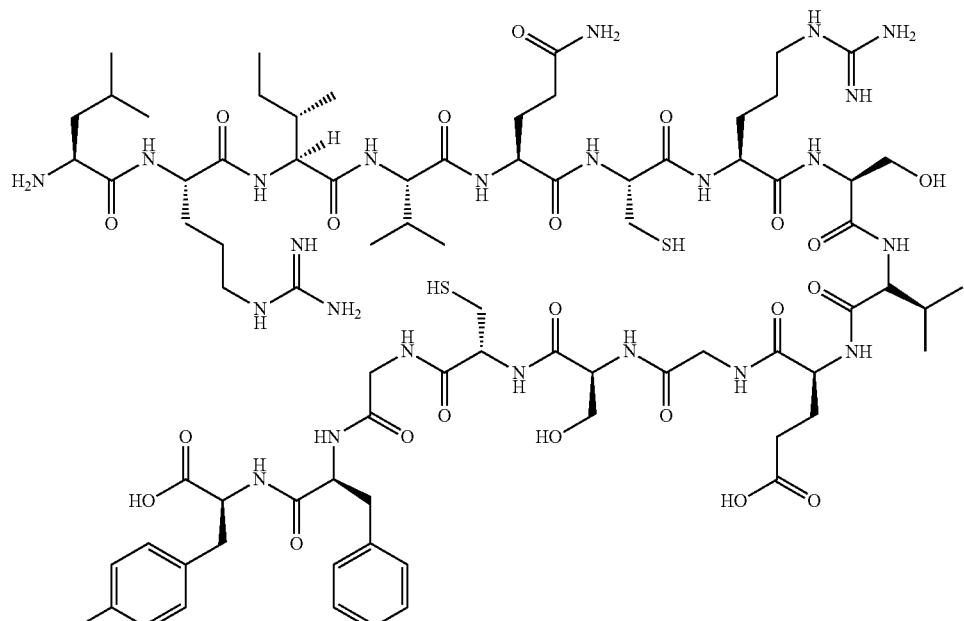

-continued
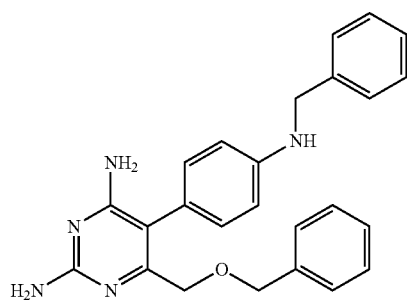
A-778193
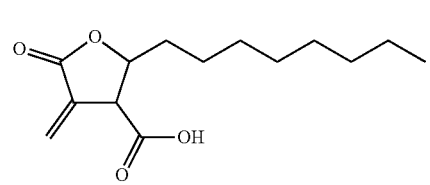
C75
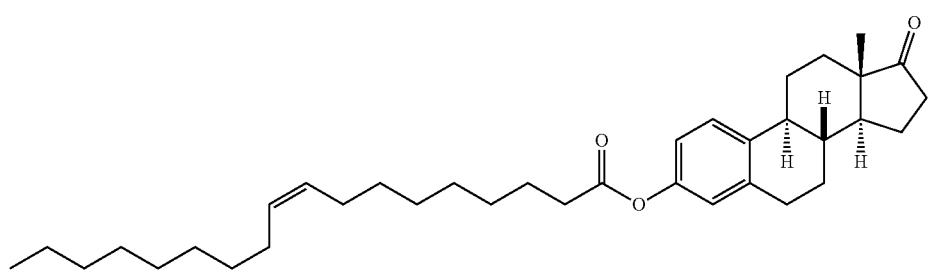
Oleoyl-Estrone
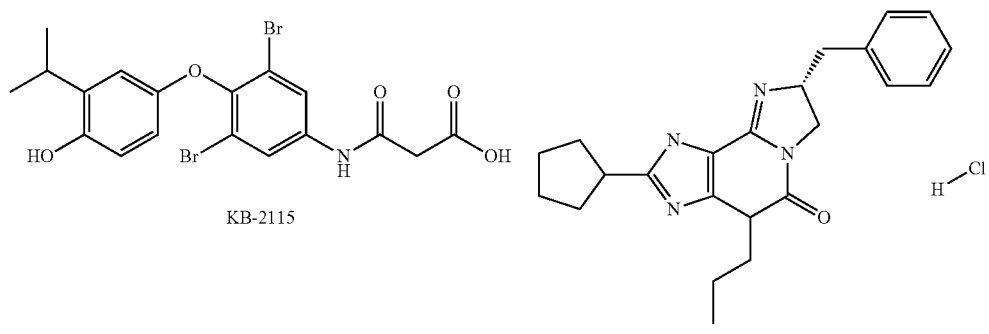
KB-2115
KCP-265
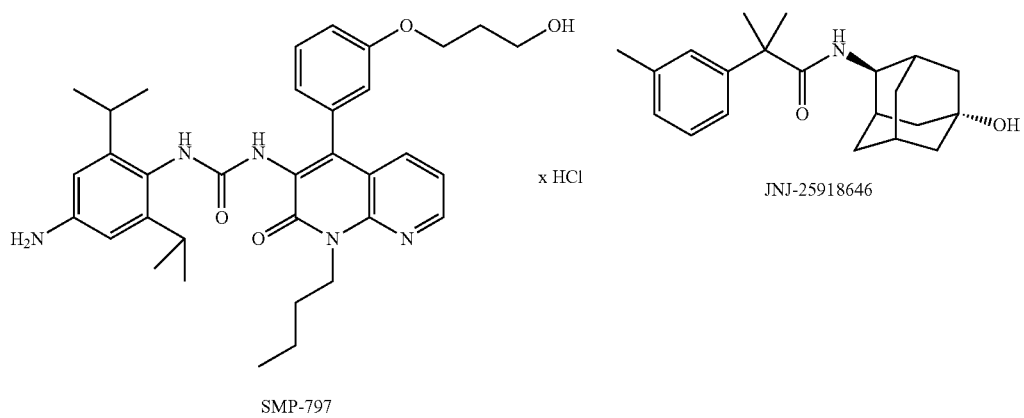
SMP-797
JNJ-25918646
x HCl

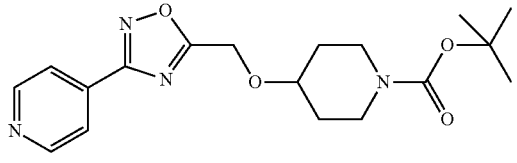
PSN-632408
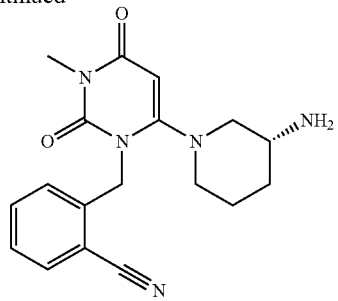
SYR-322
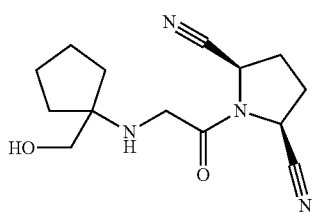
DP-893
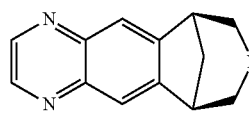
Varenicline Tartrate
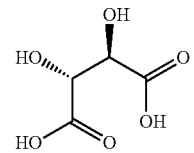
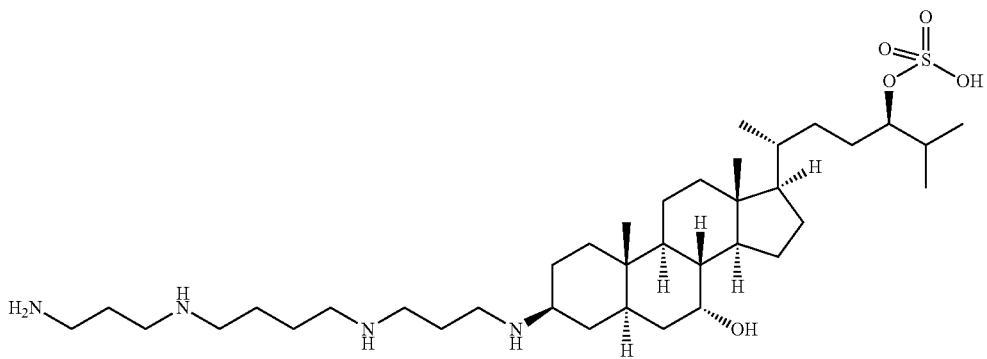
Trodusquemine
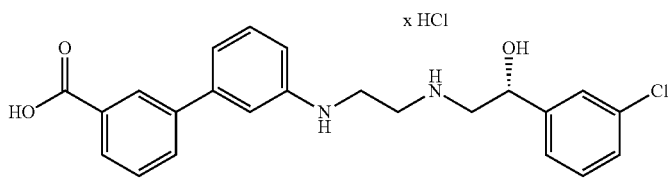
Solabegron
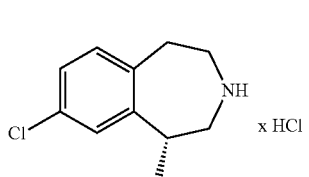
Lorcaserin Hydrochloride
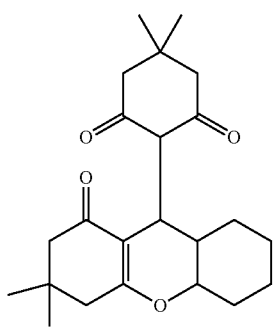
L-152804
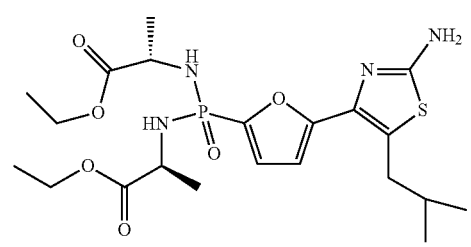
MB-06322
CS-917

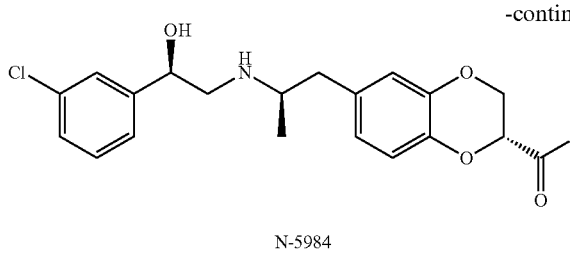

N-5984

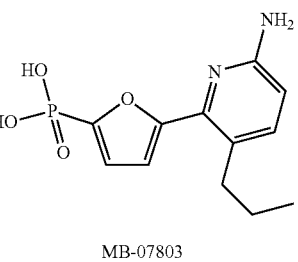

MB-07803

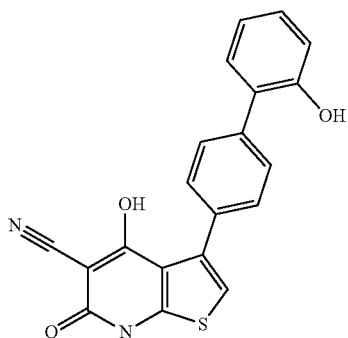

A-769662

EXAMPLES

The examples and preparation methods adduced below serve to illustrate the invention, but without limiting it.

The inventive compounds of the formula I can be prepared with the aid of reactions known in principle. For example, the compounds were prepared according to the general reaction schemes which follow.

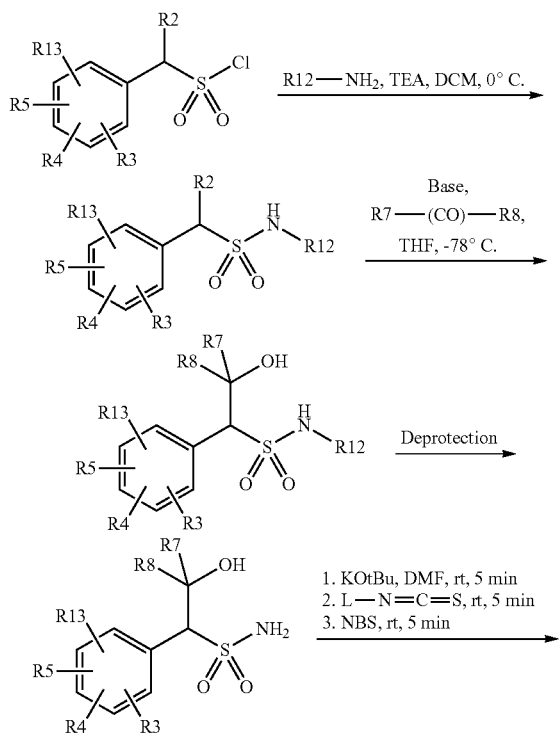

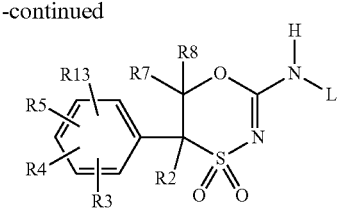

A methanesulfonyl chloride substituted by a phenyl radical and R2, through the reaction with a suitable amine and triethylamine (TEA) in a suitable solvent, for example dichloromethane (DCM), is used to prepare a corresponding phenyl- and R2-substituted methanesulfonamide protected by R12 (e.g. Boc, benzyl, 2,4-dimethoxybenzyl). By reaction with a suitable base (e.g. methyllithium) at low temperature, it is then possible to produce a dianion, which reacts with a ketone (e.g. R7-(CO)—R8) or an aldehyde (e.g. R7-CHO) in a suitable solvent, e.g. tetrahydrofuran (THF), to give the R12-protected hydroxysulfonamide. By deprotection of R12 (for example, by acid treatment in the case of a Boc group or of a 2,4-dimethoxybenzyl group, or by hydrogenation in the case of a benzyl group), the free hydroxysulfonamide is formed. The reaction of the hydroxysulfonamide thus obtained with base and an isothiocyanate (L-N=C=S), and subsequent oxidative ring closure with N-bromosuccinimide (NBS), gives the desired 4,4-dioxooxathiazines.

In the cases in which the functional groups (for example a hydroxyl group) are introduced in protected form (for example benzyl-protected or as the ester), these are released at the end of the synthesis by a suitable method (for example hydrogenation or reduction).

The isothiocyanates used are obtained by the reaction of a primary amine with thiocarbonyldiimidazole, in which case any troublesome functional groups present, for example hydroxyl groups, are blocked with suitable protecting groups, for example silyl ethers. The protecting groups are removed at the end of the sequence by suitable methods, for example silyl groups by treatment with methanolic hydrochloric acid.

In the cases in which diastereomers or racemates form during the synthesis, these can be separated from one another by preparative HPLC.

Some of the primary amines used are commercially available.

4-Fluorobicyclo[2.2.2]octan-1-amine can be prepared as described in the literature (JOC1982, 47, 1952-7).

Other inventive compounds can be obtained in other ways outlined by way of example in the scheme which follows.

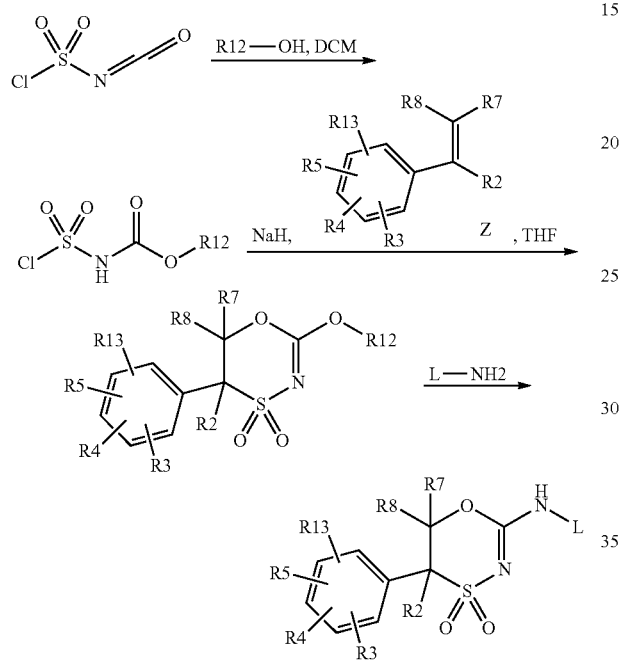

In analogy to a literature method (JACS 1972, 94, 4386-7), chlorosulfonyl isocyanate is treated with an alcohol (R12-OH, e.g. methanol), forming a corresponding carboalkoxysulfamoyl chloride (e.g. carbomethoxysulfamoyl chloride). This is deprotonated with sodium hydride, and the intermediate formed after chloride elimination (e.g. methyl-N-sulfonylurethane) reacts in a 2+4 cycloaddition with alkenes of the formula Z to give the alkoxy-substituted (e.g. methoxy-substituted) 4,4-dioxooxathiazine. The alkoxy group can be replaced here by means of an amine in a suitable solvent (e.g. dichloromethane), forming the desired 4,4-dioxooxathiazines.

In the cases in which diastereomers or racemates form during the synthesis, these can be separated from one another by preparative HPLC.

Other inventive compounds can be obtained in other ways outlined by way of example in the scheme which follows.

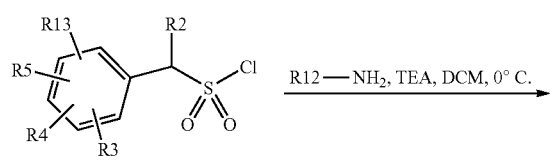

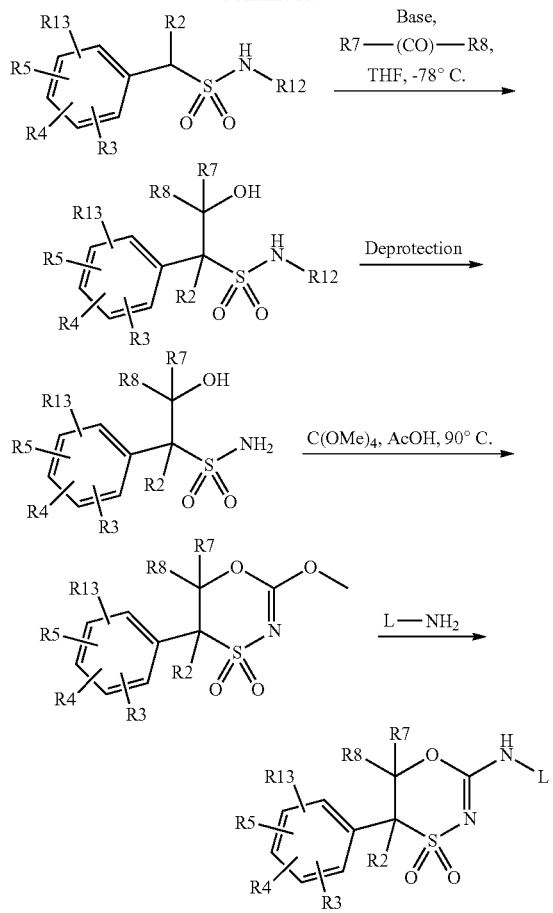

A methanesulfonyl chloride substituted by phenyl and R2, through the reaction with a suitable amine and triethylamine (TEA) in a suitable solvent, for example dichloromethane (DCM), is used to prepare a corresponding phenyl- and R2-substituted methanesulfonamide protected by R12 (e.g. Boc, benzyl, 2,4-dimethoxybenzyl). By treatment with a suitable base (e.g. methyllithium) at low temperature, it is then possible to produce a dianion, which is reacted with a ketone (e.g. R7-(CO)—R8) or an aldehyde (e.g. R7-CHO) in a suitable solvent, e.g. tetrahydrofuran (THF), to give the R12-protected hydroxysulfonamide. By deprotection of R12 (for example, by acid treatment in the case of a Boc group or of a 2,4-dimethoxybenzyl group, or by hydrogenation in the case of a benzyl group), the free hydroxysulfonamide is formed. The reaction of the hydroxysulfonamide thus obtained with tetramethyl orthocarbonate gives methoxy-substituted 4,4-dioxooxathiazines. The methoxy group (—O—CH₃) is then replaced by means of an amine (L-NH₂) in a suitable solvent (e.g. dichloromethane), forming the desired 4,4-dioxooxathiazines.

In the cases in which the functional groups (for example a hydroxyl group) are introduced in protected form (for example benzyl-protected or as the ester), these are released at the end of the synthesis by a suitable method (for example hydrogenation or reduction).

If the molecule which forms includes a haloaryl unit, the halogen can be replaced by standard metal-catalyzed coupling methods. For example, a bromide can be converted further with the aid of a Suzuki reaction or a Sonogashira reaction or a palladium-catalyzed amination. In addition, simple synthesis steps may follow in some cases; for example, a triple bond can be hydrogenated to a single bond or a Boc-protected amine can be deprotected and then alkylated.

Some of the amines used are commercially available or can be prepared by methods known from the literature.

Others among the primary amines used were prepared as outlined by way of example in the scheme which follows.

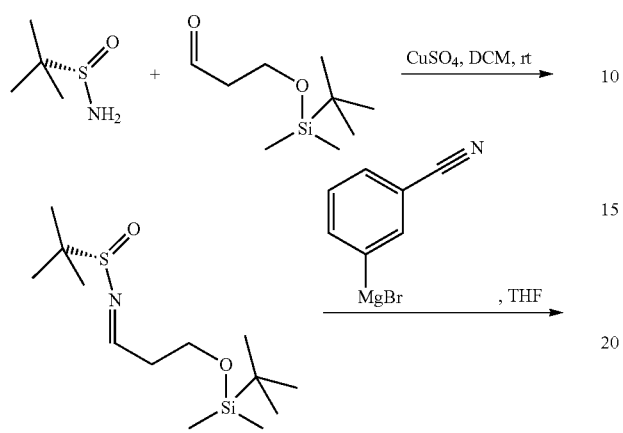

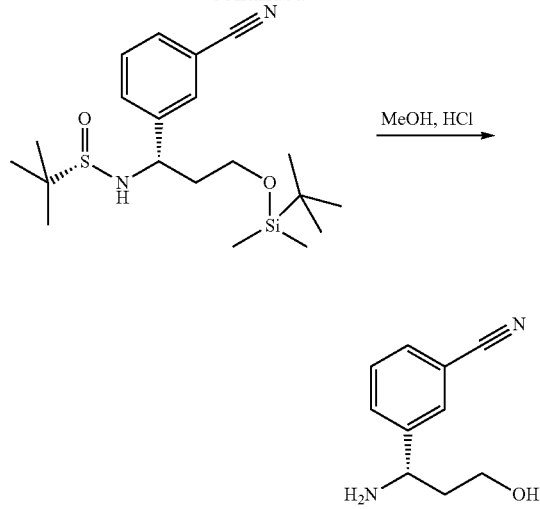

The examples adduced hereinafter serve to illustrate the invention, but without restricting it.

TABLE 1

| Example | CHEMISTR | Method | Retention time | Molar mass (g/mol) | Name |
|---|---|---|---|---|---|
| 1 | | B | 0.942 | 336.4 | Cyclohexyl-(6,6-dimethyl-4,4-dioxo-5-phenyl-5,6-dihydro-4H-4lambda6-[1,4,3]oxathiazin-2-yl)-amine |
| 2 | | B | 0.821 | 388.5 | (S)-3-(6,6-Dimethyl-4,4-dioxo-5-phenyl-5,6-dihydro-4H-4lambda6-[1,4,3]oxathiazin-2-ylamino)-3-phenyl-propan-1-ol |
| 3 | | A | 1.151 | 4125 | (5-Biphenyl-4-yl-6,6-dimethyl-4,4-dioxo-5,6-dihydro-4H-4lambda6-[1,4,3]oxathiazin-2-yl)-cyclohexyl-amine |

TABLE 1-continued

| Example | CHEMISTR | Method | Retention time | Molar mass (g/mol) | Name |
|---|---|---|---|---|---|
| 4 | | B | 0.976 | 494.6 | (S)-3-[5-(4-Benzyloxy-phenyl)-6,6-dimethyl-4,4-dioxo-5,6-dihydro-4H-4lambda6-[1,4,3]oxathiazin-2-ylamino]-3-phenyl-propan-1-ol |
| 5 | | B | 0.719 | 404.5 | 4-[2-((S)-3-Hydroxy-1-phenyl-propylamino)-6,6-dimethyl-4,4-dioxo-5,6-dihydro-4H-4lambda6-[1,4,3]oxathiazin-5-yl]-phenol |
| 6 | | B | 0.829 | 418.5 | (S)-3-[5-(4-Methoxy-phenyl)-6,6-dimethyl-4,4-dioxo-5,6-dihydro-4H-4lambda6-[1,4,3]oxathiazin-2-ylamino]-3-phenyl-propan-1-ol |
| 7 | | B | 0.898 | 467.4 | (S)-3-[5-(3-Bromophenyl)-6,6-dimethyl-4,4-dioxo-5,6-dihydro-4H-4lambda6-[1,4,3]oxathiazin-2-ylamino]-3-phenyl-propan-1-ol |
| 8 | | A | 1.038 | 464.6 | (S)-3-(5-Biphenyl-3-yl-6,6-dimethyl-4,4-dioxo-5,6-dihydro-4H-4lambda6-[1,4,3]oxathiazin-2-ylamino)-3-phenyl-propan-1-ol |
| 9 | | A | 0.942 | 402.5 | (S)-3-(6,6-Dimethyl-4,4-dioxo-5-m-tolyl-5,6-dihydro-4H-4lambda6-[1,4,3]oxathiazin-2-ylamino)-3-phenyl-propan-1-ol |

TABLE 1-continued

| Example | CHEMISTR | Method | Retention time | Molar mass (g/mol) | Name |
|---|---|---|---|---|---|
| 10 | | A | 1.063 | 478.6 | (S)-3-[5-(3-Benzyl-phenyl)-6,6-dimethyl-4,4-dioxo-5,6-dihydro-4H-4lambda6-[1,4,3]oxathiazin-2-ylamino]-3-phenyl-propan-1-ol |
| 11 | | A | 0.948 | 402.5 | (S)-3-(6,6-Dimethyl-4,4-dioxo-5-p-tolyl-5,6-dihydro-4H-4lambda6-[1,4,3]oxathiazin-2-ylamino)-3-phenyl-propan-1-ol |
| 12 | | B | 0.973 | 464.6 | (S)-3-(5-Biphenyl-4-yl-6,6-dimethyl-4,4-dioxo-5,6-dihydro-4H-4lambda6-[1,4,3]oxathiazin-2-ylamino)-3-phenyl-propan-1-ol |
| 13 | | B | 0.986 | 415.3 | [5-(3-Bromophenyl)-6,6-dimethyl-4,4-dioxo-5,6-dihydro-4H-4lambda6-[1,4,3]oxathiazin-2-yl]-cyclohexyl-amine |
| 14 | | B | 0.732 | 466.6 | (S)-3-[6,6-Dimethyl-4,4-dioxo-5-(3-pyrimidin-5-yl-phenyl)-5,6-dihydro-4H-4lambda6-[1,4,3]oxathiazin-2-ylamino]-3-phenyl-propan-1-ol |
| 15 | | B | 0.852 | 422.9 | (S)-3-[5-(2-Chlorophenyl)-6,6-dimethyl-4,4-dioxo-5,6-dihydro-4H-4lambda6-[1,4,3]oxathiazin-2-ylamino]-3-phenyl-propan-1-ol |

TABLE 1-continued

| Example | CHEMISTR | Method | Retention time | Molar mass (g/mol) | Name |
|---|---|---|---|---|---|
| 16 | | B | 0.843 | 402.5 | (S)-3-(6,6-Dimethyl-4,4-dioxo-5-o-tolyl-5,6-dihydro-4H-4lambda6-[1,4,3]oxathiazin-2-ylamino)-3-phenyl-propan-1-ol |
| 17 | | B | 0.84 | 414.5 | Cyclohexyl-[6,6-dimethyl-4,4-dioxo-5-(3-pyrimidin-5-yl-phenyl)-5,6-dihydro-4H-4lambda6-[1,4,3]oxathiazin-2-yl]-amine |
| 18 | | B | 0.938 | 350.5 | Cyclohexyl-(5,6,6-trimethyl-4,4-dioxo-5-phenyl-5,6-dihydro-4H-4lambda6-[1,4,3]oxathiazin-2-yl)-amine |
| 19 | | B | 1.095 | 442.6 | [5-(3-Benzyloxy-phenyl)-6,6-dimethyl-4,4-dioxo-5,6-dihydro-4H-4lambda6-[1,4,3]oxathiazin-2-yl]-cyclohexyl-amine |
| 20 | | B | 0.877 | 422.9 | (S)-3-[5-(3-Chloro-phenyl)-6,6-dimethyl-4,4-dioxo-5,6-dihydro-4H-4lambda6-[1,4,3]oxathiazin-2-ylamino]-3-phenyl-propan-1-ol |
| 21 | | B | 0.908 | 456.5 | (S)-3-[6,6-Dimethyl-4,4-dioxo-5-(3-trifluoromethyl-phenyl)-5,6-dihydro-4H-4lambda6-[1,4,3]oxathiazin-2-ylamino]-3-phenyl-propan-1-ol |
| 22 | | B | 0.846 | 352.4 | 3-(2-Cyclohexylamino-6,6-dimethyl-4,4-dioxo-5,6-dihydro-4H-4lambda6-[1,4,3]oxathiazin-5-yl)-phenol |

TABLE 1-continued

| Example | CHEMISTR | Method | Retention time | Molar mass (g/mol) | Name |
|---|---|---|---|---|---|
| 23 | | B | 0.935 | 366.5 | Cyclohexyl-[5-(3-methoxy-phenyl)-6,6-dimethyl-4,4-dioxo-5,6-dihydro-4H-4lambda6-[1,4,3]oxathiazin-2-yl]-amine |
| 24 | | B | 0.958 | 494.6 | (S)-3-[5-(3-Benzyloxy-phenyl)-6,6-dimethyl-4,4-dioxo-5,6-dihydro-4H-4lambda6-[1,4,3]oxathiazin-2-ylamino]-3-phenyl-propan-1-ol |
| 25 | | A | 0.883 | 352.4 | (1S,3S)-3-(6,6-Dimethyl-4,4-dioxo-5-phenyl-5,6-dihydro-4H-4lambda6-[1,4,3]oxathiazin-2-ylamino)-cyclohexanol |
| 26 | | A | 0.877 | 352.4 | (1R,3R)-3-(6,6-Dimethyl-4,4-dioxo-5-phenyl-5,6-dihydro-4H-4lambda6-[1,4,3]oxathiazin-2-ylamino)-cyclohexanol |
| 27 | | B | 0.988 | 455.3 | [5-(3-Bromophenyl)-6,6-dimethyl-4,4-dioxo-5,6-dihydro-4H-4lambda6-[1,4,3]oxathiazin-2-yl]-[(S)-1-(2-fluorophenyl)-ethyl]-amine |
| 28 | | A | 0.965 | 388.5 | (S)-3-(6,6-Dimethyl-4,4-dioxo-5-phenyl-5,6-dihydro-4H-4lambda6-[1,4,3]oxathiazin-2-ylamino)-3-phenyl-propan-1-ol * |
| 29 | | A | 0.963 | 388.5 | (S)-3-(6,6-Dimethyl-4,4-dioxo-5-phenyl-5,6-dihydro-4H-4lambda6-[1,4,3]oxathiazin-2-ylamino)-3-phenyl-propan-1-ol * |

TABLE 1-continued

| Example | CHEMISTR | Method | Retention time | Molar mass (g/mol) | Name |
|---|---|---|---|---|---|
| 30 | | B | 1.002 | 469.4 | [5-(3-Bromophenyl)-5,6,6-trimethyl-4,4-dioxo-5,6-dihydro-4H-4lambda6-[1,4,3]oxathiazin-2-yl]-[(S)-1-(2-fluorophenyl)-ethyl]-amine |
| 31 | | B | 0.939 | 376.4 | (6,6-Dimethyl-4,4-dioxo-5-phenyl-5,6-dihydro-4H-4lambda6-[1,4,3]oxathiazin-2-yl)-[(S)-1-(2-fluoro-phenyl)-ethyl]-amine |
| 32 | | B | 0.729 | 404.5 | 3-[2-((S)-3-Hydroxy-1-phenyl-propylamino)-6,6-dimethyl-4,4-dioxo-5,6-dihydro-4H-4lambda6-[1,4,3]oxathiazin-5-yl]-phenol |
| 33 | | B | 0.884 | 481.4 | (S)-3-[5-(3-Bromophenyl)-5,6,6-trimethyl-4,4-dioxo-5,6-dihydro-4H-4lambda6-[1,4,3]oxathiazin-2-ylamino]-3-phenyl-propan-1-ol |
| 34 | | B | 0.793 | 564.7 | (S)-3-{5-[3-(4-Methanesulfonyl-piperazin-1-yl)-phenyl]-5,6,6-trimethyl-4,4-dioxo-5,6-dihydro-4H-4lambda6-[1,4,3]oxathiazin-2-ylamino}-3-phenyl-propan-1-ol |
| 35 | | B | 0.907 | 552.7 | [(S)-1-(2-Fluorophenyl)-ethyl]-{5-[3-methanesulfonyl-piperazin-1-yl)-phenyl]-5,6,6-trimethyl-4,4-dioxo-5,6-dihydro-4H-4lambda6-[1,4,3]oxathiazin-2-yl}-amine |

TABLE 1-continued

| Example | CHEMISTRY | Method | Retention time | Molar mass (g/mol) | Name |
|---|---|---|---|---|---|
| 36 | | B | 0.939 | 459.6 | [(S)-1-(2-Fluorophenyl)-ethyl]-[5,6,6-trimethyl-4,4-dioxo-5-(3-pyrrolidin-1-yl-phenyl)-5,6-dihydro-4H-4lambda6-[1,4,3]oxathiazin-2-yl]-amine |
| 37 | | B | 0.832 | 418.5 | (S)-3-[5-(3-Methoxy-phenyl)-6,6-dimethyl-4,4-dioxo-5,6-dihydro-4H-4lambda6-[1,4,3]oxathiazin-2-ylamino]-3-phenyl-propan-1-ol |
| 38 | | B | 0.756 | 471.6 | (S)-3-Phenyl-3-[5,6,6-trimethyl-4,4-dioxo-5-(3-pyrrolidin-1-yl-phenyl)-5,6-dihydro-4H-4lambda6-[1,4,3]oxathiazin-2-ylamino]-propan-1-ol * |
| 39 | | B | 0.782 | 471.6 | (S)-3-Phenyl-3-[5,6,6-trimethyl-4,4-dioxo-5-(3-pyrrolidin-1-yl-phenyl)-5,6-dihydro-4H-4lambda6-[1,4,3]oxathiazin-2-ylamino]-propan-1-ol * |
| 40 | | B | 0.729 | 480.6 | (S)-3-Phenyl-3-[5,6,6-trimethyl-4,4-dioxo-5-(3-pyrimidin-5-yl-phenyl)-5,6-dihydro-4H-4lambda6-[1,4,3]oxathiazin-2-ylamino]-propan-1-ol |
| 41 | | B | 0.845 | 468.5 | [(S)-1-(2-Fluorophenyl)-ethyl]-[5,6,6-trimethyl-4,4-dioxo-5-(3-pyrimidin-5-yl-phenyl)-5,6-dihydro-4H-4lambda6-[1,4,3]oxathiazin-2-yl]-amine |

TABLE 1-continued

| Example | CHEMISTR | Method | Retention time | Molar mass (g/mol) | Name |
|---|---|---|---|---|---|
| 42 | | B | 0.816 | 402.5 | (S)-3-Phenyl-3-(5,6,6-trimethyl-4,4-dioxo-5-phenyl-5,6-dihydro-4H-4lambda6-[1,4,3]oxathiazin-2-ylamino)-propan-1-ol |
| 43 | | B | 0.94 | 390.5 | [(S)-1-(2-Fluorophenyl)-ethyl]-(5,6,6-trimethyl-4,4-dioxo-5-phenyl-5,6-dihydro-4H-4lambda6-[1,4,3]oxathiazin-2-yl)-amine |
| 44 | | B | 0.806 | 582.7 | (S)-3-(2-Fluorophenyl)-3-{5-[3-(4-methanesulfonyl-piperazin-1-yl)-phenyl]-5,6,6-trimethyl-4,4-dioxo-5,6-dihydro-4H-4lambda6-[1,4,3]oxathiazin-2-ylamino}-propan-1-ol |
| 45 | | B | 0.798 | 489.6 | (S)-3-(2-Fluorophenyl)-3-[5,6,6-trimethyl-4,4-dioxo-5-(3-pyrrolidin-1-yl-phenyl)-5,6-dihydro-4H-4lambda6-[1,4,3]oxathiazin-2-ylamino]-propan-1-ol |
| 46 | | B | 0.732 | 498.6 | (S)-3-(2-Fluorophenyl)-3-[5,6,6-trimethyl-4,4-dioxo-5-(3-pyrimidin-5-yl-phenyl)-5,6-dihydro-4H-4lambda6-[1,4,3]oxathiazin-2-ylamino]-propan-1-ol |
| 47 | | B | 0.888 | 499.4 | (S)-3-[5-(3-Bromophenyl)-5,6,6-trimethyl-4,4-dioxo-5,6-dihydro-4H-4lambda6-[1,4,3]oxathiazin-2-ylamino]-3-(2-fluorophenyl)-propan-1-ol |

TABLE 1-continued

| Example | CHEMISTRY | Method | Retention time | Molar mass (g/mol) | Name |
|---|---|---|---|---|---|
| 48 | | B | 0.82 | 420.5 | (S)-3-(2-Fluorophenyl)-3-(5,6,6-trimethyl-4,4-dioxo-5-phenyl-5,6-dihydro-4H-4lambda6-[1,4,3]oxathiazin-2-ylamino)-propan-1-ol |
| 49 | | B | 0.812 | 489.6 | (S)-3-(2-Fluorophenyl)-3-[5,6,6-trimethyl-4,4-dioxo-5-(3-pyrrolidin-1-yl-phenyl)-5,6-dihydro-4H-4lambda6-[1,4,3]oxathiazin-2-ylamino]-propan-1-ol |
| 50 | | B | 1.021 | 485.4 | (S)-3-[5-(3-Bromophenyl)-5-fluoro-6,6-dimethyl-4,4-dioxo-5,6-dihydro-4H-4lambda6-[1,4,3]oxathiazin-2-ylamino]-3-phenyl-propan-1-ol |
| 51 | | B | 0.973 | 482.6 | (S)-3-(5-Biphenyl-4-yl-6,6-dimethyl-4,4-dioxo-5,6-dihydro-4H-4lambda6-[1,4,3]oxathiazin-2-ylamino)-3-(2-fluorophenyl)-propan-1-ol |
| 52 | | B | 1.105 | 452.5 | (5-Biphenyl-4-yl-6,6-dimethyl-4,4-dioxo-5,6-dihydro-4H-4lambda6-[1,4,3]oxathiazin-2-yl)-[(S)-1-(2-fluorophenyl)-ethyl]-amine |

TABLE 1-continued

| Example | CHEMISTRY | Method | Retention time | Molar mass (g/mol) | Name |
|---|---|---|---|---|---|
| 53 | | B | 0.960 | 496.6 | (S)-3-(5-Biphenyl-4-yl-5,6,6-trimethyl-4,4-dioxo-5,6-dihydro-4H-4lambda6-[1,4,3]oxathiazin-2-ylamino)-3-(2-fluorophenyl)-propan-1-ol |
| 54 | | B | 1.003 | 478.6 | (S)-3-(5-Biphenyl-4-yl-5,6,6-trimethyl-4,4-dioxo-5,6-dihydro-4H-4lambda6-[1,4,3]oxathiazin-2-ylamino)-3-phenyl-propan-1-ol |
| 55 | | B | 1.131 | 466.6 | (5-Biphenyl-4-yl-5,6,6-trimethyl-4,4-dioxo-5,6-dihydro-4H-4lambda6-[1,4,3]oxathiazin-2-yl)-[(S)-1-(2-fluorophenyl)-ethyl]-amine |
| 56 | | B | 0.936 | 390.5 | [(S)-1-(2-Fluorophenyl)-ethyl]-(5,6,6-trimethyl-4,4-dioxo-5-phenyl-5,6-dihydro-4H-4lambda6-[1,4,3]oxathiazin-2-yl)-amine * |
| 57 | | B | 0.930 | 390.5 | [(S)-1-(2-Fluorophenyl)-ethyl]-(5,6,6-trimethyl-4,4-dioxo-5-phenyl-5,6-dihydro-4H-4lambda6-[1,4,3]oxathiazin-2-yl)-amine * |

TABLE 1-continued

| Example | CHEMISTR | Method | Retention time | Molar mass (g/mol) | Name |
|---|---|---|---|---|---|
| 58 | | B | 0.996 | 462.6 | (S)-3-[5-(4-tert-Butyl-phenyl)-6,6-dimethyl-4,4-dioxo-5,6-dihydro-4H-4lambda6-[1,4,3]oxathiazin-2-ylamino]-3-(2-fluorophenyl)-propan-1-ol |
| 59 | | B | 1.111 | 432.6 | [5-(4-tert-Butyl-phenyl)-6,6-dimethyl-4,4-dioxo-5,6-dihydro-4H-4lambda6-[1,4,3]oxathiazin-2-yl]-[(S)-1-(2-fluorophenyl)-ethyl]-amine |
| 60 | | B | 0.989 | 444.6 | (S)-3-[5-(4-tert-Butyl-phenyl)-6,6-dimethyl-4,4-dioxo-5,6-dihydro-4H-4lambda6-[1,4,3]oxathiazin-2-ylamino]-3-phenyl-propan-1-ol |
| 61 | | B | 0.998 | 476.6 | (S)-3-[5-(4-tert-Butyl-phenyl)-5,6,6-trimethyl-4,4-dioxo-5,6-dihydro-4H-4lambda6-[1,4,3]oxathiazin-2-ylamino]-3-(2-fluorophenyl)-propan-1-ol |
| 62 | | B | 0.989 | 458.6 | (S)-3-[5-(4-tert-Butyl-phenyl)-5,6,6-trimethyl-4,4-dioxo-5,6-dihydro-4H-4lambda6-[1,4,3]oxathiazin-2-ylamino]-3-phenyl-propan-1-ol |

TABLE 1-continued

| Example | CHEMISTR | Method | Retention time | Molar mass (g/mol) | Name |
|---|---|---|---|---|---|
| 63 | | B | 1.114 | 446.6 | [5-(4-tert-Butyl-phenyl)-5,6,6-trimethyl-4,4-dioxo-5,6-dihydro-4H-4lambda6-[1,4,3]oxathiazin-2-yl]-[(S)-1-(2-fluorophenyl)-ethyl]-amin |
| 64 | | C | 1.802 | 496.6 | (S)-3-[6,6-Dimethyl-5-(2'-methyl-biphenyl-4-yl)-4,4-dioxo-5,6-dihydro-4H-4lambda6-[1,4,3]oxathiazin-2-ylamino]-3-(2-fluorophenyl)-propan-1-ol |
| 65 | | C | 1.753 | 500.6 | (S)-3-[5-(4'-Fluorobiphenyl-4-yl)-6,6-dimethyl-4,4-dioxo-5,6-dihydro-4H-4lambda6-[1,4,3]oxathiazin-2-ylamino]-3-(2-fluorophenyl)-propan-1-ol |
| 66 | | C | 1.715 | 512.6 | (S)-3-(2-Fluorophenyl)-3-[5-(4'-methoxy-biphenyl-4-yl)-6,6-dimethyl-4,4-dioxo-5,6-dihydro-4H-4lambda6-[1,4,3]oxathiazin-2-ylamino]-propan-1-ol |
| 67 | | B | 0.964 | 482.6 | (S)-3-(5-Biphenyl-3-yl-6,6-dimethyl-4,4-dioxo-5,6-dihydro-4H-4lambda6-[1,4,3]oxathiazin-2-ylamino)-3-(2-fluorophenyl)-propan-1-ol |

TABLE 1-continued

| Example | CHEMISTR | Method | Retention time | Molar mass (g/mol) | Name |
|---|---|---|---|---|---|
| 68 | | B | 1.072 | 452.5 | (5-Biphenyl-3-yl-6,6-dimethyl-4,4-dioxo-5,6-dihydro-4H-4lambda6-[1,4,3]oxathiazin-2-yl)-[(S)-1-(2-fluorophenyl)-ethyl]-amine |
| 69 | | B | 0.973 | 482.6 | (S)-3-(5-Biphenyl-4-yl-6,6-dimethyl-4,4-dioxo-5,6-dihydro-4H-4lambda6-[1,4,3]oxathiazin-2-ylamino)-3-(2-fluorophenyl)-propan-1-ol * |
| 70 | | B | 0.973 | 482.6 | (S)-3-(5-Biphenyl-4-yl-6,6-dimethyl-4,4-dioxo-5,6-dihydro-4H-4lambda6-[1,4,3]oxathiazin-2-ylamino)-3-(2-fluorophenyl)-propan-1-ol * |
| 71 | | B | 0.956 | 514.6 | (S)-3-[5-(4'-Fluorobiphenyl-3-yl)-5,6,6-trimethyl-4,4-dioxo-5,6-dihydro-4H-4lambda6-[1,4,3]oxathiazin-2-ylamino]-3-(2-fluorophenyl)-propan-1-ol |
| 72 | | B | 0.972 | 478.6 | (S)-3-(5-Biphenyl-3-yl-5,6,6-trimethyl-4,4-dioxo-5,6-dihydro-4H-4lambda6-[1,4,3]oxathiazin-2-ylamino)-3-phenyl-propan-1-ol |
| 73 | | B | 1.069 | 466.6 | (5-Biphenyl-3-yl-5,6,6-trimethyl-4,4-dioxo-5,6-dihydro-4H-4lambda6-[1,4,3]oxathiazin-2-yl)-[(S)-1-(2-fluorophenyl)-ethyl]-amine |

TABLE 1-continued

| Example | CHEMISTR | Method | Retention time | Molar mass (g/mol) | Name |
|---|---|---|---|---|---|
| 74 | | B | 0.967 | 496.6 | (S)-3-(5-Biphenyl-3-yl-5,6,6-trimethyl-4,4-dioxo-5,6-dihydro-4H-4lambda6-[1,4,3]oxathiazin-2-ylamino)-3-(2-fluorophenyl)-propan-1-ol |
| 75 | | B | 0.962 | 496.6 | (S)-3-(5-Biphenyl-3-yl-5,6,6-trimethyl-4,4-dioxo-5,6-dihydro-4H-4lambda6-[1,4,3]oxathiazin-2-ylamino)-3-(2-fluorophenyl)-propan-1-ol |
| 76 | | B | 0.935 | 496.6 | (S)-3-(9-Biphenyl-4-yl-8,8-dioxo-2,5-dioxa-8lambda6-thia-7-aza-spiro[3.5]non-6-en-6-ylamino)-3-(2-fluorophenyl)-propan-1-ol |
| 77 | | B | 1.009 | 49.6 | (S)-3-(9-Biphenyl-4-yl-8,8-dioxo-5-oxa-8lambda6-thia-7-aza-spiro[3.5]non-6-en-6-ylamino)-3-(2-fluorophenyl)-propan-1-ol |
| 78 | | C | 1.796 | 508.6 | (S)-3-(10-Biphenyl-4-yl-9,9-dioxo-6-oxa-9lambda6-thia-8-aza-spiro[4.5]dec-7-en-7-ylamino)-3-(2-fluorophenyl)-propan-1-ol |

TABLE 1-continued

| Example | CHEMISTR | Method | Retention time | Molar mass (g/mol) | Name |
|---|---|---|---|---|---|
| 79 | | B | 1.028 | 510.6 | (S)-3-(2-Fluorophenyl)-3-[5,6,6-trimethyl-5-(2'-methyl-biphenyl-4-yl)-4,4-dioxo-5,6-dihydro-4H-4lambda6-[1,4,3]oxathiazin-2-ylamino]-propan-1-ol |
| 80 | | B | 1.007 | 514.6 | (S)-3-[5-(4'-Fluorobiphenyl-4-yl)-5,6,6-trimethyl-4,4-dioxo-5,6-dihydro-4H-4lambda6-[1,4,3]oxathiazin-2-ylamino]-3-(2-fluorophenyl)-propan-1-ol |
| 81 | | B | 0.988 | 526.6 | (S)-3-(2-Fluorophenyl)-3-[5-(4'-methoxy-biphenyl-4-yl)-5,6,6-trimethyl-4,4-dioxo-5,6-dihydro-4H-4lambda6-[1,4,3]oxathiazin-2-ylamino]-propan-1-ol |
| 82 | | B | 1.035 | 500.6 | 3-(5-Biphenyl-4-yl-6,6-dimethyl-4,4-dioxo-5,6-dihydro-4H-4lambda6-[1,4,3]oxathiazin-2-ylamino)-3-(2,3-difluorophenyl)-propan-1-ol |
| 83 | | B | 1.058 | 499.0 | (S)-3-(5-Biphenyl-4-yl-6,6-dimethyl-4,4-dioxo-5,6-dihydro-4H-4lambda6-[1,4,3]oxathiazin-2-ylamino)-3-(2-chloro-phenyl)-propan-1-ol |

TABLE 1-continued

| Example | CHEMISTR | Method | Retention time | Molar mass (g/mol) | Name |
|---|---|---|---|---|---|
| 84 | | B | 0.996 | 462.6 | (S)-3-[5-(4-tert-Butyl-phenyl)-6,6-dimethyl-4,4-dioxo-5,6-dihydro-4H-4lambda6-[1,4,3]oxathiazin-2-ylamino]-3-(2-fluorophenyl)-propan-1-ol * |
| 85 | | B | 0.996 | 462.6 | (S)-3-[5-(4-tert-Butyl-phenyl)-6,6-dimethyl-4,4-dioxo-5,6-dihydro-4H-4lambda6-[1,4,3]oxathiazin-2-ylamino]-3-(2-fluorophenyl)-propan-1-ol * |
| 86 | | B | 0.970 | 512.6 | S)-3-(2-Fluorophenyl)-3-[5-(3'-methoxy-biphenyl-4-yl)-6,6-dimethyl-4,4-dioxo-5,6-dihydro-4H-4lambda6-[1,4,3]oxathiazin-2-ylamino]-propan-1-ol |
| 87 | | B | 0.905 | 507.6 | 4'-{2-[(S)-1-(2-Fluorophenyl)-3-propylamino]-6,6-dimethyl-4,4-dioxo-5,6-dihydro-4H-4lambda6-[1,4,3]oxathiazin-5-yl}-biphenyl-2-carbonitrile |
| 88 | | A | 1.042 | 499.0 | (S)-3-(5-Biphenyl-4-yl-6,6-dimethyl-4,4-dioxo-5,6-dihydro-4H-4lambda6-[1,4,3]oxathiazin-2-ylamino)-3-(4-chloro-phenyl)-propan-1-ol |

TABLE 1-continued

| Example | CHEMISTR | Method | Retention time | Molar mass (g/mol) | Name |
|---|---|---|---|---|---|
| 89 | | A | 1.034 | 499.0 | (S)-3-(5-Biphenyl-4-yl-6,6-dimethyl-4,4-dioxo-5,6-dihydro-4H-4lambda6-[1,4,3]oxathiazin-2-ylamino)-3-(3-chloro-phenyl)-propan-1-ol |
| 90 | | B | 0.764 | 484.5 | (S)-3-[6,6-Dimethyl-4,4-dioxo-5-(4-pyrimidin-5-yl-phenyl)-5,6-dihydro-4H-4lambda6-[1,4,3]oxathiazin-2-ylamino]-3-(2-fluorophenyl)-propan-1-ol |
| 91 | | B | 1.068 | 523.0 | (S)-3-{5-[4-(5-Chlorothiophen-2-yl)-phenyl]-6,6-dimethyl-4,4-dioxo-5,6-dihydro-4H-4lambda6-[1,4,3]oxathiazin-2-ylamino}-3-(2-fluorophenyl)-propan-1-ol |
| 92 | | B | 1.124 | 557.5 | (S)-3-{5-[4-(2,5-Dichlorothiophen-3-yl)-phenyl]-6,6-dimethyl-4,4-dioxo-5,6-dihydro-4H-4lambda6-[1,4,3]oxathiazin-2-ylamino}-3-(2-fluorophenyl)-propan-1-ol |
| 93 | | C | 1.659 | 507.6 | 4'-{2-[(S)-1-(2-Fluorophenyl)-3-propylamino]-6,6-dimethyl-4,4-dioxo-5,6-dihydro-4H-4lambda6-[1,4,3]oxathiazin-5-yl}-biphenyl-3-carbonitrile |

TABLE 1-continued

| Example | CHEMISTRY | Method | Retention time | Molar mass (g/mol) | Name |
|---|---|---|---|---|---|
| 94 | | B | 0.969 | 512.6 | (S)-3-(2-Fluorophenyl)-3-[5-(2'-methoxy-biphenyl-4-yl)-6,6-dimethyl-4,4-dioxo-5,6-dihydro-4H-4lambda6-[1,4,3]oxathiazin-2-ylamino]-propan-1-ol |
| 95 | | B | 0.941 | 507.6 | 4'-{2-[(S)-1-(2-Fluorophenyl)-3-propylamino]-6,6-dimethyl-4,4-dioxo-5,6-dihydro-4H-4lambda6-[1,4,3]oxathiazin-5-yl}-biphenyl-4-carbonitrile |
| 96 | | A | 1.111 | 517.0 | (S)-3-(5-Biphenyl-4-yl-6,6-dimethyl-4,4-dioxo-5,6-dihydro-4H-4lambda6-[1,4,3]oxathiazin-2-ylamino)-3-(2-chloro-3-fluorophenyl)-propan-1-ol |
| 97 | | A | 1.103 | 500.6 | (S)-3-(5-Biphenyl-4-yl-6,6-dimethyl-4,4-dioxo-5,6-dihydro-4H-4lambda6-[1,4,3]oxathiazin-2-ylamino)-3-(2,4-difluorophenyl)-propan-1-ol |

TABLE 1-continued

| Example | CHEMISTR | Method | Retention time | Molar mass (g/mol) | Name |
|---|---|---|---|---|---|
| 98 | | A | 1.101 | 500.6 | (S)-3-(5-Biphenyl-4-yl-6,6-dimethyl-4,4-dioxo-5,6-dihydro-4H-4lambda6-[1,4,3]oxathiazin-2-ylamino)-3-(2,5-difluorophenyl)-propan-1-ol |
| 99 | | A | 1.104 | 517.0 | (S)-3-(5-Biphenyl-4-yl-6,6-dimethyl-4,4-dioxo-5,6-dihydro-4H-4lambda6-[1,4,3]oxathiazin-2-ylamino)-3-(5-chloro-2-fluorophenyl)-propan-1-ol |
| 99 | | A | 1.104 | 517.0 | (S)-3-(5-Biphenyl-4-yl-6,6-dimethyl-4,4-dioxo-5,6-dihydro-4H-4lambda6-[1,4,3]oxathiazin-2-ylamino)-3-(5-chloro-2-fluorophenyl)-propan-1-ol |
| 100 | | A | 1.107 | 496.6 | (S)-3-(5-Biphenyl-4-yl-6,6-dimethyl-4,4-dioxo-5,6-dihydro-4H-4lambda6-[1,4,3]oxathiazin-2-ylamino)-3-(5-fluoro-2-methyl-phenyl)-propan-1-ol |

TABLE 1-continued

| Example | CHEMISTRY | Method | Retention time | Molar mass (g/mol) | Name |
|---|---|---|---|---|---|
| 101 | | B | 0.828 | 489.6 | (S)-3-[6,6-Dimethyl-4,4-dioxo-5-(4-thiazol-4-yl-phenyl)-5,6-dihydro-4H-4lambda6-[1,4,3]oxathiazin-2-ylamino]-3-(2-fluorophenyl)-propan-1-ol |
| 102 | | B | 0.944 | 474.5 | (S)-3-[6,6-Dimethyl-4,4-dioxo-5-(4-trifluormethyl-phenyl)-5,6-dihydro-4H-4lambda6-[1,4,3]oxathiazin-2-ylamino]-3-(2-fluorophenyl)-propan-1-ol |
| 103 | | B | 0.659 | 503.6 | (S)-3-{6,6-Dimethyl-5-[4-(1-methyl-piperidin-4-phenyl]-4,4-dioxo-5,6-dihydro-4H-4lambda6-[1,4,3]oxathiazin-2-ylamino}-3-(2-fluorophenyl)-propan-1-ol |
| 104 | | B | 0.653 | 533.7 | (S)-3-(2-Fluorophenyl)-3-(5-{4-[1-(2-hydroxy-piperidin-4-yl]-phenyl}-6,6-dimethyl-4,4-dioxo-5,6-dihydro-4H-4lambda6-[1,4,3]oxathiazin-2-ylamino)-propan-1-ol |
| 105 | | B | 0.681 | 553.6 | (S)-3-(5-{4-[1-(2,2-Difluoroethyl)-piperidin-4-phenyl}-6,6-dimethyl-4,4-dioxo-5,6-dihydro-4H-4lambda6-[1,4,3]oxathiazin-2-ylamino)-3-(2-fluorophenyl)-propan-1-ol |

TABLE 1-continued

| Example | CHEMISTR | Method | Retention time | Molar mass (g/mol) | Name |
|---|---|---|---|---|---|
| 106 | | B | 0.658 | 463.6 | (S)-3-{5-[4-(3-Amino-propyl)-phenyl]-6,6-dimethyl-4,4-dioxo-5,6-dihydro-4H-4lambda6-[1,4,3]oxathiazin-2-ylamino}-3-(2-fluorophenyl)-propan-1-ol |
| 107 | | B | 0.809 | 491.6 | (S)-3-[6,6-Dimethyl-5-(4-morpholin-4-yl-phenyl)-4,4-dioxo-5,6-dihydro-4H-4lambda6-[1,4,3]oxathiazin-2-ylamino]-3-(2-fluorophenyl)-propan-1-ol |
| 108 | | B | 0.671 | 491.6 | (S)-3-{5-[4-(3-Dimethylamino-propyl)-phenyl]-6,6-dimethyl-4,4-dioxo-5,6-dihydro-4H-4lambda6-[1,4,3]oxathiazin-2-ylamino}-3-(2-fluorophenyl)-propan-1-ol |
| 109 | | C | 1.088 | 504.6 | (S)-3-{6,6-Dimethyl-5-[4-(4-methyl-piperazin-1-phenyl]-4,4-dioxo-5,6-dihydro-4H-4lambda6-[1,4,3]oxathiazin-2-ylamino}-3-(2-fluorophenyl)-propan-1-ol |
| 110 | | B | 0.648 | 533.7 | (S)-3-{6,6-Dimethyl-5-[4-(3-morpholin-4-yl-phenyl]-4,4-dioxo-5,6-dihydro-4H-4lambda6-[1,4,3]oxathiazin-2-ylamino}-3-(2-fluorophenyl)-propan-1-ol |

TABLE 1-continued

| Example | Method | Retention time | Molar mass (g/mol) | Name |
|---|---|---|---|---|
| 111 | B | 0.833 | 486.6 | (S)-3-{6,6-Dimethyl-5-[4-(2-methyl-2H-pyrazol-yl)-phenyl]-4,4-dioxo-5,6-dihydro-4H-4lambda6-[1,4,3]oxathiazin-2-ylamino}-3-(2-fluorophenyl)-propan-1-ol |
| 112 | B | 0.862 | 553.6 | 4'-{2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-biphenyl-4-carboxylic acid dimethylamide |
| 113 | B | 0.663 | 483.6 | (S)-3-[6,6-Dimethyl-4,4-dioxo-5-(4-pyridin-3-yl-phenyl)-5,6-dihydro-4H-4lambda6-[1,4,3]oxathiazin-2-ylamino]-3-(2-fluorophenyl)-propan-1-ol |
| 114 | B | 0.739 | 580.7 | (S)-3-{6,6-Dimethyl-5-[4'-(4-methyl-piperazin-1-biphenyl-4-yl]-4,4-dioxo-5,6-dihydro-4H-4lambda6-[1,4,3]oxathiazin-2-ylamino}-3-(2-fluorophenyl)-propan-1-ol |

TABLE 1-continued

| Example | CHEMISTR | Method | Retention time | Molar mass (g/mol) | Name |
|---|---|---|---|---|---|
| 115 | | B | 0.763 | 486.6 | (S)-3-{6,6-Dimethyl-5-[4-(3-methyl-1H-pyrazol-yl)-phenyl]-4,4-dioxo-5,6-dihydro-4H-4lambda6-[1,4,3]oxathiazin-2-ylamino}-3-(2-fluorophenyl)-propan-1-ol |
| 116 | | B | 0.697 | 541.6 | (S)-3-[5-(4-{3-[(2,2-Difluoroethyl)-methyl-amino]-propyl}-phenyl)-6,6-dimethyl-4,4-dioxo-5,6-dihydro-4H-4lambda6-[1,4,3]oxathiazin-2-ylamino]-3-(2-fluorophenyl)-propan-1-ol |
| 117 | | B | 0.671 | 477.6 | (S)-3-{6,6-Dimethyl-5-[4-(3-methylamino-propyl)-phenyl]-4,4-dioxo-5,6-dihydro-4H-4lambda6-[1,4,3]oxathiazin-2-ylamino}-3-(2-fluorophenyl)-propan-1-ol |
| 118 | | B | 0.898 | 574.7 | (S)-3-{6,6-Dimethyl-5-[4-(2-morpholin-4-yl-thiazol-4-yl)-phenyl]-4,4-dioxo-5,6-dihydro-4H-4lambda6-[1,4,3]oxathiazin-2-ylamino}-3-(2-fluorophenyl)-propan-1-ol |
| 119 | | B | 0.655 | 483.6 | (S)-3-[6,6-Dimethyl-4,4-dioxo-5-(4-pyridin-4-yl-phenyl)-5,6-dihydro-4H-4lambda6-[1,4,3]oxathiazin-2-ylamino]-3-(2-fluorophenyl)-propan-1-ol |

TABLE 1-continued

| Example | CHEMISTRY | Method | Retention time | Molar mass (g/mol) | Name |
|---|---|---|---|---|---|
| 120 | | B | 0.814 | 525.6 | 4'-{2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-biphenyl-4-carboxylic acid amide |
| 121 | | B | 0.782 | 472.5 | (S)-3-{6,6-Dimethyl-4,4-dioxo-5-[4-(1H-pyrazol-4-yl)-phenyl]-5,6-dihydro-4H-4lambda6-[1,4,3]oxathiazin-2-ylamino}-3-(2-fluorophenyl)-propan-1-ol |
| 122 | | B | 0.678 | 521.6 | (S)-3-(2-fluorophenyl)-3-[5-(4-{3-[(2-hydroxy-methyl-amino]-propyl}-phenyl)-6,6-dimethyl-4,4-dioxo-5,6-dihydro-4H-4lambda6-[1,4,3]oxathiazin-2-ylamino]-propan-1-ol |
| 123 | | B | 0.724 | 539.7 | (S)-3-[5-(4'-Dimethylaminomethyl-biphenyl-4-yl)-6,6-dimethyl-4,4-dioxo-5,6-dihydro-4H-4lambda6-[1,4,3]oxathiazin-2-ylamino]-3-(2-fluorophenyl)-propan-1-ol |
| 124 | | B | 0.817 | 486.6 | (S)-3-{6,6-Dimethyl-5-[4-(1-methyl-1H-pyrazol-yl)-phenyl]-4,4-dioxo-5,6-dihydro-4H-4lambda6-[1,4,3]oxathiazin-2-ylamino}-3-(2-fluorophenyl)-propan-1-ol |

TABLE 1-continued

| Example | CHEMISTR | Method | Retention time | Molar mass (g/mol) | Name |
| --- | --- | --- | --- | --- | --- |
| 125 | | B | 0.71 | 582.7 | (S)-3-(6,6-Dimethyl-5-{4-[2-(4-methyl-piperazin-1-yl)-pyrimidin-5-yl]-phenyl}-4,4-dioxo-5,6-dihydro-4H-4lambda6-[1,4,3]oxathiazin-2-ylamino)-3-(2-fluorophenyl)-propan-1-ol |
| 126 | | B | 0.734 | 526.6 | (S)-3-{5-[4-(6-Dimethylamino-pyridin-2-yl)-phenyl]-6,6-dimethyl-4,4-dioxo-5,6-dihydro-4H-4lambda6-[1,4,3]oxathiazin-2-ylamino}-3-(2-fluorophenyl)-propan-1-ol |
| 127 | | C | 1.348 | 508.6 | 4-(4-{2-[(S)-1-(2-fluorophenyl)-3-propylamino]-6,6-dimethyl-4,4-dioxo-5,6-dihydro-4H-4lambda6-[1,4,3]oxathiazin-5-yl}-phenyl)-pyridine-2-carbonitrile |
| 128 | | B | 0.75 | 472.5 | (S)-3-{6,6-Dimethyl-4,4-dioxo-5-[4-(1H-pyrazol-3-yl)-phenyl]-5,6-dihydro-4H-4lambda6-[1,4,3]oxathiazin-2-ylamino}-3-(2-fluorophenyl)-propan-1-ol |

TABLE 1-continued

| Example | CHEMISTR | Method | Retention time | Molar mass (g/mol) | Name |
|---|---|---|---|---|---|
| 129 | | B | 0.600 | 505.6 | (S)-3-[6,6-Dimethyl-5-(4-morpholin-4-ylmethyl-phenyl)-4,4-dioxo-5,6-dihydro-4H-4lambda6-[1,4,3]oxathiazin-2-ylamino]-3-(2-fluorophenyl)-propan-1-ol |
| 130 | | B | 0.763 | 499.6 | (S)-3-{6,6-Dimethyl-4,4-dioxo-5-[4-(pyrimidin-2-ylamino)-phenyl]-5,6-dihydro-4H-4lambda6-[1,4,3]oxathiazin-2-ylamino}-3-(2-fluorophenyl)-propan-1-ol |
| 131 | | B | 0.699 | 586.6 | (S)-3-(6,6-Dimethyl-4,4-dioxo-5-{4-[4-(3,3,3-trifluoropropyl)-piperazin-1-yl]-phenyl}-5,6-dihydro-4H-4lambda6-[1,4,3]oxathiazin-2-ylamino)-3-(2-fluorophenyl)-propan-1-ol |
| 132 | | B | 0.776 | 489.6 | 1-(4-{2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-phenyl)-pyrrolidin-2-one |
| 133 | | B | 0.682 | 582.7 | (S)-3-{6,6-Dimethyl-5-[4-(4-methyl-3,4,5,6-tetrahydro-2H-[1,2']bipyrazinyl-5'-yl)-phenyl]-4,4-dioxo-5,6-dihydro-4H-4lambda6-[1,4,3]oxathiazin-2-ylamino}-3-(2-fluorophenyl)-propan-1-ol |

TABLE 1-continued

| Example | CHEMISTR | Method | Retention time | Molar mass (g/mol) | Name |
|---|---|---|---|---|---|
| 134 | | B | 0.668 | 483.6 | (S)-3-[6,6-Dimethyl-4,4-dioxo-5-(4-pyridin-2-yl-phenyl)-5,6-dihydro-4H-4lambda6-[1,4,3]oxathiazin-2-ylamino]-3-(2-fluorophenyl)-propan-1-ol |
| 135 | | B | 0.638 | 534.6 | (S)-3-(2-fluorophenyl)-3-(5-{4-[4-(2-hydroxy-piperazin-1-yl]-phenyl}-6,6-dimethyl-4,4-dioxo-5,6-dihydro-4H-4lambda6-[1,4,3]oxathiazin-2-ylamino)-propan-1-ol |
| 136 | | B | 0.588 | 518.6 | (S)-3-{6,6-Dimethyl-5-[4-(4-methyl-piperazin-1-ylmethyl)-phenyl]-4,4-dioxo-5,6-dihydro-4H-4lambda6-[1,4,3]oxathiazin-2-ylamino}-3-(2-fluoro-phenyl)-propan-1-ol |
| 137 | | B | 0.618 | 548.7 | (S)-3-(6,6-Dimethyl-5-{4-[2-(4-methyl-piperazin-1-yl)-ethoxy]-phenyl}-4,4-dioxo-5,6-dihydro-4H-4lambda6-[1,4,3]oxathiazin-2-ylamino)-3-(2-fluoro-phenyl)-propan-1-ol |
| 138 | | B | 0.684 | 546.7 | (S)-3-{5-[4-(4-tert-Butyl-piperazin-1-yl)-phenyl]-dimethyl-4,4-dioxo-5,6-dihydro-4H-4lambda6-[1,4,3]oxathiazin-2-ylamino}-3-(2-fluorophenyl)-propan-1-ol |

TABLE 1-continued

| Example | CHEMISTRY | Method | Retention time | Molar mass (g/mol) | Name |
|---|---|---|---|---|---|
| 139 | | B | 0.811 | 514.6 | (S)-3-(2-fluorophenyl)-3-{5-[4-(2-methoxy-pyrimidin-5-yl)-phenyl]-6,6-dimethyl-4,4-dioxo-5,6-dihydro-4H-4lambda6-[1,4,3]oxathiazin-2-ylamino}-propan-1-ol |
| 140 | | B | 0.642 | 519.6 | (S)-3-{6,6-Dimethyl-5-[4-(2-morpholin-4-yl-phenyl]-4,4-dioxo-5,6-dihydro-4H-4lambda6-[1,4,3]oxathiazin-2-ylamino}-3-(2-fluorophenyl)-propan-1-ol |
| 141 | | B | 0.910 | 551.6 | 2-(4-{2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-phenyl)-isoindole-1,3-dione |
| 142 | | B | 0.683 | 544.7 | (S)-3-{5-[4-(1-Cyclopropyl-piperidin-4-ylamino)-phenyl]-6,6-dimethyl-4,4-dioxo-5,6-dihydro-4H-4lambda6-[1,4,3]oxathiazin-2-ylamino}-3-(2-fluoro-phenyl)-propan-1-ol |
| 143 | | B | 0.722 | 585.7 | (S)-3-(6,6-Dimethyl-4,4-dioxo-5-{4-[1-(3,3,3-trifluoropropyl)-piperidin-4-yl]-phenyl}-5,6-dihydro-4H-4lambda6-[1,4,3]oxathiazin-2-ylamino)-3-(2-fluorophenyl)-propan-1-ol |

TABLE 1-continued

| Example | CHEMISTR | Method | Retention time | Molar mass (g/mol) | Name |
|---|---|---|---|---|---|
| 144 | | B | 0.806 | 448.5 | 1-(4-{2-[(S)-1-(2-fluorophenyl)-3-propylamino]-6,6-dimethyl-4,4-dioxo-5,6-dihydro-4H-4lambda6-[1,4,3]oxathiazin-5-yl}-phenyl)-ethanone |
| 145 | | B | 0.642 | 581.7 | (S)-3-(6,6-Dimethyl-5-{4-[6-(4-methyl-piperazin-1-yl)-pyridin-3-yl]-phenyl}-4,4-dioxo-5,6-dihydro-4H-4lambda6-[1,4,3]oxathiazin-2-ylamino)-3-(2-fluoro-phenyl)-propan-1-ol |
| 146 | | B | 0.797 | 525.6 | 4'-{(S)-2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-biphenyl-4-carboxamide |
| 147 | | B | 0.799 | 525.6 | 4'-{(R)-2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-biphenyl-4-carboxamide |

TABLE 1-continued

| Example | CHEMISTRY | Method | Retention time | Molar mass (g/mol) | Name |
|---|---|---|---|---|---|
| 148 | | B | 0.597 | 532.7 | (S)-3-(6,6-Dimethyl-5-{4-[2-(4-methyl-piperazin-1-yl)-ethyl]-phenyl}-4,4-dioxo-5,6-dihydro-4H-4lambda6-[1,4,3]oxathiazin-2-ylamino)-3-(2-fluoro-phenyl)-propan-1-ol |
| 149 | | B | 0.823 | 525.6 | 4'-{(S)-2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-biphenyl-3-carboxamide |
| 150 | | B | 0.824 | 525.6 | 4'-{(R)-2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-biphenyl-3-carboxamide |
| 151 | | B | 0.714 | 545.7 | (S)-3-{5-[4-(1-tert-Butyl-piperidin-4-yl)-phenyl]-6,6-dimethyl-4,4-dioxo-5,6-dihydro-4H-4lambda6-[1,4,3]oxathiazin-2-ylamino}-3-(2-fluorophenyl)-propan-1-ol |

TABLE 1-continued

| Example | CHEMISTR | Method | Retention time | Molar mass (g/mol) | Name |
|---|---|---|---|---|---|
| 152 | | B | 0.697 | 529.7 | (S)-3-{5-[4-(1-Cyclopropyl-piperidin-4-yl)-phenyl]-6,6-dimethyl-4,4-dioxo-5,6-dihydro-4H-4lamda6-[1,4,3]oxathiazin-2-ylamino}-3-(2-fluorophenyl)-propan-1-ol |
| 153 | | B | 0.821 | 464.6 | (S)-3-(2-fluorophenyl)-3-{5-[4-(1-hydroxy-1-methyl-ethyl)-phenyl]-6,6-dimethyl-4,4-dioxo-5,6-dihydro-4H-4lambda6-[1,4,3]oxathiazin-2-ylamino}-propan-1-ol |
| 154 | | B | 0.637 | 581.7 | (S)-3-(6,6-Dimethyl-5-{4-[5-(4-methyl-piperazin-1-yl)-pyridin-2-yl]-phenyl}-4,4-dioxo-5,6-dihydro-4H-4lambda6-[1,4,3]oxathiazin-2-ylamino)-3-(2-fluoro-phenyl)-propan-1-ol |
| 155 | | B | 0.863 | 464.5 | Acetic acid 4-{2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-phenyl ester |
| 156 | | B | 0.940 | 495.6 | 4'-{2-[(S)-1-(2-fluorophenyl)-ethylamino]-6,6-dimethyl-4,4-dioxo-5,6-dihydro-4H-4lambda6-[1,4,3]oxathiazin-5-yl}-biphenyl-3-carboxamide |

TABLE 1-continued

| Example | CHEMISTR | Method | Retention time | Molar mass (g/mol) | Name |
|---|---|---|---|---|---|
| 157 | | B | 0.927 | 495.6 | 4'-{2-[(S)-1-(2-fluorophenyl)-ethylamino]-6,6-dimethyl-4,4-dioxo-5,6-dihydro-4H-4lambda6-[1,4,3]oxathiazin-5-yl}-biphenyl-4-carboxamide |
| 158 | | B | 0.783 | 459.6 | [6,6-Dimethyl-4,4-dioxo-5-(4-piperidin-4-yl-phenyl)-5,6-dihydro-4H-4lambda6-[1,4,3]oxathiazin-2-yl]-[(S)-1-(2-fluorophenyl)-ethyl]-amin |
| 159 | | B | 0.777 | 473.6 | {6,6-Dimethyl-5-[4-(1-methyl-piperidin-4-yl)-phenyl]-4,4-dioxo-5,6-dihydro-4H-4lambda6-[1,4,3]oxathiazin-2-yl}-[(S)-1-(2-fluorophenyl)-ethyl]-amine |
| 160 | | B | 0.769 | 503.6 | 2-[4-(4-{2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-piperidin-1-yl]-ethanol |
| 161 | | B | 0.619 | 407.5 | (S)-3-(6,6-Dimethyl-4,4-dioxo-5-pyridin-3-yl-5,6-dihydro-4H-4lambda6-[1,4,3]oxathiazin-2-ylamino)-3-(2-fluorophenyl)-propan-1-ol |

TABLE 1-continued

| Example | CHEMISTR | Method | Retention time | Molar mass (g/mol) | Name |
|---|---|---|---|---|---|
| 162 | | C | 1.568 | 434.5 | 2-(4-{2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-propan-2-ol |
| 163 | | B | 0.939 | 418.5 | 1-(4-{2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-ethanone |
| 164 | | B | 0.963 | 453.5 | [6,6-Dimethyl-4,4-dioxo-5-(6-phenyl-pyridin-3-yl)-5,6-dihydro-4H-4lambda6-[1,4,3]oxathiazin-2-yl]-[(S)-1-(2-fluorophenyl)-ethyl]-amine |
| 165 | | B | 0.863 | 483.6 | (S)-3-[6,6-Dimethyl-4,4-dioxo-5-(6-phenyl-pyridin-3-yl)-5,6-dihydro-4H-4lambda6-[1,4,3]oxathiazin-2-ylamino]-3-(2-fluorophenyl)-propan-1-ol |
| 166 | | B | 0.797 | 538.6 | {6,6-Dimethyl-4,4-dioxo-5-[4-(2-piperazin-1-yl-pyrimidin-5-yl)-phenyl]-5,6-dihydro-4H-4lambda6-[1,4,3]oxathiazin-2-yl}-[(S)-1-(2-fluorophenyl)-ethyl]-amine |

TABLE 1-continued

| Example | CHEMISTR | Method | Retention time | Molar mass (g/mol) | Name |
|---|---|---|---|---|---|
| 167 | | B | 0.765 | 460.6 | [6,6-Dimethyl-4,4-dioxo-5-(4-piperazin-1-yl-phenyl)-5,6-dihydro-4H-4lambda6-[1,4,3]oxathiazin-2-yl]-[(S)-1-(2-fluorophenyl)-ethyl]-amine |
| 168 | HCl | B | 0.712 | 377.4 | (6,6-Dimethyl-4,4-dioxo-5-pyridin-3-yl-5,6-dihydro-4H-4lambda6-[1,4,3]oxathiazin-2-yl)-[(S)-1-(2-fluorophenyl)-ethyl]-amine |
| 169 | HCl | B | 0.718 | 568.7 | (S)-3-{6,6-Dimethyl-4,4-dioxo-5-[4-(2-piperazin-1-yl-pyrimidin-5-yl)-phenyl]-5,6-dihydro-4H-4lambda6-[1,4,3]oxathiazin-2-ylamino}-3-(2-fluoro-phenyl)-propan-1-ol |
| 170 | HCl | B | 0.684 | 474.6 | {6,6-Dimethyl-5-[4-(4-methyl-piperazin-1-yl)-phenyl]-4,4-dioxo-5,6-dihydro-4H-4lambda6-[1,4,3]oxathiazin-2-yl}-[(S)-1-(2-fluorophenyl)-ethyl]-amine |

TABLE 1-continued

| Example | CHEMISTR | Method | Retention time | Molar mass (g/mol) | Name |
|---|---|---|---|---|---|
| 171 | 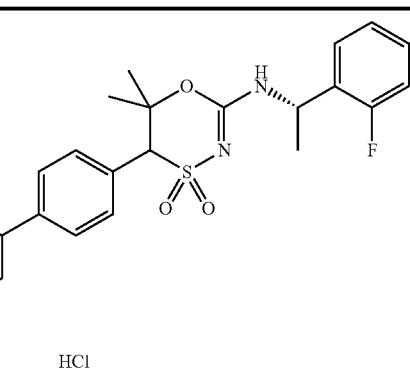 HCl | B | 0.745 | 515.7 | {5-[4-(1-tert-Butyl-piperidin-4-yl)-phenyl]-6,6-dimethyl-4,4-dioxo-5,6-dihydro-4H-4lambda6-[1,4,3]oxathiazin-2-yl}-[(S)-1-(2-fluorophenyl)-ethyl]-amine |
| 172 | 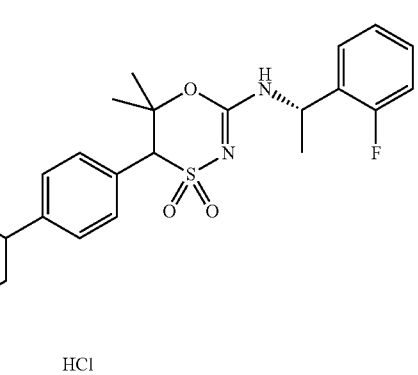 HCl | B | 0.730 | 499.6 | {5-[4-(1-Cyclopropyl-piperidin-4-yl)-phenyl]-6,6-dimethyl-4,4-dioxo-5,6-dihydro-4H-4lambda6-[1,4,3]oxathiazin-2-yl}-[(S)-1-(2-fluorophenyl)-ethyl]-amine |
| 173 | 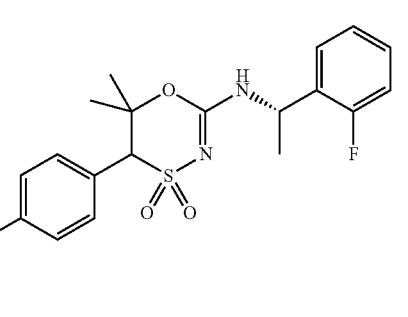 | B | 0.753 | 509.6 | [5-(2'-Dimethylaminomethyl-biphenyl-4-yl)-6,6-dimethyl-4,4-dioxo-5,6-dihydro-4H-4lambda6-[1,4,3]oxathiazin-2-yl]-[(S)-1-(2-fluorophenyl)-ethyl]-amin |
| 174 | 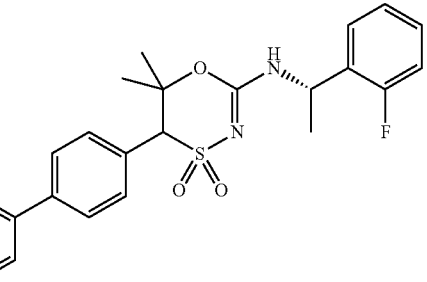 | B | 0.853 | 495.6 | 4'-{(S)-2-[(S)-1-(2-fluorophenyl)-ethylamino]-6,6-dimethyl-4,4-dioxo-5,6-dihydro-4H-4lambda6-[1,4,3]oxathiazin-5-yl}-biphenyl-3-carboxamide |

TABLE 1-continued

| Example | CHEMISTRY | Method | Retention time | Molar mass (g/mol) | Name |
|---|---|---|---|---|---|
| 175 | | B | 0.859 | 495.6 | 4'-{(R)-2-[(S)-1-(2-fluorophenyl)-ethylamino]-6,6-dimethyl-4,4-dioxo-5,6-dihydro-4H-4lambda6-[1,4,3]oxathiazin-5-yl}-biphenyl-3-carboxamide |
| 176 | | C | 1.444 | 496.6 | 3-(5-{2-[(S)-1-(2-fluorphenyl)-ethylamino]-6,6-odimethyl-4,4-dioxo-5,6-dihydro-4H-4lambda6-[1,4,3]oxathiazin-5-yl}-pyridin-2-yl)-benzamide |
| 177 | | B | 0.750 | 496.6 | 5-(4-{(S)-2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-nicotinamide |
| 178 | | B | 0.755 | 496.6 | 5-(4-{(R)-2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-nicotinamide |
| 179 | | B | 0.714 | 473.6 | {6,6-Dimethyl-5-[3-(1-methyl-piperidin-4-yl)-phenyl]-4,4-dioxo-5,6-dihydro-4H-4lambda6-[1,4,3]oxathiazin-2-yl}-[(S)-1-(2-fluorophenyl)-ethyl]-amine |

TABLE 1-continued

| Example | CHEMISTR | Method | Retention time | Molar mass (g/mol) | Name |
|---|---|---|---|---|---|
| 180 | | B | 0.788 | 496.6 | 3-(5-{2-[(S)-1-(2-fluorophenyl)-ethylamino]-6,6-dimethyl-4,4-dioxo-5,6-dihydro-4H-4lambda6-[1,4,3]oxathiazin-5-yl}-pyridin-2-yl)-benzamide |
| 181 | | B | 0.795 | 496.6 | 3-(5-{2-[(S)-1-(2-fluorophenyl)-ethylamino]-6,6-dimethyl-4,4-dioxo-5,6-dihydro-4H-4lambda6-[1,4,3]oxathiazin-5-yl}-pyridin-2-yl)-benzamide |
| 182 | | B | 0.678 | 586.6 | (S)-3-(6,6-Dimethyl-4,4-dioxo-5-{4-[4-(3,3,3-trifluoropropyl)-piperazin-1-yl]-phenyl}-5,6-dihydro-4H-4lambda6-[1,4,3]oxathiazin-2-ylamino)-3-(2-fluorophenyl)-propan-1-ol |
| 183 | | B | 0.677 | 586.6 | (S)-3-(6,6-Dimethyl-4,4-dioxo-5-{4-[4-(3,3,3-trifluoropropyl)-piperazin-1-yl]-phenyl}-5,6-dihydro-4H-4lambda6-[1,4,3]oxathiazin-2-ylamino)-3-(2-fluorophenyl)-propan-1-ol |

TABLE 1-continued

| Example | CHEMISTR | Method | Retention time | Molar mass (g/mol) | Name |
|---|---|---|---|---|---|
| 184 | | B | 0.856 | 508.6 | 4-(4-{(S)-2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-phenyl)-pyridine-2-carbonitrile |
| 185 | | B | 0.857 | 580.6 | 4-(4-{(R)-2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-phenyl)-pyridine-2-carbonitrile |
| 186 | | B | 0.964 | 478.5 | 4-(4-{(S)-2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-pyridine-2-carbonitrile |
| 187 | | B | 0.973 | 478.5 | 4-(4-{(R)-2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-pyridine-2-carbonitrile |

TABLE 1-continued

| Example | CHEMISTR | Method | Retention time | Molar mass (g/mol) | Name |
|---|---|---|---|---|---|
| 188 | | B | 0.744 | 526.6 | 4-(4-{(S)-2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-phenyl)-pyridine-2-carboxamide |
| 189 | | B | 0.745 | 526.6 | 4-(4-{(R)-2-[(S)-1-(2-fluorophenyl)-3-hydroxy-propylamino]-6,6-dimethyl-4,4-dioxo-5,6-dihydro-4H-4lambda6-[1,4,3]oxathiazin-5-yl}-phenyl)-pyridine-2-carboxamide |
| 190 | | B | 0.908 | 479.5 | 5-{2-[(S)-1-(2-fluorophenyl)-ethylamino]-6,6-dimethyl-4,4-dioxo-5,6-dihydro-4H-4lambda6-[1,4,3]oxathiazin-5-yl}-[2,4']bipyridinyl-2'-carbonitril |
| 191 | | B | 0.919 | 479.5 | 5-{2-[(S)-1-(2-fluorophenyl)-ethylamino]-6,6-dimethyl-4,4-dioxo-5,6-dihydro-4H-4lambda6-[1,4,3]oxathiazin-5-yl}-[2,4']bipyridinyl-2'-carbonitril |

TABLE 1-continued

| Example | CHEMISTR | Method | Retention time | Molar mass (g/mol) | Name |
|---|---|---|---|---|---|
| 192 | 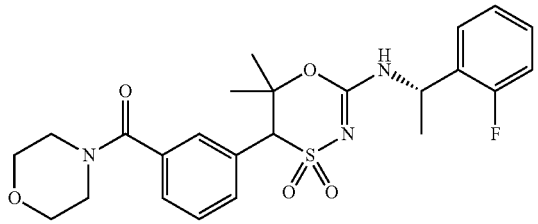 [SMILES: C[C@H](NC1=NS(=O)(=O)C(c2cccc(C(=O)N3CCOCC3)c2)C(C)(C)O1)c1ccccc1F] | C | 1.467 | 489.6 | (3-{2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-morpholin-4-yl-methanone |
| 193 | 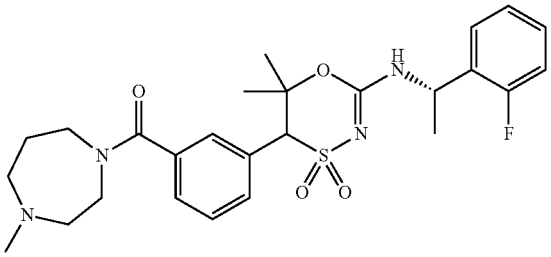 [SMILES: C[C@H](NC1=NS(=O)(=O)C(c2cccc(C(=O)N3CCCN(C)CC3)c2)C(C)(C)O1)c1ccccc1F] | C | 1.211 | 516.6 | (3-{2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-(4-methyl-[1,4]diazepan-1-yl)-methanone |
| 194 | 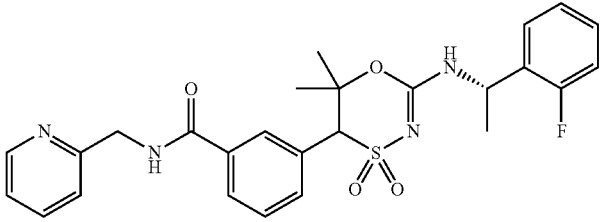 [SMILES: C[C@H](NC1=NS(=O)(=O)C(c2cccc(C(=O)NCc3ccccn3)c2)C(C)(C)O1)c1ccccc1F] | C | 1.269 | 510.6 | 3-{2-[(S)-1-(2-fluorophenyl)-ethylamino]-6,6-dimethyl-4,4-dioxo-5,6-dihydro-4H-4lambda6-[1,4,3]oxathiazin-5-yl}-N-pyridin-2-ylmethyl-benzamide |
| 195 | 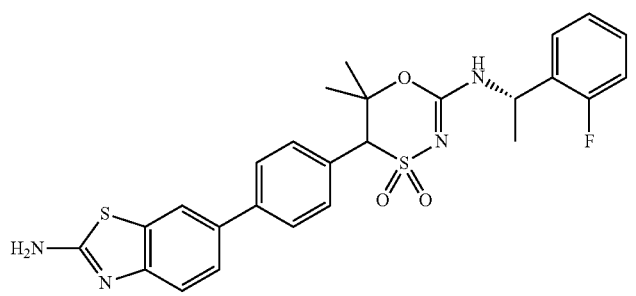 [SMILES: C[C@H](NC1=NS(=O)(=O)C(c2ccc(-c3ccc4nc(N)sc4c3)cc2)C(C)(C)O1)c1ccccc1F] | C | 1.434 | 524.6 | 6-(4-{2-[(S)-1-(2-fluorophenyl)-ethylamino]-6,6-dimethyl-4,4-dioxo-5,6-dihydro-4H-4lambda6-[1,4,3]oxathiazin-5-yl}-phenyl)-benzothiazol-2-ylamine |
| 196 | 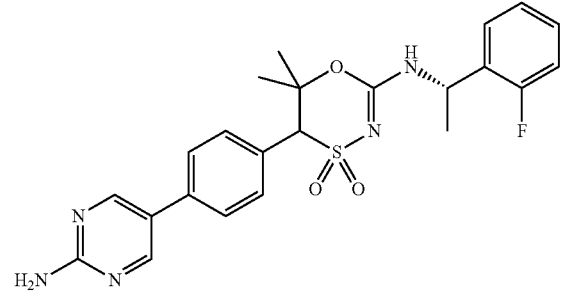 [SMILES: C[C@H](NC1=NS(=O)(=O)C(c2ccc(-c3cnc(N)nc3)cc2)C(C)(C)O1)c1ccccc1F] | C | 1.396 | 469.5 | {5-[4-(2-Amino-pyrimidin-5-yl)-phenyl]-6,6-dimethyl-4,4-dioxo-5,6-dihydro-4H-4lambda6-[1,4,3]oxathiazin-2-yl}-[(S)-1-(2-fluorophenyl)-ethyl]-amine |

\* isomerically pure compound

\*\* trans compound

Chromatography Methods:
Method A
LC UV/MS: Agilent 1200 Series
Column: Mercury MS, Luna C18(2), S-3 µm, 10×2.0 mm
Eluent: 0 min 93% $H_2O$ (0.05% TFA)—1.0 min 95% acetonitrile—1.45 min 95% acetonitrile—1.5 min 7% acetonitrile (30° C., flow rate 1.1 ml/min)
Method B
LC UV/MS: Agilent 1100 Series
Column: Mercury MS, Luna C18(2), S-3 µm, 10×2.0 mm
Eluent: 0 min 93% $H_2O$ (0.05% TFA)—1.2 min 95% acetonitrile—1.4 min 95% acetonitrile—1.45 min 7% acetonitrile (30° C., flow rate 1.1 ml/min)
Method C
LC UV/MS: Agilent 1100 Series
Column: YMC J'spere ODS H80, 80 Å, S-4 µm, 20×2.1 mm
Eluent: 0 min 96% $H_2O$ (0.05% TFA)—2.0 min 95% acetonitrile—2.4 min 95% acetonitrile—2.45 min 4% acetonitrile (30° C., flow rate 1 ml/min)

The efficacy of the compounds was tested as follows:
Enzymatic 11beta-HSD1 test:

To measure the activity of the compounds, an SPA-based detection method (Solly et al. 2005) was employed. First of all, 20 µl of the human 11β-HSD1 microsome fraction (0.2 µg of protein), prepared in 50 mM HEPES, 0.1% BSA (w/v), were applied to a plate with 384 wells. The test compounds (0.09 µl) were applied to the assay plate in 100% DMSO. The reaction was started by addition of 20 µl of [1,2-$^3$H]-cortisone (0.1 µCi/100 mM) in assay buffer comprising 25 mM HEPES, 100 mM KCl, 5 mM NaCl, 2 mM $MgCl_2$ and 0.25 mM NADPH. The plate was agitated at 37° C. for 1 hour. At the same time, a stop solution comprising 20 mg/ml SPA-PVT beads, 1.6 mg/ml monoclonal cortisol antibody and 0.01 mM SSR110887 (inhibitor from the Biovitrium patent) in 50 mM HEPES, 1 M NaCl and 1 M KCl was stirred at room temperature. To stop the reaction, 25 µl of the stop solution were added to each well. The plate was agitated gently at room temperature for 1 further hour and then centrifuged at 500 $g_{av}$ for 1 minute, in order that the SPA beads could settle out. The plate was then read in a Wallac-1450-Microbeta unit with a standard SPA program (counting time 1 min/well). The comparative compound was glycyrrhetinic acid.

Protein and radioactive substrate were dispensed with a Biomek FX unit (Beckman Coulter) for handling liquids. The test compounds were added with a Cybi-Well equipped with a 90 nl pin tool (CyBio).

Lit.: Solly S, Mundt S S, Zokian H J, Juy-Fang Ding G, Hermanowski-Vosatka A, Strulovici B and Zheng W. High-throughput screening of 11β-Hydroxysteroid dehydrogenase type 1 in scintillation proximity format. Assay Drug Dev Technol 2005; 3:377-384.

TABLE 2

| Biological activity | |
|---|---|
| Example | $IC_{50}$ (nM) |
| 1 | 113 |
| 2 | 17 |
| 3 | 1270 |
| 4 | 14 |
| 5 | 1670 |
| 6 | 29 |
| 7 | 20 |
| 8 | 22 |
| 9 | 22 |
| 10 | 15 |
| 11 | 9 |

TABLE 2-continued

| Biological activity | |
|---|---|
| Example | $IC_{50}$ (nM) |
| 12 | 45 |
| 13 | 47 |
| 14 | 32 |
| 15 | 11 |
| 16 | 11 |
| 18 | 36 |
| 19 | 352 |
| 20 | 21 |
| 21 | 22 |
| 22 | 163 |
| 23 | 114 |
| 24 | 21 |
| 27 | 13 |
| 28 | 16 |
| 29 | 23 |
| 30 | 7 |
| 31 | 10 |
| 32 | 24 |
| 33 | 8 |
| 34 | 17 |
| 35 | 15 |
| 36 | 15 |
| 37 | 13 |
| 38 | 19 |
| 39 | 24 |
| 40 | 15 |
| 41 | 10 |
| 42 | 17 |
| 43 | 7 |
| 44 | 13 |
| 45 | 11 |
| 46 | 18 |
| 47 | 5 |
| 48 | 5 |
| 49 | 24 |
| 50 | 40 |
| 51 | 15 |
| 52 | 64 |
| 53 | 8 |
| 54 | 9 |
| 55 | 28 |
| 56 | 8 |
| 57 | 7 |
| 58 | 21 |
| 59 | 55 |
| 60 | 43 |
| 61 | 14 |
| 62 | 47 |
| 63 | 32 |
| 64 | 12 |
| 65 | 21 |
| 66 | 23 |
| 67 | 15 |
| 68 | 34 |
| 69 | 13 |
| 70 | 19 |
| 71 | 22 |
| 72 | 46 |
| 73 | 28 |
| 74 | 12 |
| 75 | 44 |
| 76 | 332 |
| 77 | 26 |
| 78 | 35 |
| 79 | 8 |
| 80 | 7 |
| 81 | 10 |
| 82 | 23 |
| 83 | 17 |
| 84 | 15 |
| 85 | 9 |
| 86 | 10 |
| 87 | 7 |
| 88 | 198 |
| 89 | 21 |
| 90 | 7 |

TABLE 2-continued

Biological activity

| Example | IC$_{50}$ (nM) |
|---|---|
| 91 | 11 |
| 92 | 23 |
| 93 | 6 |
| 94 | 14 |
| 95 | 6 |
| 96 | 10 |
| 97 | 16 |
| 98 | 12 |
| 99 | 25 |
| 100 | 19 |
| 101 | 5 |
| 102 | 6 |
| 103 | 32 |
| 104 | 28 |
| 105 | 8 |
| 106 | 26 |
| 107 | 33 |
| 108 | 42 |
| 109 | 79 |
| 110 | 27 |
| 111 | 7 |
| 112 | 7 |
| 113 | 4 |
| 114 | 8 |
| 115 | 5 |
| 116 | 5 |
| 117 | 23 |
| 118 | 8 |
| 119 | 6 |
| 120 | 6 |
| 121 | 8 |
| 122 | 35 |
| 123 | 13 |
| 124 | 8 |
| 125 | 4 |
| 126 | 19 |
| 127 | 6 |
| 128 | 10 |
| 129 | 18 |
| 130 | 20 |
| 131 | 17 |
| 132 | 14 |
| 133 | 7 |
| 134 | 11 |
| 135 | 59 |
| 136 | 63 |
| 137 | 70 |
| 138 | 61 |
| 139 | 5 |
| 140 | 69 |
| 141 | 14 |
| 142 | 64 |
| 143 | 13 |
| 144 | 10 |
| 145 | 5 |
| 146 | 8 |
| 147 | 9 |
| 148 | 144 |
| 149 | 4 |
| 150 | 3 |
| 151 | 34 |
| 152 | 26 |
| 153 | 48 |
| 154 | 13 |
| 155 | 17 |
| 156 | 12 |
| 157 | 20 |
| 158 | 38 |
| 159 | 108 |
| 160 | 64 |
| 161 | 11 |
| 162 | 52 |
| 163 | 15 |
| 164 | 27 |
| 165 | 7 |
| 166 | 4 |
| 167 | 122 |
| 168 | 21 |
| 169 | 2 |
| 170 | 246 |
| 171 | 108 |
| 172 | 55 |
| 173 | 137 |
| 174 | 18 |
| 175 | 20 |
| 176 | 6 |
| 177 | 17 |
| 178 | 3 |
| 179 | 34 |
| 180 | 10 |
| 181 | 7 |
| 182 | 6 |
| 183 | 20 |
| 184 | 3 |
| 185 | 4 |
| 186 | 11 |
| 187 | 5 |
| 188 | 7 |
| 189 | 5 |
| 190 | 331 |
| 191 | 460 |
| 192 | 252 |
| 193 | 476 |
| 194 | 14 |
| 195 | 40 |
| 196 | 7 |

It can be inferred from the test data that the compounds of the formula I inhibit 11beta-HSD1 (11beta-hydroxysteroid dehydrogenase type 1), and are thus of good suitability for treatment of hyperglycemia, insulin resistance, diabetes, obesity, lipid metabolism disorders and other diseases.

The preparation of some examples is described in detail hereinafter; the remaining compounds of the formula I were obtained analogously:

Experimental:

N-[1-(2-Chloro-3-fluorophenyl)meth-(E)-ylidene]-2-methylpropane-2-sulfinamide

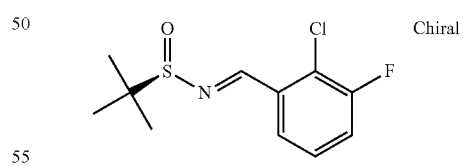

2-Chloro-3-fluorobenzaldehyde (2.5 g) and (R)-(+)-2-methyl-2-propanesulfinamide were dissolved in dichloromethane (50 ml), and then titanium(IV) isopropoxide (23.6 ml) was added. The mixture was heated for three hours under reflux, then poured onto ice (150 g) and stirred vigorously for ten minutes. The mixture was filtered through kieselguhr and the filtrate was extracted with dichloromethane (3×50 ml). The organic phase was dried (Na$_2$SO$_4$), filtered and concentrated under reduced pressure. The product (4 g) was used further without further purification.

The following compounds were prepared in the same way:

N-[1-(2,4-Difluorophenyl)meth-(E)-ylidene]-2-methylpropane-2-sulfinamide

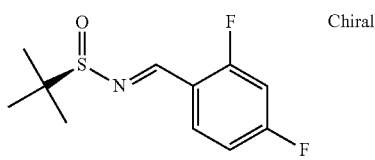 [SMILES: CC(C)(C)[S@@](=O)/N=C/c1ccc(F)cc1F]

3-Amino-3-(2,5-difluorophenyl)propionic acid

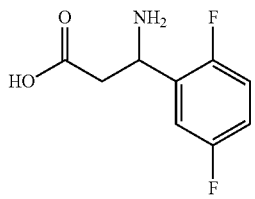 [SMILES: NC(CC(=O)O)c1cc(F)ccc1F]

A solution of 2,5-difluorobenzaldehyde (5 g), malonic acid (3.66 g) and ammonium acetate (5.42 g) in ethanol (50 ml) was heated under reflux for six hours. The mixture was cooled and left to stand overnight. The crystals formed were filtered off and washed with ethanol (5 ml).

The product (2.94 g) was used without further purification.

The following compounds were prepared in the same way:

3-Amino-3-(5-fluoro-2-methylphenyl)propionic acid

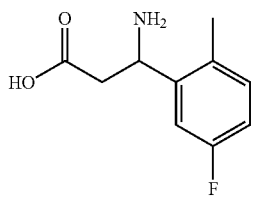

(S)-3-(2-Chloro-3-fluorophenyl)-3-((R)-2-methylpropane-2-sulfinylamino)propionic acid methyl ester

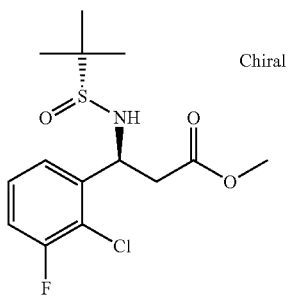 [SMILES: COC(=O)C[C@H](N[S@](=O)C(C)(C)C)c1cccc(F)c1Cl]

To diisopropylamine (4.13 ml), dissolved in THF (200 ml), was slowly added dropwise 1.6 N butyllithium (17.55 ml) at 0° C., and then the mixture was stirred for thirty minutes. Subsequently, the mixture was cooled to −75° C. and methyl acetate (2.13 ml) dissolved in THF (5 ml) was added, and the mixture was stirred for a further thirty minutes. Then chlorotitanium triisopropoxide (56.15 ml, 1 molar in hexane) was added dropwise at the same temperature and the mixture was stirred again for thirty minutes. N-[1-(2-Chloro-3-fluorophenyl)meth-(E)-ylidene]-2-methylpropane-2-sulfinamide was dissolved in THF (10 ml) and added dropwise at −75° C., and the mixture was stirred at the same temperature for three hours. The mixture was poured onto cold saturated ammonium chloride solution and admixed with ethyl acetate, and stirred for fifteen minutes. The phase mixture was then clarified using kieselguhr, the organic phase was removed and the aqueous phase was extracted with ethyl acetate (2×50 ml). The combined organic phases were dried ($Na_2SO_4$), filtered and concentrated. The residue was purified by chromatography (silica gel 40-63 μm, ethyl acetate). This gave the product (4.1 g) with a de of 72% by NMR.

The following compounds were prepared in the same way:

(S)-3-(2,4-Difluorophenyl)-3-((R)-2-methylpropane-2-sulfinylamino)propionic acid methyl ester

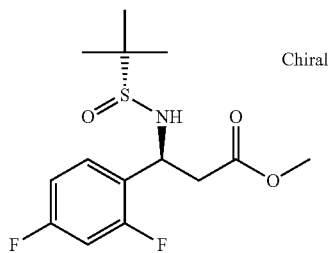 [SMILES: COC(=O)C[C@H](N[S@](=O)C(C)(C)C)c1ccc(F)cc1F]

3-Amino-3-(2,5-difluorophenyl)propionic acid ethyl ester

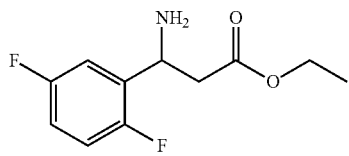 [SMILES: CCOC(=O)CC(N)c1cc(F)ccc1F]

Acetyl chloride (4 ml) was added dropwise at room temperature to a round-bottom flask containing ethanol (50 ml). 3-Amino-3-(2,5-difluorophenyl)propionic acid (2.94 g) was added to the ethanolic hydrochloric acid solution thus prepared, and the mixture was stirred at 50° C. for three hours. Subsequently, the mixture was concentrated under reduced pressure, and the residue was admixed with 1N sodium hydroxide solution (100 ml) and extracted immediately with dichloromethane (3×50 ml). The combined organic phases were dried ($Na_2SO_4$), filtered and concentrated. The product (3.2 g) was used without further purification.

The following compounds were prepared in the same way:

(S)-3-Amino-3-(5-fluoro-2-methylphenyl)propionic acid ethyl ester

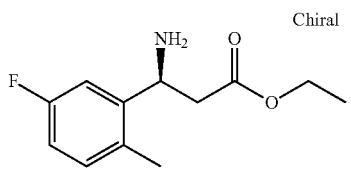 [SMILES: CCOC(=O)C[C@H](N)c1cc(F)ccc1C]

(S)-3-Amino-3-(2,5-difluorophenyl)propionic acid methyl ester

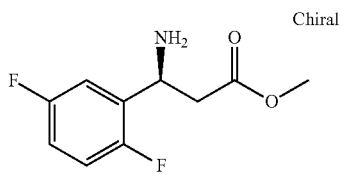

(S)-3-Amino-3-(5-fluoro-2-methylphenyl)propionic acid methyl ester

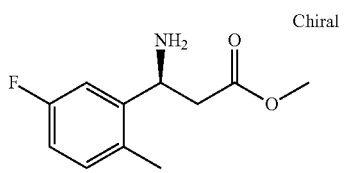

(S)-3-Amino-3-(2,5-difluorophenyl)propionic acid

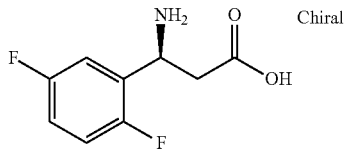 [SMILES: N[C@@H](CC(=O)O)c1cc(F)ccc1F]

3-Amino-3-(2,5-difluorophenyl)propionic acid ethyl ester (3 g) was emulsified in water (pH=9.2) and admixed with potassium dihydrogenphosphate (5 mg) (pH=8.5). After addition of Amano Lipase PS (150 mg), the mixture was stirred overnight. The pH remains at 7.5. The mixture was then admixed with water (30 ml) and filtered through kieselguhr and washed several more times with water. The aqueous phase was then extracted with dichloromethane (3×30 ml), and the organic phase was dried (Na2SO4) and concentrated. This gave the product (1.3 g) with an ee=90% by HPLC.

The following compounds were prepared in the same way:

(S)-3-Amino-3-(5-fluoro-2-methylphenyl)propionic acid

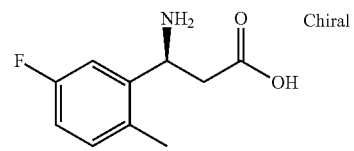

(S)-3-Amino-3-(3-chloro-2-fluorophenyl)propionic acid methyl ester

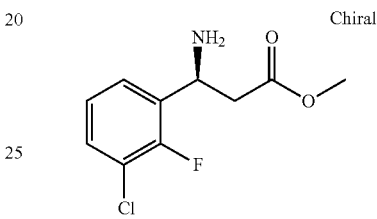

To a solution of acetyl chloride (4 ml) in methanol (50 ml) was added (S)-3-(2-chloro-3-fluorophenyl)-3-((R)-2-methylpropane-2-sulfinylamino)propionic acid methyl ester (4.1 g) dissolved in methanol (10 ml) at room temperature. After one hour, the mixture was concentrated, taken up in dichloromethane (100 ml) and washed with 1N sodium hydroxide solution (100 ml). The aqueous phase was washed twice more with dichloromethane. The combined organic phases were dried (Na$_2$SO$_4$), filtered and concentrated. The residue (2.8 g) was used without further purification.

The following compounds were prepared in the same way:

(S)-3-Amino-3-(2,4-difluorophenyl)propionic acid methyl ester

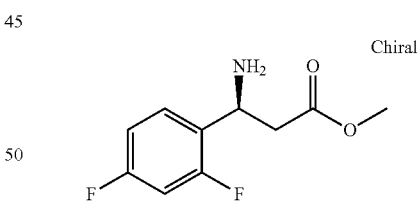

(S)-3-Amino-3-(2-chloro-3-fluorophenyl)propan-1-ol

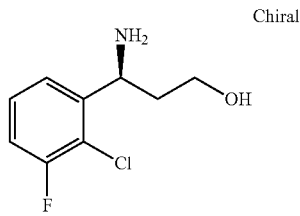 [SMILES: N[C@@H](CCO)c1cccc(F)c1Cl]

To a solution of 1N lithium aluminum hydride (24.2 ml in THF) in THF (20 ml) was added dropwise, at 0° C., (S)-3-amino-3-(3-chloro-2-fluorophenyl)propionic acid methyl ester (2.8 g) dissolved in THF (5 ml), and the mixture was stirred for one hour. Then the mixture was added dropwise to saturated sodium chloride solution (50 ml) and stirred for five minutes. Then 1N sodium hydroxide solution (50 ml) was added and the mixture was stirred for a further five minutes. The mixture was then extracted with ethyl acetate (3×50 ml), dried ($Na_2SO_4$) and concentrated. The product (2.23 g) was used without further purification.

The following compounds were prepared in the same way:

(S)-3-Amino-3-(2,4-difluorophenyl)propan-1-ol

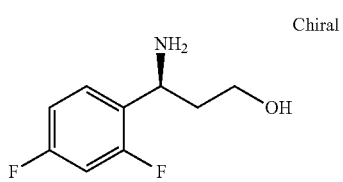 [SMILES: N[C@@H](CCO)c1ccc(F)cc1F]

(S)-3-Amino-3-(2,5-difluorophenyl)propan-1-ol

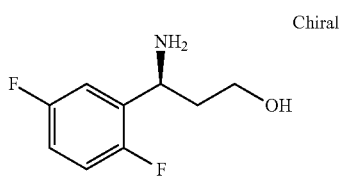 [SMILES: N[C@@H](CCO)c1cc(F)ccc1F]

(S)-3-Amino-3-(5-fluoro-2-methylphenyl)propan-1-ol

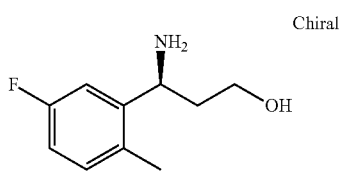

(S)-3-(tert-Butyldimethylsilanyloxy)-1-(5-chloro-2-fluorophenyl)propylamine

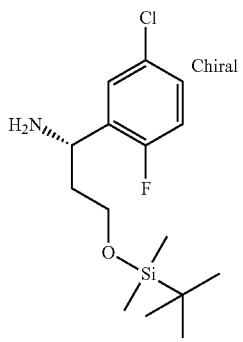

The 1N lithium aluminum hydride (100 ml) in THF was initially charged and (S)-3-amino-3-(5-chloro-2-fluorophenyl)propionic acid methyl ester (insoluble in THF) was added in portions while cooling with ice. The cooling was then removed and the mixture was stirred for 1 hour. Subsequently 5 ml of $H_2O$ and 5 ml of 5M NaOH were added dropwise under ice and 15 ml of $H_2O$ were added cautiously, then the mixture was stirred for 4 days. The precipitate was filtered through Celite and washed through with THF (3×30 ml), then the filtrate was concentrated. The residue was taken up with dichloromethane (50 ml) and dried over MgSO4, filtered and concentrated by rotary evaporation. The residue (2.95 g) was dissolved in dichloromethane (20 ml) and admixed with DIPEA and with t-butyldimethylchlorosilane in portions. The mixture was stirred at 25° C. overnight.

The mixture was washed twice with 50 ml 5% $NaHCO_3$ solution, and the organic phase was dried over $Na_2SO_4$ and concentrated. Final weight: 5.16 g. Then purification was effected with the aid of a Flashmaster. 70 g column (normal phase); fraction size: 20 ml; flow rate: 19 ml/min Fractions 17-40 combined. This gave the product (3.64 g) with a molecular weight of 317.9 ($C_{15}H_{26}ClFNOSi$); MS (ESI): 318 (M+H+).

(S)-3-(tert-Butyldimethylsilanyloxy)-1-phenylpropylamine

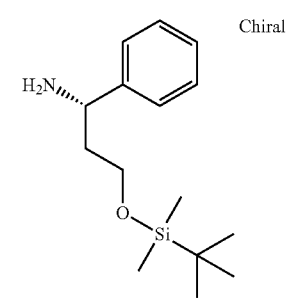 [SMILES: CC(C)(C)[Si](C)(C)OCC[C@H](N)c1ccccc1]

S-3-Amino-3-phenyl-1-propanol (4.72 g) was dissolved in dichloromethane (60 ml), admixed with triethylamine (6.36 g) and tert-butyldimethylchlorosilane (4.1 g), and the mixture was stirred at room temperature for 3 hours. Then it was washed with water (3×50 ml) and dried using a phase separator cartridge. This gave the product with a molecular weight of 265.5 g/mol (C15H27NOSi), MS (ESI): (M+H+) 266 g/mol.

The following compounds were prepared in the same way:

(S)-3-(tert-Butyl-dimethylsilanyloxy)-1-(2-fluorophenyl)propylamine

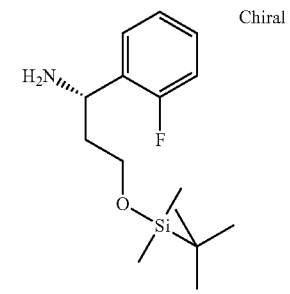 [SMILES: CC(C)(C)[Si](C)(C)OCC[C@H](N)c1ccccc1F]

(S)-3-(tert-Butyl-dimethylsilanyloxy)-1-(3-chlorophenyl)propylamine

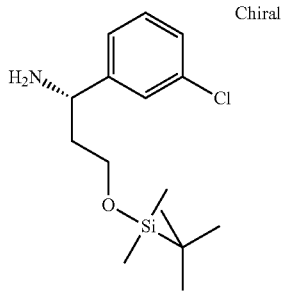 [SMILES: CC(C)(C)[Si](C)(C)OCC[C@H](N)c1cccc(Cl)c1]

(S)-3-(tert-Butyl-dimethylsilanyloxy)-1-(4-chlorophenyl)propylamine

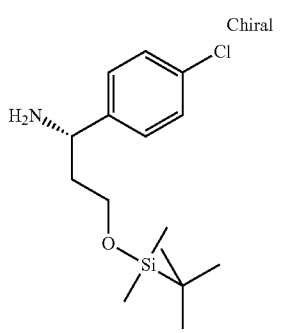 [SMILES: CC(C)(C)[Si](C)(C)OCC[C@H](N)c1ccc(Cl)cc1]

(S)-3-(tert-Butyl-dimethylsilanyloxy)-1-(2-chlorophenyl)propylamine

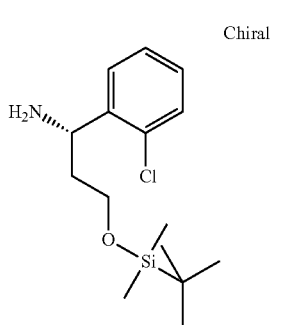 [SMILES: CC(C)(C)[Si](C)(C)OCC[C@H](N)c1ccccc1Cl]

(S)-3-(tert-Butyldimethylsilanyloxy)-1-(2-chloro-3-fluorophenyl)propylamine

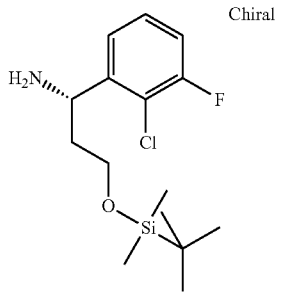 [SMILES: CC(C)(C)[Si](C)(C)OCC[C@H](N)c1cccc(F)c1Cl]

(S)-3-(tert-Butyl-dimethylsilanyloxy)-1-(2,4-difluorophenyl)propylamine

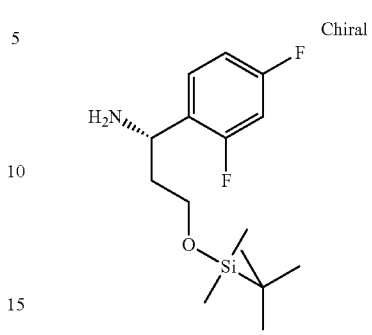

(S)-3-(tert-Butyl-dimethylsilanyloxy)-1-(2,5-difluorophenyl)propylamine

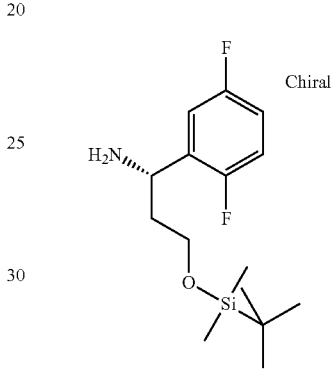

(S)-3-(tert-Butyl-dimethylsilanyloxy)-1-(5-fluoro-2-methylphenyl)propylamine

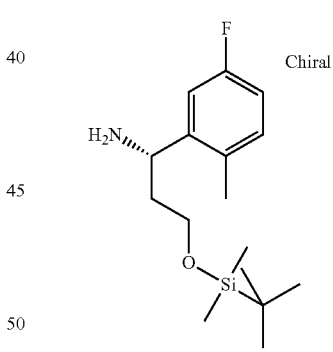

The synthesis of 2-hydroxy-2-methyl-1-phenylpropane-1-sulfonamide is described hereinafter. This unit was subsequently used in various reactions.

N-(2,4-Dimethoxybenzyl)-C-phenylmethanesulfonamide

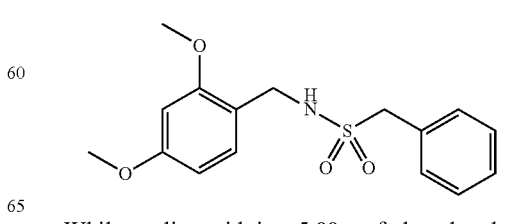

While cooling with ice, 5.00 g of phenylmethanesulfonyl chloride were initially charged in 40 ml of dichloromethane, and a solution of 8.04 ml of 2,4-dimethoxybenzylamine in 10 ml of dichloromethane was slowly added dropwise. For improved stirrability, a further 25 ml of dichloromethane were added, and the reaction mixture was allowed to come to room temperature. After stirring for 2 hours, the reaction mixture was washed with 100 ml of water, with 100 ml of 0.2 N aqueous hydrochloric acid, with 100 ml of saturated aqueous sodium hydrogencarbonate solution and finally once more with 100 ml of water. The organic phase was dried over Na₂SO₄, concentrated by rotary evaporation and dried under high vacuum. The residue (8.42 g) was used in the next reaction without further purification.

N-(2,4-Dimethoxybenzyl)-2-hydroxy-2-methyl-1-phenylpropane-1-sulfonamide

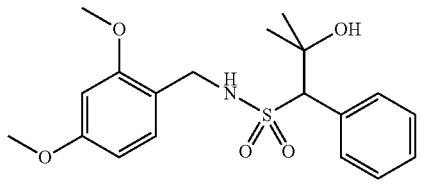 [SMILES: COc1ccc(CNS(=O)(=O)C(c2ccccc2)C(C)(C)O)c(OC)c1]

Under inert gas, 2.00 g of N-(2,4-dimethoxybenzyl)-C-phenylmethanesulfonamide were initially charged in 40 ml of THF, and then, at a temperature of −78° C., 9.54 ml of a 1.5 N butyllithium solution in hexane were added dropwise and the mixture was left to stir while cooling with ice for 5 minutes. Subsequently, the reaction solution was cooled again to −78° C. and a solution of 2.01 ml of acetone in 4 ml of THF was added. The mixture was allowed to come to room temperature and stirred for 30 minutes. The reaction solution was admixed with 0.82 ml of acetic acid and 50 ml of ethyl acetate, and washed with 30 ml of a saturated aqueous sodium hydrogencarbonate solution and 30 ml of a saturated aqueous sodium chloride solution, and the organic phase was dried over Na₂SO₄ and concentrated by rotary evaporation. The residue (2.67 g) was used in the next reaction without further purification.

2-Hydroxy-2-methyl-1-phenylpropane-1-sulfonamide

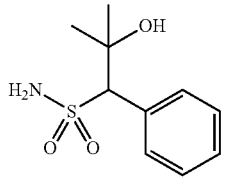

A solution of 2.67 g of N-(2,4-dimethoxybenzyl)-2-hydroxy-2-methyl-1-phenylpropane-1-sulfonamide in 20 ml of dichloromethane was admixed with 3.74 ml of trifluoroacetic acid and stirred at room temperature for 2 hours. The starting solution was coevaporated twice with 100 ml of toluene and the crude product was purified using by means of normal phase chromatography using a Flashmaster with an n-heptane/ethyl acetate gradient. The product-containing fractions were combined and concentrated by rotary evaporation. This gave the product (0.90 g) with a molecular weight of 229.3 g/mol (C₁₀H₁₅NO₃S).

Cyclohexyl-(6,6-dimethyl-4,4-dioxo-5-phenyl-5,6-dihydro-4H-4lambda6-[1,4,3]oxathiazin-2-yl)-amine

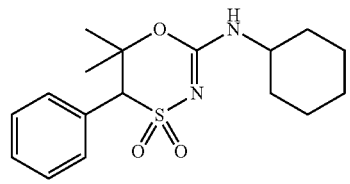 [SMILES: CC1(C)OC(NC2CCCCC2)=NS(=O)(=O)C1c1ccccc1]

A solution of 150 mg of 2-hydroxy-2-methyl-1-phenylpropane-1-sulfonamide and 97 mg of cyclohexyl isothiocyanate in 1.5 ml of NMP was admixed with 0.20 ml of a 2 N solution of sodium bis(trimethylsilyl)amide in THF. After stirring for 20 minutes, 71 mg of N-bromosuccinimide were added and the mixture was stirred at room temperature for a further 15 minutes. The reaction solution was admixed with 50 ml of water and extracted twice with 50 ml of ethyl acetate. The combined organic phases were dried over Na₂SO₄ and concentrated by rotary evaporation. The residue was purified in a purification laboratory by means of preparative HPLC, and the product-containing fractions were freed of the organic solvent under reduced pressure. The aqueous residue was extracted three times with dichloromethane, and the combined organic phases were dried using a phase separator cartridge (Chromabond® PTS) and concentrated by rotary evaporation. The residue was dissolved in a mixture of acetonitrile and water and lyophilized. This gave the product (46 mg) with a molecular weight of 336.4 g/mol (C₁₇H₂₄N₂O₃S); MS (ESI): m/e=337 (M+H⁺).

(1S,3S)-3-(6,6-Dimethyl-4,4-dioxo-5-phenyl-5,6-dihydro-4H-4lambda6-[1,4,3]oxathiazin-2-ylamino)cyclohexanol

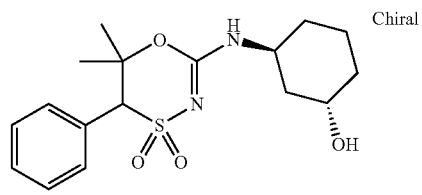 [SMILES: CC1(C)OC(N[C@H]2CCC[C@H](O)C2)=NS(=O)(=O)C1c1ccccc1]

173 mg of S,S-aminocyclohexanol were dissolved in 5 ml of dichloromethane and admixed with 311 mg of 1,1′-thiocarbonyldiimidazole. After stirring at room temperature for 5 minutes, another 5 ml of dichloromethane were added, in order to improve the stirrability of the suspension, which was stirred for a further 80 minutes. The reaction solution was admixed with a mixture of 10 ml of diethyl ether and 10 ml of n-pentane, and washed three times with 15 ml of water, dried over Na₂SO₄ and concentrated by rotary evaporation. Under inert gas, the residue and 300 mg of 2-hydroxy-2-methyl-1-phenylpropane-1-sulfonamide were dissolved in 3 ml of NMP and admixed with 0.39 ml of a 2 N solution of sodium bis(trimethylsilyl)amide in THF. After stirring for 30 minutes, 140 mg of N-bromosuccinimide were added and the resulting reaction solution was stirred at constant temperature for 45 minutes. The conversion was checked by LCMS. Since it was still incomplete, a further 70 mg of N-bromosuccinimide were added and the mixture was stirred for 48 hours. The reaction mixture was diluted with 1 ml of a mixture of acetonitrile and water (9:1) and purified in a purification laboratory by means of preparative HPLC. The product-containing fractions were combined and the aqueous residue was lyophilized. This gave the product (148 mg) with a molecular weight of 352.4 g/mol ($C_{17}H_{24}N_2O_4S$); MS (ESI): m/e=353 (M+H$^+$).

(1R,3R)-3-(6,6-Dimethyl-4,4-dioxo-5-phenyl-5,6-dihydro-4H-4lambda6-[1,4,3]oxathiazin-2-ylamino)cyclohexanol was likewise synthesized by this preparation method.

The aminocyclohexanols used were prepared as follows:

P. Bernardelli, M. Bladon, E. Lorthiois, A. C. Manage, F. Vernige, R. Wrigglesworth, *Tetrahedron: Asymmetry* 15 2004, 1451-1455

L. M. Levy, G. de Gonzalo, V. Gotor, *Tetrahedron: Asymmetry* 15 2004, 2051-2056

(S)-3-(6,6-Dimethyl-4,4-dioxo-5-phenyl-5,6-dihydro-4H-4lambda6-[1,4,3]oxathiazin-2-ylamino)-3-phenylpropan-1-ol

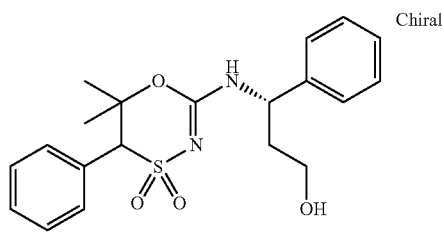 [SMILES: CC1(C)OC(N[C@@H](CCO)c2ccccc2)=NS(=O)(=O)C1c1ccccc1]

(S)-3-(tert-Butyldimethylsilanyloxy)-1-phenylpropylamine

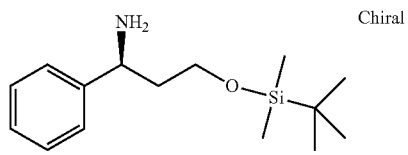 [SMILES: CC(C)(C)[Si](C)(C)OCC[C@H](N)c1ccccc1]

1.50 g of (S)-3-amino-3-phenylpropan-1-ol hydrochloride were initially charged in 20 ml of dichloromethane and then 2.77 ml of triethylamine and 1.30 g of tert-butyldimethylchlorosilane were added. After stirring at room temperature for 3 hours, the reaction solution was extracted three times with 30 ml of water, dried by means of a phase separator cartridge (Chromabond® PTS), concentrated by rotary evaporation and dried under high vacuum. This gave the product (2.06 g) with a molecular weight of 265.5 g/mol ($C_{15}H_{27}NOSi$); MS (ESI): m/e=266 (M+H$^+$).

(S)-3-(6,6-Dimethyl-4,4-dioxo-5-phenyl-5,6-dihydro-4H-4lambda6-[1,4,3]oxathiazin-2-ylamino)-3-phenylpropan-1-ol

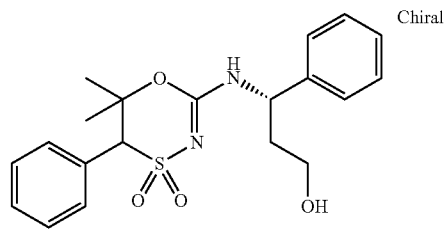 [SMILES: CC1(C)OC(N[C@@H](CCO)c2ccccc2)=NS(=O)(=O)C1c1ccccc1]

175 mg of (S)-3-(tert-butyldimethylsilanyloxy)-1-phenylpropylamine were dissolved in 2 ml of dichloromethane, and 121 mg of 1,1'-thiocarbonyldiimidazole were added. After stirring at room temperature for 20 minutes, the reaction solution was washed with a mixture of 20 ml of diethyl ether and 20 ml of n-pentane and washed three times with 30 ml of water, dried over MgSO$_4$ and concentrated by rotary evaporation. Under inert gas, the residue and 130 mg of 2-hydroxy-2-methyl-1-phenylpropane-1-sulfonamide were dissolved in 1.5 ml of NMP and admixed with 0.17 ml of a 2 N solution of sodium bis(trimethylsilyl)amide in THF. After stirring for 15 minutes, 61 mg of N-bromosuccinimide were added and the resulting reaction solution was stirred at constant temperature for 5 minutes. The reaction solution was admixed with 50 ml of water and extracted twice with 50 ml of ethyl acetate. The combined organic phases were dried over MgSO$_4$ and concentrated by rotary evaporation. To detach the protecting group, the residue was taken up in 4 ml of methanol and, after addition of 0.20 ml of concentrated hydrochloric acid, stirred at room temperature overnight. The reaction solution was admixed with DCM and water, the organic phase was dried over MgSO$_4$ and concentrated by rotary evaporation, and the residue was purified in a purification laboratory by means of preparative HPLC. The product-containing fractions were combined, the trifluoroacetic acid present was neutralized with saturated aqueous sodium hydrogencarbonate solution, and the mixture was freed of the solvent under reduced pressure. The aqueous residue was extracted three times with dichloromethane, and the combined organic phases were dried using a phase separator cartridge (Chromabond® PTS) and concentrated by rotary evaporation. The residue was dissolved in a mixture of acetonitrile and water and lyophilized. This gave the product (42 mg) with a molecular weight of 388.5 g/mol ($C_{20}H_{24}N_2O_4S$); MS (ESI): m/e=389 (M+H$^+$).

The following two compounds were prepared analogously:
(S)-3-(6,6-Dimethyl-4,4-dioxo-5-phenyl-5,6-dihydro-4H-4lambda6-[1,4,3]oxathiazin-2-ylamino)-3-phenylpropan-1-ol stereomer 1 and stereomer 2

At the N-(2,4-dimethoxybenzyl)-2-hydroxy-2-methyl-1-phenylpropane-1-sulfonamide stage, a chiral separation of 1.28 g of the racemate was conducted. Subsequently, the two stereomers were converted further individually.
HPLC system: Waters Pump 2695, PAD 2996
Column: Chiralpak AS-H/53, 5 μm, 250×4.6 mm
Eluent: n-heptane:ethanol:methanol 5:1:1 (30° C., flow rate 1 ml/min)
Retention Times:
5.323 minutes (stereomer 1, 616 mg)
6.585 minutes (stereomer 2, 630 mg)

(S)-3-[5-(4-Benzyloxyphenyl)-6,6-dimethyl-4,4-dioxo-5,6-dihydro-4H-4lambda6-1,4,3-oxathiazin-2-ylamino]-3-phenylpropan-1-ol

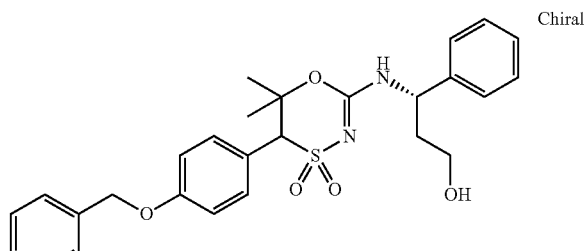

(4-Benzyloxyphenyl)methanesulfonic acid sodium salt

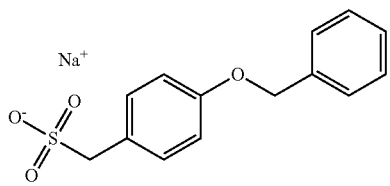 [SMILES: O=S(=O)([O-])Cc1ccc(OCc2ccccc2)cc1 ; [Na+]]

A mixture of 25.51 g of 4-benzyloxybenzyl chloride and 28.78 g of sodium sulfite in 96 ml of water was stirred at 75° C. for 21 hours. After cooling to room temperature, the reaction solution was stirred with 100 ml of tert-butyl methyl ether, and the solids were filtered off with suction, washed twice with 20 ml of tert-butyl methyl ether, once with 20 ml of ice-water, twice with 20 ml of acetone and twice with 20 ml of dichloromethane. The precipitate was dried in a vacuum drying cabinet at 40° C. overnight. This gave the product (6.20 g) with a molecular weight of 300.3 g/mol ($C_{14}H_{13}O_4S.Na$); MS (ESI): m/e=301 (M+H$^+$).

(4-Benzyloxyphenyl)methanesulfonyl chloride

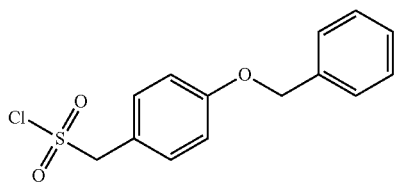 [SMILES: O=S(=O)(Cl)Cc1ccc(OCc2ccccc2)cc1]

Under inert gas, 5.70 g of (4-benzyloxyphenyl)methanesulfonic acid sodium salt and 1.48 ml of N,N-dimethylformamide were initially charged in 110 ml of THF, then, at a temperature of −20° C., 4.17 ml of oxalyl chloride were added dropwise and the reaction solution was allowed to come to 0° C. within 15 minutes. The reaction solution was diluted with 100 ml of diethyl ether and washed with water, dilute aqueous sodium hydrogencarbonate solution and saturated sodium chloride solution. The organic phase was dried over MgSO$_4$ and concentrated by rotary evaporation. The residue (4.89 g) was used in the next reaction without further purification.

C-(4-Benzyloxyphenyl)-N-(2,4-dimethoxybenzyl)methanesulfonamide

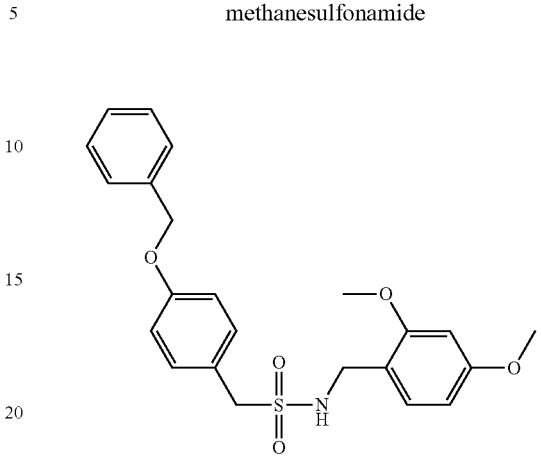

Under inert gas, 4.89 g of (4-benzyloxyphenyl)methanesulfonyl chloride were initially charged in 120 ml of THF, then, at a temperature of −20° C., 6.10 ml of 2,4-dimethoxybenzylamine were added dropwise and the reaction solution was allowed to come to 0° C. within 30 minutes. The reaction solution was diluted with 150 ml of ethyl acetate and washed with water, dilute aqueous potassium hydrogensulfate solution, saturated aqueous sodium hydrogencarbonate solution and saturated sodium chloride solution. The organic phase was dried over MgSO$_4$ and concentrated by rotary evaporation. The crude product was purified by means of normal phase chromatography using a Flashmaster with an n-heptane/ethyl acetate gradient. The product-containing fractions were combined, concentrated by rotary evaporation and dried under high vacuum. This gave the product (3.23 g) with a molecular weight of 427.5 g/mol ($C_{23}H_{25}NO_5S$).

N-(2,4-Dimethoxybenzyl)-1-(4-benzyloxyphenyl)-2-hydroxy-2-methylpropane-1-sulfonamide

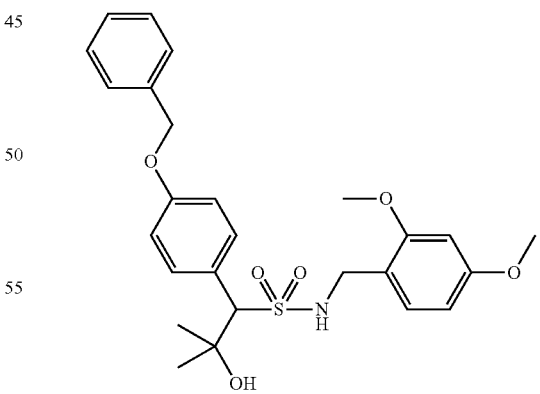

Under inert gas, 3.22 g of C-(4-benzyloxyphenyl)-N-(2,4-dimethoxybenzyl)methanesulfonamide were initially charged in 70 ml of THF, and then, at a temperature of −78° C., 12.50 ml of a 1.8 N phenyllithium solution were added dropwise. The reaction mixture was allowed to come to 0° C. and stirred briefly, then cooled again to −78° C., and 4.00 ml of acetone were added dropwise. The mixture was allowed to come to −20° C. within 15 minutes, admixed with 1.29 ml of acetic acid and 100 ml of ethyl acetate, and washed with saturated aqueous sodium hydrogencarbonate solution and saturated aqueous sodium chloride solution. The organic phase was dried over MgSO$_4$ and concentrated by rotary evaporation. The crude product was purified by means of normal phase chromatography using a Flashmaster with an n-heptane/ethyl acetate gradient. The product-containing fractions were combined and concentrated by rotary evaporation. This gave the product (3.65 g) with a molecular weight of 485.6 g/mol (C$_{26}$H$_{31}$NO$_6$S).

1-(4-Benzyloxyphenyl)-2-hydroxy-2-methylpropane-1-sulfonamide

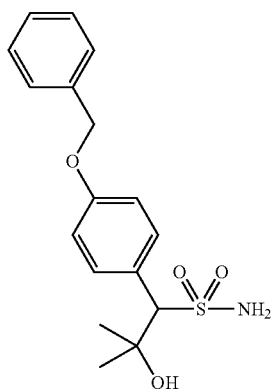 [SMILES: CC(C)(O)C(c1ccc(OCc2ccccc2)cc1)S(N)(=O)=O]

A solution of 3.65 g of N-[2,4-dimethoxybenzyl]-1-(4-benzyloxyphenyl)-2-hydroxy-2-methylpropane-1-sulfonamide in 20 ml of dichloromethane was admixed with 4.00 ml of trifluoroacetic acid and stirred at room temperature for 20 minutes. The conversion was checked by LCMS. Since it was incomplete, another 2.00 ml of trifluoroacetic acid were added and the mixture was stirred for a further 2 hours. The reaction solution was admixed with 20 ml of water and neutralized with saturated aqueous sodium hydrogencarbonate solution. The precipitate was filtered off with suction through a glass frit, washed with dichloromethane and water and dried in a desiccator over P$_2$O$_5$. This gave the product (1.95 g) with a molecular weight of 335.4 g/mol (C$_{17}$H$_{21}$NO$_4$S).

[5-(4-Benzyloxyphenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine

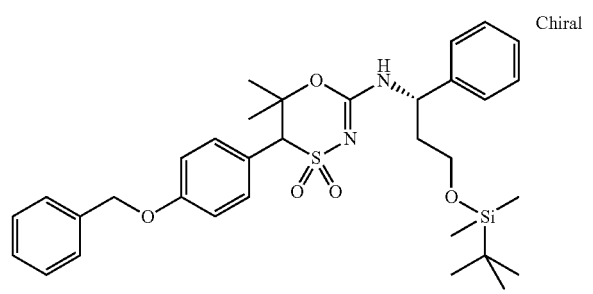 [SMILES: CC1(C)OC(N[C@@H](CCO[Si](C)(C)C(C)(C)C)c2ccccc2)=NS(=O)(=O)C1c1ccc(OCc2ccccc2)cc1]

921 mg of (S)-3-(tert-butyldimethylsilanyloxy)-1-phenylpropylamine were dissolved in 10 ml of dichloromethane, and 638 mg of 1,1′-thiocarbonyldiimidazole were added. After stirring at room temperature for 30 minutes, the reaction solution was washed with a mixture of 50 ml of diethyl ether and 50 ml of n-pentane and washed three times with 50 ml of water, dried over MgSO$_4$ and concentrated by rotary evaporation. Under inert gas, the residue and 1000 mg of 1-(4-benzyloxyphenyl)-2-hydroxy-2-methylpropane-1-sulfonamide were dissolved in 8 ml of NMP, and 1.49 ml of a 2 N solution of sodium bis(trimethylsilyl)amide in THF were added dropwise. After stirring for 15 minutes, 531 mg of N-bromosuccinimide were added and the resulting reaction solution was stirred at constant temperature for 10 minutes. The reaction solution was admixed with 100 ml of water and extracted twice with 100 ml of ethyl acetate. The combined organic phases were dried over MgSO$_4$ and concentrated by rotary evaporation, and the residue was purified by means of normal phase chromatography using a Flashmaster with an n-heptane/ethyl acetate gradient. The product-containing fractions were combined and concentrated by rotary evaporation. This gave the product (805 mg) with a molecular weight of 608.9 g/mol (C$_{33}$H$_{44}$N$_2$O$_5$SSi); MS (ESI): m/e=609 (M+H$^+$).

(S)-3-[5-(4-Benzyloxyphenyl)-6,6-dimethyl-4,4-dioxo-5,6-dihydro-4H-4lambda6-1,4,3-oxathiazin-2-ylamino]-3-phenylpropan-1-ol

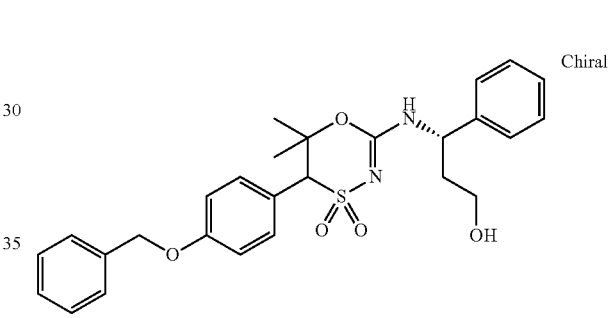

To detach the protecting group, 40 mg of [5-(4-benzyloxyphenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine were dissolved in 5 ml of methanol and, after addition of 1 ml of 2 N hydrochloric acid, stirred at room temperature for 1 hour. The reaction solution was neutralized with 2 ml of 1 N aqueous sodium hydroxide solution and concentrated by rotary evaporation, and the residue was purified in a purification laboratory by means of preparative HPLC. The product-containing fractions were combined and lyophilized. This gave the product (19.7 mg) with a molecular weight of 494.6 g/mol (C$_{27}$H$_{30}$N$_2$O$_5$S); MS (ESI): m/e=495 (M+H$^+$).

4-[2-((S)-3-Hydroxy-1-phenylpropylamino)-6,6-dimethyl-4,4-dioxo-5,6-dihydro-4H-4lambda6-1,4,3-oxathiazin-5-yl]phenol

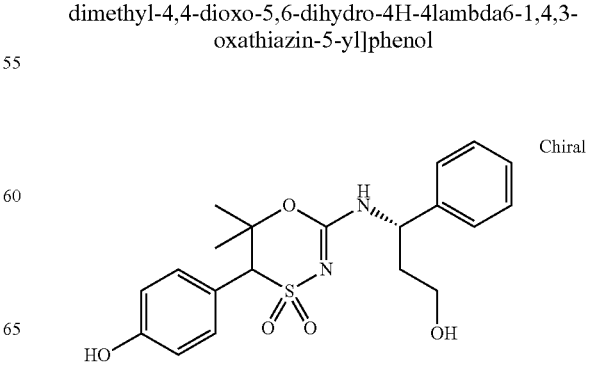

Under inert gas, 762 mg [5-(4-benzyloxyphenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine were initially charged in 20 ml of methanol and, with addition of 133 mg of 10% Pd/C, stirred under a hydrogen atmosphere for 1 hour. The completeness of the conversion was checked by LCMS, the reaction was once again admixed with 133 mg of 10% Pd/C and additionally 0.52 ml of triethylamine, and the mixture was stirred under a hydrogen atmosphere for a further 60 minutes. According to LCMS, the detachment of the silyl protecting group remained incomplete. After filtration to remove the solid residues, the filtrate was freed of the solvent under reduced pressure. The crude product was purified by means of normal phase chromatography using a Flashmaster with an n-heptane/ethyl acetate gradient. The product-containing fractions were combined and concentrated by rotary evaporation. This gave the product (104 mg) with a molecular weight of 404.5 g/mol ($C_{20}H_{24}N_2O_5S$); MS (ESI): m/e=405 (M+H$^+$).

As a result of incomplete detachment of the silyl protecting group, 4-{2-[(S)-3-(tert-butyldimethylsilanyloxy)-1-phenylpropylamino]-6,6-dimethyl-4,4-dioxo-5,6-dihydro-4H-4lambda6-1,4,3-oxathiazin-5-yl}phenol (454 mg) was isolated as a by-product with a molecular weight of 518.8 g/mol ($C_{26}H_{38}N_2O_5SSi$); MS (ESI): m/e=519 (M+H$^+$).

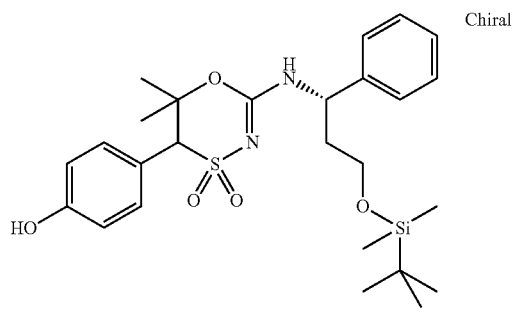 [SMILES: CC1(C)OC(N[C@@H](CCO[Si](C)(C)C(C)(C)C)c2ccccc2)=NS(=O)(=O)C1c1ccc(O)cc1]

(S)-3-[5-(4-Methoxyphenyl)-6,6-dimethyl-4,4-dioxo-5,6-dihydro-4H-4lambda6-1,4,3-oxathiazin-2-ylamino]-3-phenylpropan-1-ol To a solution of 40 mg of 4-[2-((S)-3-hydroxy-1-phenylpropylamino)-6,6-dimethyl-4,4-dioxo-5,6-dihydro-4H-4lambda6-1,4,3-oxathiazin-5-yl]phenol in 1 ml of N,N-dimethylformamide were added, at room temperature, 11 mg of potassium tert-butoxide and 28 mg of methyl iodide, and the reaction mixture was stirred at constant temperature for 3 hours. The reaction solution was purified in a purification laboratory by means of preparative HPLC. The product-containing fractions were combined and lyophilized. This gave the product (10 mg) with a molecular weight of 418.5 g/mol ($C_{21}H_{26}N_2O_5S$); MS (ESI): m/e=419 (M+H$^+$).

Trifluoromethanesulfonic acid 4-{2-[(S)-3-(tert-butyldimethylsilanyloxy)-1-phenylpropylamino]-6,6-dimethyl-4,4-dioxo-5,6-dihydro-4H-4lambda6-1,4,3-oxathiazin-5-yl}phenyl ester

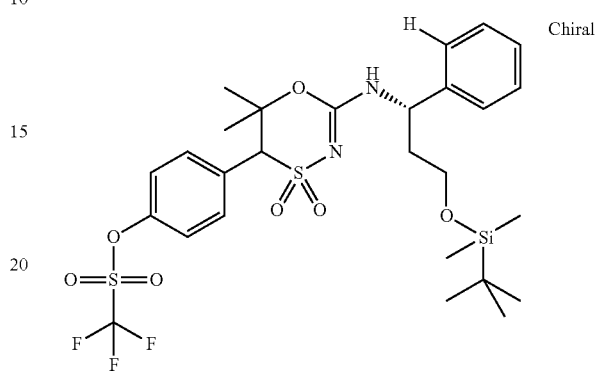

Under inert gas, 450 mg of 4-{2-[(S)-3-(tert-butyldimethylsilanyloxy)-1-phenylpropylamino]-6,6-dimethyl-4,4-dioxo-5,6-dihydro-4H-4lambda6-1,4,3-oxathiazin-5-yl}phenol were initially charged in 10 ml of methylene chloride and then, while cooling with ice, 0.18 ml of triethylamine and 0.18 ml of trifluoromethanesulfonic anhydride were added. The reaction mixture was allowed to come to room temperature and stirred for a further 2 hours. Subsequently, 20 ml of water were added, the phases were separated and the aqueous phase was extracted twice more with 20 ml of methylene chloride. The combined organic phases were washed with 1 N aqueous hydrochloric acid, dried over MgSO$_4$ and concentrated by rotary evaporation. The residue (355 mg) with a molecular weight of 650.8 g/mol ($C_{27}H_{37}F_3N_2O_7S_2Si$); MS (ESI): m/e=651 (M+H$^+$) was used in the next reaction without further purification.

(S)-3-(5-Biphenyl-4-yl-6,6-dimethyl-4,4-dioxo-5,6-dihydro-4H-4lambda6-1,4,3-oxathiazin-2-ylamino)-3-phenylpropan-1-ol

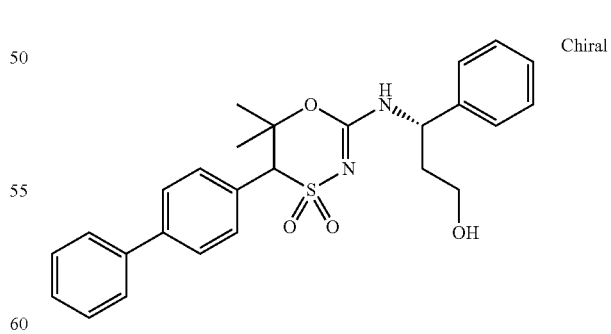

Under inert gas, 1.38 ml of a 0.5 N zinc chloride solution in THF were cooled to −78° C., and 0.26 ml of a 1.8 N phenyllithium solution in dibutyl ether was added dropwise. The reaction solution was allowed to come to room temperature and stirred for 30 minutes. Then this solution was added to a solution of 60 mg of trifluoromethanesulfonic acid 4-{2-[(S)-

3-(tert-butyldimethylsilanyloxy)-1-phenylpropylamino]-6,6-dimethyl-4,4-dioxo-5,6-dihydro-4H-4lambda6-1,4,3-oxathiazin-5-yl}phenyl ester and 8 mg of dichloro[1,1'-bis(diphenylphosphino)ferrocene]palladium in 1.5 ml of THF. After stirring at 60° C. for 45 minutes, the conversion was checked by LCMS and another 8 mg of the catalyst were added. After a further 2 hours at constant temperature, the same amount of the self-prepared solution of phenyllithium and zinc chloride was added once again, and the mixture was stirred at 60° C. for a further 60 minutes. After removal of the solvent under reduced pressure, the residue was dissolved in 1.5 ml of methanol, 0.15 ml of concentrated hydrochloric acid was added and the mixture was stirred at room temperature for 1 hour. The reaction solution was diluted with 20 ml of ethyl acetate and 10 ml of water, and neutralized with sodium hydroxide solution. The organic phase was washed once again with saturated aqueous sodium chloride solution, dried over $MgSO_4$ and concentrated by rotary evaporation. The residue was purified by means of normal phase chromatography using a Flashmaster with an n-heptane/ethyl acetate gradient. The product-containing fractions were combined and concentrated by rotary evaporation, and the crude product was purified further in a purification laboratory by means of preparative HPLC. The product-containing fractions were combined, the acetonitrile was removed under reduced pressure, and the aqueous residue was basified with saturated aqueous sodium hydrogencarbonate solution and extracted with dichloromethane. The organic phase was dried over $MgSO_4$ and concentrated by rotary evaporation, and the residue was taken up again in a mixture of acetonitrile and water and lyophilized. This gave the product (35.1 mg) with a molecular weight of 464.6 g/mol ($C_{26}H_{28}N_2O_4S$); MS (ESI): m/e=465 (M+1-1).

(S)-3-(6,6-Dimethyl-4,4-dioxo-5-p-tolyl-5,6-dihydro-4H-4lambda6-[1,4,3]oxathiazin-2-ylamino)-3-phenylpropan-1-ol

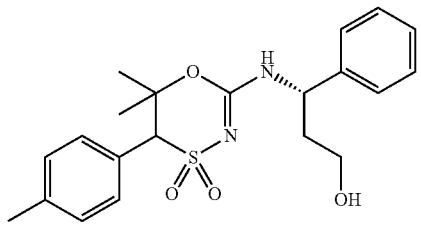 [SMILES: Cc1ccc(C2C(C)(C)OC(N[C@@H](CCO)c3ccccc3)=NS2(=O)=O)cc1]

Under inert gas, 60 mg of trifluoromethanesulfonic acid 4-{2-[(S)-3-(tert-butyldimethylsilanyloxy)-1-phenylpropylamino]-6,6-dimethyl-4,4-dioxo-5,6-dihydro-4H-4lambda6-1,4,3-oxathiazin-5-yl}phenyl ester, 5.3 mg of bis(dibenzylideneacetone)palladium and 13.1 mg of 1,2,3,4,5-pentaphenyl-1-(di-tert-butylphosphino)ferrocene were initially charged, dissolved in 1.2 ml of toluene and stirred at room temperature for 5 minutes. After the addition of 0.09 ml of a 2 N solution of trimethylaluminum, the reaction mixture was stirred at 80° C. for 2 hours. After cooling to room temperature, 1 ml of methanol was added and the solvent was removed under reduced pressure. The residue was dissolved in 2 ml of methanol, 0.2 ml of concentrated hydrochloric acid was added and the mixture was stirred at room temperature for 1 hour. The reaction solution was diluted with 20 ml of ethyl acetate and 10 ml of water, and neutralized with sodium hydroxide solution. The organic phase was washed once again with saturated aqueous sodium chloride solution, dried over $MgSO_4$ and concentrated by rotary evaporation. The residue was purified in a purification laboratory by means of preparative HPLC. The product-containing fractions were combined, the acetonitrile was removed under reduced pressure, and the aqueous residue was basified with saturated aqueous sodium hydrogencarbonate solution and extracted with dichloromethane. The organic phase was dried over $MgSO_4$ and concentrated by rotary evaporation, and the residue was taken up again in a mixture of acetonitrile and water and lyophilized. This gave the product (22.8 mg) with a molecular weight of 402.5 g/mol ($C_{21}H_{26}N_2O_4S$); MS (ESI): m/e=403 (M+H⁺).

C-(3-Bromophenyl)-N-(2,4-dimethoxybenzyl)methanesulfonamide

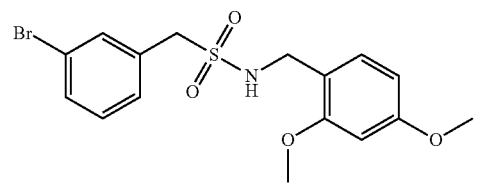 [SMILES: COc1ccc(CNS(=O)(=O)Cc2cccc(Br)c2)c(OC)c1]

While cooling with ice, 9.90 g of 3-bromobenzylsulfonyl chloride were initially charged in 120 ml of dichloromethane, and a solution of 11.55 ml of 2,4-dimethoxybenzylamine in 60 ml of dichloromethane was added dropwise within 15 minutes. The reaction mixture was allowed to come to room temperature and stirred for 1 hour. Subsequently, the mixture was washed with 50 ml of water, with 100 ml of 1 N aqueous hydrochloric acid, with 100 ml of saturated aqueous sodium hydrogencarbonate solution and finally once more with 100 ml of water. The organic phase was dried over $MgSO_4$ and concentrated by rotary evaporation. The residue (14.30 g) was used in the next reaction without further purification.

N-(2,4-Dimethoxybenzyl)-1-(3-bromophenyl)-2-hydroxy-2-methylpropane-1-sulfonamide

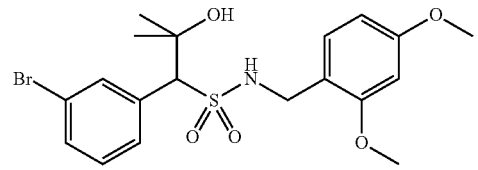 [SMILES: COc1ccc(CNS(=O)(=O)C(c2cccc(Br)c2)C(C)(C)O)c(OC)c1]

Under inert gas, 7.00 g of C-(3-bromophenyl)-N-(2,4-dimethoxybenzyl)methanesulfonamide were initially charged in 120 ml of THF, and then, at a temperature of −78° C., 25.14 ml of a 1.6 N methyllithium solution in diethyl ether were added dropwise and the mixture was stirred at constant temperature for 10 minutes. Subsequently, 7 ml of acetone were added. After stirring for 5 minutes, the reaction solution was admixed with 5 ml of acetic acid and stirred for a further 5 minutes, and 100 ml of ethyl acetate were added to the mixture, which was washed with 1×100 ml and 1×50 ml of a saturated aqueous sodium hydrogencarbonate solution and 2×50 ml of a saturated aqueous sodium chloride solution. The organic phase was dried over $MgSO_4$ and concentrated by rotary evaporation. The residue (8.63 g) was used in the next reaction without further purification.

1-(3-Bromophenyl)-2-hydroxy-2-methylpropane-1-sulfonamide

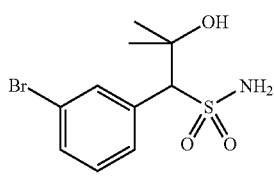 [SMILES: CC(C)(O)C(c1cccc(Br)c1)S(N)(=O)=O]

A solution of 8.63 g of N-[2,4-dimethoxybenzyl]-1-(3-bromophenyl)-2-hydroxy-2-methylpropane-1-sulfonamide in 40 ml of dichloromethane was admixed with 10 ml of trifluoroacetic acid and stirred at room temperature for 30 minutes. The reaction solution was admixed with 40 ml of water, and gradually and cautiously with 150 ml of a saturated aqueous sodium hydrogencarbonate solution. The precipitate was filtered off with suction, washed with water and dried over $P_2O_5$ under reduced pressure. The crude product was purified by means of normal phase chromatography using a Flashmaster with a dichloromethane/methanol gradient. The product-containing fractions were combined and concentrated by rotary evaporation. This gave the product (4.11 g) with a molecular weight of 308.2 g/mol ($C_{10}H_{14}BrNO_3S$); MS (ESI): m/e=325 (M+$H_2O$+$H^+$).

[5-(3-Bromophenyl)-6,6-dimethyl-4,4-dioxo-5,6-dihydro-4H-4lambda6-1,4,3-oxathiazin-2-yl]cyclohexylamine

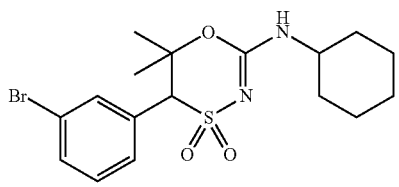 [SMILES: CC1(C)OC(NC2CCCCC2)=NS(=O)(=O)C1c1cccc(Br)c1]

A solution of 1.00 g of 1-(3-bromophenyl)-2-hydroxy-2-methylpropane-1-sulfonamide and 0.483 g of cyclohexyl isothiocyanate in 7 ml of NMP was admixed with 1.62 ml of a 2 N solution of sodium bis(trimethylsilyl)amide. After stirring for 20 minutes, 578 mg of N-bromosuccinimide were added and the mixture was stirred at room temperature for a further 60 minutes. The reaction solution was admixed with 150 ml of water and extracted twice with 150 ml of ethyl acetate. The combined organic phases were washed with saturated aqueous sodium chloride solution, dried over $MgSO_4$ and concentrated by rotary evaporation. The residue was purified in a purification laboratory by means of preparative HPLC, and the product-containing fractions were lyophilized. This gave the product (411 mg) with a molecular weight of 415.3 g/mol ($C_{17}H_{23}BrN_2O_3S$); MS (ESI): m/e=416 (M+$H^+$).

Cyclohexyl-[6,6-dimethyl-4,4-dioxo-5-(3-pyrimidin-5-ylphenyl)-5,6-dihydro-4H-4lambda6-[1,4,3]oxathiazin-2-yl]amine

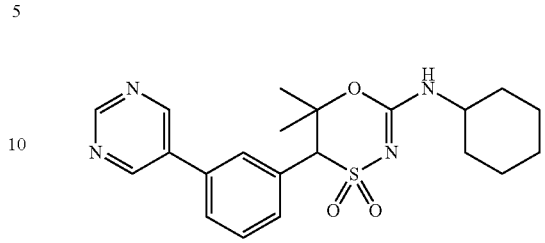

Under inert gas, 80 mg of [5-(3-bromophenyl)-6,6-dimethyl-4,4-dioxo-5,6-dihydro-4H-4lambda6-1,4,3-oxathiazin-2-yl]cyclohexylamine, 30 mg of pyrimidine-5-boronic acid and 251 mg of cesium carbonate were dissolved in a mixture of 1.2 ml of dioxane and 0.4 ml of water. After purging with argon for 10 minutes, 15 mg of dichloro[1,1'-bis(diphenylphosphino)ferrocene]palladium were added and the reaction mixture was stirred at 80° C. for 2 hours. After cooling to room temperature, the mixture was admixed with 50 ml of ethyl acetate and washed with 15 ml of water and 15 ml of saturated aqueous sodium chloride solution, and the organic phase was dried over $MgSO_4$ and concentrated by rotary evaporation. The residue was purified in a purification laboratory by means of preparative HPLC. The product-containing fractions were combined and lyophilized. This gave the product (6.4 mg) with a molecular weight of 414.5 g/mol ($C_{21}H_{26}N_4O_3S$); MS (ESI): m/e=415 (M+$H^+$).

[5-(3-Bromophenyl)-6,6-dimethyl-4,4-dioxo-5,6-dihydro-4H-4lambda6-[1,4,3]oxathiazin-2-yl]-[(S)-1-(2-fluorophenyl)ethyl]amine

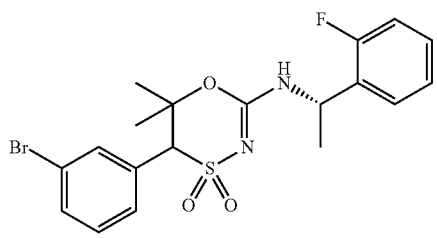 [SMILES: C[C@H](NC1=NS(=O)(=O)C(c2cccc(Br)c2)C(C)(C)O1)c1ccccc1F]

5-(3-Bromophenyl)-2-methoxy-6,6-dimethyl-5,6-dihydro-1,4,3-oxathiazine 4,4-dioxide

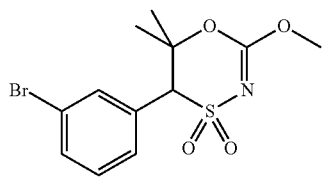 [SMILES: COC1=NS(=O)(=O)C(c2cccc(Br)c2)C(C)(C)O1]

A mixture of 500 mg of 1-(3-bromophenyl)-2-hydroxy-2-methylpropane-1-sulfonamide in 2 ml of tetramethoxymethane and 0.5 ml of acetic acid was stirred at 100° C. for 3 hours. After the removal of the solvent under reduced pressure, the residue (565 mg) was used in the next reaction without further purification.

In an analogous manner, the following intermediates were obtained:

5-(4-Bromophenyl)-2-methoxy-6,6-dimethyl-5,6-dihydro-[1,4,3]oxathiazine 4,4-dioxide

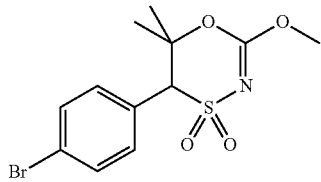

5-(6-Chloropyridin-3-yl)-2-methoxy-6,6-dimethyl-5,6-dihydro-[1,4,3]oxathiazine 4,4-dioxide

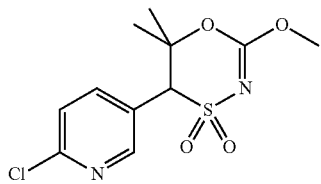 [SMILES: COC1=NS(=O)(=O)C(c2ccc(Cl)nc2)C(C)(C)O1]

[5-(3-Bromophenyl)-6,6-dimethyl-4,4-dioxo-5,6-dihydro-4H-4lambda6-[1,4,3]oxathiazin-2-yl]-[(S)-1-(2-fluorophenyl)ethyl]amine

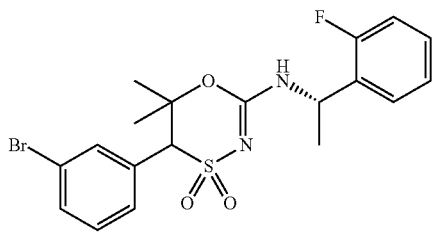 [SMILES: C[C@H](NC1=NS(=O)(=O)C(c2cccc(Br)c2)C(C)(C)O1)c1ccccc1F]

A solution of 565 mg of 5-(3-bromophenyl)-2-methoxy-6,6-dimethyl-5,6-dihydro-1,4,3-oxathiazine 4,4-dioxide and 270 mg of (S)-1-(2-fluorophenyl)ethylamine in 2 ml of methylene chloride was concentrated by rotary evaporation and the residue was left to stand at room temperature overnight. The crude product was purified by means of normal phase chromatography using a Flashmaster with an n-heptane/ethyl acetate gradient. The product-containing fractions were combined and concentrated by rotary evaporation. This gave the product (162 mg) with a molecular weight of 455.3 g/mol ($C_{19}H_{20}BrFN_2O_3S$).

The following products were obtained in the same way:

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2-fluorophenyl)propyl]amine

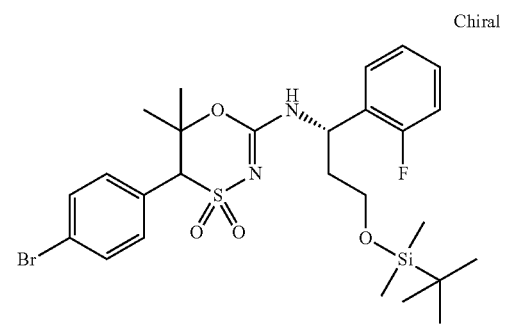 [SMILES: CC1(C)OC(N[C@@H](CCO[Si](C)(C)C(C)(C)C)c2ccccc2F)=NS(=O)(=O)C1c1ccc(Br)cc1]

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2-chlorophenyl)propyl]amine

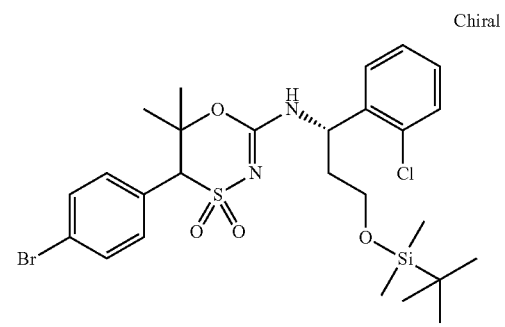 [SMILES: CC1(C)OC(N[C@@H](CCO[Si](C)(C)C(C)(C)C)c2ccccc2Cl)=NS(=O)(=O)C1c1ccc(Br)cc1]

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(3-chlorophenyl)propyl]amine

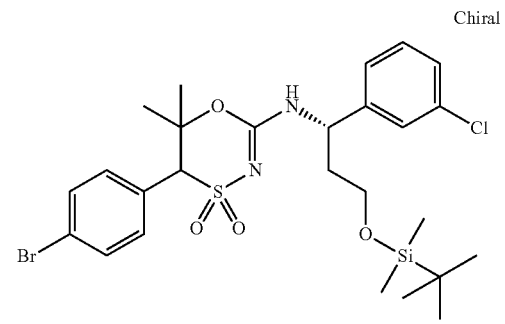 [SMILES: CC1(C)OC(N[C@@H](CCO[Si](C)(C)C(C)(C)C)c2cccc(Cl)c2)=NS(=O)(=O)C1c1ccc(Br)cc1]

145

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(4-chlorophenyl)propyl]amine

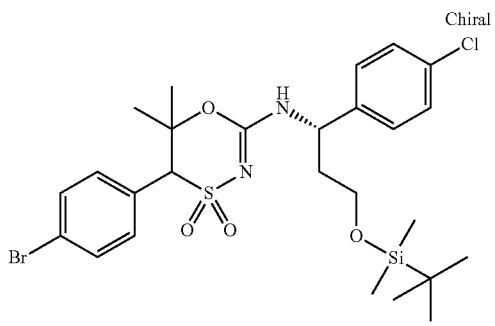 [SMILES: CC1(C)OC(N[C@@H](CCO[Si](C)(C)C(C)(C)C)c2ccc(Cl)cc2)=NS(=O)(=O)C1c1ccc(Br)cc1]

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2,3-difluorophenyl)propyl]amine

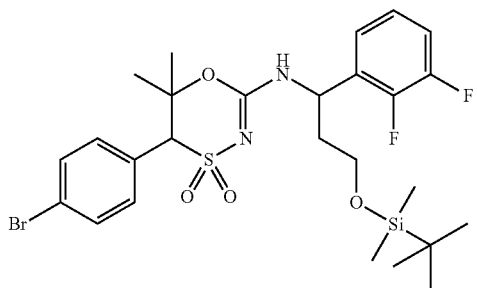 [SMILES: CC1(C)OC(NC(CCO[Si](C)(C)C(C)(C)C)c2cccc(F)c2F)=NS(=O)(=O)C1c1ccc(Br)cc1]

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2,4-difluorophenyl)propyl]amine

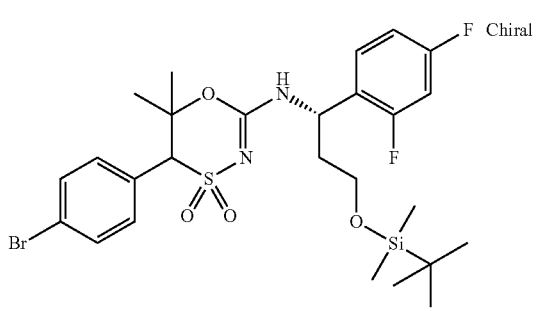 [SMILES: CC1(C)OC(N[C@@H](CCO[Si](C)(C)C(C)(C)C)c2ccc(F)cc2F)=NS(=O)(=O)C1c1ccc(Br)cc1]

146

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2,5-difluorophenyl)propyl]amine

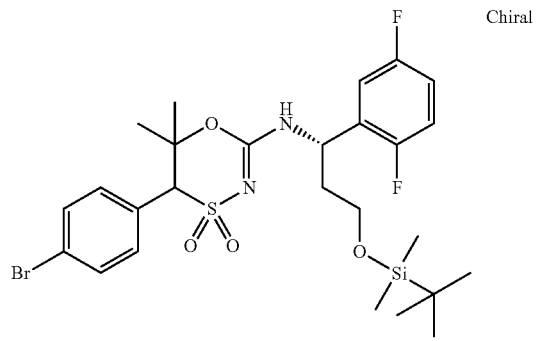

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(5-chloro-2-fluorophenyl)propyl]amine

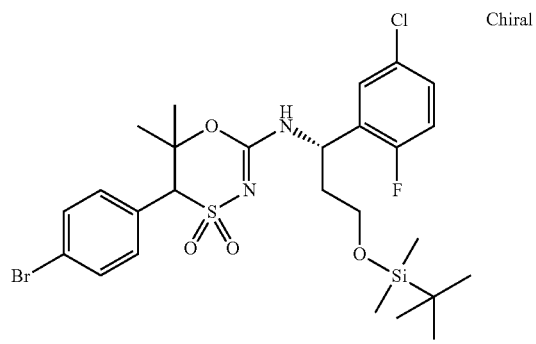

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2-chloro-3-fluorophenyl)propyl]amine

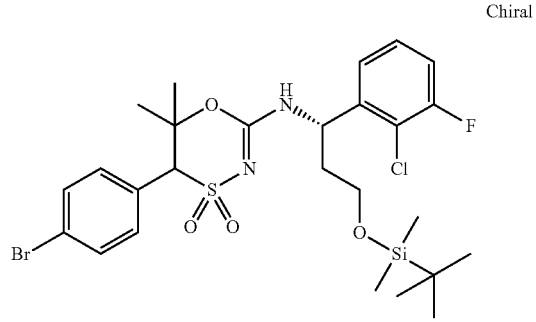 [SMILES: CC1(C)OC(N[C@@H](CCO[Si](C)(C)C(C)(C)C)c2cccc(F)c2Cl)=NS(=O)(=O)C1c1ccc(Br)cc1]

[5-(4-Bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(5-fluoro-2-methylphenyl)propyl]amine

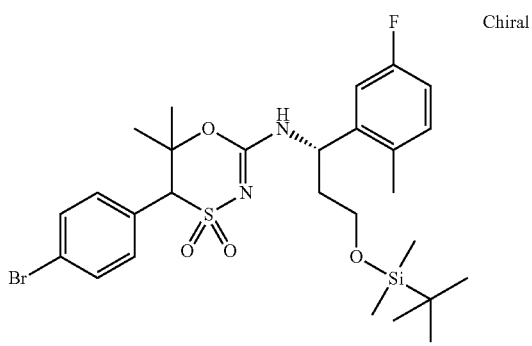 [SMILES: Cc1ccc(F)cc1[C@H](CCO[Si](C)(C)C(C)(C)C)NC1=NS(=O)(=O)C(c2ccc(Br)cc2)C(C)(C)O1]

[(S)-3-(tert-Butyldimethylsilanyloxy)-1-(2-fluorophenyl)propyl]-[5-(6-chloropyridin-3-yl)-6,6-dimethyl-4,4-dioxo-5,6-dihydro-4H-4lambda*6*-[1,4,3]oxathiazin-2-yl]amine

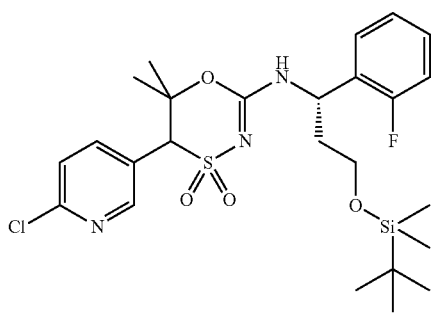 [SMILES: CC1(C)OC(N[C@@H](CCO[Si](C)(C)C(C)(C)C)c2ccccc2F)=NS(=O)(=O)C1c1ccc(Cl)nc1]

[5-(6-Chloropyridin-3-yl)-6,6-dimethyl-4,4-dioxo-5,6-dihydro-4H-4lambda*6*-[1,4,3]oxathiazin-2-yl]-[(S)-1-(2-fluorophenyl)ethyl]amine

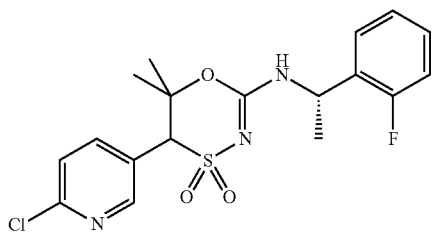 [SMILES: C[C@H](NC1=NS(=O)(=O)C(c2ccc(Cl)nc2)C(C)(C)O1)c1ccccc1F]

(6,6-Dimethyl-4,4-dioxo-5-phenyl-5,6-dihydro-4H-4lambda6-[1,4,3]oxathiazin-2-yl)-[(S)-1-(2-fluorophenyl)ethyl]amine

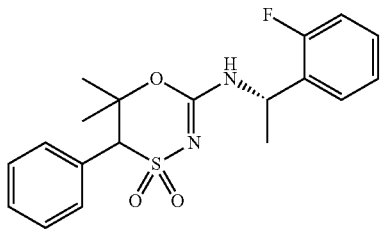 [SMILES: C[C@H](NC1=NS(=O)(=O)C(c2ccccc2)C(C)(C)O1)c1ccccc1F]

Under inert gas, 48 mg of [5-(3-bromophenyl)-6,6-dimethyl-4,4-dioxo-5,6-dihydro-4H-4lambda6-[1,4,3]oxathiazin-2-yl]-[(S)-1-(2-fluorophenyl)ethyl]amine were initially charged in 5 ml of methanol and, with addition of 22 mg of 10% Pd/C, stirred under a hydrogen atmosphere for 1.75 hours. After filtration to remove the solid residues, the filtrate was freed of the solvent under reduced pressure and the crude product was purified in a purification laboratory by means of preparative HPLC. The product-containing fractions were combined and freed of the organic solvent under reduced pressure, and the aqueous residue was lyophilized. This gave the product (27.8 mg) with a molecular weight of 376.4 g/mol ($C_{19}H_{21}FN_2O_3S$); MS (ESI): m/e=377 (M+H$^+$).

(S)-3-[6,6-Dimethyl-5-(2'-methyl-biphenyl-4-yl)-4,4-dioxo-5,6-dihydro-4H-4lambda6-[1,4,3]oxathiazin-2-ylamino-]-3-(2-fluorophenyl)propan-1-ol

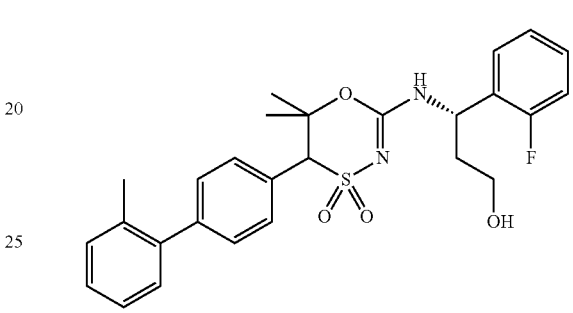

The synthesis of [5-(4-bromophenyl)-6,6-dimethyl-4,4-dioxo-5,6-dihydro-4H-4lambda6-1,4,3-oxathiazin-2-yl]-[(S)-3-(tert-butyldimethylsilanyloxy)-1-(2-fluorophenyl)propyl]amine was effected analogously to [5-(3-bromophenyl)-6,6-dimethyl-4,4-dioxo-5,6-dihydro-4H-4lambda6-[1,4,3]oxathiazin-2-yl]-[(S)-1-(2-fluorophenyl)ethyl]amine.

Under inert gas, 40 mg of dichloro[1,1'-bis(diphenylphosphino)ferrocene]palladium were added to a mixture of 97 mg of 2-methylphenylboronic acid, 350 mg of [5-(4-bromophenyl)-6,6-dimethyl-4,4-dioxo-5,6-dihydro-4H-4lambda6-1,4,3-oxathiazin-2-yl]-[(S)-3-(tert-butyldimethylsilanyloxy)-1-(2-fluorophenyl)propyl]amine and 571 mg of cesium carbonate in 4.5 ml of dioxane and 1.5 ml of water. After stirring at 95° C. for 30 minutes, the reaction was allowed to cool to room temperature, 50 ml of ethyl acetate were added and the organic phase was washed with 20 ml of water and 20 ml of saturated aqueous sodium chloride solution. The organic phase was dried over MgSO$_4$ and concentrated by rotary evaporation. The crude product was purified by means of normal phase chromatography using a Flashmaster with an n-heptane/ethyl acetate gradient. The product-containing fractions were combined and concentrated by rotary evaporation. To detach the protecting group, the residue was dissolved in 4 ml of methanol, 0.4 ml of concentrated hydrochloric acid was added and the mixture was stirred at room temperature for 16 hours. The reaction solution was concentrated by rotary evaporation, and the residue was taken up in 20 ml of dichloromethane and washed with 10 ml of water. The aqueous phase was extracted once again with 10 ml of dichloromethane, and the combined organic phases were dried using a phase separator cartridge (Chromabond® PTS) and concentrated by rotary evaporation. The crude product was purified in a purification laboratory by means of preparative HPLC. The product-containing fractions were combined, the acetonitrile was removed under reduced pressure, and the aqueous residue was basified with saturated aqueous sodium hydrogencarbonate solution and extracted with dichloromethane. The organic phase was dried over MgSO$_4$ and concentrated by rotary evaporation, and the residue was taken up again in a mixture of acetonitrile and water and lyophilized. This gave the product (120 mg) with a molecular weight of 496.6 g/mol ($C_{27}H_{29}FN_2O_4S$); MS (ESI): m/e=497 (M+H$^+$).

Compounds 65 to 68 and 71 to 75 were likewise synthesized by this preparation method:

(S)-3-[5-(4'-Fluorobiphenyl-4-yl)-6,6-dimethyl-4,4-dioxo-5,6-dihydro-4H-4lambda6-[1,4,3]oxathiazin-2-ylamino]-3-(2-fluorophenyl)propan-1-ol (S)-3-(2-Fluorophenyl)-3-[5-(4'-methoxybiphenyl-4-yl)-6,6-dimethyl-4,4-dioxo-5,6-dihydro-4H-4lambda6-[1,4,3]oxathiazin-2-ylamino]propan-1-ol (S)-3-(2-Fluorophenyl)-3-[5-(4'-methoxybiphenyl-4-yl)-6,6-dimethyl-4,4-dioxo-5,6-dihydro-4H-4lambda6-[1,4,3]oxathiazin-2-ylamino]propan-1-ol (S)-3-(5-Biphenyl-3-yl-6,6-dimethyl-4,4-dioxo-5,6-dihydro-4H-4lambda6-[1,4,3]oxathiazin-2-ylamino)-3-(2-fluorophenyl)propan-1-ol (5-Biphenyl-3-yl-6,6-dimethyl-4,4-dioxo-5,6-dihydro-4H-4lambda6-[1,4,3]oxathiazin-2-yl)-[(S)-1-(2-fluorophenyl)ethyl]amine (S)-3-[5-(4'-Fluorobiphenyl-3-yl)-5,6,6-trimethyl-4,4-dioxo-5,6-dihydro-4H-4lambda6-[1,4,3]oxathiazin-2-ylamino]-3-(2-fluorophenyl)propan-1-ol (S)-3-[5-(3-Bromophenyl)-6,6-dimethyl-4,4-dioxo-5,6-dihydro-4H-4lambda6-[1,4,3]oxathiazin-2-ylamino]-3-phenylpropan-1-ol (S)-3-[5-(4'-Fluorobiphenyl-3-yl)-5,6,6-trimethyl-4,4-dioxo-5,6-dihydro-4H-4lambda6-[1,4,3]oxathiazin-2-ylamino]-3-(2-fluorophenyl)propan-1-ol (S)-3-(5-Biphenyl-3-yl-5,6,6-trimethyl-4,4-dioxo-5,6-dihydro-4H-4lambda6-[1,4,3]oxathiazin-2-ylamino)-3-phenylpropan-1-ol (5-Biphenyl-3-yl-5,6,6-trimethyl-4,4-dioxo-5,6-dihydro-4H-4lambda6-[1,4,3]oxathiazin-2-yl)-[(S)-1-(2-fluorophenyl)ethyl]amine (5-Biphenyl-3-yl-5,6,6-trimethyl-4,4-dioxo-5,6-dihydro-4H-4lambda6-[1,4,3]oxathiazin-2-yl)-[(S)-1-(2-fluorophenyl)ethyl]amine (S)-3-(5-Biphenyl-3-yl-5,6,6-trimethyl-4,4-dioxo-5,6-dihydro-4H-4lambda6-[1,4,3]oxathiazin-2-ylamino)-3-(2-fluorophenyl)propan-1-ol (S)-3-(5-Biphenyl-3-yl-5,6,6-trimethyl-4,4-dioxo-5,6-dihydro-4H-4lambda6-[1,4,3]oxathiazin-2-ylamino)-3-(2-fluorophenyl)propan-1-ol

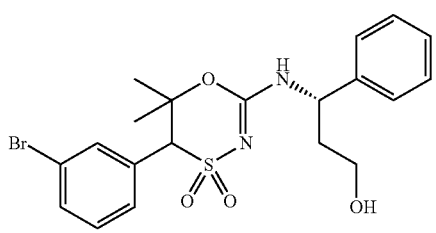 [SMILES: CC1(C)OC(N[C@@H](CCO)c2ccccc2)=NS(=O)(=O)C1c1cccc(Br)c1]

[5-(3-Bromophenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine

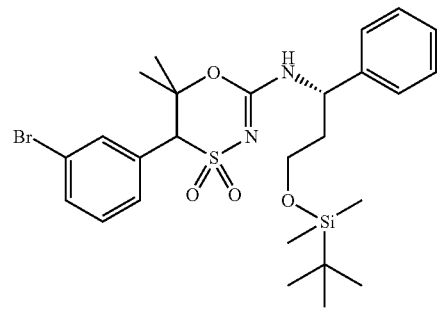 [SMILES: CC1(C)OC(N[C@@H](CCO[Si](C)(C)C(C)(C)C)c2ccccc2)=NS(=O)(=O)C1c1cccc(Br)c1]

2.04 g of (S)-3-(tert-butyldimethylsilanyloxy)-1-phenylpropylamine were initially charged in 20 ml of dichloromethane, and 1.41 g of 1,1'-thiocarbonyldiimidazole were added. After stirring at room temperature for 45 minutes, the reaction solution was washed with a mixture of 80 ml of diethyl ether and 80 ml of n-pentane and washed three times with 50 ml of water, dried over MgSO$_4$ and concentrated by rotary evaporation. Under inert gas, the residue and 2.03 g of 1-(3-bromophenyl)-2-hydroxy-2-methylpropane-1-sulfonamide were dissolved in 15 ml of NMP, and 3.29 ml of a 2 N solution of sodium bis(trimethylsilyl)amide in THF were added dropwise. After stirring for 20 minutes, 1.17 g of N-bromosuccinimide were added and the resulting reaction solution was stirred at constant temperature for 20 minutes. The reaction solution was admixed with 250 ml of water and extracted twice with 100 ml and once with 50 ml of ethyl acetate. The combined organic phases were dried over MgSO$_4$ and concentrated by rotary evaporation, and the residue was purified by means of normal phase chromatography using a Flashmaster with an n-heptane/ethyl acetate gradient. The product-containing fractions were combined and concentrated by rotary evaporation. This gave the product (1.33 g) with a molecular weight of 581.7 g/mol ($C_{26}H_{37}BrN_2O_4SSi$); MS (ESI): m/e=582 (M+H$^+$).

(S)-3-[5-(3-Bromophenyl)-6,6-dimethyl-4,4-dioxo-5,6-dihydro-4H-4lambda6-[1,4,3]oxathiazin-2-ylamino]-3-phenylpropan-1-ol

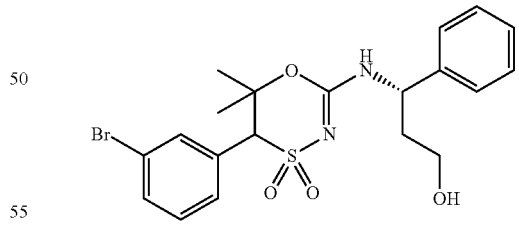

To detach the protecting group, 70 mg of [5-(3-bromophenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine were taken up in 1.5 ml of methanol and, after addition of 0.15 ml of concentrated hydrochloric acid, stirred at room temperature for 1 hour. The reaction solution was concentrated by rotary evaporation and the residue purified in a purification laboratory by means of preparative HPLC. The product-containing fractions were combined and freed of the solvent under reduced pressure. The residue was dissolved in acetonitrile and lyophilized. This gave the product (38.6 mg) with a molecular weight of 467.4 g/mol ($C_{20}H_{23}BrN_2O_4S$); MS (ESI): m/e=468 (M+H⁺).

(S)-3-(5-Biphenyl-3-yl-6,6-dimethyl-4,4-dioxo-5,6-dihydro-4H-4lambda6-[1,4,3]oxathiazin-2-ylamino)-3-phenylpropan-1-ol

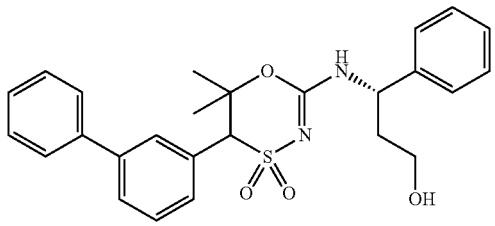 [SMILES: CC1(C)OC(N[C@@H](CCO)c2ccccc2)=NS(=O)(=O)C1c1cccc(-c2ccccc2)c1]

Under inert gas, 2.58 ml of a 0.5 N zinc chloride solution in THF were cooled to −78° C., and 0.48 ml of a 1.8 N phenyllithium solution in dibutyl ether was added dropwise. The reaction solution was allowed to come to room temperature and stirred for 30 minutes. Then this solution was added to a solution of 100 mg of [5-(3-bromophenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl] amine and 14.1 mg of dichloro[1,1'-bis(diphenylphosphino) ferrocene]palladium in 2 ml of THF. After stirring at 60° C. for 45 minutes, the reaction was allowed to cool to room temperature, 10 ml of water and 10 ml of ethyl acetate were added, and the organic phase was dried over MgSO₄ and concentrated by rotary evaporation. The residue was dissolved in 1.5 ml of methanol, 0.15 ml of concentrated hydrochloric acid was added and the mixture was stirred at room temperature for 16 hours. The reaction solution was diluted with ethyl acetate and washed with saturated aqueous sodium chloride solution, dried over MgSO₄ and concentrated by rotary evaporation. The residue was purified in a purification laboratory by means of preparative HPLC. The product-containing fractions were combined, the acetonitrile was removed under reduced pressure, and the aqueous residue was basified with saturated aqueous sodium hydrogencarbonate solution and extracted with dichloromethane. The organic phase was dried over MgSO₄ and concentrated by rotary evaporation, and the residue was taken up again in a mixture of acetonitrile and water and lyophilized. This gave the product (57.8 mg) with a molecular weight of 464.6 g/mol ($C_{26}H_{28}N_2O_4S$); MS (ESI): m/e=565 (M+H⁺).

(S)-3-(6,6-Dimethyl-4,4-dioxo-5-m-tolyl-5,6-dihydro-4H-4lambda6-[1,4,3]oxathiazin-2-ylamino)-3-phenylpropan-1-ol

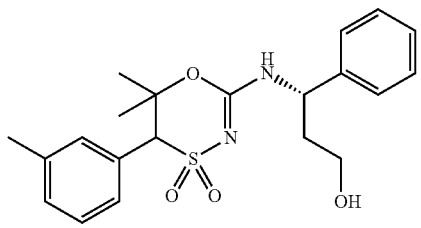 [SMILES: Cc1cccc(C2C(C)(C)OC(N[C@@H](CCO)c3ccccc3)=NS2(=O)=O)c1]

[(S)-3-(tert-Butyldimethylsilanyloxy)-1-phenylpropyl]-(6,6-dimethyl-4,4-dioxo-5-m-tolyl-5,6-dihydro-4H-4lambda6-1,4,3-oxathiazin-2-yl)amine

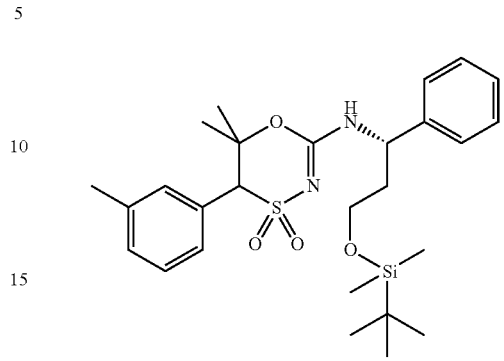

Under inert gas, 100 mg of [5-(3-bromophenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine, 8 mg of bis(dibenzylideneacetone)palladium and 19.6 mg of 1,2,3,4,5-pentaphenyl-1-(di-tert-butylphosphino)ferrocene were initially charged, dissolved in 3 ml of toluene and stirred at room temperature for 5 minutes. After the addition of 0.17 ml of a 2 N solution of trimethylaluminum, the reaction mixture was stirred at 70° C. for 1.5 hours. After cooling to room temperature, the solvent was removed under reduced pressure and the residue was purified by means of normal phase chromatography using a Flashmaster with an n-heptane/ethyl acetate gradient. The product-containing fractions were combined and concentrated by rotary evaporation. This gave the product (51.7 mg) with a molecular weight of 516.8 g/mol ($C_{27}H_{40}N_2O_4SSi$); MS (ESI): m/e=517 (M+H⁺).

(S)-3-(6,6-Dimethyl-4,4-dioxo-5-m-tolyl-5,6-dihydro-4H-4lambda6-[1,4,3]oxathiazin-2-ylamino)-3-phenylpropan-1-ol

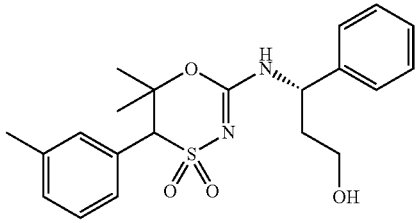 [SMILES: Cc1cccc(C2C(C)(C)OC(N[C@@H](CCO)c3ccccc3)=NS2(=O)=O)c1]

51.7 mg of [(S)-3-(tert-butyldimethylsilanyloxy)-1-phenylpropyl]-(6,6-dimethyl-4,4-dioxo-5-m-tolyl-5,6-dihydro-4H-4lambda6-1,4,3-oxathiazin-2-yl)amine were dissolved in 2 ml of methanol, 0.1 ml of concentrated hydrochloric acid was added and the mixture was stirred at room temperature for 16 hours. The reaction solution was diluted with ethyl acetate and washed with saturated aqueous sodium chloride solution, dried over MgSO₄ and concentrated by rotary evaporation. The residue was purified in a purification laboratory by means of preparative HPLC. The product-containing fractions were combined, the acetonitrile was removed under reduced pressure, and the aqueous residue was basified with saturated aqueous sodium hydrogencarbonate solution and extracted with dichloromethane. The organic phase was dried over MgSO₄ and concentrated by rotary evaporation,

(S)-3-[5-(3-Benzylphenyl)-6,6-dimethyl-4,4-dioxo-5,6-dihydro-4H-4lambda6-[1,4,3]oxathiazin-2-ylamino]-3-phenylpropan-1-ol

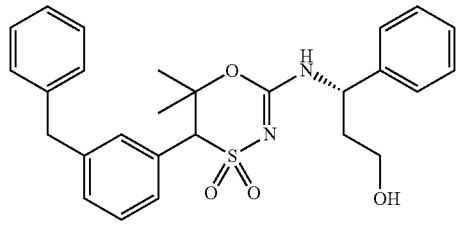 [SMILES: CC1(C)OC(N[C@@H](CCO)c2ccccc2)=NS(=O)(=O)C1c1cccc(Cc2ccccc2)c1]

Under inert gas, 1.72 ml of a 0.5 N solution of benzylzinc bromide in THF were added to a solution of 100 mg of [5-(3-bromophenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine and 14.1 mg of dichloro[1,1'-bis(diphenylphosphino)ferrocene]palladium in 2 ml of THF. After stirring at 60° C. for 18 hours, 2 ml of methanol and 0.5 ml of concentrated hydrochloric acid were added, and the reaction mixture was stirred at room temperature for 1 hour. The reaction solution was diluted with 20 ml of ethyl acetate and 10 ml of water and neutralized with aqueous sodium hydroxide solution, and the organic phase was washed once again with saturated aqueous sodium chloride solution, dried over MgSO$_4$ and concentrated by rotary evaporation. The residue was purified in a purification laboratory by means of preparative HPLC. The product-containing fractions were combined, extracted with dichloromethane and concentrated by rotary evaporation. The residue was purified further by means of normal phase chromatography using a Flashmaster with an n-heptane/ethyl acetate gradient. The product-containing fractions were combined and concentrated by rotary evaporation, and the residue was taken up again in a mixture of acetonitrile and water and lyophilized. This gave the product (38.2 mg) with a molecular weight of 478.6 g/mol ($C_{27}H_{30}N_2O_4S$); MS (ESI): m/e=479 (M+H$^+$).

(S)-3-[6,6-Dimethyl-4,4-dioxo-5-(3-pyrimidin-5-ylphenyl)-5,6-dihydro-4H-4lambda6-[1,4,3]oxathiazin-2-ylamino]-3-phenylpropan-1-ol

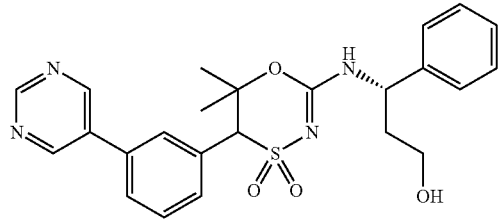 [SMILES: CC1(C)OC(N[C@@H](CCO)c2ccccc2)=NS(=O)(=O)C1c1cccc(-c2cncnc2)c1]

Under inert gas, a suspension of 100 mg of [5-(3-bromophenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine, 31 mg of pyrimidine-5-boronic acid and 110 mg of potassium phosphate in 2 ml of toluene was initially charged. After the addition of 10 mg of bis(dibenzylideneacetone)palladium and 24 mg of 1,2,3,4,5-pentaphenyl-1-(di-tert-butylphosphino)ferrocene, the reaction mixture was stirred at 80° C. for 1.5 h. The progress of the reaction was checked by LCMS. Since no conversion had taken place yet, 0.8 ml of water, 73 mg of potassium phosphate, 24 mg of pyrimidine-5-boronic acid, 10 mg of bis(dibenzylideneacetone)palladium and 24 mg of 1,2,3,4,5-pentaphenyl-1-(di-tert-butylphosphino)ferrocene were added and the mixture was stirred at constant temperature for a further 20 hours. After the removal of the solvent under reduced pressure, the residue was dissolved in 2 ml of methanol and 0.2 ml of concentrated hydrochloric acid, and the mixture was stirred at room temperature for 1.5 hours. The reaction solution was diluted with 20 ml of ethyl acetate and 10 ml of water, and the organic phase was washed once again with saturated aqueous sodium chloride solution, dried over MgSO$_4$ and concentrated by rotary evaporation. The residue was purified by means of normal phase chromatography using a Flashmaster with a dichloromethane/methanol gradient. The product-containing fractions were combined and concentrated by rotary evaporation. The crude product was purified further in a purification laboratory by means of preparative HPLC. The product-containing fractions were combined, the acetonitrile was removed under reduced pressure, and the aqueous residue was basified with saturated aqueous sodium hydrogencarbonate solution and extracted with dichloromethane. The organic phase was dried over MgSO$_4$ and concentrated by rotary evaporation, and the residue was taken up again in a mixture of acetonitrile and water and lyophilized. This gave the product (15.7 mg) with a molecular weight of 466.6 g/mol ($C_{24}H_{26}N_4O_4S$); MS (ESI): m/e=467 (M+H$^+$).

(S)-3-[5-(2-Chlorophenyl)-6,6-dimethyl-4,4-dioxo-5,6-dihydro-4H-4lambda6-[1,4,3]oxathiazin-2-ylamino]-3-phenylpropan-1-ol

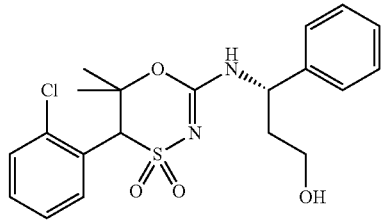 [SMILES: CC1(C)OC(N[C@@H](CCO)c2ccccc2)=NS(=O)(=O)C1c1ccccc1Cl]

C-(2-Chlorophenyl)-N-(2,4-dimethoxybenzyl)methanesulfonamide

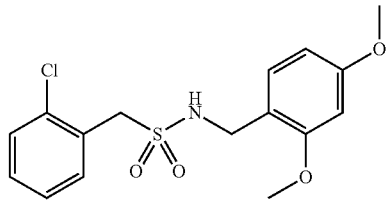 [SMILES: COc1ccc(CNS(=O)(=O)Cc2ccccc2Cl)c(OC)c1]

At room temperature, 1.24 g of (2-chlorophenyl)methanesulfonyl chloride were initially charged in 30 ml of dichloromethane, and 1.66 ml of 2,4-dimethoxybenzylamine were added dropwise. The reaction mixture was stirred for 30 minutes. Then the mixture was admixed with 50 ml of water and 50 ml of water, and then the aqueous phase was washed once more with 30 ml of ethyl acetate. The combined organic phases were washed with 1 N aqueous hydrochloric acid,

1-(2-Chlorophenyl)-2-hydroxy-2-methylpropane-1-sulfonamide

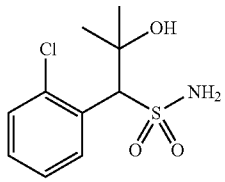 [SMILES: CC(C)(O)C(c1ccccc1Cl)S(N)(=O)=O]

Under inert gas, 1.51 g of C-(2-chlorophenyl)-N-(2,4-dimethoxybenzyl)methanesulfonamide were initially charged in 30 ml of THF, and then, at a temperature of −78° C., 6.09 ml of a 1.6 N methyllithium solution in diethyl ether were added dropwise and the mixture was stirred at constant temperature for 10 minutes. Subsequently, 1.83 ml of acetone were added. After stirring for 10 minutes, the reaction solution was admixed with 2 ml of trifluoroacetic acid and the solvent was removed under reduced pressure. The residue was dissolved in ethyl acetate, and the solution was washed with saturated aqueous sodium hydrogencarbonate solution and water, dried over MgSO$_4$ and concentrated by rotary evaporation. The residue was dissolved in 20 ml of dichloromethane, and 3 ml of trifluoroacetic acid were added. After stirring at room temperature for 2 hours, the reaction solution was concentrated by rotary evaporation and the residue was taken up in a mixture of water and dichloromethane. The solid which precipitates out was analyzed by LCMS and $^1$H NMR and subsequently discarded, since no product was present. Another solid precipitated out of the filtrate, which was identified by LCMS as product-containing (512 mg). Since further product was present in both phases of the filtrate, the aqueous phase was extracted with dichloromethane, the combined organic phases were concentrated by rotary evaporation and the residue was purified by means of normal phase chromatography using a Flashmaster with an n-heptane/ethyl acetate gradient. The product-containing fractions were combined and concentrated by rotary evaporation (707 mg). This gave the product with a molecular weight of 263.7 g/mol (C$_{10}$H$_{14}$ClNO$_3$S); MS (ESI): m/e=283 (M+H$_2$O+H$^+$).

(S)-3-[5-(2-Chlorophenyl)-6,6-dimethyl-4,4-dioxo-5,6-dihydro-4H-4lambda6-[1,4,3]oxathiazin-2-ylamino]-3-phenylpropan-1-ol

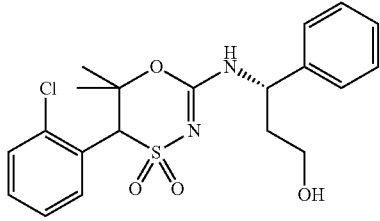 [SMILES: CC1(C)OC(N[C@@H](CCO)c2ccccc2)=NS(=O)(=O)C1c1ccccc1Cl]

443 mg of (S)-3-(tert-butyldimethylsilanyloxy)-1-phenylpropylamine were initially charged in 10 ml of dichloromethane, and 325 mg of 1,1'-thiocarbonyldiimidazole were added. After stirring at room temperature for 40 minutes, the reaction solution was washed with a mixture of 50 ml of diethyl ether and 50 ml of n-pentane and washed three times with 50 ml of water, dried over MgSO$_4$ and concentrated by rotary evaporation. Under inert gas, the residue and 400 mg of 1-(2-chlorophenyl)-2-hydroxy-2-methylpropane-1-sulfonamide were dissolved in 5 ml of NMP, and 0.68 ml of a 2 N solution of sodium bis(trimethylsilyl)amide in THF were added dropwise. After stirring for 15 minutes, 270 mg of N-bromosuccinimide were added and the resulting reaction mixture was stirred at constant temperature for 5 minutes. The reaction solution was diluted with 70 ml of ethyl acetate and washed once with 180 ml and twice with 75 ml of water. The organic phase was dried over MgSO$_4$ and concentrated by rotary evaporation, and the residue was taken up in 8 ml of methanol and, after addition of 1 ml of concentrated hydrochloric acid, stirred at room temperature for 1 hour. The reaction solution was adjusted to pH 5 with saturated aqueous sodium hydrogencarbonate solution, diluted with dichloromethane and washed with water. After drying over MgSO$_4$, the organic phase was concentrated by rotary evaporation and the residue was purified in a purification laboratory by means of preparative HPLC. The product-containing fractions were combined, the acetonitrile was removed under reduced pressure, and the aqueous residue was neutralized with saturated aqueous sodium hydrogencarbonate solution. This was followed by extraction three times with 20 ml of ethyl acetate, drying of the combined organic phases over MgSO$_4$ and concentration by rotary evaporation. The residue was taken up again in a mixture of acetonitrile and water and lyophilized. This gave the product (94.6 mg) with a molecular weight of 422.9 g/mol (C$_{20}$H$_{23}$ClN$_2$O$_4$S); MS (ESI): m/e=423 (M+H$^+$).

(S)-3-(6,6-Dimethyl-4,4-dioxo-5-o-tolyl-5,6-dihydro-4H-4lambda6-[1,4,3]oxathiazin-2-ylamino)-3-phenylpropan-1-ol

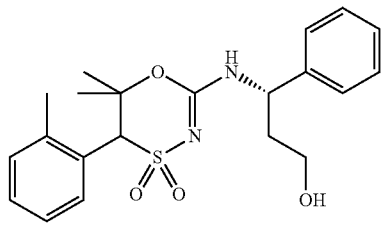 [SMILES: Cc1ccccc1C1C(C)(C)OC(N[C@@H](CCO)c2ccccc2)=NS1(=O)=O]

N-(2,4-Dimethoxybenzyl)-C-o-tolylmethanesulfonamide

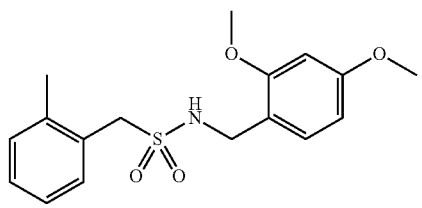 [SMILES: COc1ccc(CNS(=O)(=O)Cc2ccccc2C)c(OC)c1]

At room temperature, 1.00 g of o-tolylmethanesulfonyl chloride was initially charged in 30 ml of dichloromethane, and 1.46 ml of 2,4-dimethoxybenzylamine were added dropwise. The reaction mixture was stirred for 30 minutes. Then the mixture was admixed with 50 ml of water and 50 ml of ethyl acetate, and then the aqueous phase was washed once more with 30 ml of ethyl acetate. The combined organic phases were washed with 1 N aqueous hydrochloric acid, dried over MgSO$_4$ and concentrated by rotary evaporation. The residue (1.42 g) was used in the next reaction without further purification.

2-Hydroxy-2-methyl-1-o-tolylpropane-1-sulfonamide

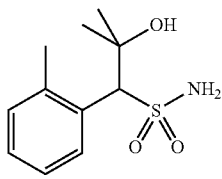 [SMILES: Cc1ccccc1C(C(C)(C)O)S(N)(=O)=O]

Under inert gas, 0.95 g of N-(2,4-dimethoxybenzyl)-C-o-tolylmethanesulfonamide was initially charged in 20 ml of THF, and then, at a temperature of −78° C., 4.06 ml of a 1.6 N methyllithium solution in diethyl ether were added dropwise and the mixture was stirred at constant temperature for 10 minutes. Subsequently, 1.22 ml of acetone were added. After stirring for 10 minutes, the reaction solution was admixed with 2 ml of trifluoroacetic acid and allowed to warm up to room temperature, and the solvent was removed under reduced pressure. The residue was dissolved in 10 ml of dichloromethane, and 1.5 ml of trifluoroacetic acid were added. After stirring at room temperature for 1.5 hours, the reaction solution was concentrated by rotary evaporation and the residue was taken up in a mixture of water and dichloromethane. The solid which precipitates out was filtered off with suction and discarded. The organic phase was dried over MgSO$_4$ and concentrated by rotary evaporation. Since the product was also present in the aqueous phase of the filtrate, this was extracted twice with 50 ml of ethyl acetate, and the combined organic phases were dried over MgSO$_4$ and concentrated by rotary evaporation. Both residues were purified by means of normal phase chromatography using a Flashmaster with an n-heptane/ethyl acetate gradient. The product-containing fractions were combined and concentrated by rotary evaporation (516 mg). This gave the product with a molecular weight of 243.3 g/mol ($C_{11}H_{17}NO_3S$).

(S)-3-(6,6-Dimethyl-4,4-dioxo-5-o-tolyl-5,6-dihydro-4H-4lambda6-[1,4,3]oxathiazin-2-ylamino)-3-phenylpropan-1-ol

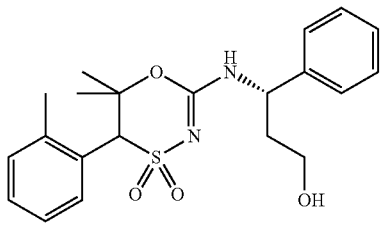 [SMILES: Cc1ccccc1C1C(C)(C)OC(N[C@@H](CCO)c2ccccc2)=NS1(=O)=O]

487 mg of (S)-3-(tert-butyldimethylsilanyloxy)-1-phenylpropylamine were initially charged in 7 ml of dichloromethane, and 357 mg of 1,1'-thiocarbonyldiimidazole were added. After stirring at room temperature for 40 minutes, the reaction solution was washed with a mixture of 30 ml of diethyl ether and 30 ml of n-pentane and washed three times with 30 ml of water, dried over MgSO$_4$ and concentrated by rotary evaporation. Under inert gas, the residue and 255 mg of 2-hydroxy-2-methyl-1-o-tolylpropane-1-sulfonamide were dissolved in 5 ml of NMP, and 0.75 ml of a 2 N solution of sodium bis(trimethylsilyl)amide in THF was added dropwise. After stirring for 5 minutes, 297 mg of N-bromosuccinimide were added and the resulting reaction mixture was stirred at constant temperature for 5 minutes. The reaction solution was diluted with 30 ml of ethyl acetate and washed once with 75 ml and twice with 40 ml of water. The organic phase was dried over MgSO$_4$ and concentrated by rotary evaporation, and the residue was taken up in 5 ml of methanol and, after addition of 1.59 ml of concentrated hydrochloric acid, stirred at room temperature for 1.75 hours. After dilution with 15 ml of water, the reaction solution was adjusted to pH 5 with saturated aqueous sodium hydrogencarbonate solution and extracted with ethyl acetate. After drying over MgSO$_4$, the organic phase was concentrated by rotary evaporation and the residue was purified in a purification laboratory by means of preparative HPLC. The product-containing fractions were combined, the acetonitrile was removed under reduced pressure, and the aqueous residue was neutralized with saturated aqueous sodium hydrogencarbonate solution. This was followed by extraction three times with 20 ml of ethyl acetate, drying of the combined organic phases over MgSO$_4$ and concentration by rotary evaporation. The residue was taken up again in a mixture of acetonitrile and water and lyophilized. This gave the product (63.4 mg) with a molecular weight of 402.5 g/mol ($C_{21}H_{26}N_2O_4S$); MS (ESI): m/e=403 (M+H$^+$).

[5-(3-Benzyloxyphenyl)-6,6-dimethyl-4,4-dioxo-5,6-dihydro-4H-4lambda6-[1,4,3]oxathiazin-2-yl]cyclohexylamine

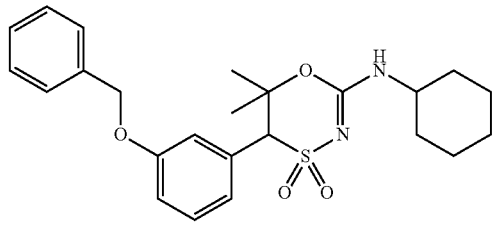 [SMILES: CC1(C)OC(NC2CCCCC2)=NS(=O)(=O)C1c1cccc(OCc2ccccc2)c1]

Methanesulfonic acid 3-benzyloxybenzyl ester

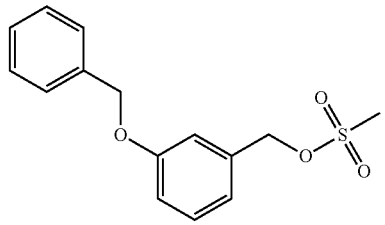 [SMILES: CS(=O)(=O)OCc1cccc(OCc2ccccc2)c1]

At room temperature, 5.00 g of o-(3-benzyloxyphenyl)methanol were initially charged in 80 ml of dichloromethane, 3.90 ml of triethylamine were added and a solution of 1.92 ml of methanesulfonyl chloride in 5 ml of DCM was added dropwise. After stirring for 45 minutes, the reaction mixture was washed with 100 ml each of water, 1 N aqueous hydrochloric acid, 1 N aqueous sodium hydroxide solution and dilute aqueous sodium chloride solution. The organic phase was dried over MgSO$_4$, concentrated by rotary evaporation and dried under high vacuum. The residue (5.86 g) was used in the next reaction without further purification.

(3-Benzyloxyphenyl)methanesulfonic acid sodium salt

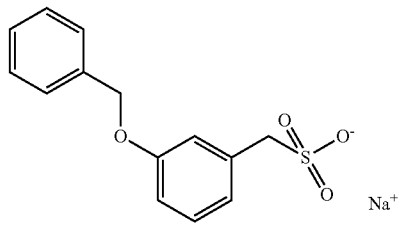 [SMILES: O=S(=O)([O-])Cc1cccc(OCc2ccccc2)c1 ; [Na+]]

5.80 g of methanesulfonic acid 3-benzyloxybenzyl ester and 5.21 g of sodium sulfite were dissolved in 50 ml of water and stirred at 90° C. for 5 hours. The mixture was allowed to cool to room temperature overnight, then 30 ml of ethyl acetate were added and the mixture was stirred in an ice bath for 1 hour. The precipitate was filtered off with suction, washed twice with 10 ml of ice-water and twice with 10 ml of ice-cold ethyl acetate, and dried in a vacuum drying cabinet at 40° C. overnight. This gave the product (2.37 g) with a molecular weight of 300.3 g/mol ($C_{14}H_{13}O_4S.Na$); MS (ESI): m/e=296 (M–$Na^+$+$H_2O$+$H^+$).

(3-Benzyloxyphenyl)methanesulfonyl chloride

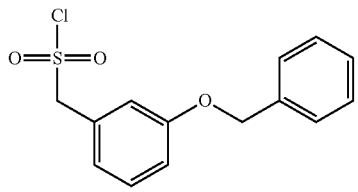 [SMILES: O=S(=O)(Cl)Cc1cccc(OCc2ccccc2)c1]

Under inert gas, 2.36 g of (3-benzyloxyphenyl)methanesulfonic acid sodium salt and 0.61 ml of N,N-dimethylformamide were initially charged in 45 ml of THF, then, at a temperature of –20° C., 4.1.73 ml of oxalyl chloride were added dropwise and the reaction solution was allowed to come to 0° C. within 15 minutes. The reaction solution was diluted with 100 ml of diethyl ether and washed with water, dilute aqueous sodium hydrogencarbonate solution and saturated sodium chloride solution. The organic phase was dried over $MgSO_4$ and concentrated by rotary evaporation. The residue (2.30 g) was used in the next reaction without further purification.

C-(3-Benzyloxyphenyl)-N-(2,4-dimethoxybenzyl) methanesulfonamide

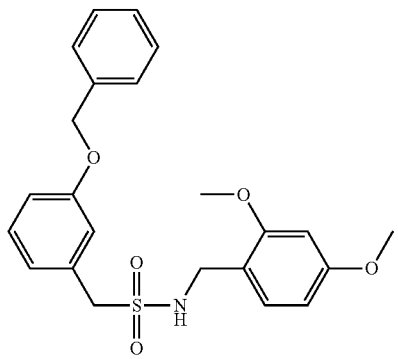 [SMILES: COc1ccc(CNS(=O)(=O)Cc2cccc(OCc3ccccc3)c2)c(OC)c1]

Under inert gas, 4.89 g of (3-benzyloxyphenyl)methanesulfonyl chloride were initially charged in 50 ml of THF, then, at a temperature of –20° C., 3.00 ml of 2,4-dimethoxybenzylamine were added dropwise and the reaction solution was allowed to come to 0° C. within 30 minutes. The reaction solution was diluted with 80 ml of ethyl acetate and washed with water, with 10% aqueous potassium hydrogensulfate solution, saturated aqueous sodium hydrogencarbonate solution and saturated sodium chloride solution. The organic phase was dried over $MgSO_4$ and concentrated by rotary evaporation. The crude product was purified by means of normal phase chromatography using a Flashmaster with an n-heptane/ethyl acetate gradient. The product-containing fractions were combined, concentrated by rotary evaporation and dried under high vacuum. This gave the product (3.12 g) with a molecular weight of 427.5 g/mol ($C_{23}H_{25}NO_5S$).

1-(3-Benzyloxyphenyl)-2-hydroxy-2-methylpropane-1-sulfonamide

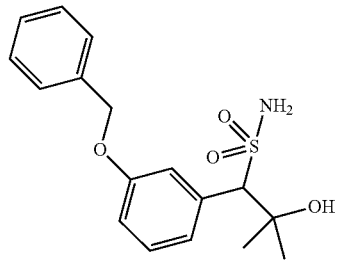 [SMILES: CC(C)(O)C(c1cccc(OCc2ccccc2)c1)S(N)(=O)=O]

Under inert gas, 3.10 g of C-(3-benzyloxyphenyl)-N-(2,4-dimethoxybenzyl)methanesulfonamide were initially charged in 60 ml of THF, and then, at a temperature of –75° C., 12.00 ml of a 1.8 N phenyllithium solution were added dropwise. The reaction mixture was allowed to come to 0° C. and stirred briefly, then cooled again to –75° C., and 3.80 ml of acetone were added dropwise. After stirring for 10 minutes, 3 ml of trifluoroacetic acid were added and the mixture was allowed to come to room temperature. After the removal of the solvent under reduced pressure, the residue was dissolved in 20 ml of dichloromethane and admixed with 5.00 ml of trifluoroacetic acid. After stirring at room temperature for 2.5 hours, the reaction solution was neutralized cautiously with 2 N aqueous sodium hydroxide solution and then stirred overnight. The precipitate formed was filtered off with suction, washed with dichloromethane and cold water, and coevaporated twice with toluene. The crude product was purified by means of normal phase chromatography using a Flashmaster with a dichloromethane/methanol gradient. The product-containing fractions were combined and concentrated by rotary evaporation. This gave the product (2.06 g) with a molecular weight of 335.4 g/mol ($C_{17}H_{21}NO_4S$).

[5-(3-Benzyloxyphenyl)-6,6-dimethyl-4,4-dioxo-5,6-dihydro-4H-4lambda6-[1,4,3]oxathiazin-2-yl]cyclohexylamine

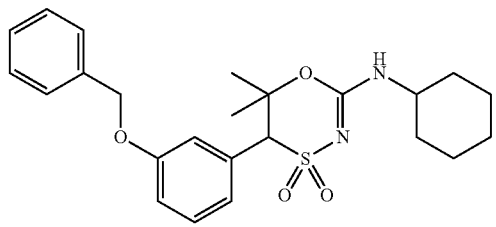 [SMILES: CC1(C)OC(NC2CCCCC2)=NS(=O)(=O)C1c1cccc(OCc2ccccc2)c1]

At room temperature, a solution of 1.00 g of 1-(3-benzyloxyphenyl)-2-hydroxy-2-methylpropane-1-sulfonamide and 0.45 ml of cyclohexyl isothiocyanate in 6.5 ml of NMP was admixed with 1.49 ml of a 2 N solution of sodium bis(trimethylsilyl)amide in THF. After stirring for 45 minutes, the conversion was checked by means of LCMS. Since the reaction was still incomplete, an additional 0.22 ml cyclohexyl isothiocyanate and 0.74 ml of a 2 N solution of sodium bis(trimethylsilyl)amide in THF were added. After stirring for 20 minutes, 0.53 g of N-bromosuccinimide was added and the mixture was stirred at room temperature for a further hour.

The reaction solution was admixed with 150 ml of water and extracted twice with 100 ml of ethyl acetate. The combined organic phases were washed with saturated aqueous sodium chloride solution, dried over MgSO$_4$ and concentrated by rotary evaporation. The residue was purified in a purification laboratory by means of preparative HPLC, and the product-containing fractions were freed of the organic solvent under reduced pressure. The aqueous residue was lyophilized. This gave the product (587 mg) with a molecular weight of 442.6 g/mol (C$_{24}$H$_{30}$N$_2$O$_4$S); MS (ESI): m/e=443 (M+H$^+$).

3-(2-Cyclohexylamino-6,6-dimethyl-4,4-dioxo-5,6-dihydro-4H-4lambda6-[1,4,3]oxathiazin-5-yl)phenol

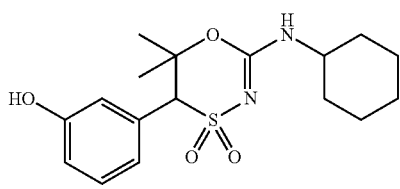

Under inert gas, 548 mg of [5-(3-benzyloxyphenyl)-6,6-dimethyl-4,4-dioxo-5,6-dihydro-4H-4lambda6-[1,4,3]oxathiazin-2-yl]cyclohexylamine were initially charged in 20 ml of methanol and, with addition of 263 mg of 10% Pd/C, stirred under a hydrogen atmosphere for 3.5 hours. The completeness of the conversion was checked by LCMS, and the reaction was once again admixed with 263 mg of 10% Pd/C and stirred under a hydrogen atmosphere for 2 days. After filtration to remove the solid residues, the filtrate was freed of the solvent under reduced pressure and dried under high vacuum. A portion (105 mg) of the residue thus obtained (468 mg) was purified in a purification laboratory by means of preparative HPLC, and the product-containing fractions were freed of the organic solvent under reduced pressure. The aqueous residue was lyophilized. This gave the product (66 mg) with a molecular weight of 352.4 g/mol (C$_{17}$H$_{24}$N$_2$O$_4$S); MS (ESI): m/e=353 (M+H$^+$).

Cyclohexyl-[5-(3-methoxyphenyl)-6,6-dimethyl-4,4-dioxo-5,6-dihydro-4H-4lambda6-[1,4,3]oxathiazin-2-yl]amine

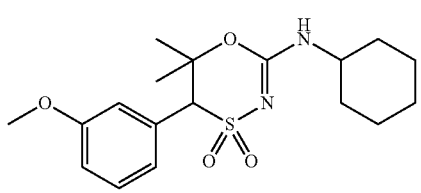 [SMILES: COc1cccc(C2C(C)(C)OC(NC3CCCCC3)=NS2(=O)=O)c1]

To a solution of 120 mg of 3-(2-cyclohexylamino-6,6-dimethyl-4,4-dioxo-5,6-dihydro-4H-4lambda6-[1,4,3]oxathiazin-5-yl)phenol in 2 ml of NMP were added, at room temperature, 38 mg of potassium tert-butoxide and 97 mg of methyl iodide, and the reaction mixture was stirred at constant temperature for 2.5 hours. The reaction solution was diluted with 60 ml of water, 5 ml of 5% aqueous sodium thiosulfate solution were added, and the mixture was extracted twice with 30 ml of ethyl acetate. The combined organic phases were dried over MgSO$_4$ and concentrated by rotary evaporation, and the residue was purified in a purification laboratory by means of preparative HPLC. The product-containing fraction was lyophilized. This gave the product (54 mg) with a molecular weight of 366.5 g/mol (C$_{18}$H$_{26}$N$_2$O$_4$S); MS (ESI): m/e=367 (M+H$^+$).

[5-(3-Benzyloxyphenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine

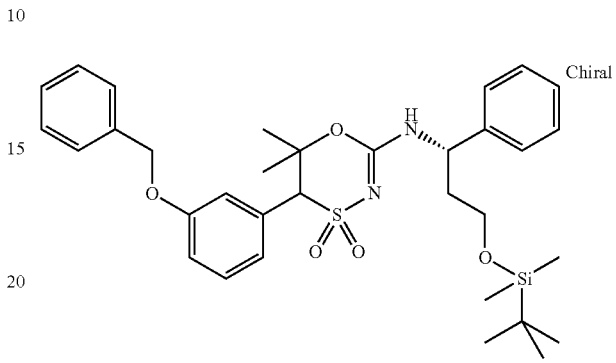

921 mg of (S)-3-(tert-butyldimethylsilanyloxy)-1-phenylpropylamine were dissolved in 10 ml of dichloromethane, and 638 mg of 1,1'-thiocarbonyldiimidazole were added. After stirring at room temperature for 30 minutes, the reaction solution was washed with a mixture of 50 ml of diethyl ether and 50 ml of n-pentane and washed three times with 50 ml of water, dried over MgSO$_4$ and concentrated by rotary evaporation. Under inert gas, the residue and 1000 mg of 1-(3-benzyloxyphenyl)-2-hydroxy-2-methylpropane-1-sulfonamide were dissolved in 8 ml of NMP, and 1.49 ml of a 2 N solution of sodium bis(trimethylsilyl)amide in THF were added dropwise. After stirring for 15 minutes, 531 mg of N-bromosuccinimide were added and the resulting reaction solution was stirred at constant temperature for 10 minutes. The reaction solution was admixed with 100 ml of water and extracted twice with 100 ml of ethyl acetate. The combined organic phases were dried over MgSO$_4$ and concentrated by rotary evaporation, and the residue was purified by means of normal phase chromatography using a Flashmaster with an n-heptane/ethyl acetate gradient. The product-containing fractions were combined and concentrated by rotary evaporation. This gave the product (1.22 g) with a molecular weight of 608.9 g/mol (C$_{33}$H$_{44}$N$_2$O$_5$SSi); MS (ESI): m/e=609 (M+H$^+$).

(S)-3-[5-(3-Benzyloxyphenyl)-6,6-dimethyl-4,4-dioxo-5,6-dihydro-4H-4lambda6-[1,4,3]oxathiazin-2-ylamino]-3-phenylpropan-1-ol

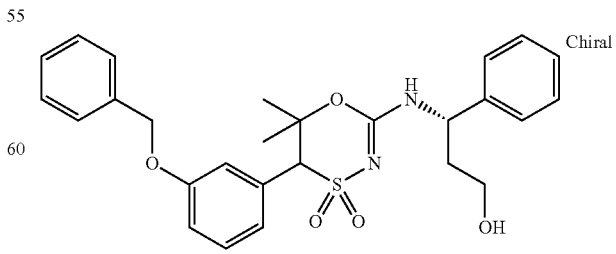

To detach the protecting group, 220 mg of [5-(3-benzyloxyphenyl)-6,6-dimethyl-4,4-dioxo-5,6-dihydro-4H-

4lambda6-1,4,3-oxathiazin-2-yl]-[(S)-3-(tert-butyldimethylsilanyloxy)-1-phenylpropyl]amine were dissolved in 4 ml of methanol and, after addition of 0.4 ml of concentrated hydrochloric acid, stirred at room temperature for 1.75 hours. The reaction solution was concentrated by rotary evaporation and coevaporated twice more with 10 ml of toluene, and the residue was purified in a purification laboratory by means of preparative HPLC. The product-containing fractions were combined, the acetonitrile was removed under reduced pressure, and the aqueous residue was basified with saturated aqueous sodium hydrogencarbonate solution. Subsequently, this aqueous residue was extracted with dichloromethane, and the combined organic phases were dried using a phase separator cartridge (Chromabond® PTS) and concentrated by rotary evaporation. The residue was taken up again in a mixture of acetonitrile and water and lyophilized. This gave the product (129 mg) with a molecular weight of 494.6 g/mol ($C_{27}H_{30}N_2O_5S$); MS (ESI): m/e=495 (M+H$^+$).

3-[2-((S)-3-Hydroxy-1-phenylpropylamino)-6,6-dimethyl-4,4-dioxo-5,6-dihydro-4H-4lambda6-[1,4,3]oxathiazin-5-yl]phenol

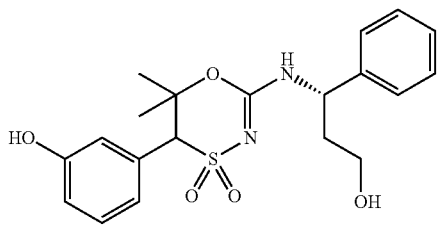 [SMILES: CC1(C)OC(N[C@@H](CCO)c2ccccc2)=NS(=O)(=O)C1c1cccc(O)c1]

3-{2-[(S)-3-(tert-Butyldimethylsilanyloxy)-1-phenylpropylamino]-6,6-dimethyl-4,4-dioxo-5,6-dihydro-4H-4lambda6-1,4,3-oxathiazin-5-yl}phenol

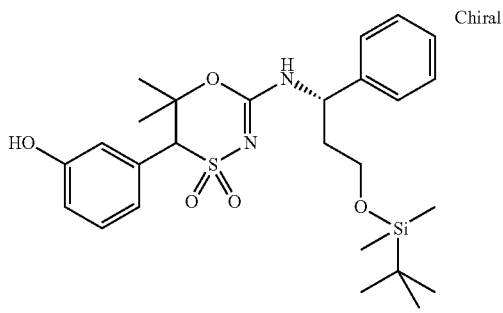 [SMILES: CC1(C)OC(N[C@@H](CCO[Si](C)(C)C(C)(C)C)c2ccccc2)=NS(=O)(=O)C1c1cccc(O)c1]

Chiral

Under inert gas, 1.03 g [5-(3-benzyloxyphenyl)-6,6-dimethyl-4,4-dioxo-5,6-dihydro-4H-4lambda6-1,4,3-oxathiazin-2-yl]-[(S)-3-(tert-butyldimethylsilanyloxy)-1-phenylpropyl]amine were initially charged in 20 ml of methanol and, with addition of 0.24 ml of triethylamine and 359 mg of 10% Pd/C, stirred under a hydrogen atmosphere for 3.75 hours. The completeness of the conversion was checked by LCMS, and the reaction was once again admixed with 359 mg of 10% Pd/C and stirred under a hydrogen atmosphere for a further 16 hours. According to LCMS, the detachment of the benzyl protecting group remained incomplete. After filtration to remove the solid residues, the filtrate was admixed again with 359 mg of 10% Pd/C. After stirring under a hydrogen atmosphere for 5 h, another 359 mg of 10% Pd/C were added and, after a further 2 hours, the reaction was found to be complete by checking with LCMS. After filtration to remove the catalyst residues, the filtrate was freed of the solvent under reduced pressure. This gave the product (764 mg) with a molecular weight of 518.8 g/mol ($C_{26}H_{38}N_2O_5SSi$); MS (ESI): m/e=519 (M+H$^+$).

3-[2-((S)-3-Hydroxy-1-phenylpropylamino)-6,6-dimethyl-4,4-dioxo-5,6-dihydro-4H-4lambda6-[1,4,3]oxathiazin-5-yl]phenol

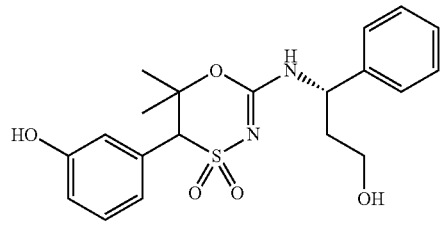 [SMILES: CC1(C)OC(N[C@@H](CCO)c2ccccc2)=NS(=O)(=O)C1c1cccc(O)c1]

To detach the protecting group, 150 mg of 3-{2-[(S)-3-(tert-butyldimethylsilanyloxy)-1-phenylpropylamino]-6,6-dimethyl-4,4-dioxo-5,6-dihydro-4H-4lambda6-1,4,3-oxathiazin-5-yl}phenol were dissolved in 3 ml of methanol and, after addition of 0.3 ml of concentrated hydrochloric acid, stirred at room temperature for 16 hours. The reaction solution was concentrated by rotary evaporation and coevaporated twice more with 10 ml of toluene, and the residue was purified in a purification laboratory by means of preparative HPLC. The product-containing fractions were combined, the acetonitrile was removed under reduced pressure, and the aqueous residue was basified with saturated aqueous sodium hydrogencarbonate solution. Subsequently, this aqueous residue was extracted with dichloromethane, and the combined organic phases were dried using a phase separator cartridge (Chromabond® PTS) and concentrated by rotary evaporation. The residue was taken up again in a mixture of acetonitrile and water and lyophilized. This gave the product (64.2 mg) with a molecular weight of 404.5 g/mol ($C_{20}H_{24}N_2O_5S$); MS (ESI): m/e=405 (M+H$^+$).

(S)-3-[5-(3-Methoxyphenyl)-6,6-dimethyl-4,4-dioxo-5,6-dihydro-4H-4lambda6-[1,4,3]oxathiazin-2-ylamino]-3-phenylpropan-1-ol

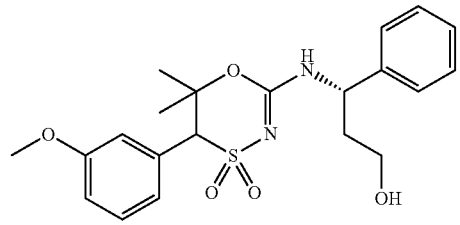 [SMILES: COc1cccc(C2C(C)(C)OC(N[C@@H](CCO)c3ccccc3)=NS2(=O)=O)c1]

To a solution of 452 mg of 3-{2-[(S)-3-(tert-butyldimethylsilanyloxy)-1-phenylpropylamino]-6,6-dimethyl-4,4-dioxo-5,6-dihydro-4H-4lambda6-1,4,3-oxathiazin-5-yl}phenol and 148 mg of methyl iodide in THF at 0° C. was added dropwise 0.44 ml of a 2 N solution of sodium bis(trimethylsilyl)amide in THF. After stirring at constant temperature for 45 minutes and then warming up to room temperature, the reaction solution was stirred for a further 4 hours and then the conversion was checked by LCMS. A further 0.20 ml of the 2 N solution of sodium bis(trimethylsilyl)

amide in THF and 114 mg of methyl iodide were added. After stirring at room temperature for 16 hours, the reaction solution was diluted with 60 ml of water, 5 ml of 5% aqueous sodium thiosulfate solution were added and the mixture was extracted twice with 30 ml of ethyl acetate. The combined organic phases were dried over $MgSO_4$ and concentrated by rotary evaporation. To detach the protecting group, the residue was dissolved in 5 ml of methanol and, after addition of 0.5 ml of concentrated hydrochloric acid, stirred at room temperature for 1 hour. The reaction solution was diluted with 50 ml of water and extracted twice with ethyl acetate. The combined organic phases were dried over $MgSO_4$ and concentrated by rotary evaporation, and the residue was purified in a purification laboratory by means of preparative HPLC. The product-containing fractions were combined and lyophilized. This gave the product (41.1 mg) with a molecular weight of 418.5 g/mol ($C_{21}H_{26}N_2O_5S$); MS (ESI): m/e=419 (M+H$^+$).

(S)-3-[5-(3-Chlorophenyl)-6,6-dimethyl-4,4-dioxo-5,6-dihydro-4H-4lambda6-[1,4,3]oxathiazin-2-ylamino]-3-phenylpropan-1-ol

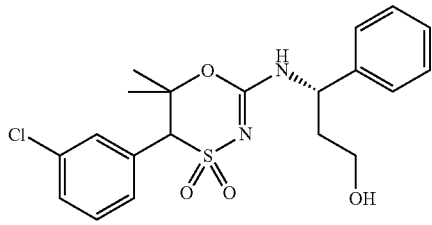 [SMILES: CC1(C)OC(N[C@@H](CCO)c2ccccc2)=NS(=O)(=O)C1c1cccc(Cl)c1]

C-(3-Chlorophenyl)-N-(2,4-dimethoxybenzyl)methanesulfonamide

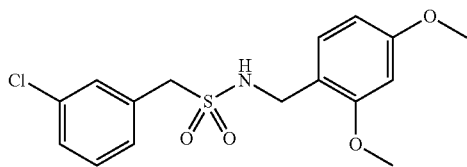 [SMILES: COc1ccc(CNS(=O)(=O)Cc2cccc(Cl)c2)c(OC)c1]

At room temperature, 1.06 g of 3-chlorophenylmethanesulfonyl chloride were initially charged in 30 ml of dichloromethane, and 1.42 ml of 2,4-dimethoxybenzylamine were added dropwise. The reaction mixture was stirred for 30 minutes. Then the mixture was admixed with 50 ml of water and 50 ml of water, and then the aqueous phase was washed once more with 30 ml of ethyl acetate. The combined organic phases were washed with 1 N aqueous hydrochloric acid, dried over $MgSO_4$ and concentrated by rotary evaporation. The residue (1.65 g) was used in the next reaction without further purification.

1-(3-Chlorophenyl)-2-hydroxy-2-methylpropane-1-sulfonamide

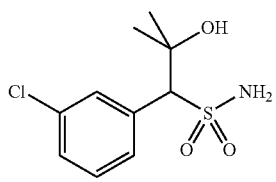 [SMILES: CC(C)(O)C(c1cccc(Cl)c1)S(N)(=O)=O]

Under inert gas, 1.65 g of C-(3-chlorophenyl)-N-(2,4-dimethoxybenzyl)methanesulfonamide were initially charged in 30 ml of THF, and then, at a temperature of −75° C., 6.67 ml of a 1.6 N methyllithium solution in diethyl ether were added dropwise and the mixture was stirred at constant temperature for 10 minutes. Subsequently, 1.86 ml of acetone were added. After stirring for 5 minutes, the reaction solution was admixed with 15 ml of trifluoroacetic acid and allowed to warm up to room temperature, and the solvent was removed under reduced pressure. The residue was dissolved in 10 ml of dichloromethane, and 2.5 ml of trifluoroacetic acid were added. After stirring at room temperature for 2 hours, the reaction solution was admixed with 50 ml of water, and the solid which precipitated out was filtered off with suction and washed with water. For drying, the product was coevaporated twice more with toluene. This gave the product (1.16 g) with a molecular weight of 263.7 g/mol ($C_{10}H_{14}ClNO_3S$).

(S)-3-[5-(3-Chlorophenyl)-6,6-dimethyl-4,4-dioxo-5,6-dihydro-4H-4lambda6-[1,4,3]oxathiazin-2-ylamino]-3-phenylpropan-1-ol

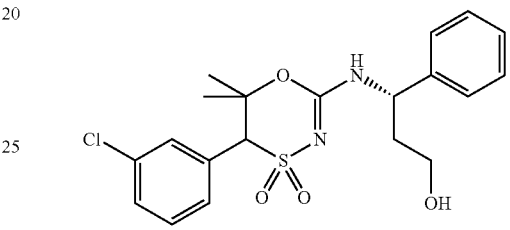

443 mg of (S)-3-(tert-butyldimethylsilanyloxy)-1-phenylpropylamine were initially charged in 10 ml of dichloromethane, and 325 mg of 1,1'-thiocarbonyldiimidazole were added. After stirring at room temperature for 45 minutes, the reaction solution was admixed with a mixture of 50 ml of diethyl ether and 50 ml of n-pentane and washed three times with 50 ml of water, dried over $MgSO_4$ and concentrated by rotary evaporation. Under inert gas, the residue and 400 mg of 1-(3-chlorophenyl)-2-hydroxy-2-methylpropane-1-sulfonamide were dissolved in 7 ml of NMP, and 0.68 ml of a 2 N solution of sodium bis(trimethylsilyl)amide in THF were added dropwise. After stirring for 10 minutes, 270 mg of N-bromosuccinimide were added and the resulting reaction mixture was stirred at constant temperature for 10 minutes. The reaction solution was diluted with 70 ml of ethyl acetate and washed once with 180 ml and twice with 75 ml of water. The organic phase was dried over $MgSO_4$ and concentrated by rotary evaporation, and the residue was taken up in 10 ml of methanol and, after addition of 1 ml of concentrated hydrochloric acid, stirred at room temperature for 1.5 hours. After dilution with 10 ml of water, the reaction solution was adjusted to pH 6 with saturated aqueous sodium hydrogencarbonate solution and extracted with 3×20 ml of ethyl acetate. After drying using a diatomaceous earth cartridge (Varian Chem Elut®), the organic phase was concentrated by rotary evaporation and the residue was purified in a purification laboratory by means of preparative HPLC. The product-containing fractions were combined, the acetonitrile was removed under reduced pressure, and the aqueous residue was brought to pH 5 with saturated aqueous sodium hydrogencarbonate solution. Subsequently, this aqueous residue was extracted three times with 20 ml of ethyl acetate, and the combined organic phases were dried using a diatomaceous earth cartridge (Varian Chem Elut®) and concentrated by rotary evaporation. The residue was taken up again in a mixture of acetonitrile and water and lyophilized. This gave the product (84.2 mg) with a molecular weight of 422.9 g/mol ($C_{20}H_{23}ClN_2O_4S$); MS (ESI): m/e=423 (M+H$^+$).

Compound 21 was synthesized by this preparation method:

(S)-3-[6,6-Dimethyl-4,4-dioxo-5-(3-trifluoromethylphenyl)-5,6-dihydro-4H-4lambda6-[1,4,3]oxathiazin-2-ylamino]-3-phenylpropan-1-ol Only at the 2-hydroxy-2-methyl-1-(3-trifluoromethylphenyl)propane-1-sulfonamide stage was the crude product additionally purified by means of normal phase chromatography using a Flashmaster with an n-heptane/ethyl acetate gradient.

Cyclohexyl-(5,6,6-trimethyl-4,4-dioxo-5-phenyl-5,6-dihydro-4H-4lambda6-[1,4,3]oxathiazin-2-yl)amine

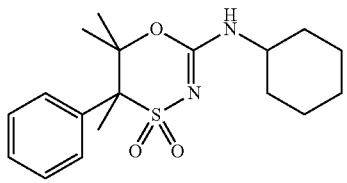 [SMILES: CC1(C)OC(NC2CCCCC2)=NS(=O)(=O)C1(C)c1ccccc1]

N-(2,4-Dimethoxybenzyl)-1-phenylethanesulfonamide

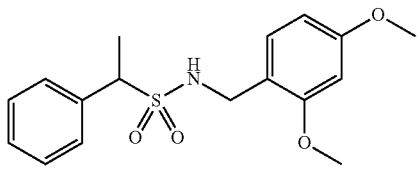 [SMILES: COc1ccc(CNS(=O)(=O)C(C)c2ccccc2)c(OC)c1]

Under inert gas, 375 mg of N-(2,4-dimethoxybenzyl)-C-phenylmethanesulfonamide were initially charged in 40 ml of THF, and then, at a temperature of −78° C., 1.46 ml of a 1.6 N butyllithium solution in hexane were added dropwise and the mixture was left to stir for 5 minutes. After the addition of 166 mg of methyl iodide, the reaction mixture was allowed to come to room temperature. The reaction solution was admixed with 50 ml of water and 50 ml of ethyl acetate, and the aqueous phase was reextracted with 50 ml of ethyl acetate. The combined organic phases were dried over MgSO$_4$ and concentrated by rotary evaporation, and the residue was purified by means of normal phase chromatography using a Flashmaster with an n-heptane/ethyl acetate gradient. The product-containing fractions were combined and concentrated by rotary evaporation. This gave the product (334 mg) with a molecular weight of 335.4 g/mol ($C_{17}H_{21}NO_4S$).

3-Hydroxy-3-methyl-2-phenylbutane-2-sulfonamide

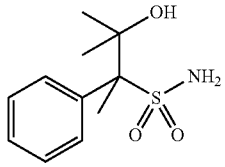 [SMILES: CC(C)(O)C(C)(c1ccccc1)S(N)(=O)=O]

Under inert gas, 330 mg of N-(2,4-dimethoxybenzyl)-1-phenylethanesulfonamide were initially charged in 5 ml of THF, and then, at a temperature of −78° C., 1.41 ml of a 1.6 N butyllithium solution in hexane were added dropwise and the mixture was stirred for 5 minutes. Subsequently, 0.22 ml of acetone was added, the mixture was stirred briefly and, after the addition of 1 ml of trifluoroacetic acid, the reaction solution was allowed to come to room temperature. The reaction mixture was admixed with 50 ml of water and 50 ml of ethyl acetate, and the aqueous phase was reextracted with 50 ml of ethyl acetate. The combined organic phases were dried over MgSO$_4$ and concentrated by rotary evaporation, and the residue was purified by means of normal phase chromatography using a Flashmaster with an n-heptane/ethyl acetate gradient. The product-containing fractions were combined and concentrated by rotary evaporation. This gave the product (113 mg) with a molecular weight of 243.3 g/mol ($C_{11}H_7NO_3S$).

[5-(3-Bromophenyl)-5,6,6-trimethyl-4,4-dioxo-5,6-dihydro-4H-4lambda6-[1,4,3]oxathiazin-2-yl]-[(S)-1-(2-fluorophenyl)ethyl]amine

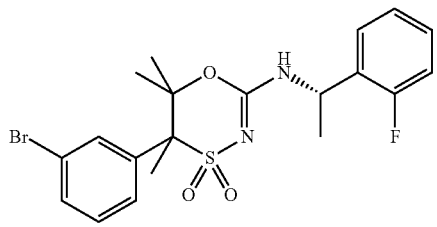 [SMILES: C[C@H](NC1=NS(=O)(=O)C(C)(c2cccc(Br)c2)C(C)(C)O1)c1ccccc1F]

N-(2,4-Dimethoxybenzyl)-1-(3-bromophenyl)ethanesulfonamide

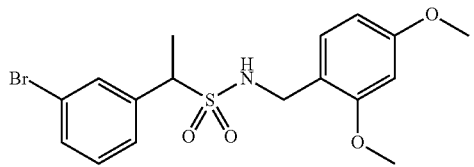 [SMILES: COc1ccc(CNS(=O)(=O)C(C)c2cccc(Br)c2)c(OC)c1]

Under inert gas, 3.50 g of C-(3-bromophenyl)-N-(2,4-dimethoxybenzyl)methanesulfonamide were initially charged in 40 ml of THF, and then, at a temperature of −76° C., 10.93 ml of a 1.6 N methyllithium solution in diethyl ether were added dropwise and the mixture was stirred for 5 minutes. After the addition of 1.24 g of methyl iodide, the reaction mixture was allowed to come to room temperature. The reaction solution was admixed with water and ethyl acetate, and the aqueous phase was reextracted with ethyl acetate. The combined organic phases were dried over MgSO$_4$ and concentrated by rotary evaporation, and the residue was purified by means of normal phase chromatography using a Flashmaster with an n-heptane/ethyl acetate gradient. The product-containing fractions were combined and concentrated by rotary evaporation. This gave the product (2.83 g) with a molecular weight of 414.3 g/mol ($C_{17}H_{20}BrNO_4S$).

2-(3-Bromophenyl)-3-hydroxy-3-methylbutane-2-sulfonamide

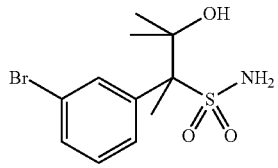 [SMILES: CC(C)(O)C(C)(c1cccc(Br)c1)S(N)(=O)=O]

Under inert gas, 2.82 g of N-(2,4-dimethoxybenzyl)-1-(3-bromophenyl)ethanesulfonamide was initially charged in 40 ml of THF, and then, at a temperature of −76° C., 10.00 ml of a 1.6 N methyllithium solution in diethyl ether were added dropwise and the mixture was stirred at constant temperature for 5 minutes. Subsequently, 1.50 ml of acetone were added. After stirring for 5 minutes, the reaction solution was allowed to warm up to room temperature, and the solvent was removed under reduced pressure. The residue was dissolved in 30 ml of dichloromethane, 2 ml of trifluoroacetic acid were added and the mixture was stirred at room temperature for 90 minutes. The conversion was checked by LCMS, a further 2 ml of trifluoroacetic acid were added and the mixture was stirred for 75 minutes. Then, 40 ml of water were added while stirring vigorously, the phases were separated and the aqueous phase was washed again with 2×30 ml of dichloromethane. The combined organic phases were concentrated by rotary evaporation and coevaporated twice with toluene. The crude product was purified by means of normal phase chromatography using a Flashmaster with a dichloromethane/methanol gradient. The product-containing fractions were combined and concentrated by rotary evaporation. This gave the product (1.10 g) with a molecular weight of 322.2 g/mol ($C_{11}H_{16}BrNO_3S$); MS (ESI): m/e=341 (M+H$_2$O+H$^+$).

5-(3-Bromophenyl)-2-methoxy-5,6,6-trimethyl-5,6-dihydro-1,4,3-oxathiazine 4,4-dioxide

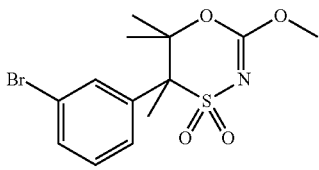 [SMILES: COC1=NS(=O)(=O)C(C)(c2cccc(Br)c2)C(C)(C)O1]

A suspension of 1.10 g of 2-(3-bromophenyl)-3-hydroxy-3-methylbutane-2-sulfonamide in 10 ml of tetramethoxymethane was admixed with 2 ml of acetic acid and stirred at 100° C. for 5 hours. After the removal of the solvent under reduced pressure, the crude product was purified by means of normal phase chromatography using a Flashmaster with an n-heptane/ethyl acetate gradient. The product-containing fractions were combined and concentrated by rotary evaporation. This gave the product (0.61 g) with a molecular weight of 362.2 g/mol ($C_{13}H_{16}BrNO_4S$).

[5-(3-Bromophenyl)-5,6,6-trimethyl-4,4-dioxo-5,6-dihydro-4H-4lambda6-1,4,3-oxathiazin-2-yl]-[(S)-1-(2-fluorophenyl)ethyl]amine

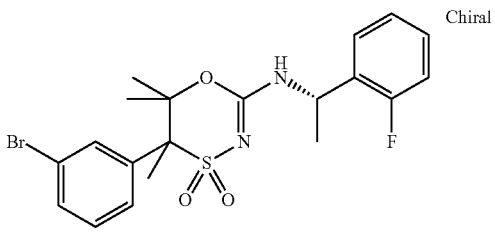 [SMILES: C[C@H](NC1=NS(=O)(=O)C(C)(c2cccc(Br)c2)C(C)(C)O1)c1ccccc1F]

A solution of 209 mg of 5-(3-bromophenyl)-2-methoxy-5,6,6-trimethyl-5,6-dihydro-1,4,3-oxathiazine 4,4-dioxide and 92 mg of (S)-1-(2-fluorophenyl)ethylamine in 5 ml of methylene chloride was stirred at room temperature for 1 hour and the conversion was checked by LCMS. Since no conversion had taken place yet, the solvent was concentrated by rotary evaporation and the residue was stirred at room temperature for 19 hours. The crude product was purified by means of normal phase chromatography using a Flashmaster with an n-heptane/ethyl acetate gradient. The product-containing fractions were combined and concentrated by rotary evaporation. This gave the product (170 mg) with a molecular weight of 469.4 g/mol ($C_{20}H_{22}BrFN_2O_3S$); MS (ESI): m/e=469 (M+H$^+$).

(S)-3-[5-(3-Bromophenyl)-5,6,6-trimethyl-4,4-dioxo-5,6-dihydro-4H-4lambda6-[1,4,3]oxathiazin-2-ylamino]-3-phenylpropan-1-ol

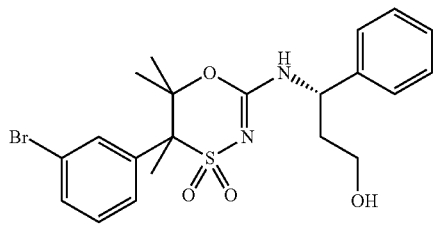

[5-(3-Bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-phenylpropyl]amine

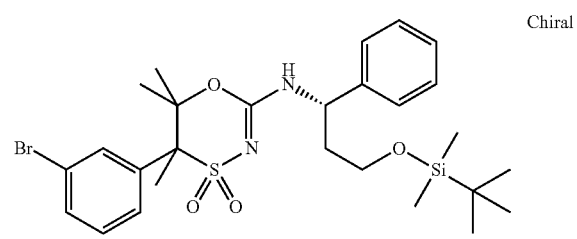 [SMILES: CC1(C)OC(N[C@@H](CCO[Si](C)(C)C(C)(C)C)c2ccccc2)=NS(=O)(=O)C1(C)c1cccc(Br)c1]

A solution of 209 mg of 5-(3-bromophenyl)-2-methoxy-5,6,6-trimethyl-5,6-dihydro-1,4,3-oxathiazine 4,4-dioxide and 181 mg of (S)-3-(tert-butyldimethylsilanyloxy)-1-phenylpropylamine in 5 ml of methylene chloride was stirred at room temperature for 1 hour and the conversion was checked by LCMS. Since no conversion had taken place yet, the solvent was concentrated by rotary evaporation and the residue was stirred at room temperature for 19 hours. The crude product was purified by means of normal phase chromatography using a Flashmaster with an n-heptane/ethyl acetate gradient. The product-containing fractions were combined and concentrated by rotary evaporation. This gave the product (237 mg) with a molecular weight of 595.7 g/mol ($C_{27}H_{39}BrN_2O_4SSi$); MS (ESI): m/e=596 (M+h$^+$).

(S)-3-[5-(3-Bromophenyl)-5,6,6-trimethyl-4,4-dioxo-5,6-dihydro-4H-4lambda6-[1,4,3]oxathiazin-2-ylamino]-3-phenylpropan-1-ol

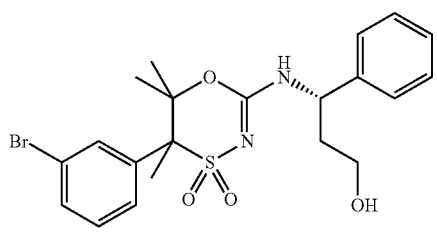 [SMILES: CC1(C)OC(N[C@@H](CCO)c2ccccc2)=NS(=O)(=O)C1(C)c1cccc(Br)c1]

To detach the protecting group, 20 mg of [5-(3-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-phenylpropyl]amine were dissolved in 1 ml of methanol and, after addition of 0.05 ml of concentrated hydrochloric acid, the mixture was stirred at room temperature for 2 hours. The reaction solution was concentrated by rotary evaporation and the residue purified in a purification laboratory by means of preparative HPLC. The product-containing fractions were combined, the acetonitrile was removed under reduced pressure, and the aqueous residue was basified with saturated aqueous sodium hydrogencarbonate solution. Subsequently, this aqueous residue was extracted with ethyl acetate, and the combined organic phases were dried using a cartridge containing diatomaceous earth (Varian Chem Elut®) and concentrated by rotary evaporation. The residue was taken up again in a mixture of acetonitrile and water and lyophilized. This gave the product (10.2 mg) with a molecular weight of 481.4 g/mol ($C_{21}H_{25}BrN_2O_4S$); MS (ESI): m/e=482 (M+H$^+$).

(S)-3-[5-(3-Bromophenyl)-5,6,6-trimethyl-4,4-dioxo-5,6-dihydro-4H-4lambda6-[1,4,3]oxathiazin-2-ylamino]-3-(2-fluorophenyl)propan-1-ol

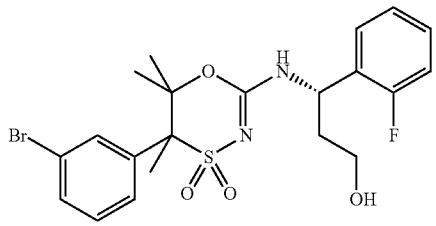 [SMILES: CC1(C)OC(N[C@@H](CCO)c2ccccc2F)=NS(=O)(=O)C1(C)c1cccc(Br)c1]

(S)-3-(tert-Butyl-dimethylsilanyloxy)-1-(2-fluorophenyl)propylamine

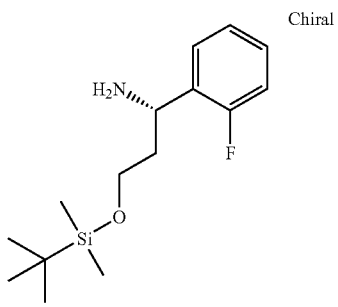 [SMILES: CC(C)(C)[Si](C)(C)OCC[C@H](N)c1ccccc1F]

Under inert gas, 2.80 g of lithium aluminum hydride were added in portions to a suspension of 0.97 g of (S)-3-amino-3-(2-fluorophenyl)propionic acid in 80 ml of THF, and the reaction mixture was then stirred at a temperature of 50° C. for 3 hours. 3 ml of water, 1 ml of 12 N aqueous sodium hydroxide solution and another 10 ml of water were added and the mixture was stirred for 10 minutes. The precipitate was filtered off, the filtrate was concentrated by rotary evaporation, the residue was dissolved once again in methylene chloride, and the solution was dried over MgSO$_4$ and concentrated by rotary evaporation. For further reaction, a solution of the residue in methylene chloride was admixed with 2.22 ml of triethylamine and 1.20 g of tert-butylchlorodimethylsilane. After stirring at room temperature overnight, the reaction solution was washed with aqueous sodium hydrogencarbonate solution, dried over MgSO$_4$ and concentrated by rotary evaporation. The crude product was purified by means of normal phase chromatography using a Flashmaster with an n-heptane/ethyl acetate gradient. The product-containing fractions were combined and concentrated by rotary evaporation. This gave the product (880 g) with a molecular weight of 283.5 g/mol ($C_{15}H_{26}FNOSi$); MS (ESI): m/e=284 (M+H$^+$).

[5-(3-Bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-(2-fluorophenyl)-propyl]amine

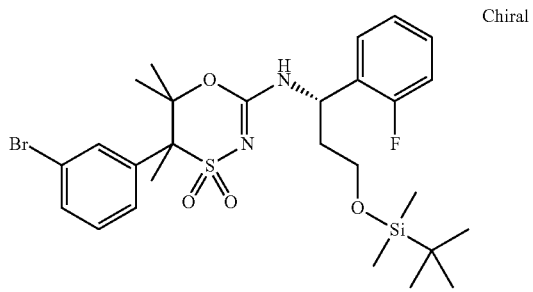 [SMILES: CC1(C)OC(N[C@@H](CCO[Si](C)(C)C(C)(C)C)c2ccccc2F)=NS(=O)(=O)C1(C)c1cccc(Br)c1]

A solution of 188 mg of 5-(3-bromophenyl)-2-methoxy-5,6,6-trimethyl-5,6-dihydro-1,4,3-oxathiazine 4,4-dioxide and 157 mg of (S)-3-(tert-butyldimethylsilanyloxy)-1-(2-fluorophenyl)propylamine in 2 ml of methylene chloride was stirred at room temperature for 3 hours and the conversion was checked by LCMS. Since no reaction had taken place yet, the solvent was concentrated by rotary evaporation and the residue with addition of 0.25 ml of methylene chloride was stirred at room temperature for 17 hours. Subsequently, the reaction mixture was stirred at 50° C. for 4 hours. The crude product was purified by means of normal phase chromatography using a Flashmaster with an n-heptane/ethyl acetate gradient. The product-containing fractions were combined and concentrated by rotary evaporation. This gave the product (206 mg) with a molecular weight of 613.7 g/mol ($C_{27}H_{38}BrFN_2O_4SSi$); MS (ESI): m/e=614 (M+H$^+$).

(S)-3-[5-(3-Bromophenyl)-5,6,6-trimethyl-4,4-dioxo-5,6-dihydro-4H-4lambda6-[1,4,3]oxathiazin-2-ylamino]-3-(2-fluorophenyl)propan-1-ol

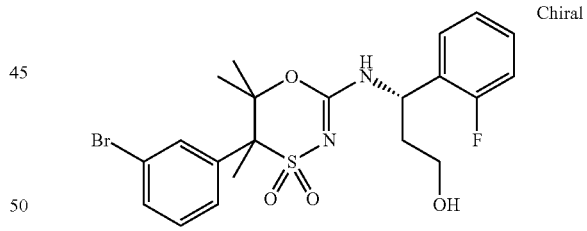

To detach the protecting group, 20 mg of [5-(3-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-(2-fluorophenyl)propyl]amine were dissolved in 1 ml of methanol and, after addition of 0.05 ml of concentrated hydrochloric acid, the mixture was stirred at room temperature for 2.5 hours. The reaction solution was concentrated by rotary evaporation and the residue purified in a purification laboratory by means of preparative HPLC. The product-containing fractions were combined, the acetonitrile was removed under reduced pressure, and the aqueous residue was basified with saturated aqueous sodium hydrogencarbonate solution. Subsequently, this aqueous residue was extracted with ethyl acetate, and the combined organic phases were dried over MgSO$_4$ and concentrated by rotary evaporation. The residue was taken up again in a mixture of acetonitrile and water and lyophilized. This gave the product (10.2 mg) with a molecular weight of 499.4 g/mol ($C_{21}H_{24}BrFN_2O_4S$); MS (ESI): m/e=500 (M+H$^+$).

(S)-3-Phenyl-3-(5,6,6-trimethyl-4,4-dioxo-5-phenyl-5,6-dihydro-4H-4lambda6-[1,4,3]oxathiazin-2-ylamino)propan-1-ol

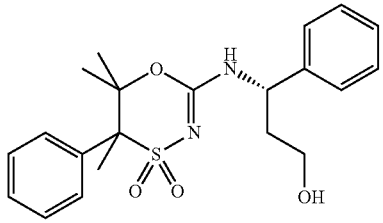 [SMILES: CC1(C)OC(N[C@@H](CCO)c2ccccc2)=NS(=O)(=O)C1(C)c1ccccc1]

Under inert gas, 50 mg of [5-(3-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-phenylpropyl]amine were initially charged in 4 ml of methanol and, with addition of 18 mg of 10% Pd/C, a gentle hydrogen stream was passed through for 1 hour. The reaction solution was concentrated by rotary evaporation and the residue purified in a purification laboratory by means of preparative HPLC. The product-containing fractions were combined, the acetonitrile was removed under reduced pressure, and the aqueous residue was basified with saturated aqueous sodium hydrogencarbonate solution. Subsequently, this aqueous residue was extracted with ethyl acetate, and the combined organic phases were dried over MgSO$_4$ and concentrated by rotary evaporation. The residue was taken up again in a mixture of acetonitrile and water and lyophilized. This gave the product (22.8 mg) with a molecular weight of 402.5 g/mol ($C_{21}H_{26}N_2O_4S$); MS (ESI): m/e=403 (M+H$^+$).

Compounds 43 and 48 were likewise synthesized by this preparation method from the bromine-containing starting compounds:
[(S)-1-(2-Fluorophenyl)ethyl]-(5,6,6-trimethyl-4,4-dioxo-5-phenyl-5,6-dihydro-4H-4lambda6-[1,4,3]oxathiazin-2-yl)amine
(S)-3-(2-Fluorophenyl)-3-(5,6,6-trimethyl-4,4-dioxo-5-phenyl-5,6-dihydro-4H-4lambda6-[1,4,3]oxathiazin-2-ylamino)propan-1-ol (S)-3-(2-Fluorophenyl)-3-[5,6,6-trimethyl-4,4-dioxo-5-(3-pyrimidin-5-ylphenyl)-5,6-dihydro-4H-4lambda6-[1,4,3]oxathiazin-2-ylamino]propan-1-ol

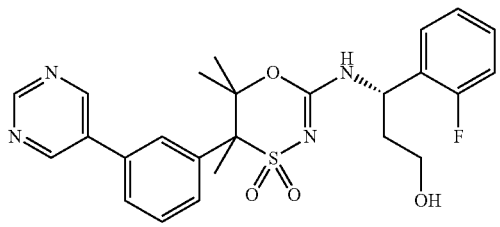 [SMILES: CC1(C)OC(N[C@@H](CCO)c2ccccc2F)=NS(=O)(=O)C1(C)c1cccc(-c2cncnc2)c1]

Under inert gas, 45 mg of [5-(3-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-(2-fluorophenyl)propyl]amine, 11 mg of pyrimidine-5-boronic acid and 96 mg of cesium carbonate were dissolved in a mixture of 1 ml of dioxane and 0.4 ml of water. After purging with argon for 10 minutes, 6 mg of dichloro[1,1'-bis(diphenylphosphino)ferrocene]palladium were added and the reaction mixture was stirred at 80° C. for 4 hours. The reaction mixture was allowed to cool to room temperature, diluted with ethyl acetate and washed with water. The organic phase was dried using a diatomaceous earth cartridge (Varian Chem Elut®) and concentrated by rotary evaporation. To detach the protecting group, the residue was dissolved in 1.5 ml of methanol, 0.18 ml of concentrated hydrochloric acid was added and the mixture was stirred at room temperature for 2.5 hours. After the removal of the solvent under reduced pressure, the crude product was purified in a purification laboratory by means of preparative HPLC. The product-containing fractions were combined, the acetonitrile was removed under reduced pressure, and the aqueous residue was basified with saturated aqueous sodium hydrogencarbonate solution and extracted with ethyl acetate. The organic phase was dried over MgSO$_4$ and concentrated by rotary evaporation, and the residue was taken up again in a mixture of acetonitrile and water and lyophilized. This gave the product (12.6 mg) with a molecular weight of 498.6 g/mol ($C_{25}H_{27}N_4O_4S$); MS (ESI): m/e=499 (M+H$^+$).

Compounds 40 and 41 were likewise synthesized by this preparation method:
(S)-3-Phenyl-3-[5,6,6-trimethyl-4,4-dioxo-5-(3-pyrimidin-5-ylphenyl)-5,6-dihydro-4H-4lambda6-[1,4,3]oxathiazin-2-ylamino]propan-1-ol
[(S)-1-(2-Fluorophenyl)ethyl]-[5,6,6-trimethyl-4,4-dioxo-5-(3-pyrimidin-5-ylphenyl)-5,6-dihydro-4H-4lambda6-[1,4,3]oxathiazin-2-yl]amine (no need to detach the protecting group)

(S)-3-(2-Fluorophenyl)-3-{5-[3-(4-methanesulfonylpiperazin-1-yl)-phenyl]-5,6,6-trimethyl-4,4-dioxo-5,6-dihydro-4H-4lambda6-[1,4,3]oxathiazin-2-ylamino}propan-1-ol

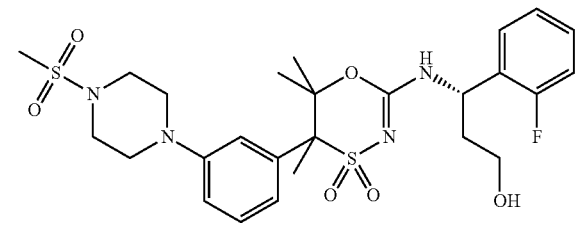 [SMILES: CC1(C)OC(N[C@@H](CCO)c2ccccc2F)=NS(=O)(=O)C1(C)c1cccc(N2CCN(S(C)(=O)=O)CC2)c1]

Under inert gas, 45 mg of [5-(3-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-(2-fluorophenyl)propyl]amine, 4 mg of bis(dibenzylideneacetone) palladium, 10 mg of 1,2,3,4,5-pentaphenyl-1-(di-tert-butylphosphino)ferrocene and 8 mg of potassium tert-butoxide were suspended in 1.5 ml of toluene. After purging with argon for 5 minutes, 15 mg of 1-methanesulfonylpiperazine were added and the reaction mixture was stirred at 80° C. for 2 hours. After cooling to room temperature, the mixture was diluted with ethyl acetate and washed with saturated aqueous sodium chloride solution. The organic phase was dried using a diatomaceous earth cartridge (Varian Chem Elut®) and concentrated by rotary evaporation. To detach the protecting group, the residue was dissolved in 1.5 ml of methanol, 0.18 ml of concentrated hydrochloric acid was added and the mixture was stirred at room temperature for 2.5 hours. After the removal of the solvent under reduced pressure, the crude product was purified in a purification laboratory by means of preparative HPLC. The product-containing fractions were combined, the acetonitrile was removed under reduced pressure, and the aqueous residue was basified with saturated aqueous sodium hydrogencarbonate solution and extracted with ethyl acetate. The organic phase was dried over MgSO₄ and concentrated by rotary evaporation, and the residue was taken up again in a mixture of acetonitrile and water and lyophilized. This gave the product (21.1 mg) with a molecular weight of 582.7 g/mol ($C_{26}H_{35}FN_4O_6S_2$); MS (ESI): m/e=583 (M+H⁺).

Compounds 34-36, 38-39, 45 and 49 were likewise synthesized by this preparation method:
(S)-3-{5-[3-(4-Methanesulfonylpiperazin-1-yl)-phenyl]-5,6,6-trimethyl-4,4-dioxo-5,6-dihydro-4H-4lambda6-[1,4,3]oxathiazin-2-ylamino}-3-phenylpropan-1-ol
[(S)-1-(2-Fluorophenyl)ethyl]-{5-[3-(4-methanesulfonylpiperazin-1-yl)-phenyl]-5,6,6-trimethyl-4,4-dioxo-5,6-dihydro-4H-4lambda6-[1,4,3]oxathiazin-2-yl}amine (no need to detach the protecting group)
[(S)-1-(2-Fluorophenyl)ethyl]-[5,6,6-trimethyl-4,4-dioxo-5-(3-pyrrolidin-1-ylphenyl)-5,6-dihydro-4H-4lambda6-[1,4,3]oxathiazin-2-yl]amine (no need to detach the protecting group)

In the case of the compounds which follow, the diastereomers were separated by means of RP chromatography in a purification laboratory.
(S)-3-Phenyl-3-[5,6,6-trimethyl-4,4-dioxo-5-(3-pyrrolidin-1-ylphenyl)-5,6-dihydro-4H-4lambda6-[1,4,3]oxathiazin-2-ylamino]propan-1-ol, stereomer 1 and 2
HPLC system: Waters Pump 2525, PAD 996, 2767 Sample Manager
MS system: Waters Micromass ZQ
Column: Waters SunFire Prep C18 OBD, 5 μm, 50×100 mm
Eluent: 0 min 90% H₂O (0.1% TFA)—2.0 min 90% H₂O—2.5 min 75% H₂O—10.5 min 75% acetonitrile—11.5 min 95% acetonitrile—13.0 min 95% acetonitrile (25° C., flow rate 120 ml/min)
Retention Times:
7.36 minutes (stereomer 1, 61.2 mg)
7.66 minutes (stereomer 2, 57.7 mg)
(S)-3-(2-Fluorophenyl)-3-[5,6,6-trimethyl-4,4-dioxo-5-(3-pyrrolidin-1-ylphenyl)-5,6-dihydro-4H-4lambda6-[1,4,3]oxathiazin-2-ylamino]propan-1-ol, stereomer 1 and 2
HPLC system: Waters Pump 2525, PAD 996, 2767 Sample Manager
MS system: Waters Micromass ZQ
Column: Waters Atlantis dC18 OBD, 5 μm, 50×100 mm
Eluent: 0 min 90% H₂O (0.1% TFA)—2.0 min 90% H₂O—2.5 min 75% H₂O—10.5 min 75% acetonitrile—11.5 min 95% acetonitrile—13.0 min 95% acetonitrile (25° C., flow rate 120 ml/min)
Retention Times:
7.31 minutes (stereomer 1, 8.7 mg)
7.51 minutes (stereomer 2, 9.1 mg)

(S)-3-[5-(3-Bromophenyl)-5-fluoro-6,6-dimethyl-4,4-dioxo-5,6-dihydro-4H-4lambda6-[1,4,3]oxathiazin-2-ylamino]-3-phenylpropan-1-ol

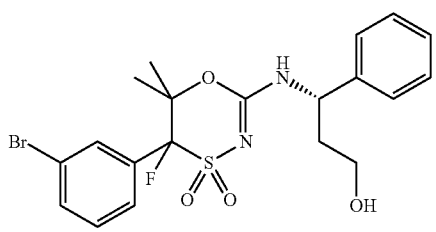 [SMILES: CC1(C)OC(N[C@@H](CCO)c2ccccc2)=NS(=O)(=O)C1(F)c1cccc(Br)c1]

C-(3-Bromophenyl)-N,N-bis(2,4-dimethoxybenzyl)methanesulfonamide

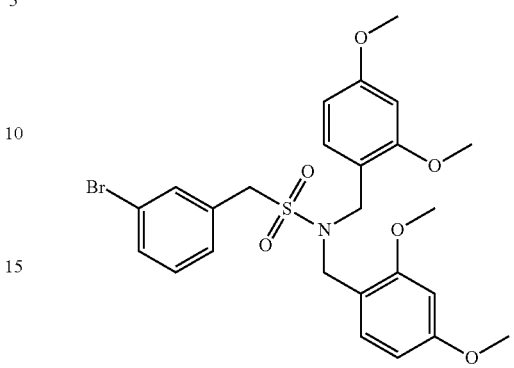

While cooling with ice, 4.94 g of 3-bromobenzylsulfonyl chloride were initially charged in 60 ml of dichloromethane and, within 15 minutes, a solution of 5.64 g of bis(2,4-dimethoxybenzyl)amine in 30 ml of dichloromethane and then a solution of 3.82 ml of N,N-diisopropylethylamine in 5 ml of dichloromethane were added dropwise. The reaction mixture was allowed to come to room temperature and stirred for 1 hour. Subsequently, the mixture was washed with 50 ml of water, with 50 ml of 1 N aqueous hydrochloric acid, with 50 ml of saturated aqueous sodium hydrogencarbonate solution and finally with 50 ml of saturated aqueous sodium chloride solution. The organic phase was dried over MgSO₄ and concentrated by rotary evaporation. The crude product was purified by means of normal phase chromatography using a Flashmaster with an n-heptane/ethyl acetate gradient. The product-containing fractions were combined and concentrated by rotary evaporation. This gave the product (9.23 g) with a molecular weight of 550.5 g/mol ($C_{25}H_{28}BrNO_6S$).

C-(3-Bromophenyl)-N,N-bis(2,4-dimethoxybenzyl)-C-fluoromethanesulfonamide

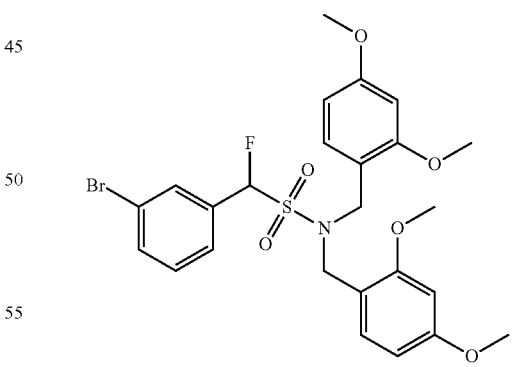

Under inert gas, 1.97 g of C-(3-bromophenyl)-N,N-bis(2,4-dimethoxybenzyl)methanesulfonamide were initially charged in 30 ml of THF, and then, at a temperature of −78° C., 3.56 ml of a 1.6 N methyllithium solution in diethyl ether were added dropwise. The reaction mixture was stirred briefly and then a solution of 1.49 g of N-fluorophenylsulfonimide in 5 ml of THF was added. After stirring at constant temperature for 10 minutes, 2 ml of acetic acid were added and the reaction mixture was allowed to come to room temperature. After concentration by rotary evaporation, the crude product was purified by means of normal phase chromatography using a Flashmaster with an n-heptane/ethyl acetate gradient. The product-containing fractions were combined and concentrated by rotary evaporation. This gave the product (0.64 g) with a molecular weight of 568.5 g/mol ($C_{25}H_{27}BrFNO_6S$).

1-(3-Bromophenyl)-1-fluoro-2-hydroxy-2-methyl-propane-1-sulfonamide

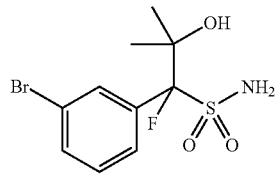 [SMILES: CC(C)(O)C(F)(c1cccc(Br)c1)S(N)(=O)=O]

Under inert gas, 310 mg of C-(3-bromophenyl)-N,N-bis(2,4-dimethoxybenzyl)-C-fluoromethanesulfonamide were initially charged in 10 ml of THF, and then, at a temperature of −78° C., 0.68 ml of a 1.6 N methyllithium solution in diethyl ether were added dropwise and the mixture was stirred at constant temperature for 10 minutes. Subsequently, 0.25 ml of acetone were added. After stirring for 10 minutes, the reaction solution was admixed with 0.10 ml of trifluoroacetic acid, and the reaction mixture was allowed to come to room temperature and concentrated by rotary evaporation. The residue was dissolved in 10 ml of dichloromethane, 1.5 ml of trifluoroacetic acid were added and the mixture was stirred at room temperature for 20 minutes. The reaction solution was freed of the solvent and the crude product was purified by means of normal phase chromatography using a Flashmaster with a dichloromethane/methanol gradient. The product-containing fractions were combined and concentrated by rotary evaporation. This gave the product (77.9 mg) with a molecular weight of 326.2 g/mol ($C_{10}H_{13}BrFNO_3S$); MS (ESI): m/e=345 (M+$H_2O$+$H^+$).

5-(3-Bromophenyl)-2-ethoxy-5-fluoro-6,6-dimethyl-5,6-dihydro-1,4,3-oxathiazine 4,4-dioxide

A mixture of 75 mg of 1-(3-bromophenyl)-1-fluoro-2-hydroxy-2-methylpropane-1-sulfonamide in 5 ml of tetraethoxymethane and 1 ml of acetic acid was stirred at 100° C. for 1.5 hours. The conversion was checked by LCMS. Since it was incomplete, the reaction mixture was stirred at 100° C. for a further 3.5 hours. After the removal of the solvents under reduced pressure, the residue was purified by means of normal phase chromatography using a Flashmaster with an n-heptane/ethyl acetate gradient. The product-containing fractions were combined and concentrated by rotary evaporation. This gave the product (45.6 mg) with a molecular weight of 380.2 g/mol ($C_{13}H_{15}BrFNO_4S$).

(S)-3-[5-(3-Bromophenyl)-5-fluoro-6,6-dimethyl-4,4-dioxo-5,6-dihydro-4H-4lambda6-[1,4,3]oxathiazin-2-ylamino]-3-phenylpropan-1-ol

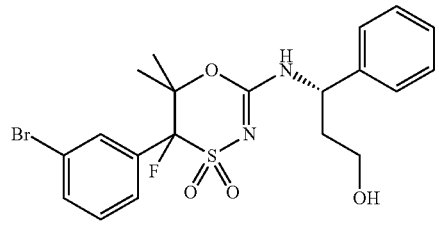 [SMILES: CC1(C)OC(N[C@@H](CCO)c2ccccc2)=NS(=O)(=O)C1(F)c1cccc(Br)c1]

In a round-bottom flask, 42 mg of 5-(3-bromophenyl)-2-ethoxy-5-fluoro-6,6-dimethyl-5,6-dihydro-1,4,3-oxathiazine 4,4-dioxide was dissolved under inert gas in 0.2 ml of dichloromethane and admixed with 20 mg of (S)-3-amino-3-phenylpropan-1-ol. After stirring at room temperature for 18 hours, the conversion was checked by LCMS. Since only traces of the product had formed, the reaction mixture was stirred at 100° C. for a further 4.5 hours. After the removal of the solvent under reduced pressure, the crude product was purified in a purification laboratory by means of preparative HPLC. The product-containing fractions were combined, the acetonitrile was removed under reduced pressure, and the aqueous residue was basified with saturated aqueous sodium hydrogencarbonate solution and extracted with ethyl acetate. The organic phase was dried over $MgSO_4$ and concentrated by rotary evaporation, and the residue was taken up again in a mixture of acetonitrile and water and lyophilized. This gave the product (13.1 mg) with a molecular weight of 485.4 g/mol ($C_{20}H_{22}BrFN_2O_4S$); MS (ESI): m/e=485 (M+$H^+$).

(S)-3-(5-Biphenyl-4-yl-6,6-dimethyl-4,4-dioxo-5,6-dihydro-4H-4lambda6-[1,4,3]oxathiazin-2-ylamino)-3-(2-fluorophenyl)propan-1-ol

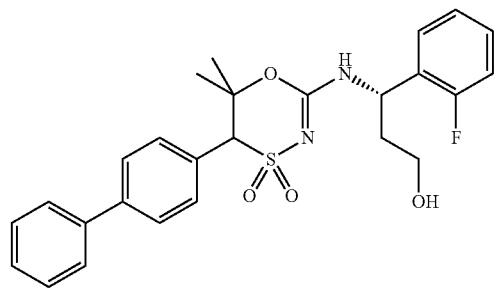 [SMILES: CC1(C)OC(N[C@@H](CCO)c2ccccc2F)=NS(=O)(=O)C1c1ccc(-c2ccccc2)cc1]

Biphenyl-4-yl-methanesulfonic acid sodium salt

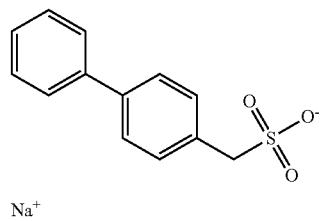 [SMILES: O=S(=O)([O-])Cc1ccc(-c2ccccc2)cc1 ; [Na+]]

A mixture of 28.69 g of 4-bromomethylbiphenyl and 29.27 g of sodium sulfite in 200 ml of a mixture of water and methanol (1:1) was stirred at 60° C. for 12 hours. After cooling to room temperature, the solvent was removed under reduced pressure and the aqueous residue was extracted twice with 100 ml of ethyl acetate. The aqueous phase was concentrated by rotary evaporation and the solid residue was stirred with 200 ml of isopropanol for 1 hour. After filtration to remove the solid constituents, the filtrate was concentrated by rotary evaporation. This gave the product (15.80 g) with a molecular weight of 270.3 g/mol ($C_{13}H_{11}O_3S \cdot Na$).

C-Biphenyl-4-yl-N-(2,4-dimethoxybenzyl)methanesulfonamide

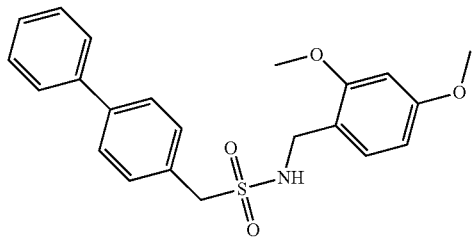 [SMILES: COc1ccc(CNS(=O)(=O)Cc2ccc(-c3ccccc3)cc2)c(OC)c1]

Under inert gas, 8.00 g of biphenyl-4-yl-methanesulfonic acid sodium salt and 2.50 ml of N,N-dimethylformamide were initially charged in 165 ml of THF, then, at a temperature of −20° C., 6.50 ml of oxalyl chloride were added dropwise and the reaction solution was allowed to come to 0° C. within 1 hour. The reaction solution was diluted with 200 ml of methyl tert-butyl ether and washed with 200 ml of water, with 200 ml of dilute aqueous sodium hydrogencarbonate solution and with 100 ml of saturated sodium chloride solution. The organic phase was dried over MgSO$_4$ and concentrated by rotary evaporation. The residue (7.41 g) was dissolved in 200 ml of THF and then, at a temperature of −20° C., 11.00 ml of 2,4-dimethoxybenzylamine were added dropwise and the reaction solution was allowed to come to room temperature within 30 minutes. After stirring for 48 hours, the reaction solution was diluted with 200 ml of ethyl acetate and washed with 100 ml each of water, 1 N aqueous hydrochloric acid, saturated aqueous sodium hydrogencarbonate solution and saturated sodium chloride solution. The organic phase was dried over MgSO$_4$ and concentrated by rotary evaporation. The crude product was purified by filtration through a silica gel column. The column was washed through with ethyl acetate until no further product eluted. The eluate was concentrated by rotary evaporation, the residue was dissolved in a little dichloromethane, the solution was concentrated again by rotary evaporation and the solids were then dried under high vacuum. This gave the product (10.89 g) with a molecular weight of 397.5 g/mol ($C_{22}H_{23}NO_4S$).

1-Biphenyl-4-yl-2-hydroxy-2-methylpropane-1-sulfonamide

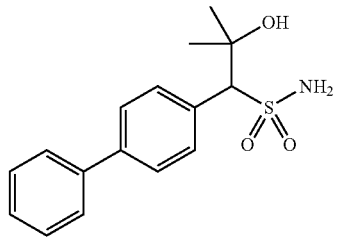 [SMILES: CC(C)(O)C(c1ccc(-c2ccccc2)cc1)S(N)(=O)=O]

Under inert gas, 4.01 g of C-biphenyl-4-yl-N-(2,4-dimethoxybenzyl)methanesulfonamide were initially charged in 100 ml of THF and then, at a temperature of −71° C., 12.60 ml of a 1.6 N butyllithium solution in hexane were added dropwise. The reaction mixture was stirred for a further 10 minutes and then admixed dropwise with 4.53 ml of acetone. The mixture was stirred at constant temperature for 10 minutes, 2 ml of trifluoroacetic acid were added and the mixture was allowed to come to room temperature. The residue was dissolved in 100 ml of dichloromethane, and 20 ml of trifluoroacetic acid were added. After stirring at room temperature for 20 minutes, the reaction solution was washed with saturated aqueous sodium hydrogencarbonate solution, and the organic phase together with the precipitate was concentrated by rotary evaporation and then coevaporated with toluene. The crude product was purified by means of normal phase chromatography using a Flashmaster with a dichloromethane/methanol gradient. The product-containing fractions were combined and concentrated by rotary evaporation. This gave the product (3.15 g) with a molecular weight of 305.4 g/mol ($C_{16}H_{19}NO_3S$).

5-Biphenyl-4-yl-2-ethoxy-6,6-dimethyl-5,6-dihydro-1,4,3-oxathiazine 4,4-dioxide

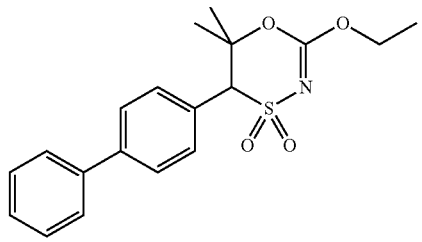 [SMILES: CCOC1=NS(=O)(=O)C(c2ccc(-c3ccccc3)cc2)C(C)(C)O1]

A mixture of 3.14 g of 1-biphenyl-4-yl-2-hydroxy-2-methylpropane-1-sulfonamide in 75 ml of tetraethoxymethane and 15 ml of acetic acid was stirred at 100° C. for 24 hours. The conversion was checked by LCMS. Since it was incomplete, the reaction mixture was admixed with a further 15 ml of acetic acid and stirred at 120° C. for 4 hours. Subsequently, a further 20 ml of tetraethoxymethane were added and the reaction mixture was stirred at 120° C. for 5 hours. Since, by checking with LCMS, no further conversion had been achieved, the solvent was removed under reduced pressure and the residue was purified by means of normal phase chromatography using a Flashmaster with an n-heptane/ethyl acetate gradient. The product-containing fractions were combined and concentrated by rotary evaporation. This gave the product (1.04 g) with a molecular weight of 359.5 g/mol ($C_{19}H_{21}NO_4S$).

(S)-3-(5-Biphenyl-4-yl-6,6-dimethyl-4,4-dioxo-5,6-dihydro-4H-4lambda6-[1,4,3]oxathiazin-2-ylamino)-3-(2-fluorophenyl)propan-1-ol

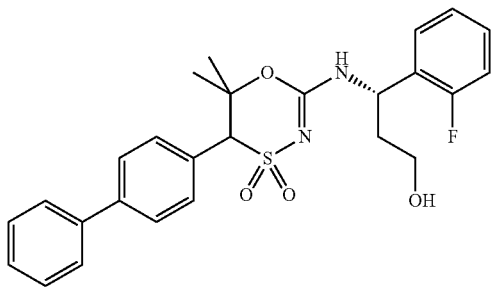 [SMILES: CC1(C)OC(N[C@@H](CCO)c2ccccc2F)=NS(=O)(=O)C1c1ccc(-c2ccccc2)cc1]

In a round-bottom flask, 346 mg of 5-biphenyl-4-yl-2-ethoxy-6,6-dimethyl-5,6-dihydro-1,4,3-oxathiazine 4,4-dioxide were dissolved under inert gas in 2 ml of dichloromethane and admixed with 328 mg of (S)-3-(tert-butyldimethylsilanyloxy)-1-(2-fluorophenyl)propylamine. After concentration by rotary evaporation, the residue was suspended in 0.5 ml of dichloromethane and stirred at room temperature for 18 hours. The conversion was checked by LCMS. Since reactant was still present, the reaction mixture, after the addition of 1 ml of toluene, was stirred at 50° C. for 1 hour. Even after stirring at 75° C. for a further 4 hours, the conversion remained incomplete. The solvent was removed under reduced pressure. To detach the protecting group, the residue was taken up in 1 ml of methanol and, after addition of 0.05 ml of concentrated hydrochloric acid, stirred at room temperature for 1 hour. After concentration by rotary evaporation, the residue was purified in a purification laboratory by means of preparative HPLC. The product-containing fractions were combined and freed of the solvent under reduced pressure. The aqueous residue was extracted with ethyl acetate, and the combined organic phases were dried using a diatomaceous earth cartridge (Varian Chem Elut®) and concentrated by rotary evaporation. The residue was dissolved in a mixture of acetonitrile and water and lyophilized. This gave the product (221 mg) with a molecular weight of 482.6 g/mol ($C_{26}H_{27}FN_2O_4S$); MS (ESI): m/e=483 (M+H$^+$).

A chiral separation of the diastereomer mixture was conducted.
HPLC system: Waters 2690UP, PAD 2996
Column: Chiralpak AD-H/83, 5 μm, 250×4.6 mm
Eluent: n-heptane:ethanol:methanol 5:1:1 (30° C., flow rate 1 ml/min)
Retention Times:
5.722 minutes (stereomer 1, 42 mg)
11.110 minutes (stereomer 2, 37 mg)

Compound 52 was likewise synthesized by this preparation method:
(5-Biphenyl-4-yl-6,6-dimethyl-4,4-dioxo-5,6-dihydro-4H-4lambda6-[1,4,3]oxathiazin-2-yl)-[(S)-1-(2-fluorophenyl)ethyl]amine (no need to detach the protecting group).

Compounds 58-60 were synthesized analogously to this preparation method. Through the reaction of 1-(4-tert-butylphenyl)-2-hydroxy-2-methylpropane-1-sulfonamide with tetramethoxymethane, 5-(4-tert-butylphenyl)-2-methoxy-6,6-dimethyl-5,6-dihydro-1,4,3-oxathiazine 4,4-dioxide was prepared, which then reacted in a further conversion with the respective amines even at room temperature.

(S)-3-[5-(4-tert-Butylphenyl)-6,6-dimethyl-4,4-dioxo-5,6-dihydro-4H-4lambda6-[1,4,3]oxathiazin-2-ylamino]-3-(2-fluorophenyl)propan-1-ol

[5-(4-tert-Butylphenyl)-6,6-dimethyl-4,4-dioxo-5,6-dihydro-4H-4lambda6-[1,4,3]oxathiazin-2-yl]-[(S)-1-(2-fluorophenyl)ethyl]amine (S)-3-[5-(4-tert-Butylphenyl)-6,6-dimethyl-4,4-dioxo-5,6-dihydro-4H-4lambda6-[1,4,3]oxathiazin-2-ylamino]-3-phenylpropan-1-ol A chiral separation of the diastereomer mixture of compound 58 was conducted.
HPLC system: Waters 2690UP, PAD 2996
Column: Chiralpak AD-H/44 250×4.6 mm
Eluent: n-heptane:ethanol:methanol 5:1:1 (1 ml/min)
Retention Times:
3.836 minutes (stereomer 1, 38 mg)
4.969 minutes (stereomer 2, 34 mg)

(S)-3-(5-Biphenyl-4-yl-5,6,6-trimethyl-4,4-dioxo-5,6-dihydro-4H-4lambda6-[1,4,3]oxathiazin-2-ylamino)-3-(2-fluorophenyl)propan-1-ol

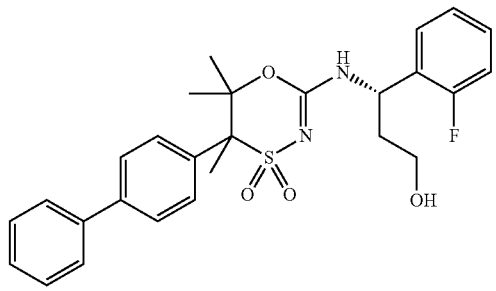 [SMILES: CC1(C)OC(N[C@@H](CCO)c2ccccc2F)=NS(=O)(=O)C1(C)c1ccc(-c2ccccc2)cc1]

The synthesis of N-[2,4-dimethoxybenzyl]-1-(4-bromophenyl)ethanesulfonamide was effected analogously to N-[2,4-dimethoxybenzyl]-1-(3-bromophenyl)ethanesulfonamide 2-(4-Bromophenyl)-3-hydroxy-3-methylbutane-2-sulfonamide

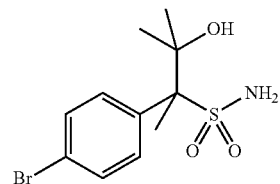 [SMILES: CC(C)(O)C(C)(c1ccc(Br)cc1)S(N)(=O)=O]

Under inert gas, 2.58 g of N-(2,4-dimethoxybenzyl)-1-(4-bromophenyl)ethanesulfonamide was initially charged in 40 ml of THF, and then, at a temperature of −78° C., 7.90 ml of a 1.6 N methyllithium solution in diethyl ether were added dropwise and the mixture was stirred at constant temperature for 10 minutes. Subsequently, 2.47 ml of acetone were added. After stirring for 15 minutes, the reaction solution was admixed with 0.96 ml of trifluoroacetic acid and allowed to warm up to room temperature. After the removal of the solvent under reduced pressure, the residue was dissolved in 50 ml of dichloromethane, 10 ml of trifluoroacetic acid were added and the mixture was stirred at room temperature for 1 hour. 100 ml of methanol were added to the reaction solution and the solvent was concentrated by rotary evaporation. The crude product was purified by filtration through a silica gel column. The column was washed through with ethyl acetate until no further product eluted. The eluate was concentrated by rotary evaporation and the residue (2.01 g) was used in the next reaction without further purification.

5-(4-Bromophenyl)-2-methoxy-5,6,6-trimethyl-5,6-dihydro-1,4,3-oxathiazine 4,4-dioxide

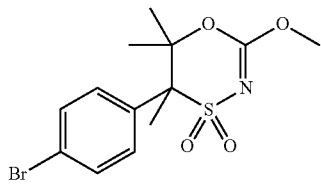 [SMILES: COC1=NS(=O)(=O)C(C)(c2ccc(Br)cc2)C(C)(C)O1]

A suspension of 2.01 g of 2-(4-bromophenyl)-3-hydroxy-3-methylbutane-2-sulfonamide in 15 ml of tetramethoxymethane was admixed with 3 ml of acetic acid and stirred at 100° C. for 1.5 hours. After the removal of the solvent under reduced pressure, the crude product was purified by means of normal phase chromatography using a Flashmaster with an n-heptane/ethyl acetate gradient. The product-containing fractions were combined, concentrated by rotary evaporation and dried under high vacuum. This gave the product (0.21 g) with a molecular weight of 362.2 g/mol ($C_{13}H_{16}BrNO_4S$).

[5-(4-Bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-(2-fluorophenyl) propyl]amine

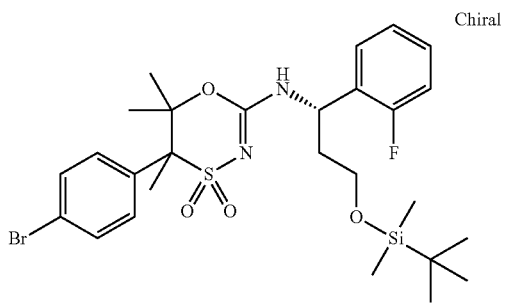 [SMILES: CC1(C)OC(N[C@@H](CCO[Si](C)(C)C(C)(C)C)c2ccccc2F)=NS(=O)(=O)C1(C)c1ccc(Br)cc1]

A solution of 70 mg of 5-(4-bromophenyl)-2-methoxy-5,6,6-trimethyl-5,6-dihydro-1,4,3-oxathiazine 4,4-dioxide and 66 mg of (S)-3-(tert-butyldimethylsilanyloxy)-1-(2-fluorophenyl)propylamine in 1 ml of methylene chloride was stirred under a gentle argon stream, such that the solvent evaporated gradually. After stirring at room temperature overnight, the residue was dissolved in 20 ml of dichloromethane and extracted with 10 ml of 0.5 N aqueous hydrochloric acid and 10 ml of water. The organic phase was dried using a phase separator cartridge (Chromabond® PTS), concentrated by rotary evaporation and dried under high vacuum. This gave the product (113 mg) with a molecular weight of 613.7 g/mol ($C_{27}H_{38}BrFN_2O_4SSi$); MS (ESI): m/e=614 (M+H$^+$).

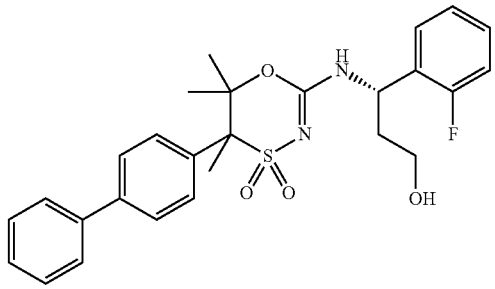 [SMILES: CC1(C)OC(N[C@@H](CCO)c2ccccc2F)=NS(=O)(=O)C1(C)c1ccc(-c2ccccc2)cc1]

Under inert gas, 5.50 ml of a 0.5 N zinc chloride solution in THF were cooled to −75° C., and 1.08 ml of a 1.8 N phenyllithium solution in dibutyl ether was added dropwise. The reaction solution was allowed to come to room temperature and stirred for 30 minutes. Then this solution was added to a solution of 113 mg of [5-(4-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-(2-fluorophenyl)-propyl]amine and 8 mg of dichloro[1,1'-bis(diphenylphosphino)ferrocene]palladium in 3 ml of THF. After stirring at 60° C. for 75 minutes, the conversion was checked by LCMS and a further 5 mg of the catalyst were added. After 1 hour at constant temperature, another half of the above-described amount of the self-prepared solution of phenyllithium and zinc chloride was added, and the mixture was stirred at 60° C. for a further 60 minutes. Since, by LCMS, there was no further conversion, the reaction solution was filtered through silica gel and concentrated by rotary evaporation. The residue was dissolved in 3 ml of THF, admixed with 8 mg of dichloro[1,1'-bis(diphenylphosphino) ferrocene]palladium and the same amount of the above-described self-prepared solution of phenyllithium and zinc chloride, and stirred again at 60° C. for a further 60 minutes. Since still no increase in conversion was observed, the reaction solution was admixed with a mixture of 1.5 ml of dioxane and 0.5 ml of water, 179 mg of cesium carbonate, 27 mg of phenylboronic acid and 8 mg of dichloro[1,1'-bis(diphenylphosphino)ferrocene]palladium, and stirred further at 60° C. After 2 hours, the conversion was checked by LCMS and found to be complete. The reaction solution was admixed with ethyl acetate and water and the organic phase was dried over MgSO$_4$. After removal of the solvent under reduced pressure, the residue was dissolved in 1.5 ml of methanol, 0.15 ml of concentrated hydrochloric acid was added and the mixture was stirred at room temperature for 1 hour. The reaction solution was concentrated by rotary evaporation, the residue was extracted with 20 ml of ethyl acetate and 10 ml of water and the aqueous phase was washed once again with ethyl acetate. The combined organic phases were dried using a phase separator cartridge (Chromabond® PTS) and concentrated by rotary evaporation. The residue was purified by means of normal phase chromatography using a Flashmaster with an n-heptane/ethyl acetate gradient. The product-containing fractions were combined and concentrated by rotary evaporation, and the crude product was purified further in a purification laboratory by means of preparative HPLC. The product-containing fractions were combined, the acetonitrile was removed under reduced pressure, and the aqueous residue was basified with saturated aqueous sodium hydrogencarbonate solution and extracted with dichloromethane. The organic phase was dried over MgSO₄ and concentrated by rotary evaporation, and the residue was taken up again in a mixture of acetonitrile and water and lyophilized. This gave the product (34.2 mg) with a molecular weight of 496.6 g/mol ($C_{27}H_{29}FN_2O_4S$); MS (ESI): m/e=497 (M+H⁺).

(S)-3-(5-Biphenyl-4-yl-5,6,6-trimethyl-4,4-dioxo-5,6-dihydro-4H-4lambda6-[1,4,3]oxathiazin-2-ylamino)-3-phenylpropan-1-ol

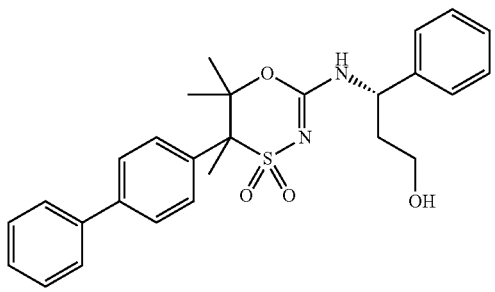 [SMILES: CC1(C)OC(N[C@@H](CCO)c2ccccc2)=NS(=O)(=O)C1(C)c1ccc(-c2ccccc2)cc1]

The synthesis of [5-(4-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-phenylpropyl]amine was effected analogously to [5-(4-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-(2-fluorophenyl)propyl]amine.

Under inert gas, 5.52 ml of a 0.5 N zinc chloride solution in THF were cooled to −75° C., and 1.02 ml of a 1.8 N phenyllithium solution in dibutyl ether was added dropwise. The reaction solution was allowed to come to room temperature and stirred for 30 minutes. Then this solution was added to a solution of 110 mg of [5-(4-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-phenylpropyl]amine and 8 mg of dichloro[1,1'-bis(diphenylphosphino)ferrocene]palladium in 3 ml of THF. After stirring at 60° C. for 75 minutes, the reaction solution was concentrated by rotary evaporation. To detach the protecting group, the residue was dissolved in 2 ml of methanol, 0.2 ml of concentrated hydrochloric acid was added and the mixture was stirred at room temperature for 1.5 hours. The reaction solution was concentrated by rotary evaporation and the residue was extracted with 20 ml of dichloromethane and 10 ml of water, and the aqueous phase was washed once again with 10 ml of dichloromethane. The combined organic phases were dried using a phase separator cartridge (Chromabond® PTS) and concentrated by rotary evaporation. The residue was purified by means of normal phase chromatography using a Flashmaster with an n-heptane/ethyl acetate gradient. The product-containing fractions were combined and concentrated by rotary evaporation, and the crude product was purified further in a purification laboratory by means of preparative HPLC. The product-containing fractions were combined, the acetonitrile was removed under reduced pressure, and the aqueous residue was basified with saturated aqueous sodium hydrogencarbonate solution and extracted with dichloromethane. The organic phase was dried over MgSO₄ and concentrated by rotary evaporation, and the residue was taken up again in a mixture of acetonitrile and water and lyophilized. This gave the product (39.7 mg) with a molecular weight of 478.6 g/mol ($C_{27}H_{30}N_2O_4S$); MS (ESI): m/e=479 (M+H⁺).

(5-Biphenyl-4-yl-5,6,6-trimethyl-4,4-dioxo-5,6-dihydro-4H-4lambda6-[1,4,3]oxathiazin-2-yl)-[(S)-1-(2-fluorophenyl)ethyl]amine

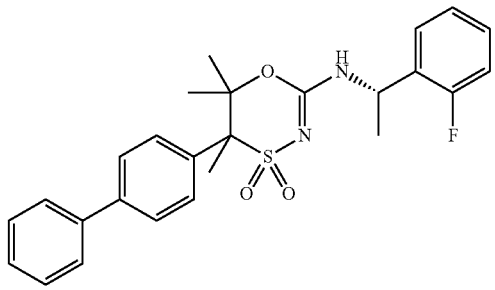 [SMILES: C[C@H](NC1=NS(=O)(=O)C(C)(c2ccc(-c3ccccc3)cc2)C(C)(C)O1)c1ccccc1F]

The synthesis of [5-(4-bromophenyl)-5,6,6-trimethyl-4,4-dioxo-5,6-dihydro-4H-4lambda6-1,4,3-oxathiazin-2-yl]-[(S)-1-(2-fluorophenyl)ethyl]amine was effected analogously to [544-bromophenyl)-5,6,6-trimethyl-4,4-dioxo-5,6-dihydro-4H-4lambda6-1,4,3-oxathiazin-2-yl]-[(S)-3-(tert-butyldimethylsilanyloxy)-1-(2-fluorophenyl)propyl]amine.

Under inert gas, 5.56 ml of a 0.5 N zinc chloride solution in THF were cooled to −75° C., and 1.03 ml of a 1.8 N phenyllithium solution in dibutyl ether was added dropwise. The reaction solution was allowed to come to room temperature and stirred for 30 minutes. Then this solution was added to a solution of 87 mg of [5-(4-bromophenyl)-5,6,6-trimethyl-4,4-dioxo-5,6-dihydro-4H-4lambda6-1,4,3-oxathiazin-2-yl]-[(S)-1-(2-fluorophenyl)ethyl]amine and 8 mg of dichloro[1,1'-bis(diphenylphosphino)ferrocene]palladium in 3 ml of THF. After stirring at 60° C. for 75 minutes, the conversion was checked by LCMS. Since it was incomplete, the reaction mixture was stirred at 60° C. for a further 2.5 hours. Since, by LCMS, no further conversion had taken place, another 30% of the above-described amount of the self-prepared solution of phenyllithium and zinc chloride was added, and the mixture was stirred at 60° C. for a further 60 minutes. Since, by LCMS, there was no further conversion, the reaction solution was concentrated by rotary evaporation. The residue was admixed with dichloromethane and water, and the organic phase was dried over MgSO₄ and concentrated by rotary evaporation. The residue was purified by means of normal phase chromatography using a Flashmaster with an n-heptane/ethyl acetate gradient. The product-containing fractions were combined and concentrated by rotary evaporation, and the crude product was purified further in a purification laboratory by means of preparative HPLC. The product-containing fractions were combined and lyophilized. This gave the product (29.1 mg) with a molecular weight of 466.6 g/mol ($C_{26}H_{27}FN_2O_3S$); MS (ESI): m/e=467 (M+H⁺).

[(S)-1-(2-Fluorophenyl)ethyl]-(5,6,6-trimethyl-4,4-dioxo-5-phenyl-5,6-dihydro-4H-4lambda6-[1,4,3]oxathiazin-2-yl)amine, stereomer 1

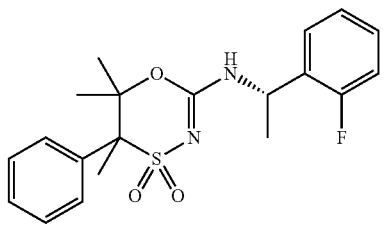 [SMILES: C[C@H](NC1=NS(=O)(=O)C(C)(c2ccccc2)C(C)(C)O1)c1ccccc1F]

5-(3-Bromophenyl)-2-ethoxy-5,6,6-trimethyl-5,6-dihydro-1,4,3-oxathiazine 4,4-dioxide

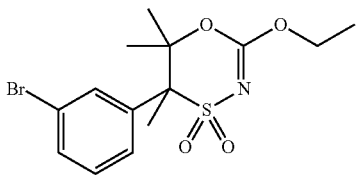 [SMILES: CCOC1=NS(=O)(=O)C(C)(c2cccc(Br)c2)C(C)(C)O1]

A suspension of 14.40 g of 2-(3-bromophenyl)-3-hydroxy-3-methylbutane-2-sulfonamide (50%, contaminated with 1-(3-bromophenyl)ethanesulfonamide)) in 100 ml of tetraethoxymethane was admixed with 12 ml of acetic acid and stirred at 100° C. under a strong argon stream for 6 hours. After the removal of the solvent under reduced pressure (bath temperature 70° C.), the viscous residue was dried at 50° C. in a vacuum drying cabinet for 16 hours. The conversion was checked by LCMS and found to be incomplete. Therefore, the oily residue was left to react on the rotary evaporator under reduced pressure (bath temperature 80° C.) for 4 hours. After the addition of 10 ml of acetic acid, the bath temperature was increased to 85° C. and the pressure was adjusted to 150 mbar. Subsequently, the volatile constituents were removed, again under reduced pressure, and the crude product was purified by means of normal phase chromatography using a Flashmaster with an n-heptane/ethyl acetate gradient. The product-containing fractions were combined and concentrated by rotary evaporation. This gave the product (5.97 g) with a molecular weight of 376.3 g/mol ($C_{14}H_{18}BrNO_4S$).

A chiral separation of the racemate was conducted. Subsequently, the two stereomers were converted further individually.
HPLC system: Waters 2690UP, PAD 2996
Column: Chiralpak AS-H/52, 5 μm, 250×4.6 mm
Eluent: n-heptane:ethanol 15:1+0.1% trifluoroacetic acid (30° C., flow rate 1 ml/min)
Retention Times:
8.348 minutes (stereomer 1, 1.22 g)
9.862 minutes (stereomer 2, 1.54 g)

[(S)-1-(2-Fluorophenyl)ethyl]-(5,6,6-trimethyl-4,4-dioxo-5-phenyl-5,6-dihydro-4H-4lambda6-[1,4,3]oxathiazin-2-yl)amine, stereomer 1

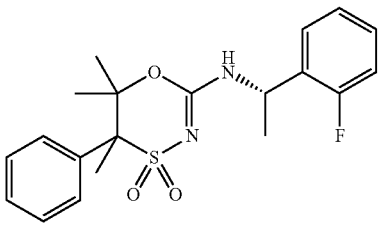 [SMILES: C[C@H](NC1=NS(=O)(=O)C(C)(c2ccccc2)C(C)(C)O1)c1ccccc1F]

In a round-bottom flask, 92 mg of 5-(3-bromophenyl)-2-ethoxy-5,6,6-trimethyl-5,6-dihydro-1,4,3-oxathiazine 4,4-dioxide stereomer 1 were dissolved in 1.3 ml of dichloromethane and admixed with 45 mg of (S)-1-(2-fluorophenyl)ethylamine. After stirring at room temperature and under a gentle argon stream for 18 hours, the conversion was checked by LCMS. Since it was incomplete, the reaction mixture was taken up in 1.5 ml of THF and stirred at 50° C. for 5 hours. After the removal of the solvent under reduced pressure, the oily residue was stirred at 95° C. for 2 hours and then at room temperature for 48 hours. According to LCMS, the reaction remained incomplete. The residue was dissolved under inert gas in 2 ml of ethanol and, with addition of 50 mg of 10% Pd/C, stirred under a hydrogen atmosphere at room temperature for 16 hours. After the addition of a further 50 mg of 10% Pd/C, the reaction mixture was stirred under the same conditions for a further 24 hours. After filtration to remove solid constituents, the filtrate was concentrated by rotary evaporation and the residue was purified in a purification laboratory by means of preparative HPLC. The product-containing fractions were combined, the acetonitrile was removed under reduced pressure, and the aqueous residue was lyophilized. This gave the product (45.7 mg) with a molecular weight of 390.5 g/mol ($C_{20}H_{23}FN_2O_3S$); MS (ESI): m/e=391 (M+H$^+$).

Compound 57 was likewise synthesized by this preparation method:
[(S)-1-(2-Fluorophenyl)ethyl]-(5,6,6-trimethyl-4,4-dioxo-5-phenyl-5,6-dihydro-4H-4lambda6-[1,4,3]oxathiazin-2-yl)amine, stereomer 2

(S)-3-[5-(4-tert-Butylphenyl)-5,6,6-trimethyl-4,4-dioxo-5,6-dihydro-4H-4lambda6-[1,4,3]oxathiazin-2-ylamino]-3-(2-fluorophenyl)propan-1-ol

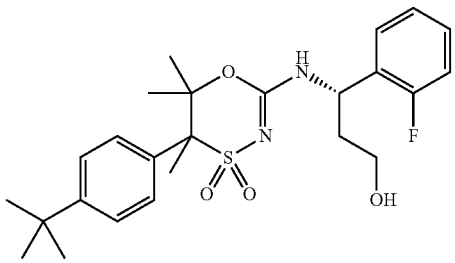 [SMILES: CC(C)(C)c1ccc(C2(C)C(C)(C)OC(N[C@@H](CCO)c3ccccc3F)=NS2(=O)=O)cc1]

N-[2,4-Dimethoxybenzyl]-2-(4-tert-butylphenyl)-3-hydroxy-3-methylbutane-2-sulfonamide

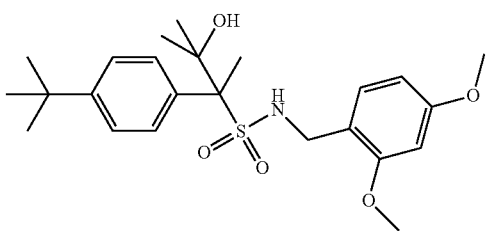 [SMILES: COc1ccc(CNS(=O)(=O)C(C)(c2ccc(C(C)(C)C)cc2)C(C)(C)O)c(OC)c1]

N-[2,4-Dimethoxybenzyl]-1-(4-tert-butylphenyl)ethanesulfonamide was prepared analogously to N-(2,4-dimethoxybenzyl)-1-phenylethanesulfonamide.

Under inert gas, 1.01 g of N-[2,4-dimethoxybenzyl]-1-(4-tert-butylphenyl)ethanesulfonamide were initially charged in 20 ml of THF and then, at a temperature of −75° C., 3.23 ml of a 1.6 N butyllithium solution in hexane were added dropwise and the mixture was stirred for 10 minutes. After the addition of 1.16 ml of acetone, the reaction mixture was stirred at constant temperature for 10 minutes. Subsequently, 0.45 ml of trifluoroacetic acid was added and the reaction solution was allowed to come to room temperature. After concentration by rotary evaporation, the crude product was purified using a Flashmaster with an n-heptane/ethyl acetate gradient. The product-containing fractions were combined and concentrated by rotary evaporation. This gave the product (484 mg) with a molecular weight of 449.6 g/mol ($C_{24}H_{35}NO_5S$).

2-(4-tert-Butylphenyl)-3-hydroxy-3-methylbutane-2-sulfonamide

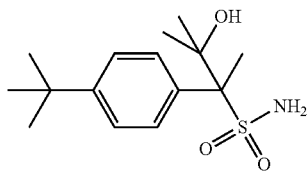 [SMILES: CC(C)(C)c1ccc(C(C)(C(C)(C)O)S(N)(=O)=O)cc1]

A solution of 480 mg of N-[2,4-dimethoxybenzyl]-2-(4-tert-butylphenyl)-3-hydroxy-3-methylbutane-2-sulfonamide in a mixture of 21 ml of acetonitrile and 7 ml of water was admixed at 0° C. with 2342 mg of cerium(IV) ammonium nitrate in portions. After stirring at room temperature for 1 hour, the reaction solution was diluted with 100 ml of dichloromethane and 15 ml of water and, after phase separation, the organic phase was dried using a phase separator cartridge (Chromabond® PTS) and concentrated by rotary evaporation. The crude product was purified by means of normal phase chromatography using a Flashmaster with a dichloromethane/methanol gradient. The product-containing fractions were combined and concentrated by rotary evaporation. This gave the product (202 mg) with a molecular weight of 299.4 g/mol ($C_{15}H_{25}NO_3S$).

The further conversion to (S)-3-[5-(4-tert-butylphenyl)-5,6,6-trimethyl-4,4-dioxo-5,6-dihydro-4H-4lambda6-[1,4,3]oxathiazin-2-ylamino]-3-(2-fluorophenyl)propan-1-ol was effected via the 5-(4-tert-butylphenyl)-2-methoxy-5,6,6-trimethyl-5,6-dihydro-1,4,3-oxathiazine 4,4-dioxide intermediate in analogy to the preparation of (S)-3-[5-(3-bromophenyl)-5,6,6-trimethyl-4,4-dioxo-5,6-dihydro-4H-4lambda6-[1,4,3]oxathiazin-2-ylamino]-3-phenylpropan-1-ol.

Compounds 62 and 63 were likewise synthesized by this preparation method:
(S)-3-[5-(4-tert-Butylphenyl)-5,6,6-trimethyl-4,4-dioxo-5,6-dihydro-4H-4lambda6-[1,4,3]oxathiazin-2-ylamino]-3-phenylpropan-1-ol
[5-(4-tert-Butylphenyl)-5,6,6-trimethyl-4,4-dioxo-5,6-dihydro-4H-4lambda6-[1,4,3]oxathiazin-2-yl]-[(S)-1-(2-fluorophenyl)ethyl]amine (no need to detach protecting group)

(S)-3-[5,6,6-Trimethyl-5-(2'-methylbiphenyl-4-yl)-4,4-dioxo-5,6-dihydro-4H-4lambda6-[1,4,3]oxathiazin-2-ylamino]-3-(2-fluorophenyl)propan-1-ol

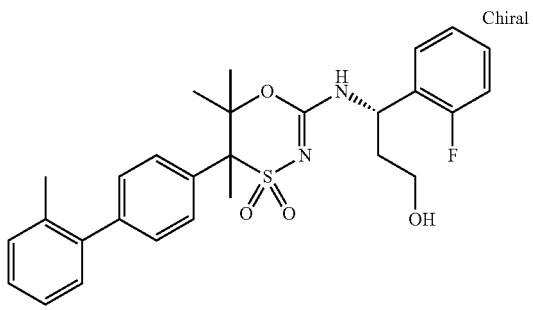 [SMILES: Cc1ccccc1-c1ccc(C2(C)C(C)(C)OC(N[C@@H](CCO)c3ccccc3F)=NS2(=O)=O)cc1]

A solution of 2-methylphenylboronic acid (57 mg), cesium carbonate (335 mg) and [5-(4-bromophenyl)-5,6,6-trimethyl-4,4-dioxo-5,6-dihydro-4H-4lambda6-[1,4,3]oxathiazin-2-yl]-[(S)-3-(tert-butyldimethylsilanyloxy)-1-(2-fluorophenyl)propyl]amine (210 mg) in dioxane (3 ml)/water (1 ml) was purged with argon for twenty minutes. Then 1,1'-bis(diphenylphosphino)ferrocenepalladium(II) chloride (24 mg) was added and the mixture was stirred at 80° C. for forty-five minutes. Subsequently, ethyl acetate (20 ml) was added and the mixture was washed with water (10 ml). The organic phase was dried using a kieselguhr cartridge, filtered and concentrated under reduced pressure. This was followed by purification by column chromatography (ethyl acetate/heptane). The residue of the fractions of value (197 mg) was taken up in methanol (4 ml), concentrated hydrochloric acid was added and the mixture was stirred overnight. The solvent was removed, and the residue was taken up in dichloromethane (20 ml) and washed with water (20 ml). The organic phase was dried with a phase separator cartridge and concentrated. The residue was purified by column chromatography (ethyl acetate/heptane). This gave the product (124 mg) with a molecular weight of 496.6 g/mol ($C_{27}H_{29}FN_2O_4S$), MS (ESI): (M+H+) 421 g/mol.

The following compounds were obtained in the same way:

(S)-3-[5-(4'-Fluorobiphenyl-4-yl)-5,6,6-trimethyl-4,4-dioxo-5,6-dihydro-4H-4lambda6-[1,4,3]oxathiazin-2-ylamino]-3-(2-fluorophenyl)propan-1-ol

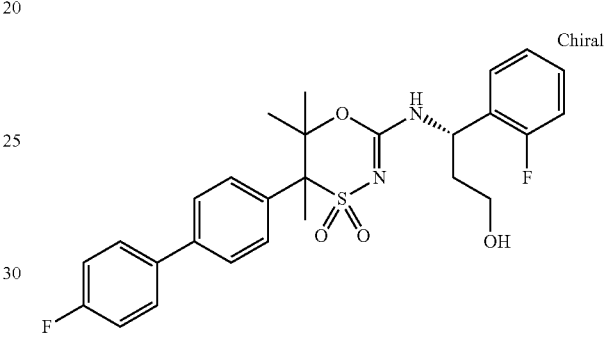

(S)-3-(2-Fluorophenyl)-3-[5-(4'-methoxybiphenyl-4-yl)-5,6,6-trimethyl-4,4-dioxo-5,6-dihydro-4H-4lambda6-[1,4,3]oxathiazin-2-ylamino]propan-1-ol

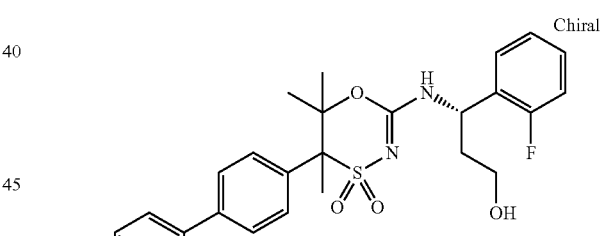

(S)-3-(5-Biphenyl-4-yl-6,6-dimethyl-4,4-dioxo-5,6-dihydro-4H-4lambda6-[1,4,3]oxathiazin-2-ylamino)-3-(2,4-difluorophenyl)propan-1-ol

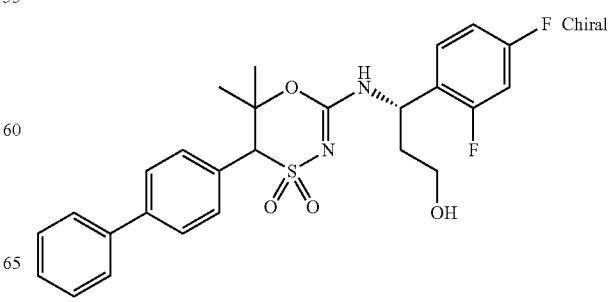

A solution of phenylboronic acid (88 mg), cesium carbonate (423 mg) and [5-(4-bromophenyl)-6,6-dimethyl-4,4-dioxo-5,6-dihydro-4H-4lambda6-[1,4,3]oxathiazin-2-yl]-[(S)-3-(tert-butyldimethylsilanyloxy)-1-(2,4-difluorophenyl)propyl]amine (360 mg) in dioxane (3.8 ml)/water (1.2 ml) was purged with argon for twenty minutes. Then 1,1'-bis(diphenylphosphino)ferrocenepalladium(II) chloride (50 mg) was added and the mixture was stirred for 65° C. for thirty minutes. Subsequently, ethyl acetate (20 ml) was added and the mixture was washed with water (10 ml). The organic phase was dried using a kieselguhr cartridge, filtered and concentrated under reduced pressure. This was followed by purification by column chromatography (ethyl acetate/heptane). The residue of the fractions of value (197 mg) was taken up in methanol (4 ml), concentrated hydrochloric acid was added and the mixture was stirred overnight. The solvent was removed, and the residue was taken up in dichloromethane (20 ml) and washed with water (20 ml). The organic phase was dried with a phase separator cartridge and concentrated. The residue was purified by column chromatography (ethyl acetate/heptane). This gave the product (150 mg) with a molecular weight of 500.5 g/mol ($C_{26}H_{26}F_2N_2O_4S$), MS (ESI): (M+H+) 501 g/mol.

The following compounds were obtained in the same way:

3-(5-Biphenyl-4-yl-6,6-dimethyl-4,4-dioxo-5,6-dihydro-4H-4lambda6-[1,4,3]oxathiazin-2-ylamino)-3-(2,3-difluorophenyl)propan-1-ol

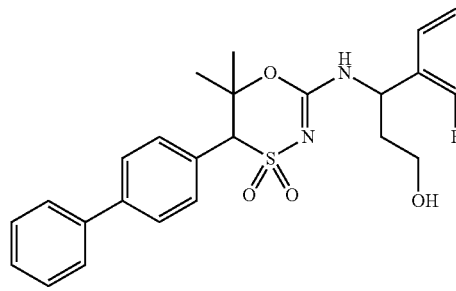

(S)-3-(5-Biphenyl-4-yl-6,6-dimethyl-4,4-dioxo-5,6-dihydro-4H-4lambda6-[1,4,3]oxathiazin-2-ylamino)-3-(2-chlorophenyl)propan-1-ol

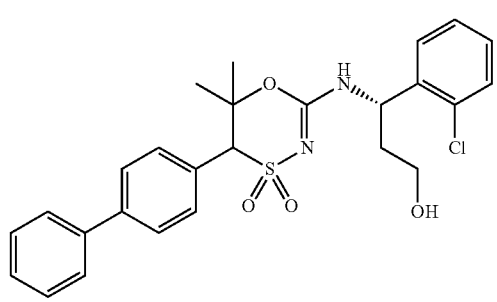

(S)-3-(2-Fluorophenyl)-3-[5-(3'-methoxybiphenyl-4-yl)-6,6-dimethyl-4,4-dioxo-5,6-dihydro-4H-4lambda6-[1,4,3]oxathiazin-2-ylamino]propan-1-ol

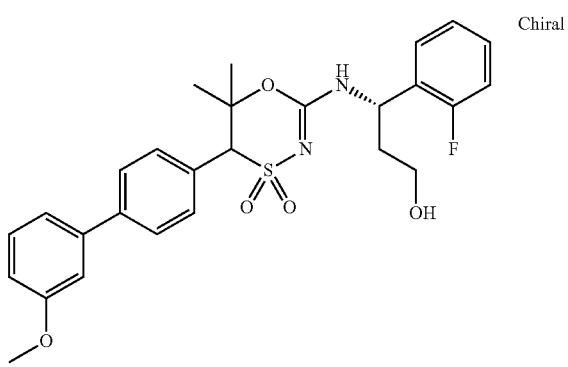 [SMILES: COc1cccc(-c2ccc(C3C(C)(C)OC(N[C@@H](CCO)c4ccccc4F)=NS3(=O)=O)cc2)c1]

4'-{2-[(S)-1-(2-Fluorophenyl)-3-hydroxypropylamino]-6,6-dimethyl-4,4-dioxo-5,6-dihydro-4H-4lambda6-[1,4,3]oxathiazin-5-yl}-biphenyl-2-carbonitrile

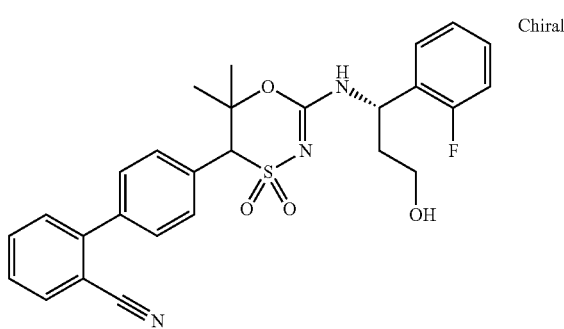 [SMILES: CC1(C)OC(N[C@@H](CCO)c2ccccc2F)=NS(=O)(=O)C1c1ccc(-c2ccccc2C#N)cc1]

(S)-3-(5-Biphenyl-4-yl-6,6-dimethyl-4,4-dioxo-5,6-dihydro-4H-4lambda6-[1,4,3]oxathiazin-2-ylamino)-3-(4-chlorophenyl)propan-1-ol

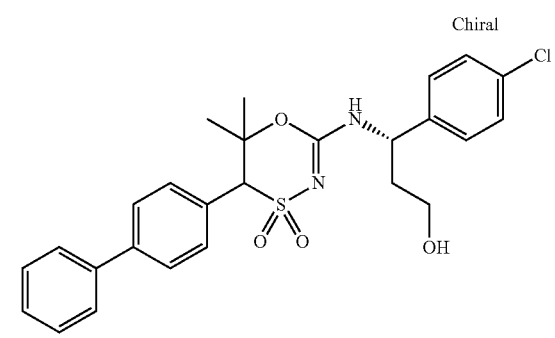 [SMILES: CC1(C)OC(N[C@@H](CCO)c2ccc(Cl)cc2)=NS(=O)(=O)C1c1ccc(-c2ccccc2)cc1]

193

(S)-3-(5-Biphenyl-4-yl-6,6-dimethyl-4,4-dioxo-5,6-dihydro-4H-4lambda6-[1,4,3]oxathiazin-2-ylamino)-3-(3-chlorophenyl)propan-1-ol

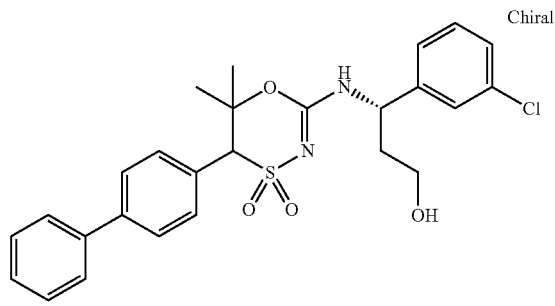 [SMILES: CC1(C)OC(N[C@@H](CCO)c2cccc(Cl)c2)=NS(=O)(=O)C1c1ccc(-c2ccccc2)cc1]

(S)-3-[6,6-Dimethyl-4,4-dioxo-5-(4-pyrimidin-5-ylphenyl)-5,6-dihydro-4H-4lambda6-[1,4,3]oxathiazin-2-ylamino]-3-(2-fluorophenyl)propan-1-ol

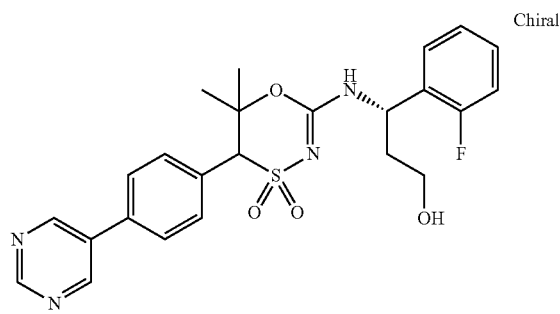 [SMILES: CC1(C)OC(N[C@@H](CCO)c2ccccc2F)=NS(=O)(=O)C1c1ccc(-c2cncnc2)cc1]

(S)-3-{5-[4-(5-Chlorothiophen-2-yl)-phenyl]-6,6-dimethyl-4,4-dioxo-5,6-dihydro-4H-4lambda6-[1,4,3]oxathiazin-2-ylamino}-3-(2-fluorophenyl)propan-1-ol

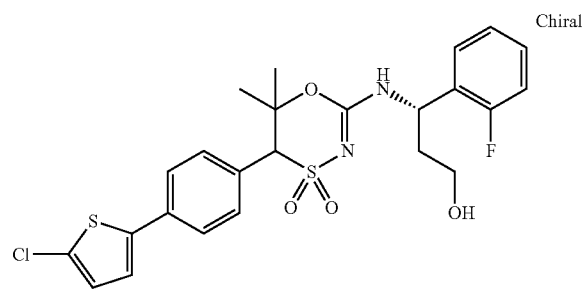 [SMILES: CC1(C)OC(N[C@@H](CCO)c2ccccc2F)=NS(=O)(=O)C1c1ccc(-c2ccc(Cl)s2)cc1]

194

(S)-3-{5-[4-(2,5-Dichlorothiophen-3-yl)-phenyl]-6,6-dimethyl-4,4-dioxo-5,6-dihydro-4H-4lambda6-[1,4,3]oxathiazin-2-ylamino}-3-(2-fluorophenyl)propan-1-ol

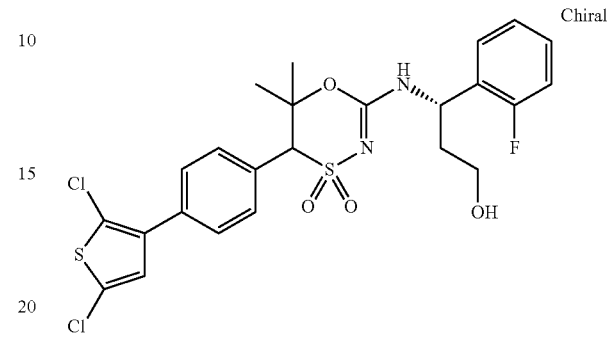

4'-{2-[(S)-1-(2-Fluorophenyl)-3-hydroxypropylamino]-6,6-dimethyl-4,4-dioxo-5,6-dihydro-4H-4lambda6-[1,4,3]oxathiazin-5-yl}-biphenyl-3-carbonitrile

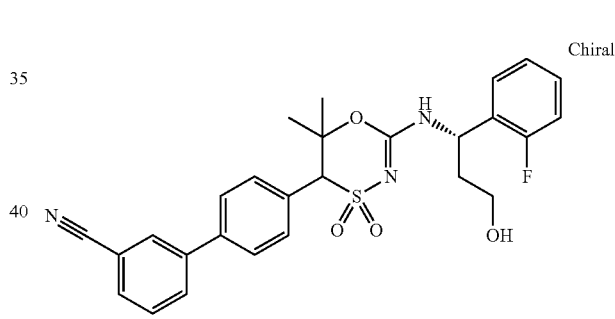

(S)-3-(2-Fluorophenyl)-3-[5-(2'-methoxybiphenyl-4-yl)-6,6-dimethyl-4,4-dioxo-5,6-dihydro-4H-4lambda6-[1,4,3]oxathiazin-2-ylamino]propan-1-ol

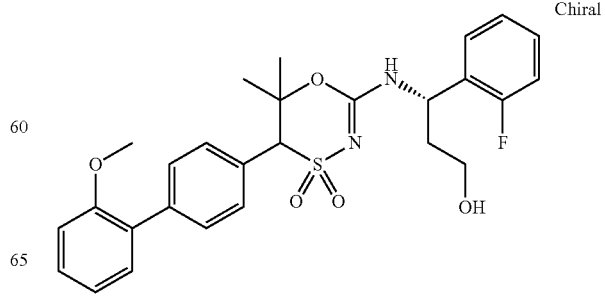

| 195 | 196 |
|---|---|
| 4'-{2-[(S)-1-(2-Fluorophenyl)-3-hydroxypropylamino]-6,6-dimethyl-4,4-dioxo-5,6-dihydro-4H-4lambda6-[1,4,3]oxathiazin-5-yl}-biphenyl-4-carbonitrile | (S)-3-(5-Biphenyl-4-yl-6,6-dimethyl-4,4-dioxo-5,6-dihydro-4H-4lambda6-[1,4,3]oxathiazin-2-ylamino)-3-(5-chloro-2-fluorophenyl)propan-1-ol |

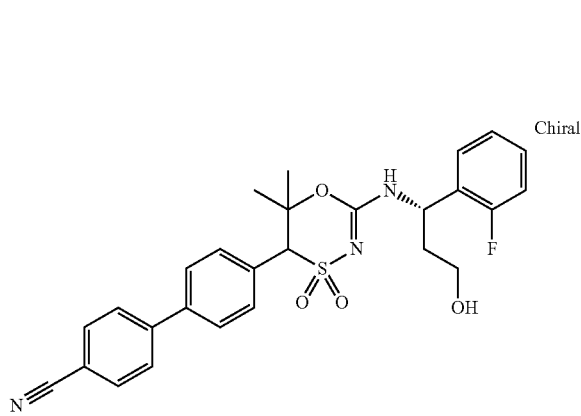 [SMILES: CC1(C)OC(N[C@@H](CCO)c2ccccc2F)=NS(=O)(=O)C1c1ccc(-c2ccc(C#N)cc2)cc1]

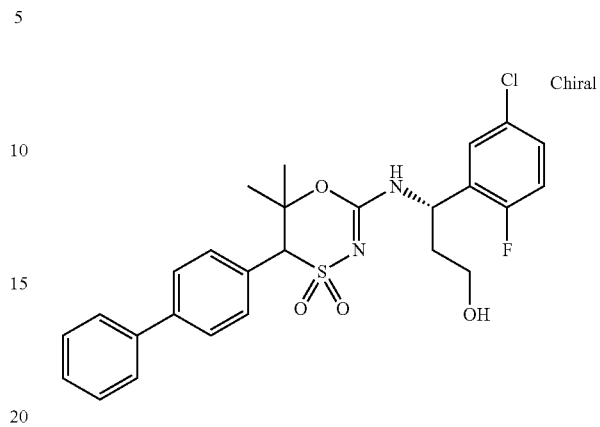

(S)-3-(5-Biphenyl-4-yl-6,6-dimethyl-4,4-dioxo-5,6-dihydro-4H-4lambda6-[1,4,3]oxathiazin-2-ylamino)-3-(2-chloro-3-fluorophenyl)propan-1-ol (S)-3-(5-Biphenyl-4-yl-6,6-dimethyl-4,4-dioxo-5,6-dihydro-4H-4lambda6-[1,4,3]oxathiazin-2-ylamino)-3-(5-fluoro-2-methylphenyl)propan-1-ol

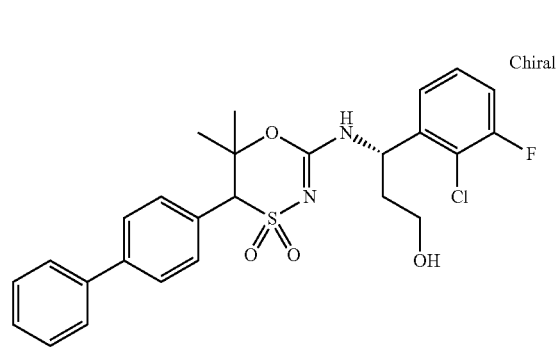 [SMILES: CC1(C)OC(N[C@@H](CCO)c2cccc(F)c2Cl)=NS(=O)(=O)C1c1ccc(-c2ccccc2)cc1]

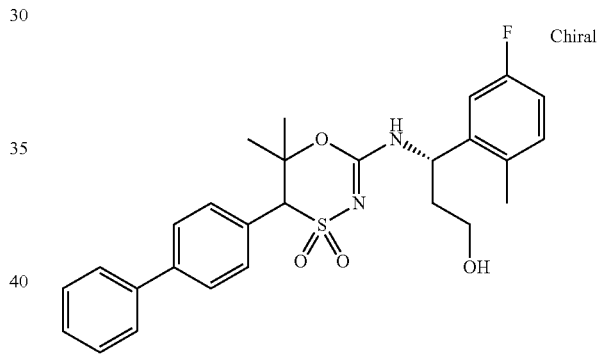

(S)-3-(5-Biphenyl-4-yl-6,6-dimethyl-4,4-dioxo-5,6-dihydro-4H-4lambda6-[1,4,3]oxathiazin-2-ylamino)-3-(2,5-difluorophenyl)propan-1-ol (S)-3-[6,6-Dimethyl-4,4-dioxo-5-(4-thiazol-4-ylphenyl)-5,6-dihydro-4H-4lambda6-[1,4,3]oxathiazin-2-ylamino]-3-(2-fluorophenyl)propan-1-ol

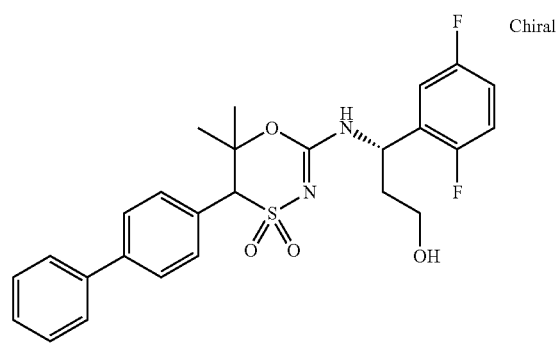 [SMILES: CC1(C)OC(N[C@@H](CCO)c2cc(F)ccc2F)=NS(=O)(=O)C1c1ccc(-c2ccccc2)cc1]

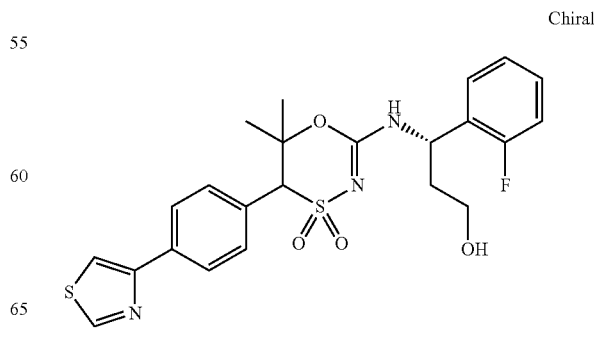

| 197 | 198 |
|---|---|
| (S)-3-{6,6-Dimethyl-5-[4-(2-methyl-2H-pyrazol-3-yl)-phenyl]-4,4-dioxo-5,6-dihydro-4H-4lambda*6*-[1,4,3]oxathiazin-2-ylamino}-3-(2-fluorophenyl)propan-1-ol | (S)-3-[6,6-Dimethyl-4,4-dioxo-5-(4-pyridin-3-ylphenyl)-5,6-dihydro-4H-4lambda*6*-[1,4,3]oxathiazin-2-ylamino]-3-(2-fluorophenyl)propan-1-ol |

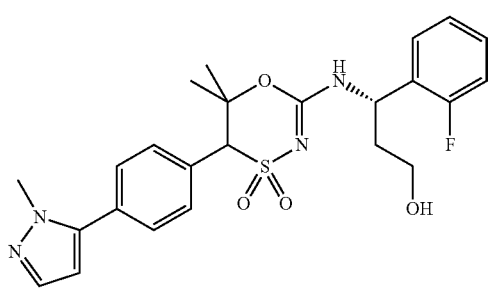 [SMILES: Cn1nccc1-c1ccc(C2C(C)(C)OC(N[C@@H](CCO)c3ccccc3F)=NS2(=O)=O)cc1]
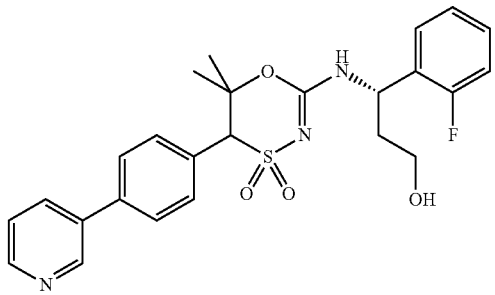

| | |
|---|---|
| 4'-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}biphenyl-4-carboxamide | (S)-3-[6,6-Dimethyl-4,4-dioxo-5-(4-pyridin-4-ylphenyl)-5,6-dihydro-4H-4lambda*6*-[1,4,3]oxathiazin-2-ylamino]-3-(2-fluorophenyl)propan-1-ol |

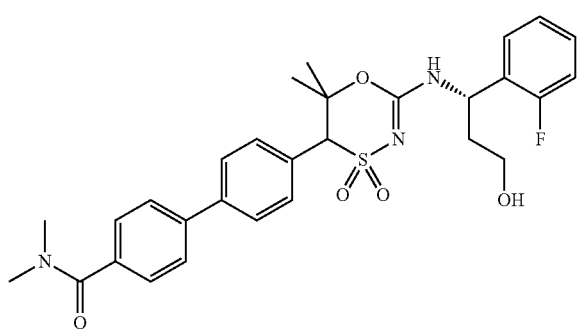 [SMILES: CN(C)C(=O)c1ccc(-c2ccc(C3C(C)(C)OC(N[C@@H](CCO)c4ccccc4F)=NS3(=O)=O)cc2)cc1]
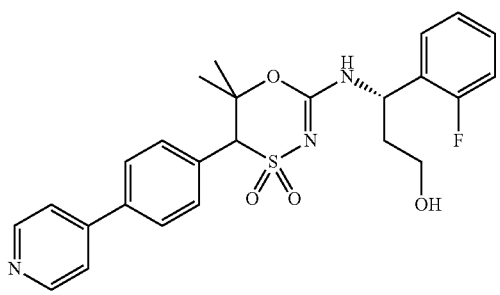

| | |
|---|---|
| 4'-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}biphenyl-4-carboxamide | (S)-3-[6,6-Dimethyl-5-[4-(3-methyl-1H-pyrazol-4-yl)phenyl]-4,4-dioxo-5,6-dihydro-4H-4lambda*6*-[1,4,3]oxathiazin-2-ylamino]-3-(2-fluorophenyl)propan-1-ol |

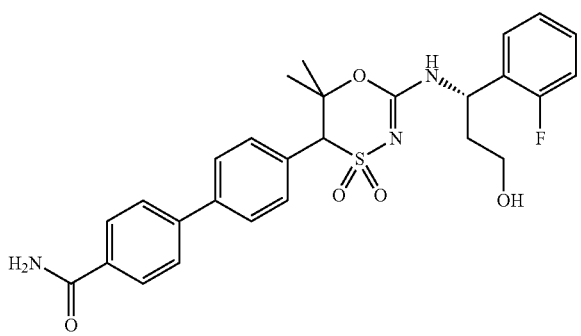 [SMILES: CC1(C)OC(N[C@@H](CCO)c2ccccc2F)=NS(=O)(=O)C1c1ccc(-c2ccc(C(N)=O)cc2)cc1]
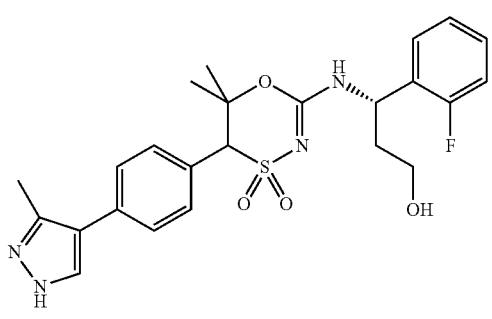 [SMILES: Cc1n[nH]cc1-c1ccc(C2C(C)(C)OC(N[C@@H](CCO)c3ccccc3F)=NS2(=O)=O)cc1]

199

(S)-3-{6,6-Dimethyl-5-[4-(2-morpholin-4-ylthiazol-4-yl)phenyl]-4,4-dioxo-5,6-dihydro-4H-4lambda*6*-[1,4,3]oxathiazin-2-ylamino}-3-(2-fluorophenyl)propan-1-ol

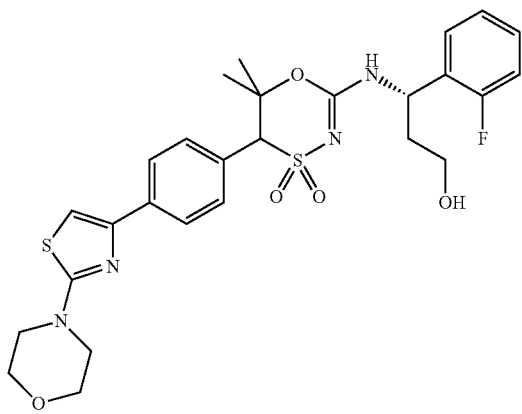 [SMILES: CC1(C)OC(N[C@@H](CCO)c2ccccc2F)=NS(=O)(=O)C1c1ccc(-c2csc(N3CCOCC3)n2)cc1]

(S)-3-{6,6-Dimethyl-4,4-dioxo-5-[4-(1H-pyrazol-4-yl)phenyl]-5,6-dihydro-4H-4lambda*6*-[1,4,3]oxathiazin-2-ylamino}-3-(2-fluorophenyl)propan-1-ol

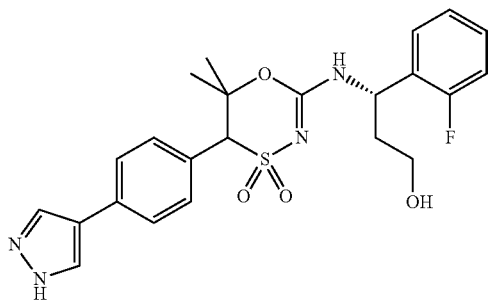 [SMILES: CC1(C)OC(N[C@@H](CCO)c2ccccc2F)=NS(=O)(=O)C1c1ccc(-c2cn[nH]c2)cc1]

(S)-3-[5-(4'-Dimethylaminomethylbiphenyl-4-yl)-6,6-dimethyl-4,4-dioxo-5,6-dihydro-4H-4lambda*6*-[1,4,3]oxathiazin-2-ylamino]-3-(2-fluorophenyl)propan-1-ol

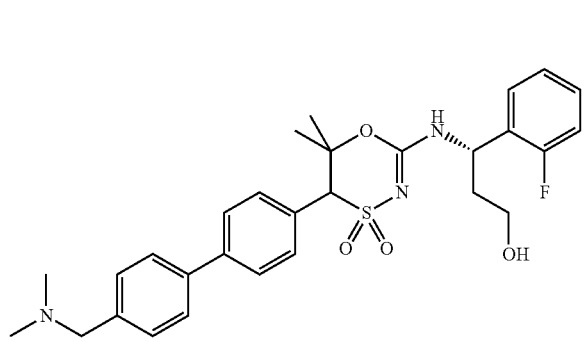 [SMILES: CN(C)Cc1ccc(-c2ccc(C3C(C)(C)OC(N[C@@H](CCO)c4ccccc4F)=NS3(=O)=O)cc2)cc1]

200

(S)-3-{6,6-Dimethyl-5-[4-(1-methyl-1H-pyrazol-4-yl)phenyl]-4,4-dioxo-5,6-dihydro-4H-4lambda*6*-[1,4,3]oxathiazin-2-ylamino}-3-(2-fluorophenyl)propan-1-ol

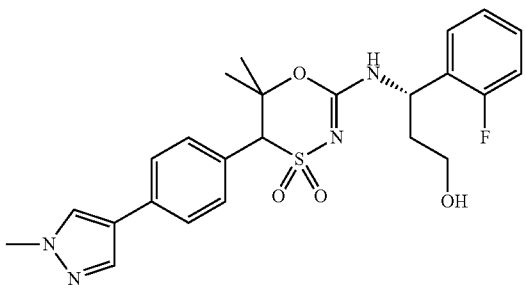 [SMILES: Cn1cc(-c2ccc(C3C(C)(C)OC(N[C@@H](CCO)c4ccccc4F)=NS3(=O)=O)cc2)cn1]

(S)-3-(6,6-Dimethyl-5-{4-[2-(4-methylpiperazin-1-yl)pyrimidin-5-yl]phenyl}-4,4-dioxo-5,6-dihydro-4H-4lambda*6*-[1,4,3]oxathiazin-2-ylamino)-3-(2-fluorophenyl)propan-1-ol

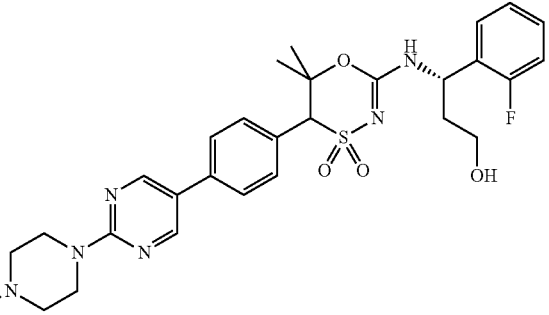

(S)-3-{5-[4-(6-Dimethylaminopyridin-2-yl)phenyl]-6,6-dimethyl-4,4-dioxo-5,6-dihydro-4H-4lambda*6*-[1,4,3]oxathiazin-2-ylamino}-3-(2-fluorophenyl)propan-1-ol

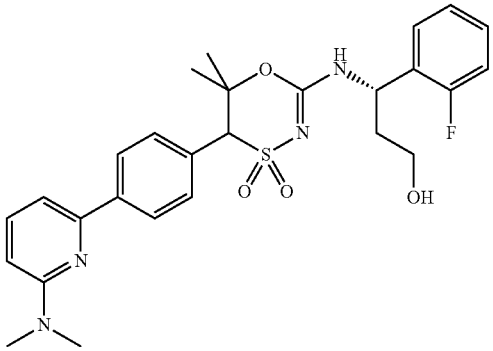 [SMILES: CN(C)c1cccc(-c2ccc(C3C(C)(C)OC(N[C@@H](CCO)c4ccccc4F)=NS3(=O)=O)cc2)n1]

201

4-(4-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}phenyl)pyridine-2-carbonitrile

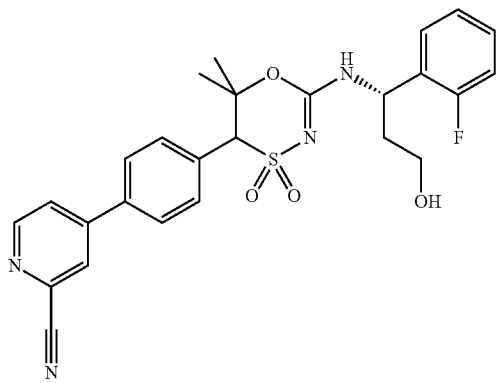 [SMILES: CC1(C)OC(N[C@@H](CCO)c2ccccc2F)=NS(=O)(=O)C1c1ccc(-c2ccnc(C#N)c2)cc1]

(S)-3-{6,6-Dimethyl-5-[4-(4-methyl-3,4,5,6-tetrahydro-2H-[1,2']bipyrazinyl-5'-yl)phenyl]-4,4-dioxo-5,6-dihydro-4H-4lambda*6*-[1,4,3]oxathiazin-2-ylamino}-3-(2-fluorophenyl)-propan-1-ol

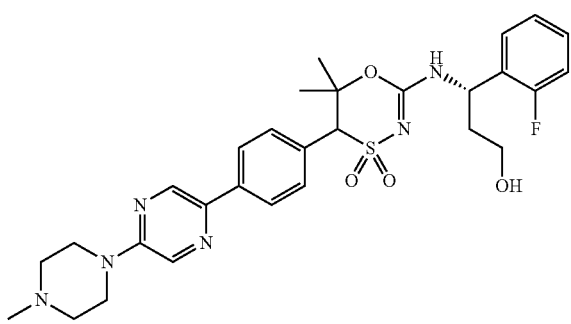

(S)-3-(2-Fluorophenyl)-3-{5-[4-(2-methoxypyrimidin-5-yl)phenyl]-6,6-dimethyl-4,4-dioxo-5,6-dihydro-4H-4lambda*6*-[1,4,3]oxathiazin-2-ylamino}propan-1-ol

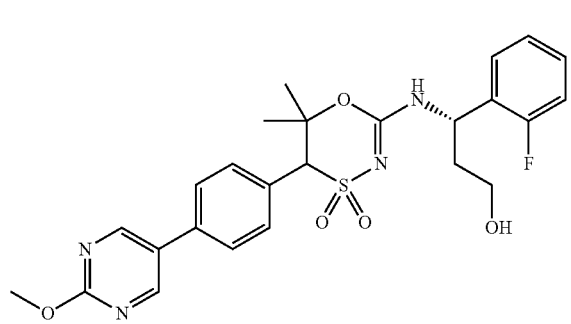 [SMILES: COc1ncc(-c2ccc(C3C(C)(C)OC(N[C@@H](CCO)c4ccccc4F)=NS3(=O)=O)cc2)cn1]

202

(S)-3-(6,6-Dimethyl-5-{4-[6-(4-methylpiperazin-1-yl)pyridin-3-yl]phenyl}-4,4-dioxo-5,6-dihydro-4H-4lambda*6*-[1,4,3]oxathiazin-2-ylamino)-3-(2-fluorophenyl)propan-1-ol

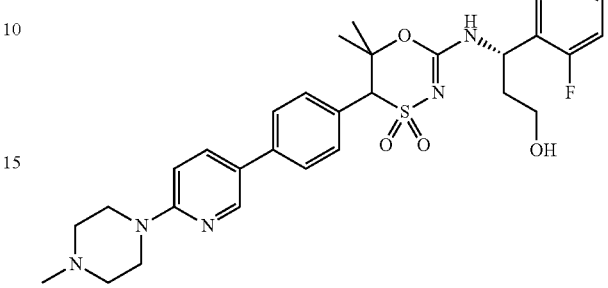

4'-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}biphenyl-3-carboxamide

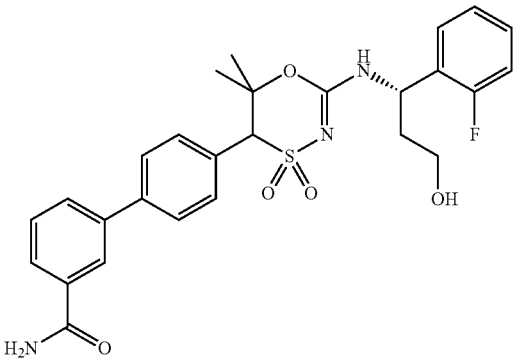

4'-{2-[(S)-1-(2-Fluorophenyl)ethylamino]-6,6-dimethyl-4,4-dioxo-5,6-dihydro-4H-4lambda*6*-[1,4,3]oxathiazin-5-yl}biphenyl-3-carboxamide

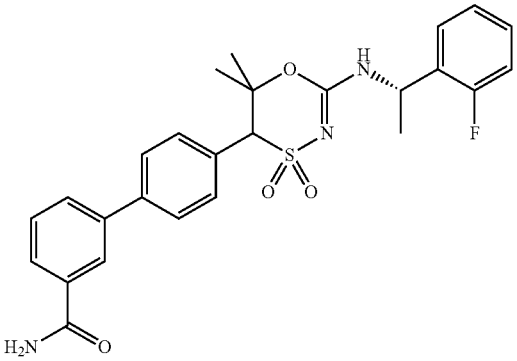 [SMILES: C[C@H](NC1=NS(=O)(=O)C(c2ccc(-c3cccc(C(N)=O)c3)cc2)C(C)(C)O1)c1ccccc1F]

| 203 | 204 |
|---|---|
| 4'-{2-[(S)-1-(2-Fluorophenyl)ethylamino]-6,6-dimethyl-4,4-dioxo-5,6-dihydro-4H-4lambda*6*-[1,4,3]oxathiazin-5-yl}biphenyl-4-carboxamide | {6,6-Dimethyl-4,4-dioxo-5-[4-(2-piperazin-1-ylpyrimidin-5-yl)phenyl]-5,6-dihydro-4H-4lambda*6*-[1,4,3]oxathiazin-2-yl}-[(S)-1-(2-fluorophenyl)ethyl]amine |

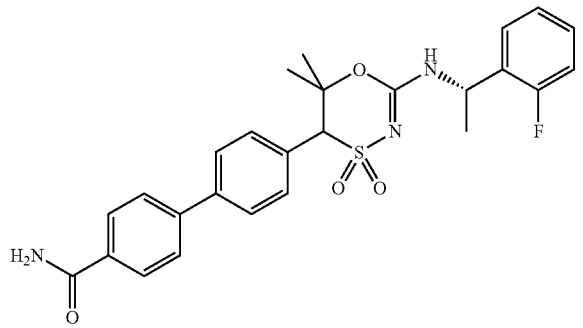 [SMILES: C[C@H](NC1=NS(=O)(=O)C(c2ccc(-c3ccc(C(N)=O)cc3)cc2)C(C)(C)O1)c1ccccc1F]

| | |
|---|---|
| [6,6-Dimethyl-4,4-dioxo-5-(6-phenylpyridin-3-yl)-5,6-dihydro-4H-4lambda*6*-[1,4,3]oxathiazin-2-yl]-[(S)-1-(2-fluorophenyl)ethyl]amine | (S)-3-{6,6-Dimethyl-4,4-dioxo-5-[4-(2-piperazin-1-ylpyrimidin-5-yl)phenyl]-5,6-dihydro-4H-4lambda*6*-[1,4,3]oxathiazin-2-ylamino}-3-(2-fluorophenyl)propan-1-ol |

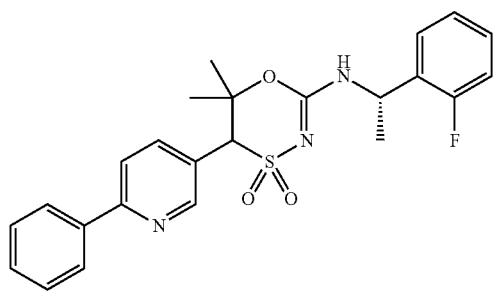 [SMILES: C[C@H](NC1=NS(=O)(=O)C(c2ccc(-c3ccccc3)nc2)C(C)(C)O1)c1ccccc1F]

| | |
|---|---|
| (S)-3-[6,6-Dimethyl-4,4-dioxo-5-(6-phenyl-pyridin-3-yl)-5,6-dihydro-4H-4lambda*6*[1,4,3]oxathiazin-2-ylamino]-3-(2-fluorophenyl)propan-1-ol | [5-(2'-Dimethylaminomethylbiphenyl-4-yl)-6,6-dimethyl-4,4-dioxo-5,6-dihydro-4H-4lambda*6*-[1,4,3]oxathiazin-2-yl]-[(S)-1-(2-fluorophenyl)ethyl]amine |

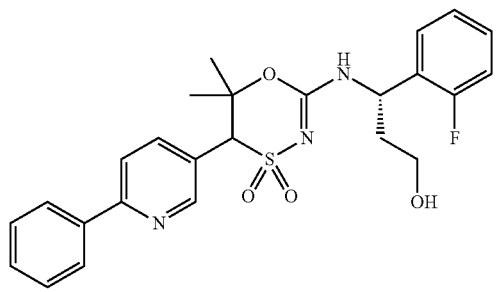 [SMILES: CC1(C)OC(N[C@@H](CCO)c2ccccc2F)=NS(=O)(=O)C1c1ccc(-c2ccccc2)nc1]
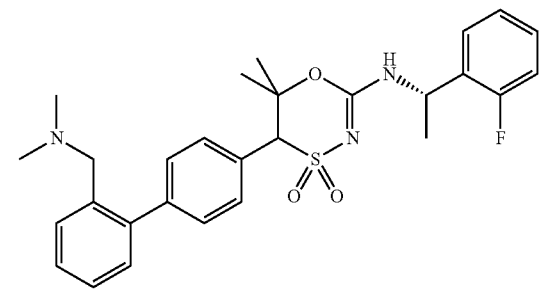 [SMILES: C[C@H](NC1=NS(=O)(=O)C(c2ccc(-c3ccccc3CN(C)C)cc2)C(C)(C)O1)c1ccccc1F]

| 205 | 206 |
|---|---|
| 3-(5-{2-[(S)-1-(2-Fluorophenyl)ethylamino]-6,6-dimethyl-4,4-dioxo-5,6-dihydro-4H-4lambda*6*-[1,4,3]oxathiazin-5-yl}pyridin-2-yl)benzamide | 4-(4-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}phenyl)pyridine-2-carbonitrile |

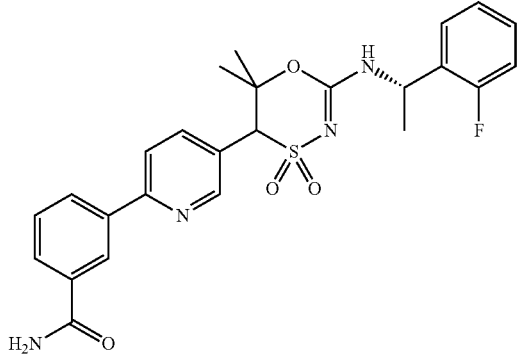 [SMILES: C[C@H](NC1=NS(=O)(=O)C(c2ccc(-c3cccc(C(N)=O)c3)nc2)C(C)(C)O1)c1ccccc1F]

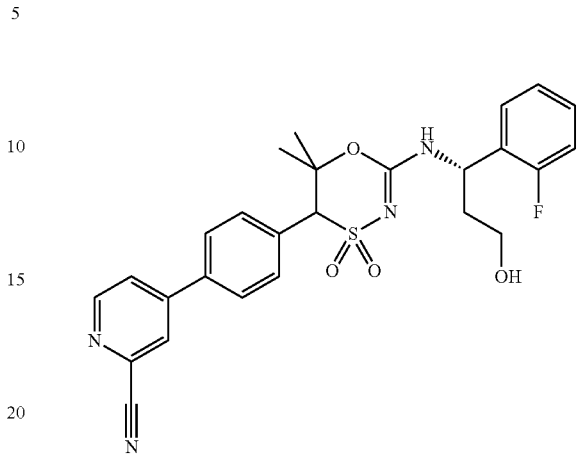

5-(4-{2-[(S)-1-(2-Fluorophenyl)ethylamino]-6,6-dimethyl-4,4-dioxo-5,6-dihydro-4H-4lambda*6*-[1,4,3]oxathiazin-5-yl}phenyl)nicotinamide 4-(4-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}-phenyl)pyridine-2-carboxamide

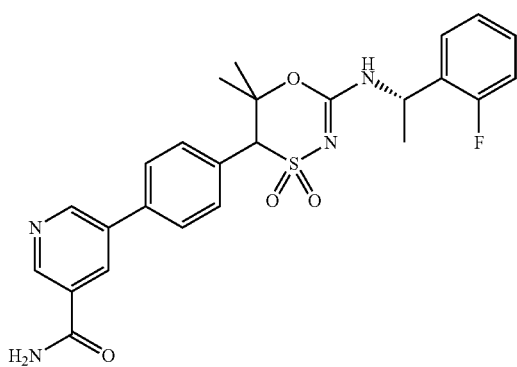 [SMILES: C[C@H](NC1=NS(=O)(=O)C(c2ccc(-c3cncc(C(N)=O)c3)cc2)C(C)(C)O1)c1ccccc1F]

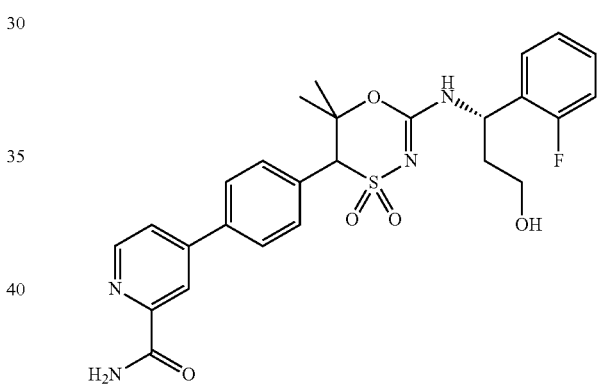

4-(4-{2-[(S)-1-(2-Fluorophenyl)ethylamino]-6,6-dimethyl-4,4-dioxo-5,6-dihydro-4H-4lambda*6*-[1,4,3]oxathiazin-5-yl}phenyl)pyridine-2-carbonitrile 4-(4-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}phenyl)pyridine-2-carbonitrile

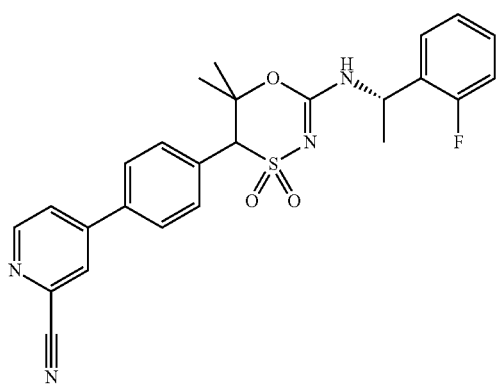 [SMILES: C[C@H](NC1=NS(=O)(=O)C(c2ccc(-c3ccnc(C#N)c3)cc2)C(C)(C)O1)c1ccccc1F]

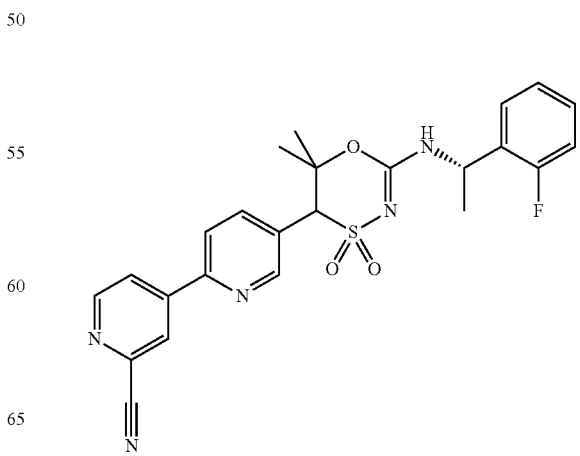

6-(4-{2-[(S)-1-(2-Fluorophenyl)ethylamino]-6,6-dimethyl-4,4-dioxo-5,6-dihydro-4H-4lambda*6*-[1,4,3]oxathiazin-5-yl}phenyl)benzothiazol-2-ylamine

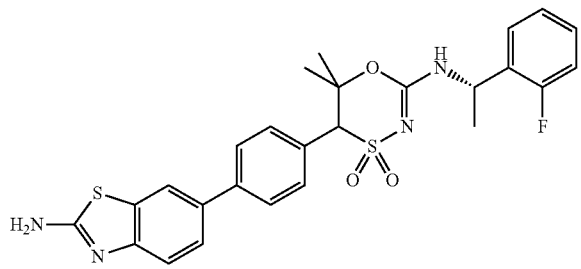 [SMILES: C[C@H](NC1=NS(=O)(=O)C(c2ccc(-c3ccc4nc(N)sc4c3)cc2)C(C)(C)O1)c1ccccc1F]

{5-[4'-(2-Aminopyrimidin-5-yl)-biphenyl-4-yl]-6,6-dimethyl-4,4-dioxo-5,6-dihydro-4H-4lambda*6*-[1,4,3]oxathiazin-2-yl}-[(S)-1-(2-fluorophenyl)ethyl]amine

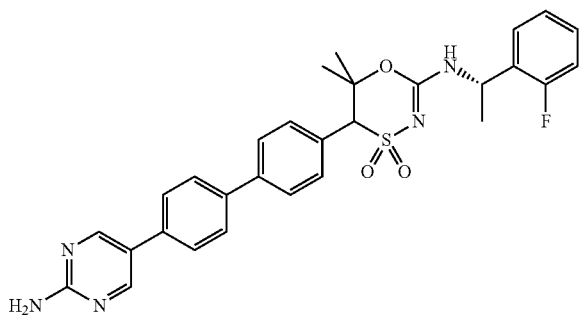 [SMILES: C[C@H](NC1=NS(=O)(=O)C(c2ccc(-c3ccc(-c4cnc(N)nc4)cc3)cc2)C(C)(C)O1)c1ccccc1F]

(S)-3-(9-Biphenyl-4-yl-8,8-dioxo-2,5-dioxa-8lambda6-thia-7-azaspiro[3.5]non-6-en-6-ylamino)-3-(2-fluorophenyl)propan-1-ol

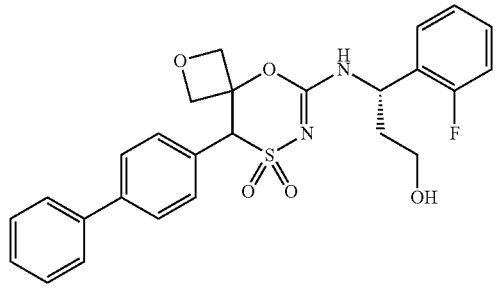 [SMILES: O=S1(=O)N=C(N[C@@H](CCO)c2ccccc2F)OC2(COC2)C1c1ccc(-c2ccccc2)cc1]

Biphenyl-4-yl-(3-hydroxyoxetan-3-yl)methanesulfonamide

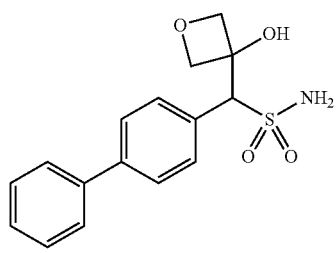 [SMILES: NS(=O)(=O)C(c1ccc(-c2ccccc2)cc1)C1(O)COC1]

Under inert gas, 0.500 g of C-biphenyl-4-yl-N-(2,4-dimethoxybenzyl)methanesulfonamide was initially charged in 5 ml of THF and then, at −78° C., 1.8 ml of a 1.6 N butyllithium solution in hexane were added dropwise. The reaction mixture was stirred for 5 minutes and then admixed dropwise with 0.24 ml of 3-oxetanone. The mixture was stirred at constant temperature for 5 minutes, 0.28 ml of trifluoroacetic acid were added and the mixture was allowed to come to room temperature. The solvent was removed under reduced pressure. The residue was dissolved in 2 ml of dichloromethane, and 2 ml of trifluoroacetic acid were added. After stirring at room temperature for 60 minutes, 50 ml of saturated potassium carbonate solution were added and the mixture was extracted with dichloromethane, dried over magnesium sulfate and concentrated. The crude product was purified by means of normal phase chromatography using a Flashmaster with an n-heptane/ethyl acetate gradient. This gave the product (170 mg) with a molecular weight of 319.4 g/mol ($C_{16}H_{17}NO_4S$).

9-Biphenyl-4-yl-6-methoxy-2,5-dioxa-8-thia-7-azaspiro[3.5]non-6-ene 8,8-dioxide

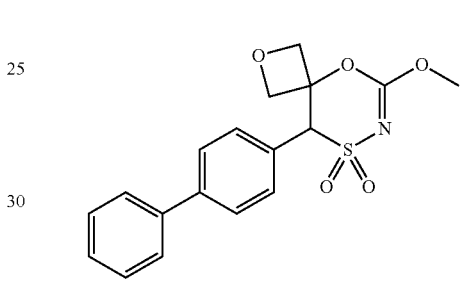

A mixture of 0.17 g of biphenyl-4-yl-(3-hydroxyoxetan-3-yl)methanesulfonamide in 4 ml of tetraethoxymethane and 1 ml of acetic acid was stirred at 90° C. for 3 hours. The solvent was removed under reduced pressure. This gave the crude product, which was used without further purification.

(S)-3-(9-Biphenyl-4-yl-8,8-dioxo-2,5-dioxa-8lambda*6*-thia-7-azaspiro[3.5]non-6-en-6-ylamino)-3-(2-fluorophenyl)propan-1-ol

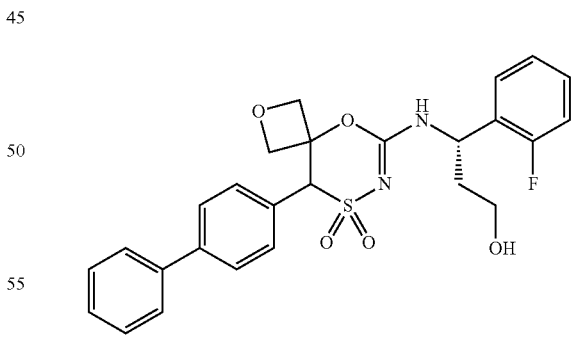

In a round-bottom flask, 9-biphenyl-4-yl-6-methoxy-2,5-dioxa-8-thia-7-azaspiro[3.5]non-6-ene 8,8-dioxide was dissolved under inert gas in 2 ml of dichloromethane, and 151 mg of (S)-3-(tert-butyldimethylsilanyloxy)-1-(2-fluorophenyl)propylamine were added. After concentration by rotary evaporation, the residue was left to stand at room temperature for 18 hours. To detach the protecting group, the residue was taken up in 1 ml of methanol and, after addition of 0.05 ml of concentrated hydrochloric acid, stirred at room temperature for 1 hour. After concentration by rotary evaporation, the residue was purified in a purification laboratory by means of preparative HPLC. The product-containing fractions were combined and freed of the solvent under reduced pressure. This gave the product (8 mg) with a molecular weight of 496.6 g/mol ($C_{26}H_{25}FN_2O_5S$); MS (ESI): m/e=497 (M+H$^+$).

The following products were obtained in the same way:

(S)-3-(9-Biphenyl-4-yl-8,8-dioxo-5-oxa-8lambda*6*-thia-7-azaspiro[3.5]non-6-en-6-ylamino)-3-(2-fluorophenyl)propan-1-ol

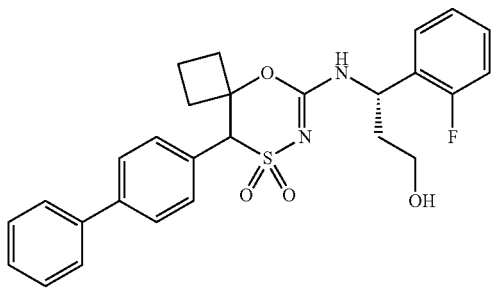 [SMILES: O=S1(=O)N=C(N[C@@H](CCO)c2ccccc2F)OC2(CCC2)C1c1ccc(-c2ccccc2)cc1]

(S)-3-(10-Biphenyl-4-yl-9,9-dioxo-6-oxa-9lambda*6*-thia-8-azaspiro[4.5]dec-7-en-7-ylamino)-3-(2-fluorophenyl)propan-1-ol

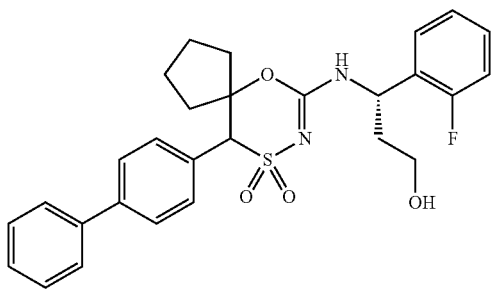 [SMILES: O=S1(=O)N=C(N[C@@H](CCO)c2ccccc2F)OC2(CCCC2)C1c1ccc(-c2ccccc2)cc1]

(S)-3-{6,6-Dimethyl-5-[4-(1-methylpiperidin-4-yl)phenyl]-4,4-dioxo-5,6-dihydro-4H-4lambda*6*-[1,4,3]oxathiazin-2-ylamino}-3-(2-fluorophenyl)propan-1-ol

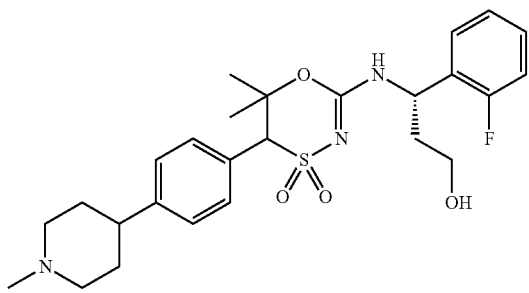 [SMILES: CN1CCC(c2ccc(C3C(C)(C)OC(N[C@@H](CCO)c4ccccc4F)=NS3(=O)=O)cc2)CC1]

1-Boc-4-(4-{2-[(S)-3-(tert-Butyldimethylsilanyloxy)-1-(2-fluorophenyl)propylamino]-6,6-dimethyl-4,4-dioxo-5,6-dihydro-4H-4lambda*6*-[1,4,3]oxathiazin-5-yl}phenyl)-3,6-dihydro-2H-pyridine

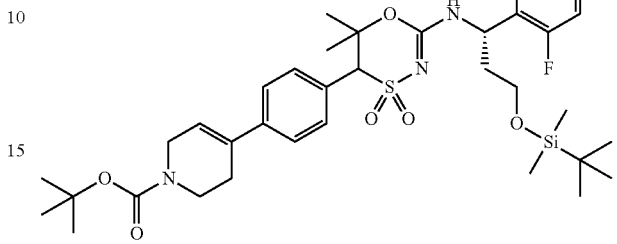

A solution of N-boc-4-(4,4,5,5-Tetramethyl-[1,3,2]dioxaborolan-2-yl)-3,6-dihydro-2H-pyridine (408 mg), cesium carbonate (696 mg) and [5-(4-bromophenyl)-6,6-dimethyl-4,4-dioxo-5,6-dihydro-4H-4lambda*6*-[1,4,3]oxathiazin-2-yl]-[(S)-3-(tert-butyldimethylsilanyloxy)-1-(2-fluorophenyl)-propyl]amine (600 mg) in dioxane (7.0 ml)/water (2.8 ml) was purged with argon for twenty minutes. Then 1,2,3,4,5-pentaphenyl-1'-(di-t-butylphosphino)ferrocene (142 mg) and bis(dibenzylideneacetone)palladium (58 mg) were added and the mixture was stirred at 65° C. for thirty minutes. Subsequently, ethyl acetate (20 ml) was added and the mixture was washed with water (10 ml). The organic phase was dried using a kieselguhr cartridge, filtered and concentrated under reduced pressure. This was followed by purification by column chromatography (ethyl acetate/heptane). This gave the product (584 mg) with a molecular weight of 701.0 g/mol ($C_{36}H_{52}FN_3O_6SSi$).

(S)-3-[6,6-Dimethyl-4,4-dioxo-5-(4-piperidin-4-ylphenyl)-5,6-dihydro-4H-4lambda*6*-[1,4,3]oxathiazin-2-ylamino]-3-(2-fluorophenyl)propan-1-ol

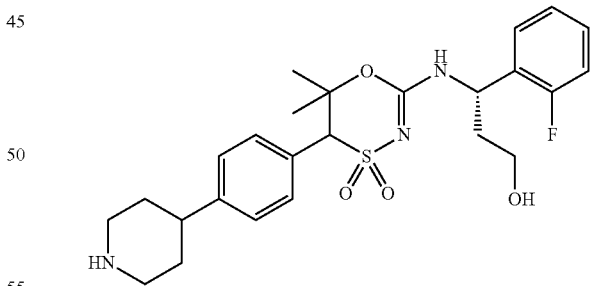

A solution of 1-Boc-4-(4-{2-[(S)-3-(tert-butyldimethylsilanyloxy)-1-(2-fluorophenyl)propylamino]-6,6-dimethyl-4,4-dioxo-5,6-dihydro-4H-4lambda*6*-[1,4,3]oxathiazin-5-yl}phenyl)-3,6-dihydro-2H-pyridine (575 mg) in methanol (25 ml) was admixed with palladium on charcoal (10%, 260 mg) and stirred in a hydrogen atmosphere for 1.5 h. The mixture was filtered and concentrated. The residue was dissolved in 5 ml of dichloromethane, and 1 ml of trifluoroacetic acid was added. After stirring at room temperature for 1 h, the solvent was removed under reduced pressure and TFA ester formed was cleaved by treatment with 1 N HCl. Extraction with ethyl acetate gave the crude product (91%), which was used without further purification.

(S)-3-{6,6-Dimethyl-5-[4-(1-methylpiperidin-4-yl)phenyl]-4,4-dioxo-5,6-dihydro-4H-4lambda*6*-[1,4,3]oxathiazin-2-ylamino}-3-(2-fluorophenyl)propan-1-ol

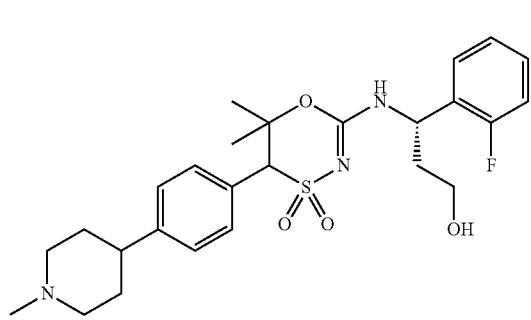 [SMILES: CN1CCC(c2ccc(C3C(C)(C)OC(N[C@@H](CCO)c4ccccc4F)=NS3(=O)=O)cc2)CC1]

To a solution of (S)-3-[6,6-dimethyl-4,4-dioxo-5-(4-piperidin-4-ylphenyl)-5,6-dihydro-4H-4lambda*6*-[1,4,3]oxathiazin-2-ylamino]-3-(2-fluorophenyl)propan-1-ol (100 mg) in 5 ml of 4:1 THF/acetic acid were added paraformaldehyde (74 mg) and polymer-bound sodium cyanoborohydride (238 mg), and the mixture was stirred at room temperature overnight. After filtration and concentration by rotary evaporation, the residue was purified in a purification laboratory by means of preparative HPLC. This gave the product (75 mg as the HCl salt after treatment with hydrochloric acid) with a molecular weight of 503.2 g/mol ($C_{26}H_{34}FN_3O_4S$); MS (ESI): m/e=504 (M+H$^+$).

(S)-3-(2-Fluorophenyl)-3-(5-{4-[1-(2-hydroxyethyl)piperidin-4-yl]phenyl}-6,6-dimethyl-4,4-dioxo-5,6-dihydro-4H-4lambda*6*-[1,4,3]oxathiazin-2-ylamino)propan-1-ol

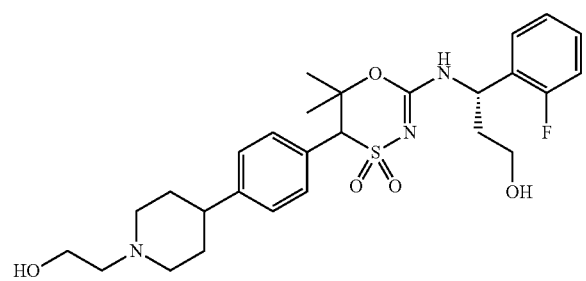 [SMILES: CC1(C)OC(N[C@@H](CCO)c2ccccc2F)=NS(=O)(=O)C1c1ccc(C2CCN(CCO)CC2)cc1]

To a solution of (S)-3-[6,6-dimethyl-4,4-dioxo-5-(4-piperidin-4-ylphenyl)-5,6-dihydro-4H-4lambda*6*-[1,4,3]oxathiazin-2-ylamino]-3-(2-fluorophenyl)propan-1-ol (100 mg) in DMF (1.5 ml) were added DIPEA (40 mg) and 2-bromoethanol (31 mg), and the mixture was stirred overnight. The resulting mixture was purified in a purification laboratory by means of preparative HPLC. This gave the product (66 mg as the HCl salt after treatment with hydrochloric acid) with a molecular weight of 533.2 g/mol ($C_{27}H_{36}FN_3O_5S$); MS (ESI): m/e=534 (M+H$^+$).

In an analogous manner, the following compounds were obtained:

(S)-3-(5-{4-[1-(2,2-Difluoroethyl)piperidin-4-yl]phenyl}-6,6-dimethyl-4,4-dioxo-5,6-dihydro-4H-4lambda*6*-[1,4,3]oxathiazin-2-ylamino)-3-(2-fluorophenyl)propan-1-ol

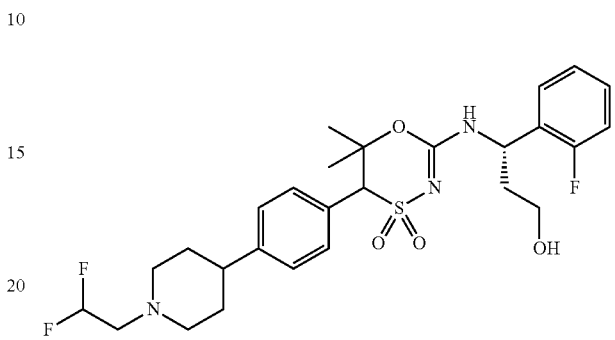

(S)-3-(6,6-Dimethyl-4,4-dioxo-5-{4-[1-(3,3,3-trifluoropropyl)piperidin-4-yl]phenyl}-5,6-dihydro-4H-4lambda*6*-[1,4,3]oxathiazin-2-ylamino)-3-(2-fluorophenyl)propan-1-ol

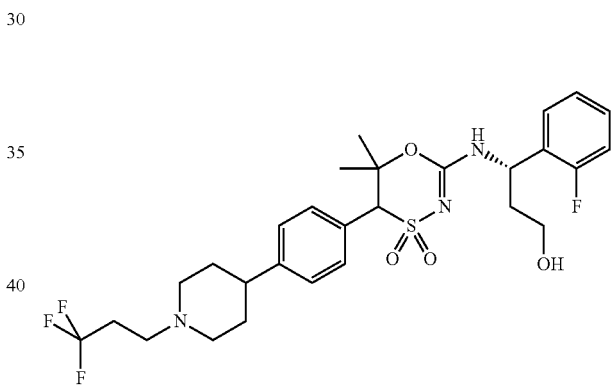

In an analogous manner, the following compounds were obtained:

[6,6-Dimethyl-4,4-dioxo-5-(4-piperidin-4-ylphenyl)-5,6-dihydro-4H-4lambda*6*-[1,4,3]oxathiazin-2-yl]-[(S)-1-(2-fluorophenyl)ethyl]amine

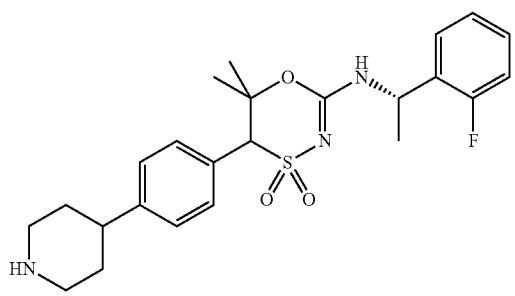 [SMILES: C[C@H](NC1=NS(=O)(=O)C(c2ccc(C3CCNCC3)cc2)C(C)(C)O1)c1ccccc1F]

213

{6,6-Dimethyl-5-[4-(1-methylpiperidin-4-yl)phenyl]-4,4-dioxo-5,6-dihydro-4H-4lambda*6*-[1,4,3]oxathiazin-2-yl}-[(S)-1-(2-fluorophenyl)ethyl]amine

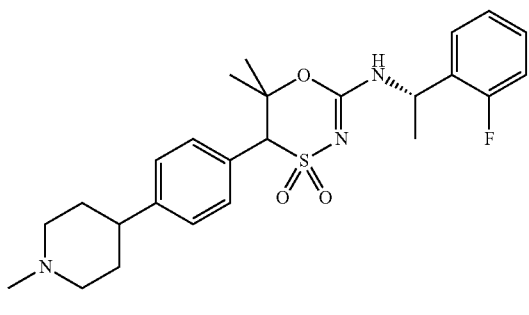 [SMILES: C[C@H](NC1=NS(=O)(=O)C(c2ccc(C3CCN(C)CC3)cc2)C(C)(C)O1)c1ccccc1F]

{6,6-Dimethyl-5-[3-(1-methylpiperidin-4-yl)phenyl]-4,4-dioxo-5,6-dihydro-4H-4lambda*6*-[1,4,3]oxathiazin-2-yl}-[(S)-1-(2-fluorophenyl)ethyl]amine

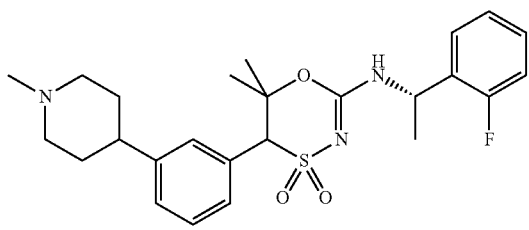 [SMILES: C[C@H](NC1=NS(=O)(=O)C(c2cccc(C3CCN(C)CC3)c2)C(C)(C)O1)c1ccccc1F]

2-[4-(4-{2-[(S)-1-(2-Fluorophenyl)ethylamino]-6,6-dimethyl-4,4-dioxo-5,6-dihydro-4H-4lambda*6*-[1,4,3]oxathiazin-5-yl}phenyl)piperidin-1-yl]ethanol

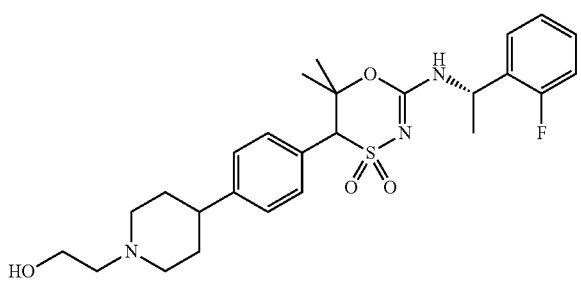 [SMILES: C[C@H](NC1=NS(=O)(=O)C(c2ccc(C3CCN(CCO)CC3)cc2)C(C)(C)O1)c1ccccc1F]

(S)-3-{5-[4-(3-Aminopropyl)phenyl]-6,6-dimethyl-4,4-dioxo-5,6-dihydro-4H-4lambda*6*-[1,4,3]oxathiazin-2-ylamino}-3-(2-fluorophenyl)propan-1-ol

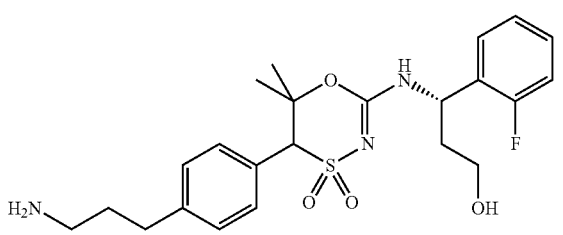

214

[3-(4-{2-[(S)-3-(tert-Butyldimethylsilanyloxy)-1-(2-fluorophenyl)propylamino]-6,6-dimethyl-4,4-dioxo-5,6-dihydro-4H-4lambda*6*-[1,4,3]oxathiazin-5-yl}phenyl)prop-2-ynyl]carbamic acid tert-butyl ester

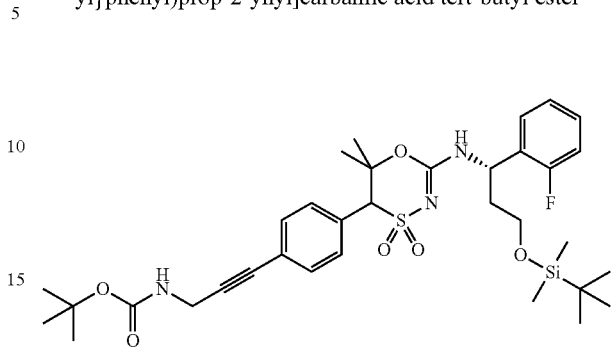

To a suspension of bis(triphenylphosphine)palladium(II) dichloride (10 mg) and copper(I) iodide (5 mg) in dry dioxane (0.6 ml) were added successively triethylamine (120 µl) and a solution of [5-(4-bromophenyl)-6,6-dimethyl-4,4-dioxo-5,6-dihydro-4H-4lambda*6*-[1,4,3]oxathiazin-2-yl]-[(S)-3-(tert-butyldimethylsilanyloxy)-1-(2-fluorophenyl)propyl]amine (100 mg) in dry dioxane (0.7 ml), and the mixture was stirred at 80° C. for 3 h and at 100° C. for 1 h. Subsequently, ethyl acetate was added and the mixture was washed with water. The organic phase was dried using a kieselguhr cartridge, filtered and concentrated under reduced pressure. This was followed by purification by column chromatography (ethyl acetate/heptane). This gave the product (89 mg) with a molecular weight of 673.2 g/mol ($C_{34}H_{48}FN_3O_6SSi$).

[3-(4-{2-[(S)-3-(tert-Butyldimethylsilanyloxy)-1-(2-fluorophenyl)propylamino]-6,6-dimethyl-4,4-dioxo-5,6-dihydro-4H-4lambda*6*-[1,4,3]oxathiazin-5-yl}phenyl)propyl]carbamic acid tert-butyl ester

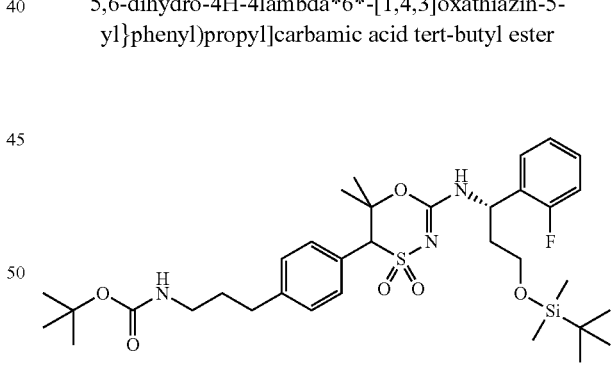

To a solution of [3-(4-{2-[(S)-3-(tert-Butyldimethylsilanyloxy)-1-(2-fluorophenyl)propylamino]-6,6-dimethyl-4,4-dioxo-5,6-dihydro-4H-4lambda*6*-[1,4,3]oxathiazin-5-yl}phenyl)prop-2-ynyl]carbamic acid tert-butyl ester (89 mg) in methanol (25 ml) was added palladium on charcoal (5%, 25 mg), and the solution was stirred in a hydrogen atmosphere for 1 h. The mixture was filtered and the filtrate was concentrated. This was followed by purification by column chromatography (ethyl acetate/heptane). This gave the product (49 mg) with a molecular weight of 678.0 g/mol ($C_{34}H_{52}FN_3O_6SSi$).

215

(S)-3-{5-[4-(3-Aminopropyl)phenyl]-6,6-dimethyl-4,4-dioxo-5,6-dihydro-4H-4lambda*6*-[1,4,3]oxathiazin-2-ylamino}-3-(2-fluorophenyl)propan-1-ol

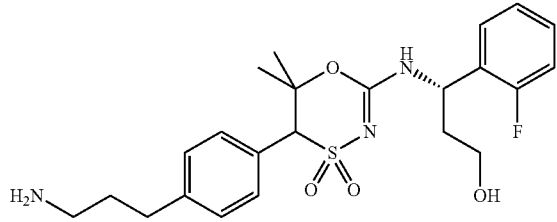 [SMILES: CC1(C)OC(N[C@@H](CCO)c2ccccc2F)=NS(=O)(=O)C1c1ccc(CCCN)cc1]

To a solution of [3-(4-{2-[(S)-3-(tert-butyldimethylsilanyloxy)-1-(2-fluorophenyl)-propylamino]-6,6-dimethyl-4,4-dioxo-5,6-dihydro-4H-4lambda*6*-[1,4,3]oxathiazin-5-yl}phenyl)propyl]carbamic acid tert-butyl ester (49 mg) in methanol (2 ml) was added concentrated hydrochloric acid (0.2 ml), and the mixture was stirred for 2 days. The resulting mixture was purified in a purification laboratory by means of preparative HPLC. This gave the product (6 mg as the HCl salt after treatment with hydrochloric acid) with a molecular weight of 463.2 g/mol ($C_{22}H_{30}FN_3O_4S$); MS (ESI): m/e=464 (M+H$^+$).

In an analogous manner, the following compounds were obtained:

(S)-3-{5-[4-(3-Dimethylaminopropyl)phenyl]-6,6-dimethyl-4,4-dioxo-5,6-dihydro-4H-4lambda*6*-[1,4,3]oxathiazin-2-ylamino}-3-(2-fluorophenyl)propan-1-ol

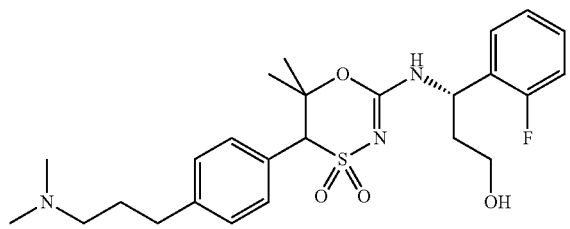 [SMILES: CN(C)CCCc1ccc(C2C(C)(C)OC(N[C@@H](CCO)c3ccccc3F)=NS2(=O)=O)cc1]

(S)-3-{6,6-Dimethyl-5-[4-(3-morpholin-4-ylpropyl)phenyl]-4,4-dioxo-5,6-dihydro-4H-4lambda*6*-[1,4,3]oxathiazin-2-ylamino}-3-(2-fluorophenyl)propan-1-ol

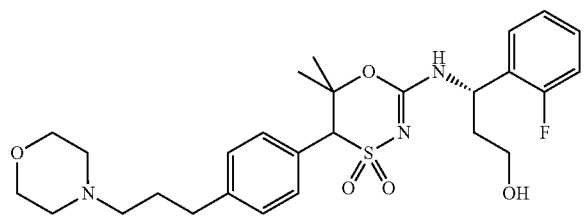 [SMILES: CC1(C)OC(N[C@@H](CCO)c2ccccc2F)=NS(=O)(=O)C1c1ccc(CCCN2CCOCC2)cc1]

216

(S)-3-{6,6-Dimethyl-5-[4-(3-methylaminopropyl)phenyl]-4,4-dioxo-5,6-dihydro-4H-4lambda*6*-[1,4,3]oxathiazin-2-ylamino}-3-(2-fluorophenyl)propan-1-ol

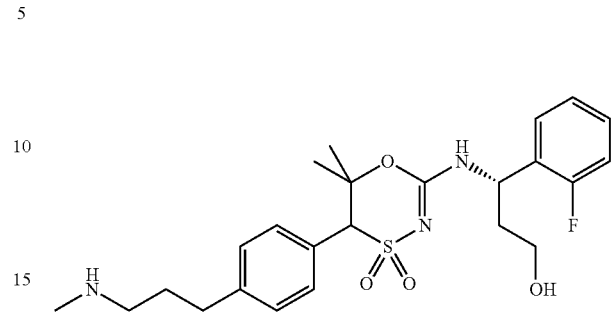

(S)-3-(2-Fluorophenyl)-3-[5-(4-{3-[(2-hydroxyethyl)methylamino]propyl}phenyl)-6,6-dimethyl-4,4-dioxo-5,6-dihydro-4H-4lambda*6*-[1,4,3]oxathiazin-2-ylamino]propan-1-ol

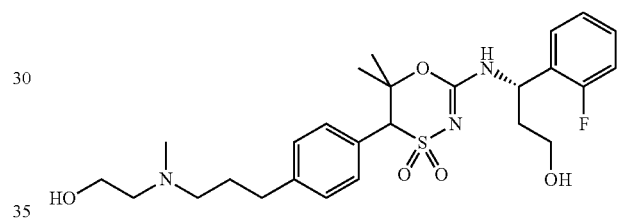

A solution of (S)-3-{6,6-dimethyl-5-[4-(3-methylaminopropyl)phenyl]-4,4-dioxo-5,6-dihydro-4H-4lambda*6*-[1,4,3]oxathiazin-2-ylamino}-3-(2-fluorophenyl)propan-1-ol (175 mg) and 2-bromoethanol (51 mg) in DMF (2.5 ml) was stirred at 50° C. for 8 h. The resulting mixture was purified in a purification laboratory by means of preparative HPLC. This gave the product (75 mg as the HCl salt after treatment with hydrochloric acid) with a molecular weight of 521.2 g/mol ($C_{26}H_{36}FN_3O_5S$); MS (ESI): m/e=522 (M+H$^+$).

In an analogous manner, the following compound was obtained:

(S)-3-[5-(4-{3-[(2,2-Difluoroethyl)methylamino]propyl}phenyl)-6,6-dimethyl-4,4-dioxo-5,6-dihydro-4H-4lambda*6*-[1,4,3]oxathiazin-2-ylamino]-3-(2-fluorophenyl)propan-1-ol

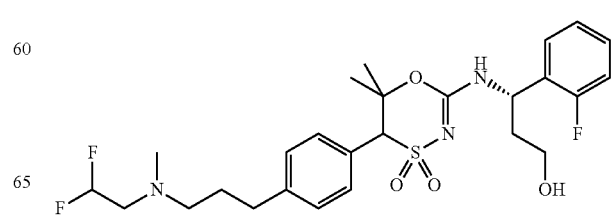

(S)-3-[6,6-Dimethyl-5-(4-morpholin-4-ylphenyl)-4,
4-dioxo-5,6-dihydro-4H-4lambda*6*-[1,4,3]oxathi-
azin-2-ylamino]-3-(2-fluorophenyl)propan-1-ol

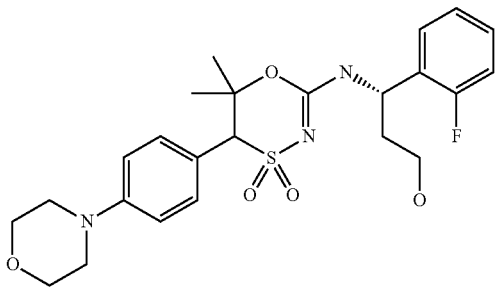 [SMILES: CC1(C)OC(N[C@@H](CCO)c2ccccc2F)=NS(=O)(=O)C1c1ccc(N2CCOCC2)cc1]

N-(2,4-Dimethoxybenzyl)-C-(4-morpholin-4-ylphe-
nyl)methanesulfonamide

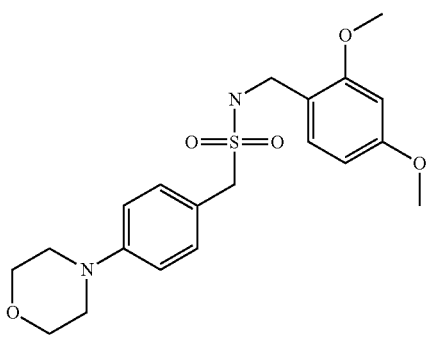 [SMILES: COc1ccc(CNS(=O)(=O)Cc2ccc(N3CCOCC3)cc2)c(OC)c1]

A mixture of C-(4-bromophenyl)-N-(2,4-dimethoxyben-zyl)methanesulfonamide (1 g), morpholine (0.3 ml), Pd$_2$(dba)$_3$ (51 mg) and cesium carbonate (1.3 g) in dioxane was stirred at 80° C. for 16 h. The mixture was diluted with ethyl acetate, washed with water, dried over magnesium sulfate and concentrated. This was followed by purification by column chromatography (ethyl acetate/heptane). This gave the product (267 mg) with a molecular weight of 406.5 g/mol ($C_{20}H_{26}N_2O_5S$).

2-Hydroxy-2-methyl-1-(4-morpholin-4-ylphenyl)
propane-1-sulfonamide

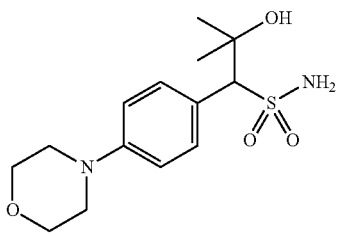 [SMILES: CC(C)(O)C(c1ccc(N2CCOCC2)cc1)S(N)(=O)=O]

Under inert gas, 0.264 g of N-(2,4-dimethoxybenzyl)-C-(4-morpholin-4-ylphenyl)methanesulfonamide was initially charged in 3 ml of THF and then, at −78° C., 0.85 ml of a 1.6 N butyllithium solution in hexane was added dropwise. The reaction mixture was stirred for 10 minutes and then 0.22 ml of acetone was added dropwise. The mixture was stirred at constant temperature for 30 minutes, 0.102 ml of trifluoroacetic acid was added and the mixture was allowed to come to room temperature. The solvent was removed under reduced pressure. The residue was dissolved in 4 ml of dichloromethane, and 1.2 ml of trifluoroacetic acid was added. After stirring at room temperature for 16 h, the crude product was purified in a purification laboratory by means of preparative HPLC. This gave the product with a molecular weight of 428.43 g/mol ($C_{14}H_{22}N_2O_4S$).

2-Methoxy-6,6-dimethyl-5-(4-morpholin-4-ylphe-
nyl)-5,6-dihydro-[1,4,3]oxathiazine 4,4-dioxide

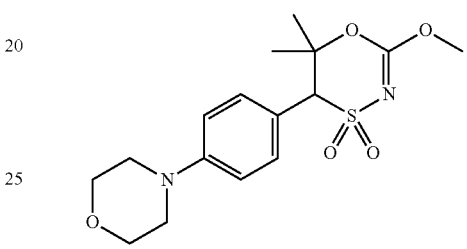

2-Hydroxy-2-methyl-1-(4-morpholin-4-ylphenyl)pro-pane-1-sulfonamide (41 mg) was stirred with tetramethyl orthocarbonate (0.2 ml), glacial acetic acid (0.01 ml) and dioxane (0.1 ml) at 90° C. for 4 hours. The solvents were removed under reduced pressure and the residue was used further without further purification.

(S)-3-[6,6-Dimethyl-5-(4-morpholin-4-ylphenyl)-4,
4-dioxo-5,6-dihydro-4H-4lambda*6*-[1,4,3]oxathi-
azin-2-ylamino]-3-(2-fluorophenyl)propan-1-ol

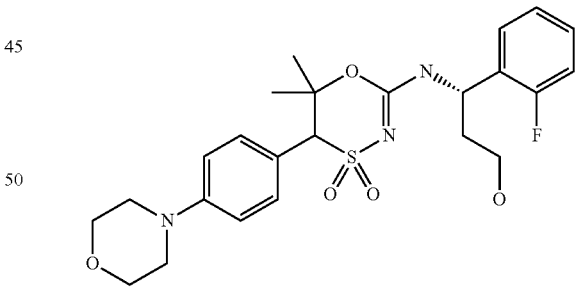

To a solution of 2-methoxy-6,6-dimethyl-5-(4-morpholin-4-ylphenyl)-5,6-dihydro-[1,4,3]oxathiazine 4,4-dioxide (50 mg) in dichloromethane (1 ml) was added (S)-3-(tert-butyldimethylsilanyloxy)-1-(2-fluorophenyl)propylamine (50 mg), and the solvent was evaporated. The residue was left to stand for 16 h and then dissolved in methanol (0.5 ml), and 0.05 ml of conc. HCl was added. The resulting mixture was purified in a purification laboratory by means of preparative HPLC. This gave the product (28 mg as the HCl salt after treatment with hydrochloric acid) with a molecular weight of 491.2 g/mol ($C_{24}H_{30}FN_3O_5S$); MS (ESI): m/e=492 (M+H$^+$).

(S)-3-{6,6-Dimethyl-5-[4-(4-methylpiperazin-1-yl)phenyl]-4,4-dioxo-5,6-dihydro-4H-4lambda*6*-[1,4,3]oxathiazin-2-ylamino}-3-(2-fluorophenyl)propan-1-ol

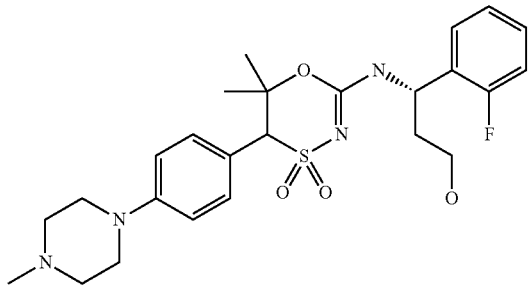 [SMILES: CN1CCN(c2ccc(C3C(C)(C)OC(N[C@@H](CCO)c4ccccc4F)=NS3(=O)=O)cc2)CC1]

[(S)-3-(tert-Butyldimethylsilanyloxy)-1-(2-fluorophenyl)propyl]-{6,6-dimethyl-4,4-dioxo-5-[4-(4,4,5,5-tetramethyl-[1,3,2]dioxaborolan-2-yl)phenyl]-5,6-dihydro-4H-4lambda*6*-[1,4,3]oxathiazin-2-yl}amine

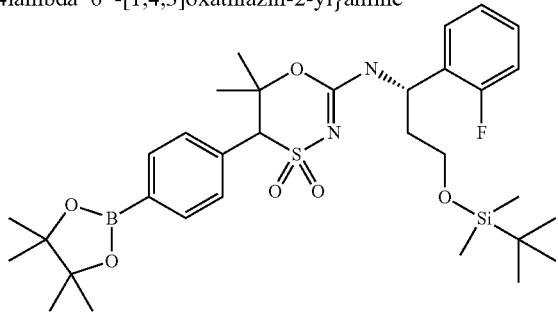

To a solution of [5-(4-bromophenyl)-6,6-dimethyl-4,4-dioxo-5,6-dihydro-4H-4lambda*6*-[1,4,3]oxathiazin-2-yl]-[(S)-3-(tert-butyldimethylsilanyloxy)-1-(2-fluorophenyl)propyl]amine (490 mg) in dioxane were added Pd(dppf)Cl$_2$ (67 mg), bis(pinacolato)diboron (311 mg) and potassium acetate (241 mg), and the mixture was stirred at 80° C. for 1 h. After dilution with ethyl acetate, the mixture was washed with water and sodium chloride solution, dried over kieselguhr and concentrated. This was followed by purification by column chromatography (ethyl acetate/heptane). This gave the product (447 mg) with a molecular weight of 646.7 g/mol ($C_{32}H_{48}BFN_2O_6SSi$).

[5-(4-Boroxyphenyl)-6,6-dimethyl-4,4-dioxo-5,6-dihydro-4H-4lambda*6*-[1,4,3]oxathiazin-2-yl]-[(S)-3-(tert-butyldimethylsilanyloxy)-1-(2-fluorophenyl)propyl]amine

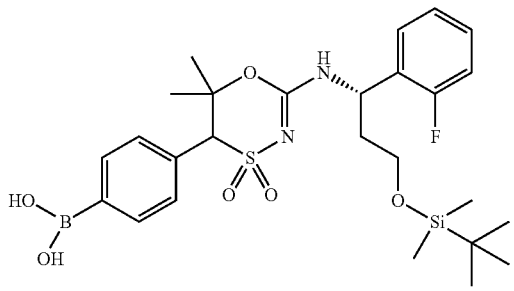 [SMILES: CC1(C)OC(N[C@@H](CCO[Si](C)(C)C(C)(C)C)c2ccccc2F)=NS(=O)(=O)C1c1ccc(B(O)O)cc1]

To a solution of [(S)-3-(tert-butyldimethylsilanyloxy)-1-(2-fluorophenyl)propyl]-{6,6-dimethyl-4,4-dioxo-5-[4-(4,4,5,5-tetramethyl-[1,3,2]dioxaborolan-2-yl)-phenyl]-5,6-dihydro-4H-4lambda*6*-[1,4,3]oxathiazin-2-yl}amine (1.15 g) in 1:1 acetone/water (24 ml) at room temperature were added ammonium acetate (308 mg) and sodium periodate (859 mg), and the mixture was stirred for 16 h. After dilution with ethyl acetate, the mixture was washed with water and sodium chloride solution, dried over magnesium sulfate and concentrated. This was followed by purification by column chromatography (ethyl acetate/heptane). This gave the product (567 mg) with a molecular weight of 564.6 g/mol ($C_{26}H_{38}BFN_2O_6SSi$).

In an analogous manner, the following intermediate was prepared:

[5-(3-Boroxyphenyl)-6,6-dimethyl-4,4-dioxo-5,6-dihydro-4H-4lambda*6*-[1,4,3]oxathiazin-2-yl]-[(S)-1-(2-fluorophenyl)ethyl]amine

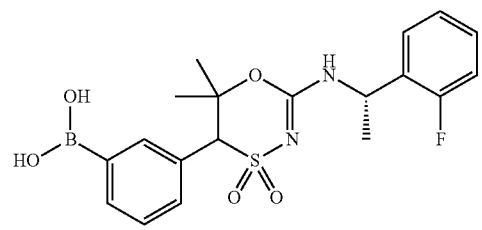 [SMILES: C[C@H](NC1=NS(=O)(=O)C(c2cccc(B(O)O)c2)C(C)(C)O1)c1ccccc1F]

(S)-3-{6,6-Dimethyl-5-[4-(4-methylpiperazin-1-yl)phenyl]-4,4-dioxo-5,6-dihydro-4H-4lambda*6*-[1,4,3]oxathiazin-2-ylamino}-3-(2-fluorophenyl)propan-1-ol

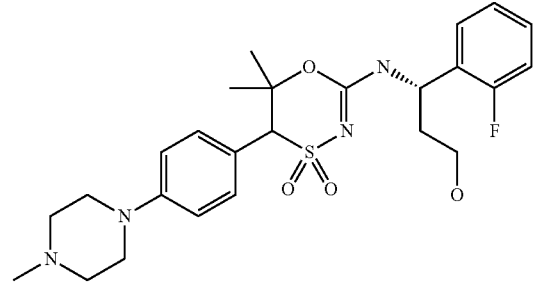 [SMILES: CN1CCN(c2ccc(C3C(C)(C)OC(N[C@@H](CCO)c4ccccc4F)=NS3(=O)=O)cc2)CC1]

To a solution of [(S)-3-(tert-butyldimethylsilanyloxy)-1-(2-fluorophenyl)propyl]-{6,6-dimethyl-4,4-dioxo-5-[4-(4,4,5,5-tetramethyl-[1,3,2]dioxaborolan-2-yl)phenyl]-5,6-dihydro-4H-4lambda*6*-[1,4,3]oxathiazin-2-yl}amine (270 mg) in pyridine were added copper(II) acetate (76 mg) and 0.4 nm molecular sieve, and the mixture was stirred for 10 min. Subsequently, N-methylpiperazine (63 mg) was added and the mixture was stirred at 80° C. for 16 h. After dilution with ethyl acetate, the mixture was washed with sodium bicarbonate solution and sodium chloride solution, dried over magnesium sulfate and concentrated. The residue was dissolved in methanol (5 ml) and treated with conc. HCl (0.5 ml). After 16 h, the solution was purified in a purification laboratory by means of preparative HPLC. This gave the product (61 mg as the HCl salt after treatment with hydrochloric acid) with a molecular weight of 504.2 g/mol ($C_{25}H_{33}FN_4O_4S$); MS (ESI): m/e=505 (M+H$^+$).

In an analogous manner, the following compounds were obtained:

221

(S)-3-{6,6-Dimethyl-4,4-dioxo-5-[4-(pyrimidin-2-ylamino)phenyl]-5,6-dihydro-4H-4lambda*6*-[1,4,3]oxathiazin-2-ylamino}-3-(2-fluorophenyl)propan-1-ol

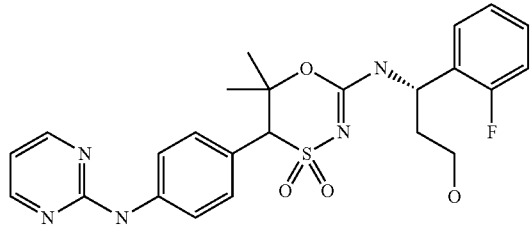 [SMILES: CC1(C)OC(N[C@@H](CCO)c2ccccc2F)=NS(=O)(=O)C1c1ccc(Nc2ncccn2)cc1]

(S)-3-[6,6-Dimethyl-4,4-dioxo-5-(4-piperazin-1-ylphenyl)-5,6-dihydro-4H-4lambda*6*-[1,4,3]oxathiazin-2-ylamino]-3-(2-fluorophenyl)propan-1-ol

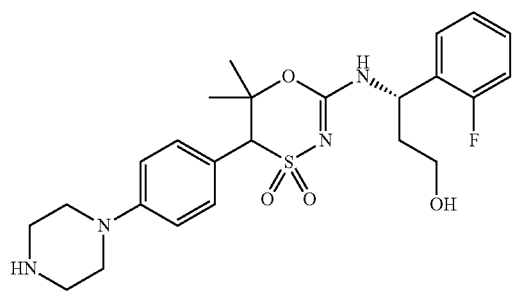 [SMILES: CC1(C)OC(N[C@@H](CCO)c2ccccc2F)=NS(=O)(=O)C1c1ccc(N2CCNCC2)cc1]

[6,6-Dimethyl-4,4-dioxo-5-(4-piperazin-1-ylphenyl)-5,6-dihydro-4H-4lambda*6*-[1,4,3]oxathiazin-2-yl]-[(S)-1-(2-fluorophenyl)ethyl]amine

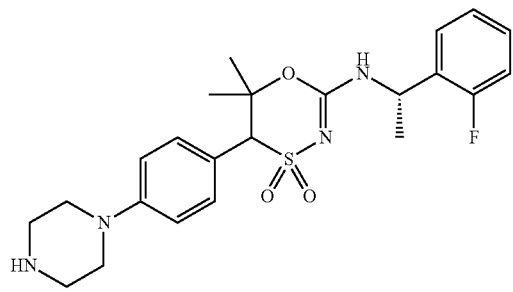 [SMILES: C[C@H](NC1=NS(=O)(=O)C(c2ccc(N3CCNCC3)cc2)C(C)(C)O1)c1ccccc1F]

{6,6-Dimethyl-5-[4-(4-methylpiperazin-1-yl)phenyl]-4,4-dioxo-5,6-dihydro-4H-4lambda*6*-[1,4,3]oxathiazin-2-yl}-[(S)-1-(2-fluorophenyl)ethyl]amine

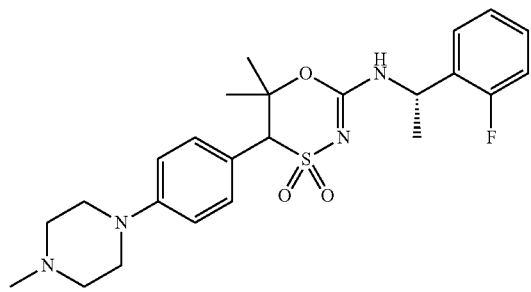 [SMILES: C[C@H](NC1=NS(=O)(=O)C(c2ccc(N3CCN(C)CC3)cc2)C(C)(C)O1)c1ccccc1F]

222

1-(4-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}phenyl)pyrrolidin-2-one

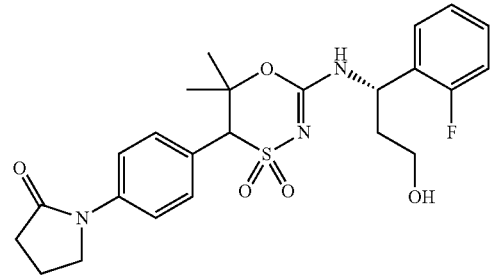 [SMILES: CC1(C)OC(N[C@@H](CCO)c2ccccc2F)=NS(=O)(=O)C1c1ccc(N2CCCC2=O)cc1]

(S)-3-(2-Fluorophenyl)-3-(5-{4-[4-(2-hydroxyethyl)piperazin-1-yl]phenyl}-6,6-dimethyl-4,4-dioxo-5,6-dihydro-4H-4lambda*6*-[1,4,3]oxathiazin-2-ylamino)propan-1-ol

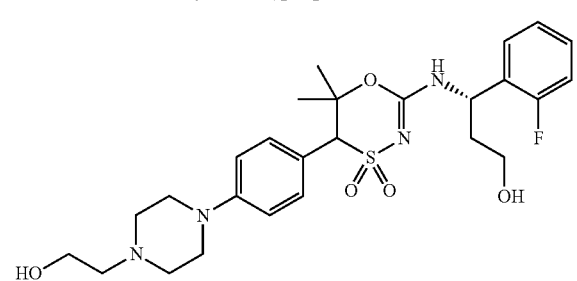

(S)-3-{6,6-Dimethyl-4,4-dioxo-5-[4-(2-piperazin-1-ylethoxy)phenyl]-5,6-dihydro-4H-4lambda*6*-[1,4,3]oxathiazin-2-ylamino}-3-(2-fluorophenyl)propan-1-ol

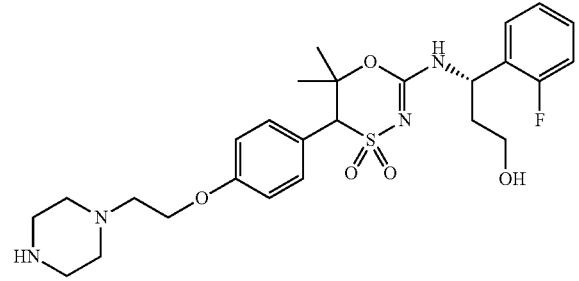 [SMILES: CC1(C)OC(N[C@@H](CCO)c2ccccc2F)=NS(=O)(=O)C1c1ccc(OCCN2CCNCC2)cc1]

(S)-3-{5-[4-(4-tert-Butylpiperazin-1-yl)phenyl]-6,6-dimethyl-4,4-dioxo-5,6-dihydro-4H-4lambda*6*-[1,4,3]oxathiazin-2-ylamino}-3-(2-fluorophenyl)propan-1-ol

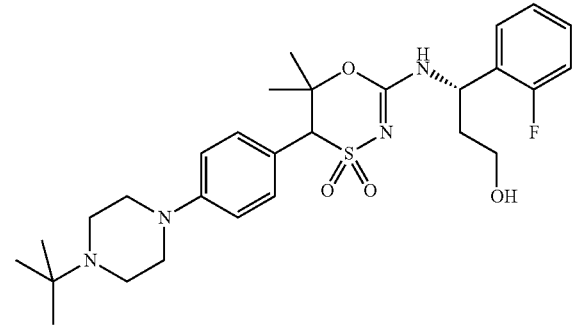 [SMILES: CC1(C)OC(N[C@@H](CCO)c2ccccc2F)=NS(=O)(=O)C1c1ccc(N2CCN(C(C)(C)C)CC2)cc1]

2-(4-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}phenyl)isoindole-1,3-dione

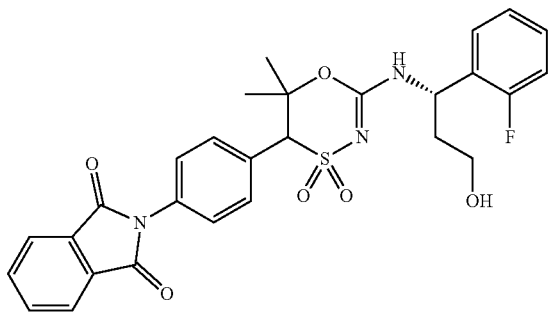 [SMILES: CC1(C)OC(N[C@@H](CCO)c2ccccc2F)=NS(=O)(=O)C1c1ccc(N2C(=O)c3ccccc3C2=O)cc1]

(S)-3-{5-[4-(1-Cyclopropylpiperidin-4-ylamino)phenyl]-6,6-dimethyl-4,4-dioxo-5,6-dihydro-4H-4lambda*6*-[1,4,3]oxathiazin-2-ylamino}-3-(2-fluorophenyl)propan-1-ol

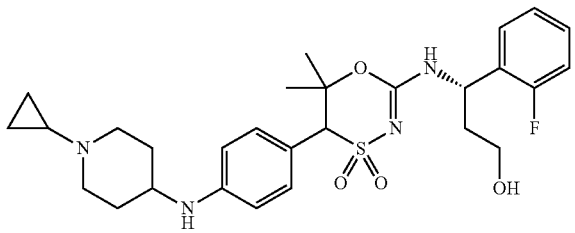 [SMILES: CC1(C)OC(N[C@@H](CCO)c2ccccc2F)=NS(=O)(=O)C1c1ccc(NC2CCN(C3CC3)CC2)cc1]

(6,6-Dimethyl-4,4-dioxo-5-{4-[4-(3,3,3-trifluoropropyl)piperazin-1-yl]phenyl}-5,6-dihydro-4H-4lambda*6*-[1,4,3]oxathiazin-2-yl)-[(S)-1-(2-fluorophenyl)ethyl]amine

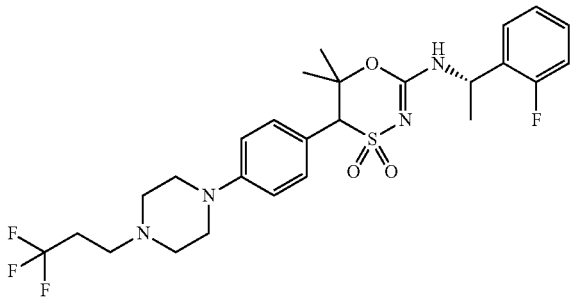 [SMILES: C[C@H](NC1=NS(=O)(=O)C(c2ccc(N3CCN(CCC(F)(F)F)CC3)cc2)C(C)(C)O1)c1ccccc1F]

(S)-3-[6,6-Dimethyl-4,4-dioxo-5-(4-pyridin-2-ylphenyl)-5,6-dihydro-4H-4lambda*6*-[1,4,3]oxathiazin-2-ylamino]-3-(2-fluorophenyl)propan-1-ol

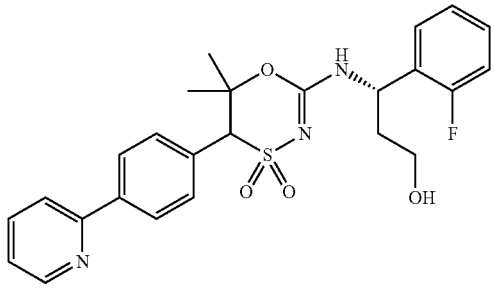 [SMILES: CC1(C)OC(N[C@@H](CCO)c2ccccc2F)=NS(=O)(=O)C1c1ccc(-c2ccccn2)cc1]

To a solution of [(S)-3-(tert-butyldimethylsilanyloxy)-1-(2-fluorophenyl)propyl]-{6,6-dimethyl-4,4-dioxo-5-[4-(4,4,5,5-tetramethyl-[1,3,2]dioxaborolan-2-yl)phenyl]-5,6-dihydro-4H-4lambda*6*-[1,4,3]oxathiazin-2-yl}amine (300 mg) in 3:1 dioxane/water (4 ml) were added 2-bromopyridine (92 mg), Pd(dba)₂ (27 mg) and CTC-Q-Phos (66 mg), and the mixture was stirred at 62° C. for 40 minutes. After dilution with ethyl acetate, the mixture was washed with water, dried using a kieselguhr cartridge and concentrated. This was followed by purification by column chromatography (ethyl acetate/heptane). The still silylated intermediate was dissolved in methanol (2 ml) and treated with conc. HCl (0.25 ml). After 2 h, the solution was purified in a purification laboratory by means of preparative HPLC. This gave the product (129 mg as the HCl salt after treatment with hydrochloric acid) with a molecular weight of 483.6 g/mol ($C_{25}H_{26}FN_3O_4S$); MS (ESI): m/e=484 (M+H⁺).

In an analogous manner, the following compound was obtained:

(S)-3-(6,6-Dimethyl-5-{4-[5-(4-methylpiperazin-1-yl)pyridin-2-yl]phenyl}-4,4-dioxo-5,6-dihydro-4H-4lambda*6*-[1,4,3]oxathiazin-2-ylamino)-3-(2-fluorophenyl)propan-1-ol

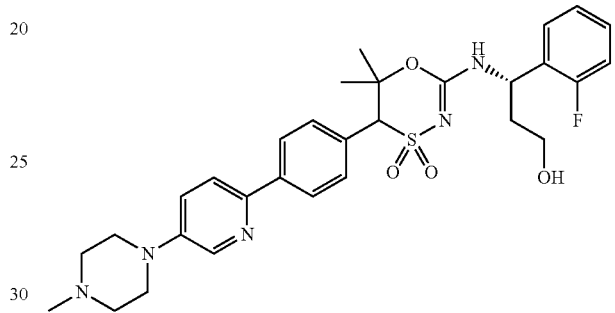

(S)-3-{5-[4-(1-tert-Butylpiperidin-4-yl)phenyl]-6,6-dimethyl-4,4-dioxo-5,6-dihydro-4H-4lambda*6*-[1,4,3]oxathiazin-2-ylamino}-3-(2-fluorophenyl)propan-1-ol

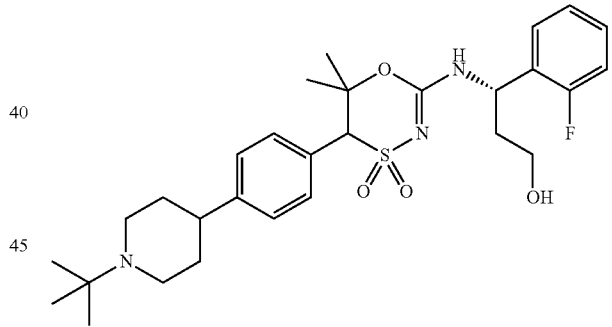

[(S)-3-(tert-Butyldimethylsilanyloxy)-1-(2-fluorophenyl)propyl]-{5-[4-(1-tert-butyl-1,2,3,6-tetrahydropyridin-4-yl)phenyl]-6,6-dimethyl-4,4-dioxo-5,6-dihydro-4H-4lambda*6*-[1,4,3]oxathiazin-2-yl}amine

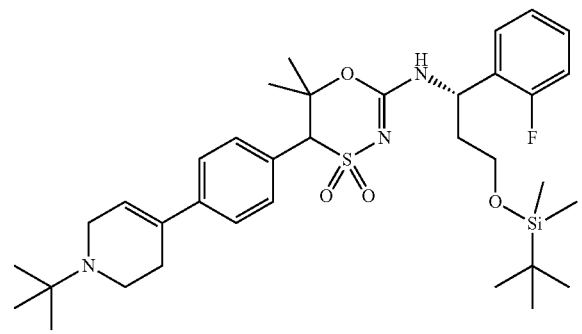 [SMILES: CC1(C)OC(N[C@@H](CCO[Si](C)(C)C(C)(C)C)c2ccccc2F)=NS(=O)(=O)C1c1ccc(C2=CCN(C(C)(C)C)CC2)cc1]

To a solution of [(S)-3-(tert-butyldimethylsilanyloxy)-1-(2-fluorophenyl)propyl]-{6,6-dimethyl-4,4-dioxo-5-[4-(4,4,5,5-tetramethyl-[1,3,2]dioxaborolan-2-yl)phenyl]-5,6-dihydro-4H-4lambda*6*-[1,4,3]oxathiazin-2-yl}amine (300 mg), trifluoromethanesulfonic acid 1-tert-butyl-1,2,3,6-tetrahydropyridin-4-yl ester (208 mg) and cesium carbonate (519 mg) in 3:1 dioxane/water (4 ml) were added Pd(dba)$_2$ (31 mg) and CTC-Q-Phos (75 mg), and the mixture was stirred at 62° C. for 40 min. After dilution with ethyl acetate, the mixture was washed with water, dried using a kieselguhr cartridge and concentrated. This was followed by purification by column chromatography (ethyl acetate/heptane). This gave the product (207 mg) with a molecular weight of 658.0 g/mol ($C_{35}H_{52}FN_3O_4SSi$).

(S)-3-{5-[4-(1-tert-Butylpiperidin-4-yl)phenyl]-6,6-dimethyl-4,4-dioxo-5,6-dihydro-4H-4lambda*6*-[1,4,3]oxathiazin-2-ylamino}-3-(2-fluorophenyl)propan-1-ol

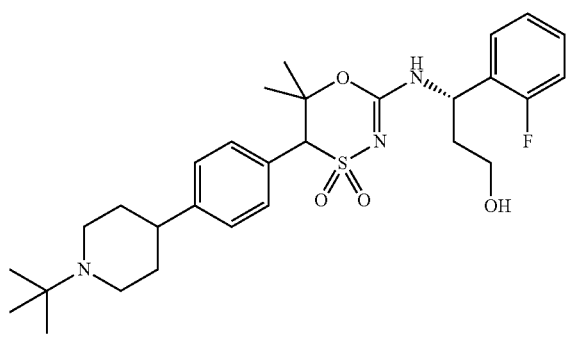 [SMILES: CC1(C)OC(N[C@@H](CCO)c2ccccc2F)=NS(=O)(=O)C1c1ccc(C2CCN(C(C)(C)C)CC2)cc1]

To a solution of [(S)-3-(tert-butyldimethylsilanyloxy)-1-(2-fluorophenyl)-propyl]-{5-[4-(1-tert-butyl-1,2,3,6-tetrahydropyridin-4-yl)phenyl]-6,6-dimethyl-4,4-dioxo-5,6-dihydro-4H-4lambda*6*-[1,4,3]oxathiazin-2-yl}amine (203 mg) in methanol (10 ml) was added palladium on charcoal (5%, 66 mg), and the mixture was stirred in a hydrogen atmosphere for 11 h. The mixture was filtered and the filtrate was concentrated. The residue was dissolved in methanol (10 ml) and treated with conc. HCl (1 ml). After 2 h, the solution was purified in a purification laboratory by means of preparative HPLC. This gave the product (69 mg as the HCl salt after treatment with hydrochloric acid) with a molecular weight of 545.7 g/mol ($C_{29}H_{40}FN_3O_4S$); MS (ESI): m/e=546 (M+H$^+$).

In an analogous manner, the following compounds were obtained:

(S)-3-{5-[4-(1-Cyclopropylpiperidin-4-yl)phenyl]-6,6-dimethyl-4,4-dioxo-5,6-dihydro-4H-4lambda*6*-[1,4,3]oxathiazin-2-ylamino}-3-(2-fluorophenyl)propan-1-ol

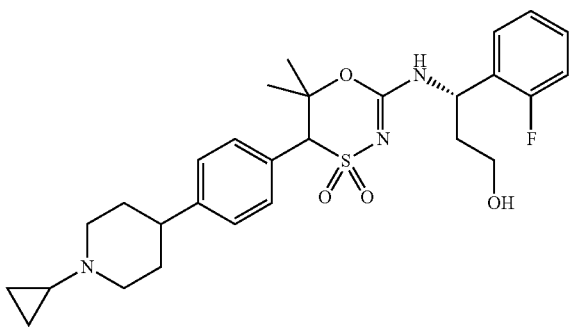 [SMILES: CC1(C)OC(N[C@@H](CCO)c2ccccc2F)=NS(=O)(=O)C1c1ccc(C2CCN(C3CC3)CC2)cc1]

{5-[4-(1-Cyclopropylpiperidin-4-yl)phenyl]-6,6-dimethyl-4,4-dioxo-5,6-dihydro-4H-4lambda*6*-[1,4,3]oxathiazin-2-yl}-[(S)-1-(2-fluorophenyl)ethyl]amine

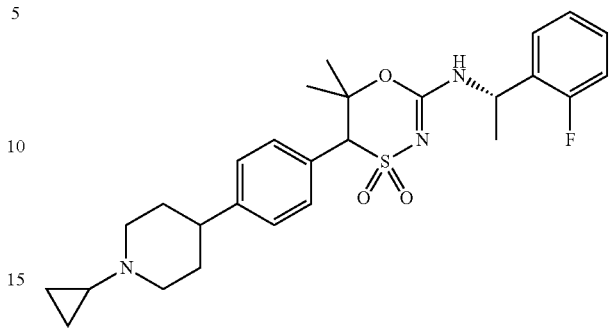

{5-[4-(1-tert-Butylpiperidin-4-yl)phenyl]-6,6-dimethyl-4,4-dioxo-5,6-dihydro-4H-4lambda*6*-[1,4,3]oxathiazin-2-yl}-[(S)-1-(2-fluorophenyl)ethyl]amine

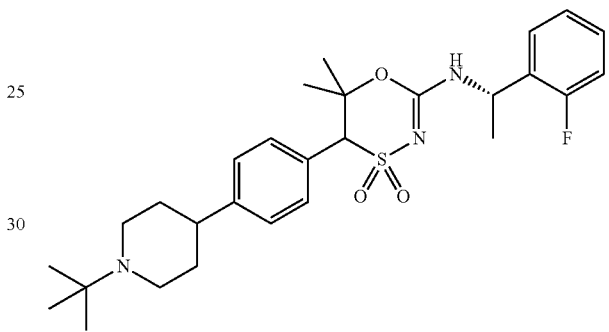

(S)-3-[6,6-Dimethyl-5-(4-morpholin-4-ylmethylphenyl)-4,4-dioxo-5,6-dihydro-4H-4lambda*6*-[1,4,3]oxathiazin-2-ylamino]-3-(2-fluorophenyl)propan-1-ol

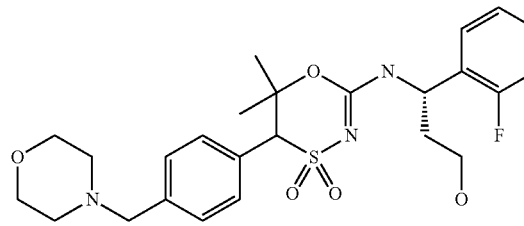

4-[(2,4-Dimethoxybenzylsulfamoyl)methyl]benzoic acid methyl ester

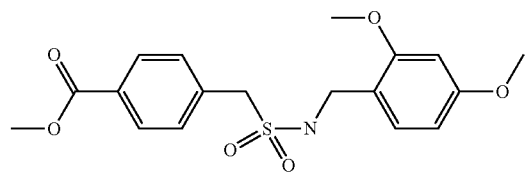

Under inert gas, 10 g of 4-[(chlorosulfonyl)methyl]benzoic acid methyl ester were initially charged in 100 ml of DCM, then, at a temperature of 0° C., 12.1 ml of 2,4-dimethoxybenzylamine were added dropwise. The reaction mixture was filtered and the filtrate was washed with 1 N HCl. The organic phase was dried over MgSO$_4$ and concentrated by rotary evaporation. This gave the product (14.2 g) with a molecular weight of 379.4 g/mol ($C_{18}H_{21}NO_6S$).

In an analogous manner, the following intermediate was synthesized:

3-[(2,4-Dimethoxybenzylsulfamoyl)methyl]benzoic acid methyl ester

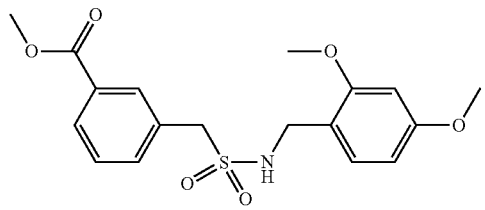

N-(2,4-Dimethoxybenzyl)-C-[4-(morpholine-4-carbonyl)phenyl]methanesulfonamide

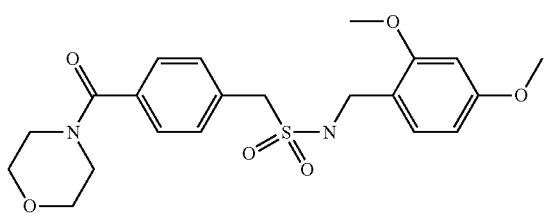 [SMILES: COc1ccc(CNS(=O)(=O)Cc2ccc(C(=O)N3CCOCC3)cc2)c(OC)c1]

To a solution of morpholine (0.69 ml) in THF (10 ml) was added, at −78° C., N-butyllithium (1.6 M, 3.3 ml), and the solution was stirred for 10 min. A solution of 4-[(2,4-dimethoxybenzylsulfamoyl)methyl]benzoic acid methyl ester (1 g) was added and the solution was warmed up to room temperature and stirred for a further 30 minutes. After the addition of water (100 ml), the mixture was extracted with ethyl acetate (2×50 ml). The organic phases were dried over magnesium sulfate and concentrated. This was followed by purification by column chromatography (ethyl acetate/heptane). This gave the product (450 mg) with a molecular weight of 434.5 g/mol ($C_{21}H_{26}N_2O_6S$).

N-(2,4-Dimethoxybenzyl)-C-(4-morpholin-4-ylmethylphenyl)methanesulfonamide

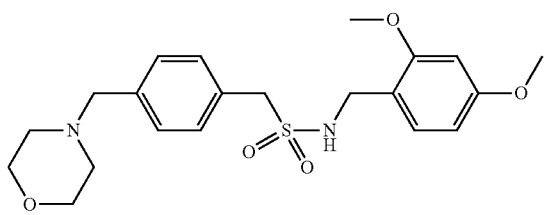 [SMILES: COc1ccc(CNS(=O)(=O)Cc2ccc(CN3CCOCC3)cc2)c(OC)c1]

To a solution of N-(2,4-dimethoxybenzyl)-C-[4-(morpholine-4-carbonyl)phenyl]methanesulfonamide (440 mg) in THF (5 ml) was added, at 0° C., LAH (96 mg), and the mixture was warmed up to room temperature and stirred for a further 60 minutes. After the addition of water (100 μl), sodium hydroxide solution (300 μl) and water again (300 μl), the mixture was filtered and the filtrate was concentrated. This gave the product (415 mg) with a molecular weight of 420.5 g/mol ($C_{21}H_{28}N_2O_5S$).

2-Hydroxy-2-methyl-1-(4-morpholin-4-ylmethylphenyl)propane-1-sulfonamide

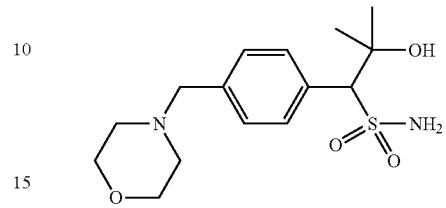

Under inert gas, 0.410 g of N-(2,4-dimethoxybenzyl)-C-(4-morpholin-4-ylmethylphenyl)methanesulfonamide was initially charged in 5 ml of THF and then, at −78° C., 1.34 ml of a 1.6 N butyllithium solution in hexane were added dropwise. The reaction mixture was stirred for 5 minutes and then 0.29 ml of acetone was added dropwise. The mixture was stirred at constant temperature for 5 minutes, 0.22 ml of trifluoroacetic acid were added and the mixture was allowed to come to room temperature. The solvent was removed under reduced pressure. The residue was dissolved in 10 ml of dichloromethane, and 2 ml of trifluoroacetic acid were added. After stirring at room temperature for 16 h, 20 ml of 1M HCl were added and the aqueous phase was removed and concentrated. This gave the crude product with a molecular weight of 364.9 g/mol ($C_{15}H_{25}N_2O_4S$), which was used without further purification.

2-Methoxy-6,6-dimethyl-5-(4-morpholin-4-ylmethylphenyl)-5,6-dihydro-[1,4,3]oxathiazine 4,4-dioxide

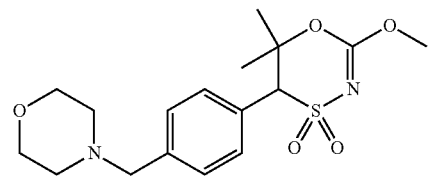 [SMILES: COC1=NS(=O)(=O)C(c2ccc(CN3CCOCC3)cc2)C(C)(C)O1]

2-Hydroxy-2-methyl-1-(4-morpholin-4-ylmethylphenyl)propane-1-sulfonamide (350 mg) was stirred with tetramethyl orthocarbonate (5 ml) and glacial acetic acid (1 ml) at 80° C. for 16 hours. The solvents were removed under reduced pressure and the residue was used further without further purification.

(S)-3-[6,6-Dimethyl-5-(4-morpholin-4-ylmethylphenyl)-4,4-dioxo-5,6-dihydro-4H-4lambda*6*-[1,4,3]oxathiazin-2-ylamino]-3-(2-fluorophenyl)propan-1-ol

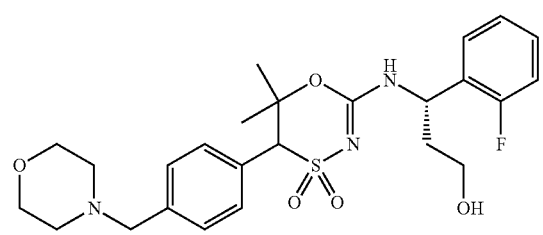 [SMILES: CC1(C)OC(N[C@@H](CCO)c2ccccc2F)=NS(=O)(=O)C1c1ccc(CN2CCOCC2)cc1]

To a solution of 2-methoxy-6,6-dimethyl-5-(4-morpholin-4-ylmethylphenyl)-5,6-dihydro-[1,4,3]oxathiazine 4,4-dioxide in dichloromethane (1 ml) was added (S)-3-(tert-butyldimethylsilanyloxy)-1-(2-fluorophenyl)propylamine (283 mg), and the solvent was evaporated. The residue was left to stand for 16 h and then dissolved in methanol (0.5 ml), and 0.05 ml of conc. HCl was added. The resulting mixture was purified in a purification laboratory by means of preparative HPLC. This gave the product (230 mg as the HCl salt after treatment with hydrochloric acid) with a molecular weight of 505.2 g/mol ($C_{25}H_{32}FN_3O_5S$); MS (ESI): m/e=506 (M+H$^+$).

In an analogous manner, the following compound was obtained:

(S)-3-{6,6-Dimethyl-5-[4-(4-methylpiperazin-1-ylmethyl)phenyl]-4,4-dioxo-5,6-dihydro-4H-4lambda*6*-[1,4,3]oxathiazin-2-ylamino}-3-(2-fluorophenyl)propan-1-ol

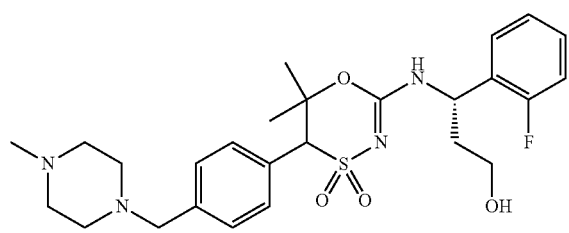 [SMILES: CN1CCN(Cc2ccc(C3C(C)(C)OC(N[C@@H](CCO)c4ccccc4F)=NS3(=O)=O)cc2)CC1]

(S)-3-(6,6-Dimethyl-4,4-dioxo-5-{4-[4-(3,3,3-trifluoropropyl)piperazin-1-yl]phenyl}-5,6-dihydro-4H-4lambda*6*-[1,4,3]oxathiazin-2-ylamino)-3-(2-fluorophenyl)propan-1-ol

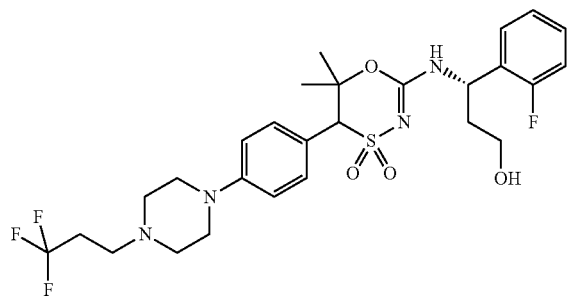

To a solution of (S)-3-[6,6-dimethyl-4,4-dioxo-5-(4-piperazin-1-ylphenyl)-5,6-dihydro-4H-4lambda*6*-[1,4,3]oxathiazin-2-ylamino]-3-(2-fluorophenyl)propan-1-ol (73 mg) in DMF (1 ml) was added 3-bromo-1,1,1-trifluoropropane (105 mg), and the mixture was stirred at 50° C. for 16 h. The resulting mixture was purified in a purification laboratory by means of preparative HPLC. This gave the product (61 mg as the HCl salt after treatment with hydrochloric acid) with a molecular weight of 586.6 g/mol ($C_{27}H_{34}F_4N_4O_4S$); MS (ESI): m/e=587 (M+H$^+$).

(S)-3-(6,6-Dimethyl-5-{4-[2-(4-methylpiperazin-1-yl)ethoxy]phenyl}-4,4-dioxo-5,6-dihydro-4H-4lambda*6*-[1,4,3]oxathiazin-2-ylamino)-3-(2-fluorophenyl)propan-1-ol

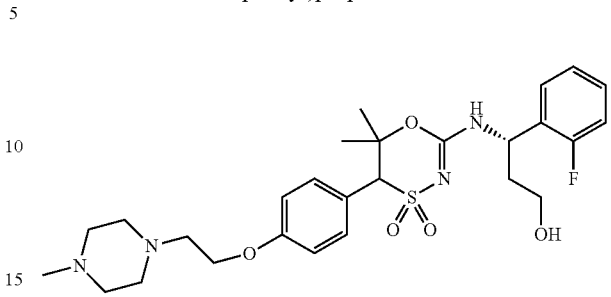

To a solution of (S)-3-{6,6-dimethyl-4,4-dioxo-5-[4-(2-piperazin-1-ylethoxy)phenyl]-5,6-dihydro-4H-4lambda*6*-[1,4,3]oxathiazin-2-ylamino}-3-(2-fluorophenyl)propan-1-ol (26 mg) in 1.3 ml of 4:1 THF/acetic acid were added paraformaldehyde (17 mg) and polymer-bound sodium cyanoborohydride (56 mg), and the mixture was stirred at room temperature overnight. After filtration and concentration by rotary evaporation, the residue was purified in a purification laboratory by means of preparative HPLC. This gave the product (16 mg as the HCl salt after treatment with hydrochloric acid) with a molecular weight of 548.7 g/mol ($C_{27}H_{37}FN_4O_5S$); MS (ESI): m/e=549 (M+H$^+$).

(S)-3-{6,6-Dimethyl-5-[4-(2-morpholin-4-ylethyl)phenyl]-4,4-dioxo-5,6-dihydro-4H-4lambda*6*-[1,4,3]oxathiazin-2-ylamino}-3-(2-fluorophenyl)propan-1-ol

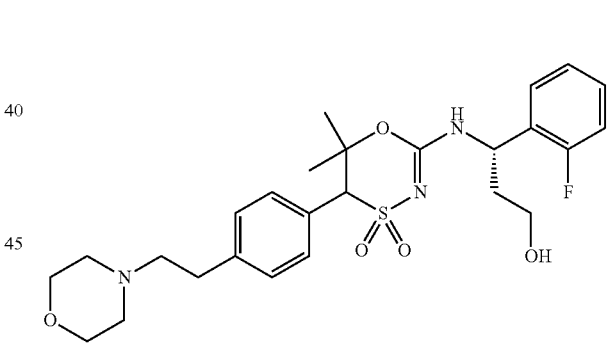

N-(2,4-Dimethoxybenzyl)-C-(4-hydroxymethylphenyl)methanesulfonamide

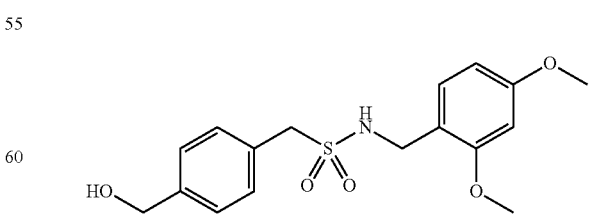

To a solution of 4-[(2,4-dimethoxybenzylsulfamoyl)methyl]benzoic acid methyl ester (6 g) in THF (300 ml) was added, at 0° C., lithium aluminum hydride (1.5 g) in portions, and the mixture was stirred at room temperature for 1 h. Then water (9 ml), 6 M NaOH (7 ml) and water again (27 ml) were added successively. The solids were filtered off and dichloromethane was added to the filtrate. The organic phase was removed, dried over magnesium sulfate and concentrated. This gave the product (6 g) with a molecular weight of 351.4 g/mol ($C_{17}H_{21}NO_5S$).

Methanesulfonic acid 4-[(2,4-dimethoxybenzylsulfamoyl)methyl]benzyl ester

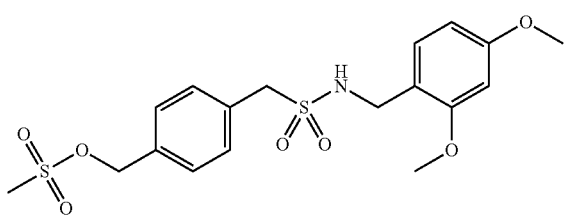

To a solution of N-(2,4-dimethoxybenzyl)-C-(4-hydroxymethylphenyl)methanesulfonamide (6 g) were added, at 0° C., triethylamine (4.5 ml) and, gradually, methanesulfonyl chloride in dichloromethane (2.2 ml in 50 ml). The mixture was stirred for 1.5 h and then diluted with ethyl acetate. After washing with water, 1 M hydrochloric acid and sodium chloride solution, the organic phase was dried over magnesium sulfate and concentrated. This gave the product (7 g) with a molecular weight of 429.5 g/mol ($C_{18}H_{23}NO_7S_2$).

C-(4-Cyanomethylphenyl)-N-(2,4-dimethoxybenzyl)methanesulfonamide

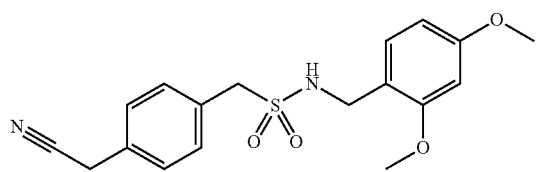 [SMILES: COc1ccc(CNS(=O)(=O)Cc2ccc(CC#N)cc2)c(OC)c1]

To a solution of C-(4-cyanomethylphenyl)-N-(2,4-dimethoxybenzyl)methanesulfonamide (4.8 g) in DMF (30 ml) was added sodium cyanide (1.4 g), and the mixture was stirred at 85° C. for 1.5 h. The mixture was added to water (400). After extraction with ethyl acetate, the organic phase was washed with water and sodium chloride solution, dried over magnesium sulfate and concentrated. This was followed by purification by column chromatography (ethyl acetate/heptane). This gave the product (1.8 g) with a molecular weight of 360.4 g/mol ($C_{18}H_{20}N_2O_4S$).

{4-[(2,4-Dimethoxybenzylsulfamoyl)methyl]phenyl}acetic acid

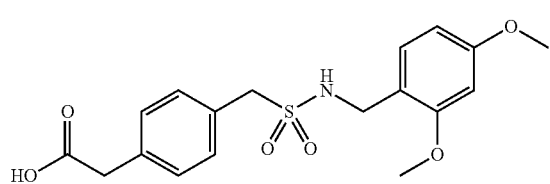 [SMILES: COc1ccc(CNS(=O)(=O)Cc2ccc(CC(=O)O)cc2)c(OC)c1]

To a suspension of C-(4-cyanomethylphenyl)-N-(2,4-dimethoxybenzyl)methanesulfonamide (1.7 g) in ethanol (50 ml) was added 25% NaOH, and the mixture was stirred at 60° C. for 5 h. After cooling, the organic solvent was removed by rotary evaporation and the remaining solution was washed with diethyl ether. The aqueous phase was slightly acidified with conc. HCl and then extracted with ethyl acetate. The organic phase was dried over magnesium sulfate and concentrated. This gave the product (1 g) with a molecular weight of 379.4 g/mol ($C_{18}H_{21}NO_6S$).

N-(2,4-Dimethoxybenzyl)-C-[4-(2-morpholin-4-yl-2-oxoethyl)phenyl]methanesulfonamide

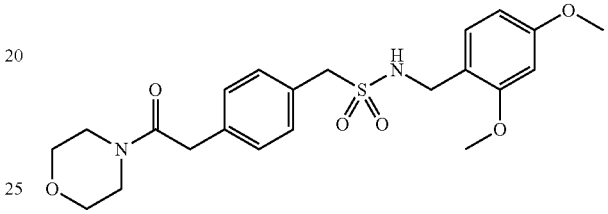

To a solution of {4-[(2,4-dimethoxybenzylsulfamoyl)methyl]phenyl}acetic acid (356 mg) in DMF (15 ml) were added triethylamine (237 mg), morpholine (97 mg) and HATU (392 mg). The mixture was stirred at room temperature for 17 h, then added to water (200 ml) and extracted with ethyl acetate. After washing with water, 1 M hydrochloric acid, sodium hydrogencarbonate solution and sodium chloride solution, the organic phase was dried over magnesium sulfate and concentrated. This gave the product (313 mg) with a molecular weight of 448.5 g/mol ($C_{22}H_{28}N_2O_6S$).

N-(2,4-Dimethoxybenzyl)-C-[4-(2-morpholin-4-ylethyl)phenyl]methanesulfonamide

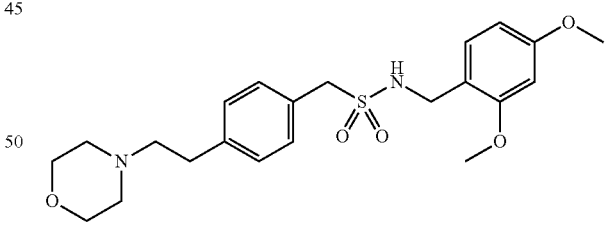

To a solution of N-(2,4-dimethoxybenzyl)-C-[4-(2-morpholin-4-yl-2-oxoethyl)phenyl]methanesulfonamide (313 mg) in THF (10 ml) was added, at 0° C., lithium aluminum hydride (66 mg) in portions, and the mixture was stirred at room temperature for 1 h. Then water (0.4 ml), 6 M NaOH (0.3 ml) and water again (1.2 ml) were added successively. The solids were filtered off and dichloromethane was added to the filtrate. The organic phase was removed, dried over magnesium sulfate and concentrated. The crude product was purified by means of preparative HPLC. This gave the product (57 mg) with a molecular weight of 434.6 g/mol ($C_{22}H_{30}N_2O_5S$).

2-Hydroxy-2-methyl-1-[4-(2-morpholin-4-ylethyl)phenyl]propane-1-sulfonamide

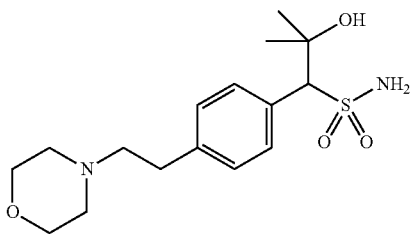 [SMILES: CC(C)(O)C(c1ccc(CCN2CCOCC2)cc1)S(N)(=O)=O]

A solution of N-(2,4-dimethoxybenzyl)-C-[4-(2-morpholin-4-ylethyl)phenyl]methanesulfonamide (50 mg) in THF (1 ml) was initially charged and then, at −78° C., 1.6 N butyllithium solution in hexane (0.3 ml) was added dropwise. The reaction mixture was stirred for 10 minutes, and then acetone (50 μl) was added dropwise. The mixture was stirred at constant temperature for 30 minutes, trifluoroacetic acid (40 μl) was added and the mixture was allowed to come to room temperature. The solvent was removed under reduced pressure. The residue was dissolved in 2 ml of dichloromethane, and 250 μl of trifluoroacetic acid were added. After stirring at room temperature for 2 h, the mixture was diluted with dichloromethane and extracted with 1 M hydrochloric acid. The aqueous phase was concentrated and the residue was coevaporated with toluene. This gave the crude product with a molecular weight of 378.9 g/mol ($C_{16}H_{26}N_2O_4S$), which was used without further purification.

2-Methoxy-6,6-dimethyl-5-[4-(2-morpholin-4-ylethyl)phenyl]-5,6-dihydro-[1,4,3]oxathiazine 4,4-dioxide

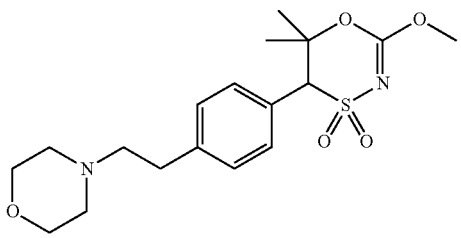 [SMILES: COC1=NS(=O)(=O)C(c2ccc(CCN3CCOCC3)cc2)C(C)(C)O1]

2-Hydroxy-2-methyl-1-[4-(2-morpholin-4-ylethyl)phenyl]propane-1-sulfonamide (44 mg) was stirred with tetramethyl orthocarbonate (1 ml) and glacial acetic acid (0.2 ml) at 80° C. for 17 hours. The solvents were removed under reduced pressure. This gave the crude product with a molecular weight of 382.5 g/mol ($C_{18}H_{26}N_2O_5S$), which was used without further purification.

(S)-3-{6,6-Dimethyl-5-[4-(2-morpholin-4-ylethyl)phenyl]-4,4-dioxo-5,6-dihydro-4H-4lambda*6*-[1,4,3]oxathiazin-2-ylamino}-3-(2-fluorophenyl)propan-1-ol

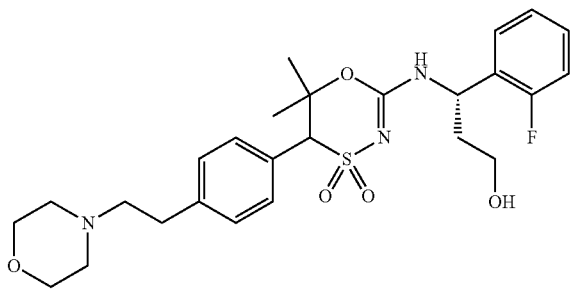 [SMILES: CC1(C)OC(N[C@@H](CCO)c2ccccc2F)=NS(=O)(=O)C1c1ccc(CCN2CCOCC2)cc1]

To a solution of 2-methoxy-6,6-dimethyl-5-[4-(2-morpholin-4-ylethyl)phenyl]-5,6-dihydro-[1,4,3]oxathiazine 4,4-dioxide (19 mg) in dichloromethane (1 ml) was added (S)-3-(tert-butyldimethylsilanyloxy)-1-(2-fluorophenyl)propylamine (15 mg), and the solvent was evaporated. The residue was left to stand for 2.5 days and then dissolved in methanol (1 ml), and 0.1 ml of conc. HCl was added. The resulting mixture was purified in a purification laboratory by means of preparative HPLC. This gave the product (2.7 mg as the HCl salt after treatment with hydrochloric acid) with a molecular weight of 519.6 g/mol ($C_{26}H_{34}FN_3O_5S$); MS (ESI): m/e=520 (M+H$^+$).

In an analogous manner, the following compound was obtained:

(S)-3-(6,6-Dimethyl-5-{4-[2-(4-methylpiperazin-1-yl)ethyl]phenyl}-4,4-dioxo-5,6-dihydro-4H-4lambda*6*-[1,4,3]oxathiazin-2-ylamino)-3-(2-fluorophenyl)propan-1-ol

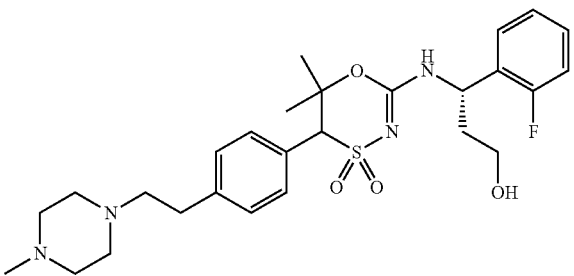 [SMILES: CN1CCN(CCc2ccc(C3C(C)(C)OC(N[C@@H](CCO)c4ccccc4F)=NS3(=O)=O)cc2)CC1]

(S)-3-(2-Fluorophenyl)-3-{5-[4-(1-hydroxy-1-methylethyl)phenyl]-6,6-dimethyl-4,4-dioxo-5,6-dihydro-4H-4lambda*6*-[1,4,3]oxathiazin-2-ylamino}propan-1-ol

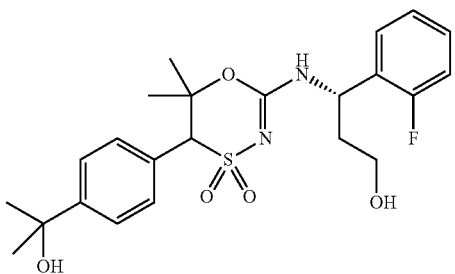 [SMILES: CC(C)(O)c1ccc(C2C(C)(C)OC(N[C@@H](CCO)c3ccccc3F)=NS2(=O)=O)cc1]

[5-(4-Boroxyphenyl)-6,6-dimethyl-4,4-dioxo-5,6-dihydro-4H-4lambda*6*-[1,4,3]oxathiazin-2-yl]-[(S)-3-(tert-butyldimethylsilanyloxy)-1-(2-fluorophenyl)propyl]amine

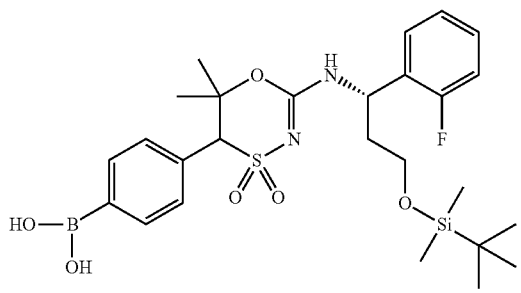 [SMILES: CC1(C)OC(N[C@@H](CCO[Si](C)(C)C(C)(C)C)c2ccccc2F)=NS(=O)(=O)C1c1ccc(B(O)O)cc1]

To a solution of [(S)-3-(tert-butyldimethylsilanyloxy)-1-(2-fluorophenyl)propyl]-{6,6-dimethyl-4,4-dioxo-5-[4-(4,4,5,5-tetramethyl-[1,3,2]dioxaborolan-2-yl)-phenyl]-5,6-dihydro-4H-4lambda*6*-[1,4,3]oxathiazin-2-yl}amine (1.7 g) in 1:1 acetone/water (36 ml) were added ammonium acetate (463 mg) and sodium periodate (1.3 g), and the mixture was stirred at room temperature for 16 h and then at 50° C. for 1 h. The mixture was diluted with ethyl acetate, washed with water, dried over magnesium sulfate and concentrated. This was followed by purification by column chromatography (ethyl acetate/heptane/methanol). This gave the product (1.1 g) with a molecular weight of 564.6 g/mol ($C_{26}H_{38}BN_2O_6SSi$).

1-(4-{2-[(S)-3-(tert-Butyldimethylsilanyloxy)-1-(2-fluorophenyl)propylamino]-6,6-dimethyl-4,4-dioxo-5,6-dihydro-4H-4lambda*6*-[1,4,3]oxathiazin-5-yl}phenyl)ethanone

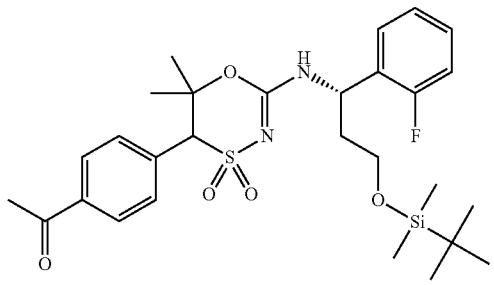 [SMILES: CC(=O)c1ccc(C2C(C)(C)OC(N[C@@H](CCO[Si](C)(C)C(C)(C)C)c3ccccc3F)=NS2(=O)=O)cc1]

To a suspension of [5-(4-boroxyphenyl)-6,6-dimethyl-4,4-dioxo-5,6-dihydro-4H-4lambda*6*-[1,4,3]oxathiazin-2-yl]-[(S)-3-(tert-butyldimethylsilanyloxy)-1-(2-fluorophenyl)propyl]amine (400 mg) and potassium acetate (140 mg) in dioxane (6 ml) were added bis(triphenylphosphine)palladium(II)dichloride (60 mg) and acetyl chloride (120 µl), and the mixture was stirred at 50° C. overnight. The mixture was diluted with ethyl acetate, washed with water, dried over magnesium sulfate and concentrated. This was followed by purification by column chromatography (ethyl acetate/heptane). This gave the product (172 mg) with a molecular weight of 562.8 g/mol ($C_{28}H_{39}FN_2O_5SSi$).

A further product obtained in this reaction was:

Acetic acid 4-{2-[(S)-3-(tert-butyldimethylsilanyloxy)-1-(2-fluorophenyl)propylamino]-6,6-dimethyl-4,4-dioxo-5,6-dihydro-4H-4lambda*6*-[1,4,3]oxathiazin-5-yl}phenyl ester

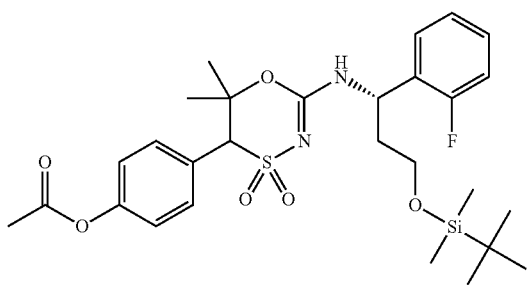 [SMILES: CC(=O)Oc1ccc(C2C(C)(C)OC(N[C@@H](CCO[Si](C)(C)C(C)(C)C)c3ccccc3F)=NS2(=O)=O)cc1]

(S)-3-(2-Fluorophenyl)-3-{5-[4-(1-hydroxy-1-methylethyl)phenyl]-6,6-dimethyl-4,4-dioxo-5,6-dihydro-4H-4lambda*6*-[1,4,3]oxathiazin-2-ylamino}propan-1-ol

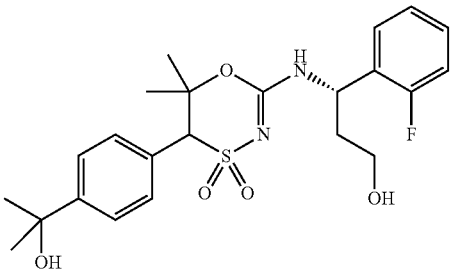 [SMILES: CC(C)(O)c1ccc(C2C(C)(C)OC(N[C@@H](CCO)c3ccccc3F)=NS2(=O)=O)cc1]

To a solution of 1-(4-{2-[(S)-3-(tert-butyldimethylsilanyloxy)-1-(2-fluorophenyl)propylamino]-6,6-dimethyl-4,4-dioxo-5,6-dihydro-4H-4lambda*6*-[1,4,3]oxathiazin-5-yl}phenyl)ethanone (174 mg) in THF (2.5 ml) was added dropwise, at −78° C., a solution of methylmagnesium bromide (1.4 M, 0.44 ml). After 30 min at −78° C., ammonium chloride solution was added to the mixture. After the addition of water, the mixture was extracted with ethyl acetate, dried over magnesium sulfate and concentrated. The residue was dissolved in methanol (2 ml), and 0.2 ml of conc. HCl was added. The resulting mixture was purified in a purification laboratory by means of preparative HPLC. This gave the product (28 mg) with a molecular weight of 464.6 g/mol ($C_{23}H_{29}FN_2O_5S$); MS (ESI): m/e=465 (M+H$^+$).

In this reaction, the following was likewise isolated:

1-(4-{2-[(S)-1-(2-Fluorophenyl)-3-hydroxypropylamino]-6,6-dimethyl-4,4-dioxo-5,6-dihydro-4H-4lambda*6*-[1,4,3]oxathiazin-5-yl}phenyl)ethanone

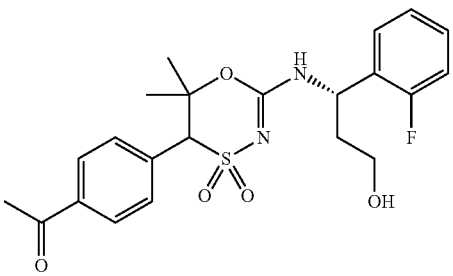 [SMILES: CC(=O)c1ccc(C2C(C)(C)OC(N[C@@H](CCO)c3ccccc3F)=NS2(=O)=O)cc1]

In an analogous manner, the following compounds were obtained:

2-(4-[2-[(S)-1-(2-Fluorophenyl)ethylamino]-6,6-dimethyl-4,4-dioxo-5,6-dihydro-4H-4lambda*6*-[1,4,3]oxathiazin-5-yl]phenyl)propan-2-ol

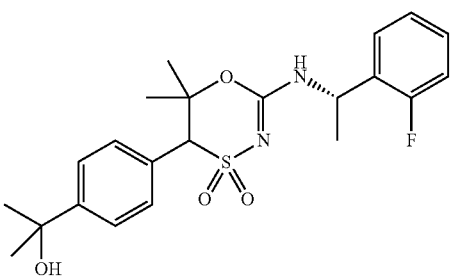 [SMILES: C[C@H](NC1=NS(=O)(=O)C(c2ccc(C(C)(C)O)cc2)C(C)(C)O1)c1ccccc1F]

1-(4-{2-[(S)-1-(2-Fluorophenyl)ethylamino]-6,6-dimethyl-4,4-dioxo-5,6-dihydro-4H-4lambda*6*-[1,4,3]oxathiazin-5-yl}phenyl)ethanone

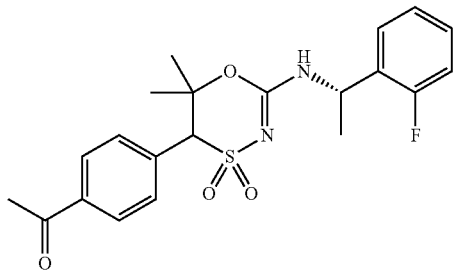 [SMILES: CC(=O)c1ccc(C2C(C)(C)OC(N[C@@H](C)c3ccccc3F)=NS2(=O)=O)cc1]

Acetic acid 4-[2-[(S)-1-(2-fluorophenyl)-3-hydroxypropylamino]-6,6-dimethyl-4,4-dioxo-5,6-dihydro-4H-4lambda*6*-[1,4,3]oxathiazin-5-yl]phenyl ester

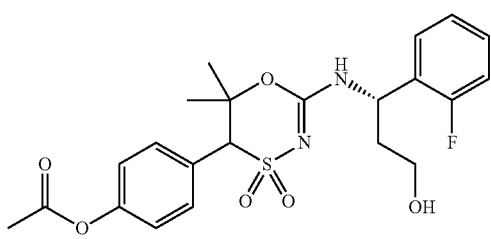 [SMILES: CC(=O)Oc1ccc(C2C(C)(C)OC(N[C@@H](CCO)c3ccccc3F)=NS2(=O)=O)cc1]

This compound was obtained by acidic deprotection of acetic acid 4-{2-[(S)-3-(tert-butyldimethylsilanyloxy)-1-(2-fluorophenyl)propylamino]-6,6-dimethyl-4,4-dioxo-5,6-dihydro-4H-4lambda*6*-[1,4,3]oxathiazin-5-yl}phenyl ester.

(S)-3-(6,6-Dimethyl-4,4-dioxo-5-pyridin-3-yl-5,6-dihydro-4H-4lambda*6*-[1,4,3]oxathiazin-2-ylamino)-3-(2-fluorophenyl)propan-1-ol

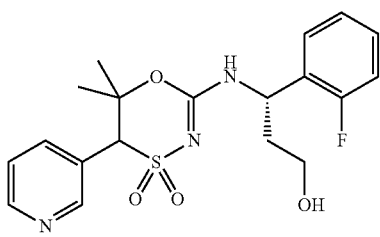 [SMILES: CC1(C)OC(N[C@@H](CCO)c2ccccc2F)=NS(=O)(=O)C1c1cccnc1]

To a solution of [(S)-3-(tert-butyldimethylsilanyloxy)-1-(2-fluorophenyl)propyl]-[5-(6-chloropyridin-3-yl)-6,6-dimethyl-4,4-dioxo-5,6-dihydro-4H-4lambda*6*-[1,4,3]oxathiazin-2-yl]amine (310 mg) in methanol was added palladium on charcoal (5%, 119 mg), and the mixture was stirred in a hydrogen atmosphere for 19 h. The mixture was filtered and the filtrate was concentrated. The residue was dissolved in methanol (10 ml) and treated with conc. HCl (1 ml). After 2 h, the solution was purified in a purification laboratory by means of preparative HPLC. This gave the product (108 mg) with a molecular weight of 407.5 g/mol ($C_{19}H_{22}FN_3O_4S$); MS (ESI): m/e=408 (M+H$^+$).

In an analogous manner, the following compound was obtained:

(6,6-Dimethyl-4,4-dioxo-5-pyridin-3-yl-5,6-dihydro-4H-4lambda*6*-[1,4,3]oxathiazin-2-yl)-[(S)-1-(2-fluorophenyl)ethyl]amine

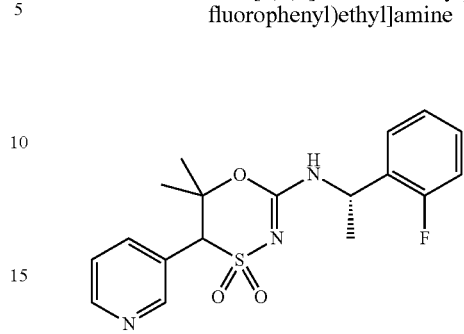

3-[(2,4-Dimethoxybenzylsulfamoyl)methyl]benzoic acid

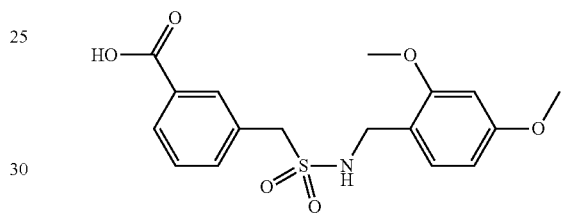

To a solution of 3-[(2,4-dimethoxybenzylsulfamoyl)methyl]benzoic acid methyl ester (5 g) in methanol (20 ml) was added 2M NaOH (20 ml), and the solution was stirred at room temperature for 16 h. The methanol was removed under reduced pressure and the aqueous solution was washed with ethyl acetate, acidified with HCl and extracted with ethyl acetate. The organic phase was dried over magnesium sulfate and concentrated. This gave the product (4.1 g) with a molecular weight of 365.4 g/mol ($C_{17}H_{19}NO_6S$).

3-(2-Hydroxy-2-methyl-1-sulfamoylpropyl)benzoic acid

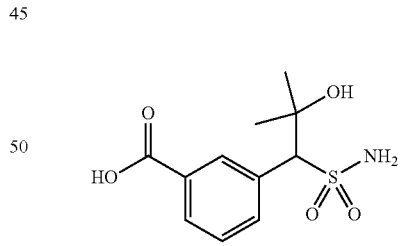

To a solution of 3-[(2,4-dimethoxybenzylsulfamoyl)methyl]benzoic acid (4.1 g) in THF (50 ml) was added dropwise, at −78° C., butyllithium (1.6 M, 25 ml). The mixture was stirred for 10 min. Subsequently, acetone (4.5 ml) was added and the mixture was stirred at −78° C. for a further 30 min. The reaction mixture was then admixed with trifluoroacetic acid (4 ml) and concentrated. The residue was suspended in dichloromethane and trifluoroacetic acid (10 ml) admixed. After 2 h, water was added and the mixture was filtered. The aqueous phase was removed and freeze-dried. The residue was purified by means of preparative HPLC. This gave the product (1.1 g) with a molecular weight of 273.3 g/mol ($C_{11}H_{15}NO_5S$).

3-(2-Methoxy-6,6-dimethyl-4,4-dioxo-5,6-dihydro-4H-4lambda*6*-[1,4,3]oxathiazin-5-yl)benzoic acid methyl ester

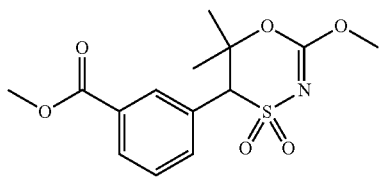

A suspension of 3-(2-hydroxy-2-methyl-1-sulfamoylpropyl)benzoic acid (1.1 g) in tetramethyl orthocarbonate (12 ml) and acetic acid (60 µl) was stirred at 85° C. for 16 h. The mixture was concentrated, admixed with ethyl acetate and washed with sodium bicarbonate solution and with sodium chloride solution. The organic phase was dried over magnesium sulfate and concentrated. This gave the product (1.3 g) with a molecular weight of 327.4 g/mol ($C_{14}H_{17}NO_6S$).

3-{2-[(S)-1-(2-Fluorophenyl)ethylamino]-6,6-dimethyl-4,4-dioxo-5,6-dihydro-4H-4lambda*6*-[1,4,3]oxathiazin-5-yl}benzoic acid methyl ester

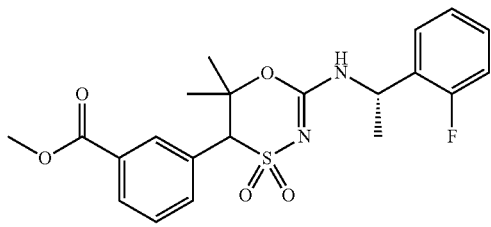 [SMILES: COC(=O)c1cccc(C2C(C)(C)OC(N[C@@H](C)c3ccccc3F)=NS2(=O)=O)c1]

A solution of 3-(2-methoxy-6,6-dimethyl-4,4-dioxo-5,6-dihydro-4H-4lambda*6*-[1,4,3]oxathiazin-5-yl)benzoic acid methyl ester (1.3 g) and (S)-1-(2-fluorophenyl)ethylamine (713 mg) in dichloromethane (15 ml) was stirred under an argon stream and thus concentrated. The residue was left to stand for 4 h, dissolved in ethyl acetate, washed with 1 M HCl and sodium bicarbonate solution, dried over magnesium sulfate and concentrated. This was followed by purification by column chromatography (ethyl acetate/heptane). This gave the product (1.2 g) with a molecular weight of 434.5 g/mol ($C_{21}H_{23}FN_2O_5S$).

3-{2-[(S)-1-(2-Fluorophenyl)ethylamino]-6,6-dimethyl-4,4-dioxo-5,6-dihydro-4H-4lambda*6*-[1,4,3]oxathiazin-5-yl}benzoic acid

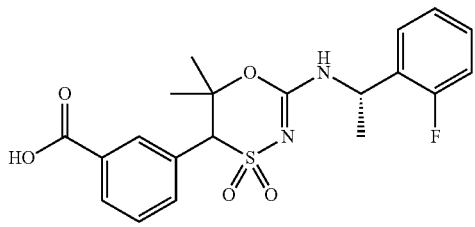

To a solution of 3-{2-[(S)-1-(2-fluorophenyl)ethylamino]-6,6-dimethyl-4,4-dioxo-5,6-dihydro-4H-4lambda*6*-[1,4,3]oxathiazin-5-yl}benzoic acid methyl ester (1.7 mg) in dioxane (15 ml) were added water (5 ml) and sulfuric acid (0.3 ml), and the mixture was stirred at 100° C. for 16 h. The mixture was alkalized with sodium carbonate solution, diluted with water and washed with ethyl acetate. The aqueous phase was acidified, extracted with ethyl acetate, dried over magnesium sulfate and concentrated. This gave the product (551 mg) with a molecular weight of 420.5 g/mol ($C_{20}H_{21}FN_2O_5S$).

(3-{2-[(S)-1-(2-Fluorophenyl)ethylamino]-6,6-dimethyl-4,4-dioxo-5,6-dihydro-4H-4lambda*6*-[1,4,3]oxathiazin-5-yl}phenyl)-(4-methylpiperazin-1-yl)methanone

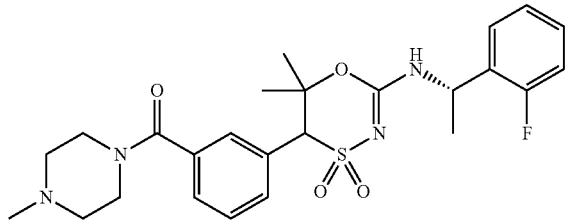 [SMILES: C[C@H](NC1=NS(=O)(=O)C(c2cccc(C(=O)N3CCN(C)CC3)c2)C(C)(C)O1)c1ccccc1F]

To a solution of 3-{2-[(S)-1-(2-fluorophenyl)ethylamino]-6,6-dimethyl-4,4-dioxo-5,6-dihydro-4H-4lambda*6*-[1,4,3]oxathiazin-5-yl}benzoic acid (100 mg) in DMF (2.5 ml) were added DIPEA (0.1 ml), N-methylpiperazine (29 mg) and HATU (100 mg). The mixture was stirred at room temperature for 1.5 h. The mixture was diluted with ethyl acetate, washed with sodium hydrogencarbonate solution and sodium chloride solution, dried over magnesium sulfate and concentrated. The resulting mixture was purified in a purification laboratory by means of preparative HPLC. This gave the product (87 mg as the HCl salt after treatment with hydrochloric acid) with a molecular weight of 502.2 g/mol ($C_{25}H_{31}FN_4O_4S$); MS (ESI): m/e=503 (M+H$^+$).

In an analogous manner, the following compounds were prepared:

(3-{2-[(S)-1-(2-Fluorophenyl)ethylamino]-6,6-dimethyl-4,4-dioxo-5,6-dihydro-4H-4lambda*6*-[1,4,3]oxathiazin-5-yl}phenyl)-(4-methyl-[1,4]diazepan-1-yl)methanone

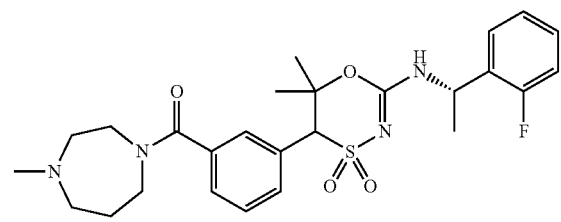 [SMILES: C[C@H](NC1=NS(=O)(=O)C(c2cccc(C(=O)N3CCCN(C)CC3)c2)C(C)(C)O1)c1ccccc1F]

(3-{2-[(S)-1-(2-Fluorophenyl)ethylamino]-6,6-dimethyl-4,4-dioxo-5,6-dihydro-4H-4lambda*6*-[1,4,3]oxathiazin-5-yl}phenyl)morpholin-4-ylmethanone

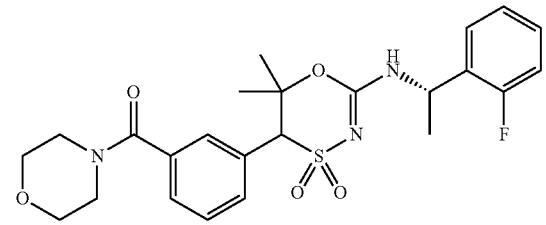 [SMILES: C[C@H](NC1=NS(=O)(=O)C(c2cccc(C(=O)N3CCOCC3)c2)C(C)(C)O1)c1ccccc1F]

3-{2-[(S)-1-(2-Fluorophenyl)ethylamino]-6,6-dimethyl-4,4-dioxo-5,6-dihydro-4H-4lambda*6*-[1,4,3]oxathiazin-5-yl}-N-pyridin-2-ylmethylbenzamide

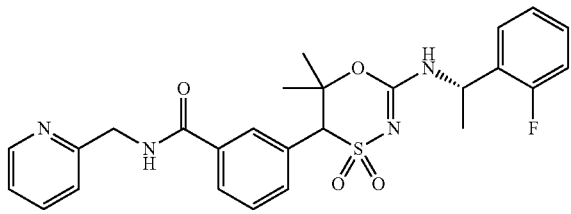 [SMILES: C[C@H](NC1=NS(=O)(=O)C(c2cccc(C(=O)NCc3ccccn3)c2)C(C)(C)O1)c1ccccc1F]

The invention claimed is:
1. A compound of the formula I

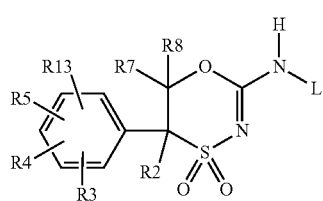

in which
L is R1, —CH(R10)(R11);
R10, R11 are each independently H, F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$, ($C_1$-$C_6$)-alkylene-(R6), ($C_3$-$C_8$)-cycloalkylene-(R6), ($C_1$-$C_6$)-alkylene-($C_3$-$C_8$)-cycloalkylene-(R6), ($C_6$-$C_{10}$)-aryl, ($C_1$-$C_6$)-alkylene-(($C_6$-$C_{10}$)-aryl;
where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
R1 is

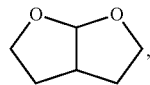

($C_6$-$C_{10}$)-aryl, ($C_3$-$C_8$)-cycloalkyl,
where the

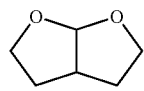

radical, aryl radical or cycloalkyl radical may be mono- to trisubstituted by F, Cl, Br, I, OH, $CF_3$, $CHF_2$, $CH_2F$, $NO_2$, CN, $OCF_3$, $OCHF_2$, —O($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
R2 is H, F, ($C_1$-$C_3$)-alkyl where the alkyl radical may be mono- to trisubstituted by fluorine;
R3, R4, R5, R13 are each independently
H, F, Cl, Br, I, OH, $CF_3$, $CHF_2$, $CH_2F$, $NO_2$, CN, $OCF_3$, $OCHF_2$, —($C_1$-$C_6$)-alkylene-(R9), O—($C_1$-$C_6$)-alkylene-(R9), tert-butyl, isopropylene-(R9), (C=O)—($C_1$-$C_6$)-alkylene-(R9), ($C_1$-$C_6$)-alkylene-(R9), $NH_2$, NH($C_1$-$C_6$)-alkylene-(R9), N(($C_1$-$C_6$)-alkylene-R9)$_2$, ($C_1$-$C_6$)-alkylene-$NH_2$, ($C_1$-$C_6$)-alkylene-NH($C_1$-$C_6$)-alkylene-(R9), ($C_1$-$C_6$)-alkylene-N(($C_1$-$C_6$)-alkylene-R9)$_2$, —O—($C_1$-$C_6$)-alkylene-$NH_2$, —O—($C_1$-$C_6$)-alkylene-NH($C_1$-$C_6$)-alkylene-(R9), —O—($C_1$-$C_6$)-alkylene-N(($C_1$-$C_6$)-alkylene-R9)$_2$, —NH—($C_1$-$C_6$)-alkylene-$NH_2$, —NH—($C_1$-$C_6$)-alkylene-NH($C_1$-$C_6$)-alkylene-(R9), —NH—($C_1$-$C_6$)-alkylene-N(($C_1$-$C_6$)-alkylene-R9)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
($C_6$-$C_{10}$)-aryl, —($C_1$-$C_6$)-alkylene-($C_6$-$C_{10}$)-aryl,
where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$, ($C_6$-$C_{10}$)-aryl, ($C_3$-$C_8$)-cycloalkyl, 4- to 12-membered heterocycle;
where the ($C_6$-$C_{10}$)-aryl radical, ($C_3$-$C_8$)-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
4- to 12-membered heterocycle, —($C_1$-$C_6$)-alkylene-4- to −12-membered heterocycle,
where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, NH($C_1$-$C_6$)-alkylene-(R9), N(($C_1$-$C_6$)-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—NH($C_1$-$C_6$)-alkylene-(R9), $SO_2$—N(($C_1$-$C_6$)-alkyl)$_2$, COOH, COO—($C_1$-$C_6$)-alkylene-(R9), $CONH_2$, CONH($C_1$-$C_6$)-alkylene-(R9), CON(($C_1$-$C_6$)-alkyl)$_2$, $SF_5$, ($C_6$-$C_{10}$)-aryl, ($C_3$-$C_8$)-cycloalkyl, 4- to 12-membered heterocycle;
where the ($C_6$-$C_{10}$)-aryl radical, ($C_3$-$C_8$)-cycloalkyl radical, 4- to 12-membered heterocycle radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, $CONH_2$, CONH($C_1$-$C_6$)-alkyl, CON(($C_1$-$C_6$)-alkyl)$_2$, $SF_5$;
R6 is H, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, $SO_2$—$NH_2$, $SO_2$—NH($C_1$-$C_6$)-alkyl, $SO_2$—N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, O—(CO)—NH$_2$, SF$_5$;
R7, R8 are each independently H, ($C_1$-$C_3$)-alkyl, where the alkyl radical may be mono- to trisubstituted by fluorine, or R7 and R8 together with the carbon atom to which they are bonded form a 3-8-membered carbocycle or heterocycle;
R9 is H, OH, OCH$_3$, OCF$_3$, CHF$_2$, CF$_3$;
and pharmaceutically acceptable salts thereof.

2. The compound of claim 1, wherein
L is R1, —CH(R10)(R11);
R10 is F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$, ($C_1$-$C_6$)-alkylene-(R6), ($C_3$-$C_8$)-cycloalkylene-(R6), ($C_1$-$C_6$)-alkylene-($C_3$-$C_8$)-cycloalkylene-(R6), ($C_6$-$C_{10}$)-aryl, ($C_1$-$C_6$)-alkylene-($C_6$-$C_{10}$)-aryl;
where the aryl radical may be mono- to trisubstituted by F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, SO$_2$—NH$_2$, SO$_2$—NH($C_1$-$C_6$)-alkyl, SO$_2$—N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$;
R11 is H, F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$, ($C_1$-$C_6$)-alkylene-(R6), ($C_3$-$C_8$)-cycloalkylene-(R6), ($C_1$-$C_6$)-alkylene-($C_3$-$C_8$)-cycloalkylene-(R6), ($C_6$-$C_{10}$)-aryl, ($C_1$-$C_6$)-alkylene-($C_6$-$C_{10}$)-aryl;
where the aryl radical may be mono- to trisubstituted by F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, SO$_2$—NH$_2$, SO$_2$—NH($C_1$-$C_6$)-alkyl, SO$_2$—N(($C_1$-$C_6$)-alkyl)$_2$, COOH, COO—($C_1$-$C_6$)-alkyl, CONH$_2$, CONH(C alkyl, CON(($C_1$-$C_6$)-alkyl)$_2$, SF$_5$;
R1 is ($C_3$-$C_8$)-cycloalkyl,
where the cycloalkyl radical may be mono- to trisubstituted by F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, SO$_2$—NH$_2$, SO$_2$—NH($C_1$-$C_6$)-alkyl, SO$_2$—N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$;
R2 is H, F, ($C_1$-$C_3$)-alkyl where the alkyl radical may be mono- to trisubstituted by fluorine;
R3, R4, R5, R13 are each independently H, F, Cl, Br, I, OH, CF$_3$, CHF$_2$, CH$_2$F, NO$_2$, CN, OCF$_3$, OCHF$_2$, O—($C_1$-$C_6$)-alkylene-(R9), —($C_1$-$C_6$)-alkylene-(R9), (C=O)—(C1-C6)-alkylene-(R9), ($C_1$-$C_6$)-alkylene-(R9), NH$_2$, NH($C_1$-$C_6$)-alkylene-(R9), N(($C_1$-$C_6$)-alkyl)$_2$, SO$_2$—CH$_3$, SO$_2$—NH$_2$, SO$_2$—NH($C_1$-$C_6$)-alkyl, SO$_2$—N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$;
($C_6$-$C_{10}$)-aryl, —($C_1$-$C_6$)-alkylene-($C_6$-$C_{10}$-aryl,
where the aryl radical may be mono- to trisubstituted by F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, SO$_2$—NH$_2$, SO$_2$—NH($C_1$-$C_6$)-alkyl, SO$_2$—N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$;
4- to 12-membered heterocycle, —($C_1$-$C_6$)-alkylene-4- to -12-membered heterocycle,
where the heterocyclyl radical may be mono- to trisubstituted by F, Cl, Br, I, OH, CF$_3$, CHF$_2$, CH$_2$F, NO$_2$, CN, OCF$_3$, OCHF$_2$, O—($C_1$-$C_6$)-alkylene-(R9), ($C_1$-$C_6$)-alkylene-(R9), NH$_2$, NH($C_1$-$C_6$)-alkylene-(R9), N(($C_1$-$C_6$)-alkyl)$_2$, SO$_2$—($C_1$-$C_6$)-alkylene-(R9), SO$_2$—$C_2$H$_2$F$_3$, SO$_2$—CH$_3$, SO$_2$—NH$_2$, SO$_2$—NH($C_1$-$C_6$)-alkylene-(R9), SO$_2$—N(($C_1$-$C_6$)-alkyl)$_2$, COOH, COO—($C_1$-$C_6$)-alkylene-(R9), CONH$_2$, CONH($C_1$-$C_6$)-alkylene-(R9), CON(($C_1$-$C_6$)-alkyl)$_2$, SF$_5$, ($C_6$-$C_{10}$)-aryl, ($C_3$-$C_8$)-cycloalkyl, 4- to 12-membered heterocycle;
R6 is H, OH, O—(CO)—NH$_2$, SO$_2$NH$_2$;
R7, R8 are each independently H, ($C_1$-$C_3$)-alkyl where the alkyl radical may be mono- to trisubstituted by fluorine;
R9 is H, OH, OCH$_3$, OCF$_3$, CHF$_2$, CF$_3$;
and pharmaceutically acceptable salts thereof.

3. The compound of claim 1, wherein
L is R1, —CH(R10)(R11);
R10 is ($C_6$-$C_{10}$)-aryl, ($C_1$-$C_6$)-alkylene-($C_6$-$C_{10}$)-aryl;
where the aryl radical may be mono- to trisubstituted by F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, SO$_2$—NH$_2$, SO$_2$—NH($C_1$-$C_6$)-alkyl, SO$_2$—N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$;
R11 is F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$, ($C_1$-$C_6$)-alkylene-(R6);
R1 is ($C_3$-$C_8$)-cycloalkyl,
where the cycloalkyl radical may be mono- to trisubstituted by F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, SO$_2$—NH$_2$, SO$_2$—NH($C_1$-$C_6$)-alkyl, SO$_2$—N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$;
R2 is H, ($C_1$-$C_3$)-alkyl;
R3, R4, R5, R13 are each independently H, F, Cl, Br, I, OH, CF$_3$, CHF$_2$, CH$_2$F, NO$_2$, CN, OCF$_3$, OCHF$_2$, O—($C_1$-$C_6$)-alkylene-(R9), —($C_1$-$C_6$)-alkylene-(R9), (C=O)—(C1-C6)-alkylene-(R9), ($C_1$-$C_6$)-alkylene-(R9), NH$_2$, NH($C_1$-$C_6$)-alkylene-(R9), N(($C_1$-$C_6$)-alkyl)$_2$, SO$_2$—CH$_3$, SO$_2$—NH$_2$, SO$_2$—NH($C_1$-$C_6$)-alkyl, SO$_2$—N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$;
($C_6$-$C_{10}$)-aryl, —($C_1$-$C_6$)-alkylene-($C_6$-$C_{10}$-aryl, where the aryl radical may be mono- to trisubstituted by F, Cl, Br, I, OH, CF$_3$, CHF$_2$, CH$_2$F, NO$_2$, CN, OCF$_3$, OCHF$_2$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, SO$_2$—NH$_2$, SO$_2$—NH($C_1$-$C_6$)-alkyl, SO$_2$—N(($C_1$-$C_6$)-alkyl)$_2$, COOH, COO—($C_1$-$C_6$)-alkyl, CONH$_2$, CONH($C_1$-$C_6$)-alkyl, CON(($C_1$-$C_6$)-alkyl)$_2$, SF$_5$;
4- to 12-membered heterocycle, —($C_1$-$C_6$)-alkylene-4- to -12-membered heterocycle, where the heterocyclyl radical may be mono- to trisubstituted by F, Cl, Br, I, OH, CF$_3$, CHF$_2$, CH$_2$F, NO$_2$, CN, OCF$_3$, OCHF$_2$, O—($C_1$-$C_6$)-alkylene-(R9), ($C_1$-$C_6$)-alkylene-(R9), NH$_2$, NH($C_1$-$C_6$)-alkylene-(R9), N(($C_1$-$C_6$)-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—$NH(C_1$-$C_6)$-alkylene-(R9), $SO_2$—$N((C_1$-$C_6)$-alkyl)$_2$, COOH, COO—($C_1$-$C_6$)-alkylene-(R9), $CONH_2$, $CONH(C_1$-$C_6)$-alkylene-(R9), $CON((C_1$-$C_6)$-alkyl)$_2$, $SF_5$, ($C_6$-$C_{10}$-aryl, ($C_3$-$C_8$)-cycloalkyl, 4- to 12-membered heterocycle;

R6 is H, OH, O—(CO)—$NH_2$, $SO_2NH_2$;

R7, R8 are each independently ($C_1$-$C_3$)-alkyl;

R9 is H, OH, $OCH_3$, $OCF_3$, $CHF_2$, $CF_3$;

and pharmaceutically acceptable salts thereof.

4. The compound of claim 1, wherein

L is R1, —CH(R10)(R11);

R10 is phenyl, where the phenyl radical may be mono- to trisubstituted by F, Cl, Br, —($C_1$-$C_6$)-alkyl;

R11 is ($C_1$-$C_6$)-alkyl, ($C_1$-$C_6$)-alkylene-(R6);

R1 is ($C_3$-$C_8$)-cycloalkyl, where the cycloalkyl radical may be mono- to trisubstituted by F, Cl, Br, OH;

R2 is H, ($C_1$-$C_3$)-alkyl;

R3, R4, R5, R13 are each independently H, F, Cl, Br, I, OH, $CF_3$, $CHF_2$, $CH_2F$, $NO_2$, CN, $OCF_3$, $OCHF_2$, O—($C_1$-$C_6$)-alkylene-(R9), —($C_1$-$C_6$)-alkylene-(R9), (C=O)—(C1-C6)-alkylene-(R9), ($C_1$-$C_6$)-alkylene-(R9), $NH_2$, $NH(C_1$-$C_6)$-alkylene-(R9), $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;

($C_6$-$C_{10}$-aryl, —($C_1$-$C_6$)-alkylene-($C_6$-$C_{10}$-aryl, where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, $SO_2$—$NH_2$, $SO_2$—$NH(C_1$-$C_6)$-alkyl, $SO_2$—$N((C_1$-$C_6)$-alkyl)$_2$, COOH, COO—($C_1$-$C_6$)-alkyl, $CONH_2$, $CONH(C_1$-$C_6)$-alkyl, $CON((C_1$-$C_6)$-alkyl)$_2$, $SF_5$;

4- to 12-membered heterocycle, —($C_1$-$C_6$)-alkylene-4- to -12-membered heterocycle, where the heterocyclyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkylene-(R9), ($C_1$-$C_6$)-alkylene-(R9), $NH_2$, $NH(C_1$-$C_6)$-alkylene-(R9), $N((C_1$-$C_6)$-alkyl)$_2$, $SO_2$—($C_1$-$C_6$)-alkylene-(R9), $SO_2$—$C_2H_2F_3$, $SO_2$—$CH_3$, $SO_2$—$NH_2$, $SO_2$—$NH(C_1$-$C_6)$-alkylene-(R9), $SO_2$—$N((C_1$-$C_6)$-alkyl)$_2$, COOH, COO—($C_1$-$C_6$)-alkylene-(R9), $CONH_2$, $CONH(C_1$-$C_6)$-alkylene-(R9), $CON((C_1$-$C_6)$-alkyl)$_2$, $SF_5$, ($C_6$-$C_{10}$)-aryl, ($C_3$-$C_8$)-cycloalkyl, 4- to 12-membered heterocycle;

R6 is OH;

R7, R8 are each independently ($C_1$-$C_3$)-alkyl;

R9 is H, OH, $OCH_3$, $OCF_3$, $CHF_2$, $CF_3$;

and pharmaceutically acceptable salts thereof.

5. A pharmaceutical composition comprising the compound of claim 1, or pharmaceutically acceptable salts thereof, and a pharmaceutically acceptable carrier and/or excipient.

6. The pharmaceutical composition of claim 5, further comprising at least one further active ingredient.

7. The pharmaceutical composition of claim 6, wherein said active ingredient is one or more antidiabetics, active hypoglycemic ingredients, HMG-CoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose 1,6-biphosphatase, modulators of glucose transporter 4, inhibitors of glutamine:fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, GPR40 modulators, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists, lipase/amylase inhibitors, PPAR modulators, RXR modulators or TRβ agonists or amphetamines.

8. A process for preparing a pharmaceutical composition comprising mixing the compound of claim 1 with a pharmaceutically suitable carrier and converting said mixture to a form suitable for administration.

9. A method of treating hyperglycemia comprising administering to a patient in need thereof a therapeutically effective amount of the pharmaceutical composition of claim 5.

10. A method of treating diabetes comprising administering to a patient in need thereof a therapeutically effective amount of the pharmaceutical composition of claim 5.

11. A method of treating insulin resistance comprising administering to a patient in need thereof a therapeutically effective amount of the pharmaceutical composition of claim 5.

12. A kit consisting of separate packages of
a) an effective amount of the compound of claim 1 and
b) an effective amount of a further active medicament ingredient.

\* \* \* \* \*

UNITED STATES PATENT AND TRADEMARK OFFICE
CERTIFICATE OF CORRECTION

PATENT NO. : 8,895,547 B2  
APPLICATION NO. : 14/003329  
DATED : November 25, 2014  
INVENTOR(S) : Thomas Boehme et al.

Page 1 of 1

It is certified that error appears in the above-identified patent and that said Letters Patent is hereby corrected as shown below:

In the Claims:

Column 241, claim number 1, line number 65, please replace "-O($C_1$-$C_6$)-alkyl," with -- -O-($C_1$-$C_6$)-alkyl,--;

Column 243, claim number 2, line number 34, please replace "($C_6$-$C_{10}$-aryl," with --($C_6$-$C_{10}$)-aryl,--;

Column 243, claim number 2, line number 42, please replace "CONH(C alkyl," with --CONH($C_1$-$C_6$)-alkyl,--;

Column 243, claim number 2, line number 62, please replace "-($C_1$-$C_6$)-alkylene-($C_6$-$C_{10}$-aryl," with -- -($C_1$-$C_6$)-alkylene-($C_6$-$C_{10}$)-aryl,--;

Column 244, claim number 3, line number 54, please replace "-($C_1$-$C_6$)-alkylene-($C_6$-$C_{10}$-aryl," with -- -($C_1$-$C_6$)-alkylene-($C_6$-$C_{10}$)-aryl,--;

Column 245, claim number 3, line number 5, please replace "($C_6$-$C_{10}$-aryl," with --($C_6$-$C_{10}$)-aryl,--;

Column 245, claim number 4, line number 30, please replace "($C_6$-$C_{10}$-aryl, -($C_1$-$C_6$)-alkylene-($C_6$-$C_{10}$-aryl," with --($C_6$-$C_{10}$)-aryl, -($C_1$-$C_6$)-alkylene-($C_6$-$C_{10}$)-aryl,--.

Signed and Sealed this  
Eighth Day of September, 2015

Michelle K. Lee  
*Director of the United States Patent and Trademark Office*